(12) United States Patent
Song et al.

(10) Patent No.: US 11,773,132 B2
(45) Date of Patent: Oct. 3, 2023

(54) CYCLIC DI-NUCLEOTIDES AS STIMULATOR OF INTERFERON GENES MODULATORS

(71) Applicant: Beijing Xuanyi PharmaSciences Co., Ltd., Beijing (CN)

(72) Inventors: Yuntao Song, Palo Alto, CA (US); Anrong Li, Foster City, CA (US); Xiaoqi Chen, Palo Alto, CA (US)

(73) Assignee: Beijing Xuanyi PharmaSciences Co., Ltd., Beijing (CN)

( * ) Notice: Subject to any disclaimer, the term of this patent is extended or adjusted under 35 U.S.C. 154(b) by 407 days.

(21) Appl. No.: 16/643,127

(22) PCT Filed: Aug. 30, 2018

(86) PCT No.: PCT/IB2018/056658
§ 371 (c)(1),
(2) Date: Feb. 28, 2020

(87) PCT Pub. No.: WO2019/043634
PCT Pub. Date: Mar. 7, 2019

(65) Prior Publication Data
US 2020/0331957 A1    Oct. 22, 2020

Related U.S. Application Data

(60) Provisional application No. 62/660,565, filed on Apr. 20, 2018, provisional application No. 62/552,148, filed on Aug. 30, 2017.

(51) Int. Cl.
*C07H 21/04*    (2006.01)
*C07H 21/02*    (2006.01)

(52) U.S. Cl.
CPC ............. *C07H 21/04* (2013.01); *C07H 21/02* (2013.01)

(58) Field of Classification Search
CPC ..... C07H 21/02; C07H 21/04; A61K 31/7084
See application file for complete search history.

(56) References Cited

U.S. PATENT DOCUMENTS

| | | | |
|---|---|---|---|
| 6,106,864 A | 8/2000 | Dolan et al. | |
| 7,867,493 B2 | 1/2011 | Damiano et al. | |
| 8,562,997 B2 | 10/2013 | Jaiswal et al. | |
| 8,728,476 B2 | 5/2014 | van den Berg | |
| 8,895,705 B2 | 11/2014 | Medema et al. | |
| 9,718,848 B2 | 8/2017 | Adams et al. | |
| 11,001,605 B2 * | 5/2021 | Genieser | C07H 21/00 |
| 11,401,295 B2 * | 8/2022 | Guo | C07H 21/02 |
| 2005/0203051 A1 | 9/2005 | Karaolis et al. | |
| 2007/0244059 A1 * | 10/2007 | Karaolis | A61K 31/00 514/44 R |
| 2014/0341976 A1 | 11/2014 | Dubensky, Jr. et al. | |
| 2015/0056224 A1 | 2/2015 | Dubensky, Jr. et al. | |
| 2017/0044206 A1 † | 2/2017 | Altman | |
| 2018/0369268 A1 † | 12/2018 | Katibah | |

FOREIGN PATENT DOCUMENTS

| | | | |
|---|---|---|---|
| WO | WO 1991/11172 A1 | 8/1991 | |
| WO | WO 1994/02518 A1 | 2/1994 | |
| WO | WO 1998/55148 A1 | 12/1998 | |
| WO | WO 2000/35298 A1 | 6/2000 | |

(Continued)

OTHER PUBLICATIONS

Morisette et al., "High-throughput crystallization: polymorphs, salts, co-crystals and solvates of pharmaceutical solids" Advanced Drug Delivery Reviews vol. 56 pp. 275-300 doi:10.1016/j.addr.2003.10.020 (Year: 2004).*

(Continued)

*Primary Examiner* — Eric Olson
(74) *Attorney, Agent, or Firm* — Cooley LLP

(57) ABSTRACT

The present disclosure relates to a compound of formulae (I) or (II), or a pharmaceutically acceptable salt, a solvate, a hydrate thereof, a pharmaceutical composition comprising a compound of formulae (I) or (II), and use thereof, wherein various Markush groups are as described herein.

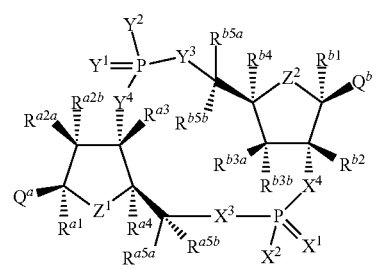

(I)

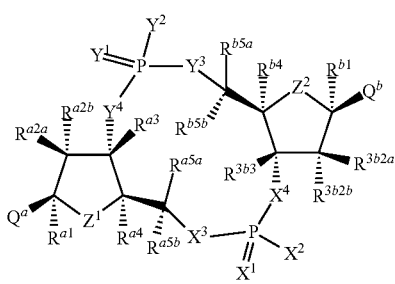

(II)

15 Claims, 1 Drawing Sheet

(56) References Cited

FOREIGN PATENT DOCUMENTS

| WO | WO 2004/045532 A2 | 6/2004 | | |
|---|---|---|---|---|
| WO | WO 2005/005450 A1 | 1/2005 | | |
| WO | WO 2005/030186 A2 | 4/2005 | | |
| WO | WO 2009/133560 A1 | 11/2009 | | |
| WO | WO 2012/022814 A1 | 2/2012 | | |
| WO | WO 2014/093936 A1 | 6/2014 | | |
| WO | WO 2014/160160 A2 | 10/2014 | | |
| WO | WO 2014/179335 A1 | 11/2014 | | |
| WO | WO 2014/189805 A1 | 11/2014 | | |
| WO | WO 2015/061294 A2 | 4/2015 | | |
| WO | WO 2015/074145 A1 | 5/2015 | | |
| WO | WO 2015/185565 A1 | 12/2015 | | |
| WO | WO 2016/096174 A1 | 6/2016 | | |
| WO | WO 2016/096577 A1 | 6/2016 | | |
| WO | WO 2016/120305 A1 | 8/2016 | | |
| WO | WO 2017/027645 A1 | 2/2017 | | |
| WO | WO 2017/027646 A1 | 2/2017 | | |
| WO | WO 2017/075477 A1 | 5/2017 | | |
| WO | WO 2017/093933 A1 | 6/2017 | | |
| WO | WO 2017/106740 A1 | 6/2017 | | |
| WO | WO 2017/123657 A1 | 7/2017 | | |
| WO | WO 2017/123669 A1 | 7/2017 | | |
| WO | 2017161349 A1 † | 9/2017 | | |
| WO | WO 2017/161349 A1 | 9/2017 | | |
| WO | WO-2017186711 A1 * | 11/2017 | ......... | A61K 31/7076 |
| WO | WO 2018/009466 A1 | 1/2018 | | |
| WO | WO 2018/045204 A1 | 3/2018 | | |
| WO | WO 2018/060323 A1 | 4/2018 | | |
| WO | WO 2018/065360 A1 | 4/2018 | | |
| WO | WO 2018/098203 A1 | 5/2018 | | |
| WO | WO 2018/100558 A2 | 6/2018 | | |
| WO | WO 2018/118665 A1 | 6/2018 | | |
| WO | WO-2018119274 A1 * | 6/2018 | ............ | A61K 35/17 |
| WO | WO 2018/138684 A1 | 8/2018 | | |
| WO | WO 2018/138685 A2 | 8/2018 | | |
| WO | WO-2018138685 A2 * | 8/2018 | ............ | A61P 31/12 |
| WO | WO 2019/043634 A2 | 3/2019 | | |

OTHER PUBLICATIONS

Xin et al., "Solvate Prediction for Pharmaceutical Organic Molecules with Machine Learning" Cryst Growth Des vol. 19 pp. 1903-1911 DOI: 10.1021/acs.cgd.8b01883 (Year: 2019).*
Boothroyd et al., "Why Do Some Molecules Form Hydrates or Solvates?" Cryst Growth Des vol. 18 pp. 1903-1908 DOI: 10.1021/acs.cgd.8b00160 (Year: 2018).*
Third Party Observations submission in European Patent Application No. 18850228.0, (mailed to agent of record on Feb. 26, 2021), 27 pages.
Third Party Observations issued in Japanese Patent Application No. 2020-533876, dated Jan. 5, 2021 (mailed to agent of record on Feb. 12, 2021), 30 pages including English translation.
Belikov, Farmatsevticheskaya Khimiya (Pharmaceutical Chemistry: A Scholarly Manual), Moscow: MEDpress-Inform, 2007, pp. 27-29 (Non-English).
Dyson et al., Chemistry of Synthetic Drugs Revised and Rewritten by G. M. Dyson, in consultation with Percy May, London: Longmans, Green and Co., Ltd., 1959 (in Russian translation: G. Daison and P.

Mei, "Khimiya Sinteticheskikh Lekarstvennykh Veshchestv," Moscow: Mir, 1964, pp. 12-19 (Non-English).
"Khimicheskiy entsiklopedicheskiy slovarm" (Chemical Encyclopedic Dictionary), Moscow: Sovetskaya Entsiklopediy, 1983, pp. 130-131 (Non-English).
Smirnova et al., "Optical Isomerism and Biological Activity of Drug," Vestnik Moskovskogo Universiteta, Ser. 2: Khim., 2012, 53(3), pp. 147-156 (Non-English).
Extended European Search Report issued by the European Patent Office for Application No. EP20180850228 dated Sep. 17, 2021, 11 pages.
Office Action issued by the Russian Patent Office for Application No. RU2020112502 , dated Oct. 8, 2021, 27 pages including English translation.
Ablasser et al., "cGAS Produces a 2'-5'-linked Cyclic Dinucleotide Second Messenger That Activates STING," Nature 498(7454): 380-384 (2013).
Azimi, "Tumor-infiltrating Lymphocyte Grade Is an Independent Predictor of Sentinel Lymph Node Status and Survival in Patients With Cutaneous Melanoma," J Clin Oncol. 30(21):2678-83 (2012).
Burdette, D.L., et al., "STING Is a Direct Innate Immune Sensor of Cyclic di-GMP," Naure. 478(7370):515518 (2011).
Davies, B. W., et al., "Coordinated Regulation of Accessory Genetic Elements Produces Cyclic Di-Nucleotides for V. cholerae Virulence," Cell 149:358-370 (2012).
Diner et al., The Innate Immune DNA Sensor cGAS Produces a Noncanonical Cyclic Dinucleotide that Activates Human STING. Cell Reports 3:1355-1361 (2013).
Galon J. et al., "Type, Density, and Location of Immune Cells Within Human Colorectal Tumors Predict Clinical Outcome," Science 313(5795):1960-1964 (2006).
Jin, Y.; Just, G.,"The synthesis of the Sp and Rp diastereomers of dithymidine boranophosphate," Tetrahedron Lett. 39:6429-6432 (1998).
Keating et al., "Cytosolic DNA sensors regulating type I interferon induction," Trends Immunol. 32:574-581 (2011).
Corrales, et al., "Molecular Pathways: Targeting the Stimulator of Interferon Genes (STING) in the Immunotherapy of Cancer," Clin Cancer Res 21:4774-4779 (2015).
Li et al., "Nucleoside and Oligonucleoside Boranophosphates: Chemistry and Properties," Chem. Rev. 107:4746-4796 (2007).
Mahmoud SM et al., "Tumor-infiltrating CD8+ Lymphocytes Predict Clinical Outcome in Breast Cancer," J Clin Oncol. 29(15):1949-55 (2011).
Verma et al, "Current Status of Drug Delivery Technologies and Future Directions," Pharmaceutical Technology Online, 25(2), 1-14 (2001).
Woo et al., "STING-Dependent Cytosolic DNA Sensing Mediates Innate Immune Recognition of Immunogenic Tumors," Immunity 41(5): 830-842 (2014).
Yan et al., "Synthesis and immunostimulatory properties of the phosphorothioate analogues of cdiGMP," Biorganic & Medicinal Chemistry Letters 18(20):5631-5634 (2008).
Zhang Let al., "Intratumoral T Cells, Recurrence, and Survival in Epithelial Ovarian Cancer," N Engl J Med 348(3):203-213 (2003).
Zhang X et al. Cyclic GMP-AMP Containing Mixed Phosphodiester Linkages Is An Endogenous High-Affinity Ligand for STING. Molecular cell 51:226-235 (2013).

* cited by examiner
† cited by third party

CYCLIC DI-NUCLEOTIDES AS STIMULATOR OF INTERFERON GENES MODULATORS

CROSS-REFERENCE TO RELATED APPLICATIONS

This application is a U.S. National Stage Application under 35 U.S.C. § 371 of International Application No. PCT/IB2018/056658 filed Aug. 30, 2018, which claims priority to and the benefit of U.S. Provisional Patent Application No. 62/552,148, filed Aug. 30, 2017, and U.S. Provisional Patent Application No. 62/660,565, filed Apr. 20, 2018, the disclosure of each of which is hereby incorporated by reference in its entirety for all purposes.

FIELD OF THE DISCLOSURE

The present invention relates to compounds of formulae (I), (II), (A), or (B), or any subgenera thereof, or a pharmaceutically acceptable salt thereof, and pharmaceutical compositions, combinations and medicaments comprising the compounds of formulae (I), (II), (A), or (B), or any subgenera thereof, or a pharmaceutically acceptable salt thereof, The invention also relates to the use of such compounds, combinations, compositions and medicaments, in the treatment of diseases and conditions in which modulation of STING (stimulator of interferon genes) is beneficial, such as inflammation, allergic and autoimmune diseases, infectious diseases, cancer, pre-cancerous syndromes and as vaccine adjuvants.

BACKGROUND OF THE DISCLOSURE

Novel immunotherapy approaches are transforming the treatment of cancer, yet only a fraction of patients respond to these immunotherapy. One hypothesis for the failure of an immunotherapy is that a tumor microenvironment fails to support recruitment of immune cells, including CD8+ T cells. It is known that the presence of CD8+ T cells in solid tumors correlates with better prognosis in colorectal cancer (Galon J et al., 2006), breast cancer (Mahmoud S M et al., 2011), melanoma (Azimi F et al., 2012), ovarian (Zhang L et al., 2003) and others. Recent work has demonstrated that activation of STING pathway in tumor-resident host antigen presenting cells is required for induction of a spontaneous CD8+ T cells response against tumor-derived antigen in vivo (Woo. et al., 2014).

STING (Stimulator of interferon genes; also known as THEM173, MITA, ERIS and MPYS) is an endoplasmic reticulum (ER) transmembrane protein, expressed in thymus, spleen, placenta as well as THP1 human monocytic cells. The STING pathway is activated either by exogenous cyclic dinucleotides (CDNs) produced by bacteria infection or structurally distinct endogenous CDNs, such as cyclic GMP-AMP (cGAMP) produced by cyclic GMP-AMP synthase (cGAS) in response to sensing cytosolic double-stranded DNA (dsDNA) (Ablasser et al., 2013; Diner et al., 2013). The cytoplasmic domain of STING forms dimers, and the CDNs bind at the dimer interface (Burdette, D. L., et al., 2011). Upon ligand binding, the cytoplasmic tail of STING serves as adaptor for TBK-1 and IRF-3, resulting in their phosphorylation. The phosphorylated IRF-3 gets into nucleus to induce transcription of genes encoding type I IFN and cytokines for promoting intercellular host immune defense (Keating et al., 2011).

cGAMP is a heterodimer linked by one 3'-5' phosphodiester and one 2'-5' phosphodiester (2',3'-cGAMP), while the bacteria CDNs linked through two 3'-5' phosphodiester linkages (3',3'-CDNs), which can contain two guanosines, two adenosines or one of each (Davies, B. W., 2012). The affinity of 2',3'-cGAMP for human STING is very high, with a dissociation constant of 4.59 nM compared to >1 uM for bacteria 3',3'-CDNs (Zhang, X. et al., 2013; Ablasser, A. et al., 2013; Diner et al., 2013). However, native CDNs are sensitive to degradation by phosphodiesterases that are present in host cell or in the systemic circulation (Yan et al., 2008). In order to improve hydrolytic stability, synthetic CDN compounds were developed with the substitution of non-bridging oxygen atoms at phosphate bridge with sulfur atoms. It has been found that bisphosphothionate anologue of endogenous cGAMP (ML cGAMP) is resistant to hydrolysis by ENPP1 phosphodiesterase; therefore, more potent in inducing IFN-βsecretion in human THP-1 cells (Li et al., 2014). Similarly, R, R-dithio modified cyclic di-AMP (CDA) (ML RR-S2 CDA and RR-S2 CDA showed increased type I IFN production over CDA (Leticia C., et al., 2015). In addition, intratumoral injection of ML RR-S2 CDA into B16 melanoma tumors resulted in complete tumor elimination in most of the ML RR-S2 CDA-treated mice and induced lasting systemic antigen-specific CD8+T-cell immunity. Furthermore, they were completely protected against second tumor rechallenge. Similar results were seen in the 4T-1 breast cancer and MC26 colon cancer models.

SUMMARY OF THE INVENTION

In one embodiment of the present disclosure, a compound of formulae (I), (II), (A), or (B), or a pharmaceutically acceptable salt, stereoisomers, solvate or hydrate thereof, is provided.

In one embodiment, the compound of formula (I) or formula (II):

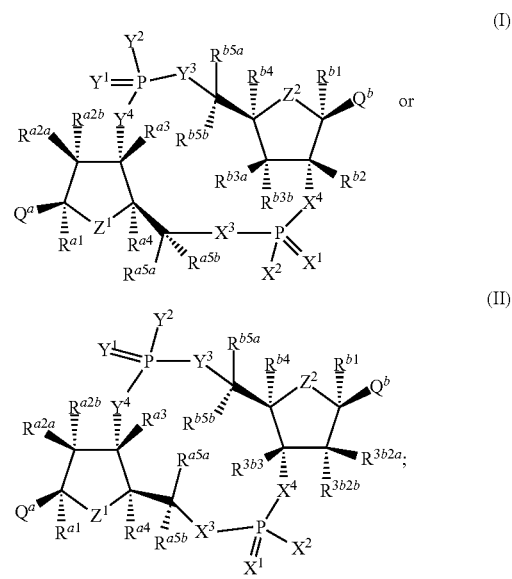

or a pharmaceutically acceptable salt, stereoisomer, solvate or hydrate thereof, wherein:

$Q^a$ and $Q^b$ are each independently cycloalkyl, heterocyclyl, aryl, or heteroaryl, wherein the cycloalkyl, heterocyclyl, aryl, and heteroaryl can be optionally substituted with one, two, three, four, or five $R^1$;

$R^1$ is each independently hydrogen, halogen, —$NO_2$, —CN, —$OR^{cl}$, —$SR^{cl}$, —$N(R^{cl})_2$, —$C(O)R^{cl}$, —$CO_2R^{cl}$, —$C(O)C(O)R^{cl}$, —$C(O)CH_2C(O)R^{cl}$, —$C(O)N(R^{cl})_2$, —$C(=NR^{cl})N(R^{cl})_2$, —$C(=NOR^{cl})R^{cl}$, —$S(O)R^{cl}$, —$S(O)_2R^{cl}$, —$SO_2N(R^{cl})_2$, —$OC(O)R^{cl}$, —$N(R^{cl})C(O)R^{cl}$, —$NR^{cl}N(R^{cl})_2$, —$N(R^{cl})C(=NR^{cl})N(R^{cl})_2$, —$N(R^{cl})C(O)N(R^{cl})_2$, —$N(R^{cl})SO_2N(R^{cl})_2$, —$N(R^{cl})SO_2R^{cl}$, —$N(R^{cl})SO_2NR^{cl}C(=O)OR^{cl}$, —$OC(O)N(R^{cl})_2$, or $R^{cl}$;

$R^{cs}$ is each independently H, $C_{1-12}$ alkyl, $C_{2-12}$ alkenyl, $C_{2-12}$ alkynyl, $C_{3-12}$ cycloalkyl, $C_{3-12}$ cycloalkyl-$C_{1-6}$ alkyl-, heterocyclyl, heterocyclyl-$C_{1-6}$ alkyl-, aryl, aryl-$C_{1-6}$ alkyl-, heteroaryl, or heteroaryl-$C_{1-6}$ alkyl-, wherein $C_{1-12}$ alkyl, $C_{2-12}$ alkenyl, $C_{2-12}$ alkynyl, $C_{3-12}$ cycloalkyl, $C_{3-12}$ cycloalkyl-$C_{1-6}$ alkyl-, heterocyclyl, heterocyclyl-$C_{1-6}$ alkyl-, aryl, aryl-$C_{1-6}$ alkyl-, heteroaryl, and heteroaryl-$C_{1-6}$ alkyl- can be substituted one or more substituents selected from $C_{1-6}$ alkyl, halogen, $C_{1-6}$ alkoxy, —$NO_2$, —$NR^{ns}R^{ns}$, —OH, =O, or $COOR^{cs}$; or alternatively, two $R^{cl}$ attached to the same N atom can together with the N atom form a 4-7 membered heterocyclic ring, containing up to one other heteroatom selected from O, S, or $NR^{ns}$, and wherein the 4-7 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

$R^{ns}$ is each independently H, $R^{cs}$, $R^{cs}$—C(O)—, $R^{cs}$—S(O)_2—, $R^{cs}R^{cs}$N—C(O)—, or $R^{cs}R^{cs}$NS(O)_2—;

$R^{cs}$ is each independently H, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, or $C_2$-$C_6$ haloalkynyl; or alternatively, two $R^{cs}$ attached to the same N atom can together with the N atom form a 4-7 membered heterocyclic ring, containing up to one other heteroatom chosen from O, S, or $NR^{ns}$, wherein the 4-7 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

$R^{a1}$ and $R^{b1}$ are each independently H, CN, $C_{3-6}$ cycloakyl, $R^{cs}$, —$OR^{cs}$, —$SR^{cs}$, —$CH_2N_3$, —$CH_2NR^{cs}R^{cs}$ or —$CH_2OR^{cs}$, wherein $C_{3-6}$ cycloakyl and $R^{cs}$ is optionally substituted with one, two or three substituents selected from halogen, OH, OMe, $NMe_2$, CN or $N_3$;

$R^{a4}$ and $R^{b4}$ are each independently selected from the group consisting of H, halogen, OH, CN, $N_3$, $R^{cs}$, —$CH_2OR^{cs}$, —$CH_2SR^{cs}$, —$CH_2N_3$, —$CH_2NR^{cs}R^{cs}$, —$CO_2R^{cs}$, —$SR^{cs}$, and —$OR^{cs}$, where said $R^{cs}$ is substituted by 0-3 substituents selected from the group consisting of halogen, OH, OMe, $NMe_2$, CN and $N_3$;

$R^{a2a}$, $R^{a2b}$, $R^{b3a}$, $R^{b3b}$, $R^{3b2a}$, $R^{3b2b}$, $R^{2a3a}$ and $R^{2a3b}$ are each independently H, halogen, CN, $N_3$, —$CH_2N_3$, —$CH_2NR^{cs}R^{cs}$, —$CO_2R^{cs}$, —$CH_2OR^{cs}$, —$CH_2SR^{cs}$, —$C_{3-6}$ cycloalkyl, —$R^{cs}$, —$NR^{cs}R^{cs}$, —$OCH_2CO_2R^{cs}$, or —$OR^{cs}$, wherein the —$R^{cs}$ and the $R^{cs}$ in —$CH_2NR^{cs}R^{cs}$, —$CO_2R^{cs}$, —$CH_2OR^{cs}$, —$CH_2SR^{cs}$, and —$OCH_2CO_2R^{cs}$, the $R''$ in —$NR''R''$, and the $R^0$ in —$OR^0$ can be optionally substituted with up to three substituents selected from halogen, CN, —$NMe_2$, $C_{1-6}$ alkoxy, —$NO_2$, —$NR^{cs}R^{cs}$, —OH, OMe, =O, or $COOR^{cs}$; or alternatively, $R^{a2a}$ and $R^{a2b}$, $R^{b3a}$ and $R^{b3b}$, $R^{3b2a}$ and $R^{3b2b}$, or $R^{2a3a}$ and $R^{2a3b}$, can be taken together with the carbon atom to which they are attached, form a 4-6 membered heterocyclic ring, containing up to one other heteroatom chosen from O, S, or $NR^{ns}$, and wherein the 4-6 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, $NMe_2$, cyano or halo;

$R^0$ is hydrogen, $R^{cl}$, or $R^{cl}$—C(O)—;

$R^{a3}$, $R^{b2}$, $R^{3b3}$ and $R^{2a2}$ are each independently H, halogen, CN, $N_3$, —P(=O)(OR^{cs})_2$, $C_{3-6}$ cycloalkyl, $R^{cs}$, —C≡C—Cl, —$CH_2N_3$, —$CH_2NR^{cs}R^{cs}$, —$CO_2R^{cs}$, —$CH_2OR^{cs}$ or —$CH_2SR^{cs}$; wherein the $C_{3-6}$ cycloakyl and $R^{cs}$ is optionally substituted with one, two, or three substituents selected from halogen, OH, OMe, oxo, $NMe_2$, CN or $N_3$;

$R^{a5a}$, $R^{a5b}$, $R^{b5a}$ and $R^{b5b}$ are each independently H, F, $R^{cs}$, wherein the $R^{cs}$ is optionally substituted with one, two, or three substituents selected from halogen, OH, OMe, $NMe_2$, CN or $N_3$;

$R''$ is independently hydrogen, $R^{cl}$, $R^{cl}$—C(=O)—, $R^{cl}$—S(=O)_2—, $R^{cl}R^{cl}$N—C(=O)—, $R^{cl}$O—C(=O)—, $R^{cl}R^{cl}$N—S(=O)_2—, or $R^{cl}OC(=O)NR^{cl}$—S(=O)_2—, wherein, two $R^{cl}$ attached to the same N atom can together with the N atom form a 4-7 membered heterocyclic ring, containing up to one other heteroatom selected from O, S, or $NR^{ns}$, wherein the 4-7 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo; or alternatively, two $R''$ attached to the same N atom can together with the N atom form a 4-7 membered heterocyclic ring, containing up to one other heteroatom chosen from O, S, or $NR^{ns}$, wherein the 4-7 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

$X^1$ and $Y^1$ are each independently O or S;

$X^2$ and $Y^2$ are each independently $SR^4$, $OR^4$, $NR^4R^4$, $BH(OR^7)_2^-$, or $BH(R^b)_2^-$; wherein, at least one of $X^2$ and $Y^2$ is $BH(R^b)_2^-$;

$R^b$ is each independently H, CN, carboxyl, carboxyl salts, $C_{1-6}$ alkyl, alkylaryl, aryl, alkoxycarbonyl, or alkylaminocarbonyl, wherein the $C_{1-6}$ alkyl, alkylaryl, aryl, alkoxycarbonyl and alkylaminocarbonyl is each optionally substituted with up to 3 substituents selected from OH, —P(O)(OH)_2, —OP(O)(OH)_2, $CO_2H$, or F; or alternatively, two $R^b$ taken together with the B atom to which they are both attached, form a 4-7 membered heterocyclic ring, containing up to one other heteroatom selected from O, S, or $NR^{ns}$, wherein the 4-7 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano, $CO_2H$, —P(O)(OH)_2, —OP(O)(OH)_2, or halo;

$R^4$ is each independently H, $R^{cl}$, $C_{1-20}$ alkyl, $CH_2COOR^5$, $CH_2OC(O)R^5$, $CH_2OCO_2R^5$, $CH_2CH_2SC(O)R^5$,

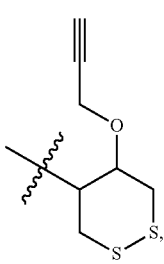 [SMILES: *C1CSSCC1OCC#C]

or CH$_2$CH$_2$SSCH$_2$R$^5$;

R$^5$ is each independently R$^{cl}$, C$_{1-20}$ alkyl, C$_{1-20}$ alkenyl, or C$_{1-20}$ alkynyl, wherein the R$^{cl}$, C$_{1-20}$ alkyl, C$_{1-20}$ alkenyl and C$_{1-20}$ alkynyl is each optionally substituted with 1 to 5 substituents independently selected from OH, —P(O)(OH)$_2$, —OP(O)(OH)$_2$, CO$_2$H, aryl, cycloalkyl, hydroxy or fluorine;

R$^6$ is selected from the group consisting of H, R$^n$, and R$^4$;

R$^7$ is H, R$^{cl}$, or R$^4$; or alternatively, two R$^7$ taken together with the —O—B(H)—O— group to which they are both attached, form a 5-7 membered heterocyclic ring, containing up to one other heteroatom selected from O, S, or NR$^{ns}$, wherein the 5-7 membered heterocyclic ring is optionally substituted with up to three substituents selected from hydroxyl, C$_{1-6}$ alkoxy, C$_{1-6}$ hydroxyalkyl, C$_{1-6}$ alkoxy-C$_{1-6}$ alkyl, C$_{1-6}$ alkoxy-C$_{1-6}$ alkoxy, C$_{2-6}$ hydroxyalkoxy, oxo, thiono, cyano, CO$_2$H, —P(O)(OH)$_2$, —OP(O)(OH)$_2$, CO$_2$H, or halo;

X$^3$, X$^4$, Y$^3$ and Y$^4$ are each independently selected from the group consisting of O, S and NR$^6$; and Z$^1$ and Z$^2$ are independently selected from O, S, S(O), SO$_2$, NR$^{ns}$, CH$_2$, CHF, CF$_2$, CH$_2$O, OCH$_2$, CH$_2$CH$_2$, CHFCHF, or CH=CH;

provided that, in Formula (I), if Q$^b$ is

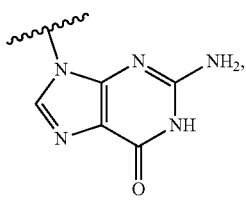 [SMILES: *n1cnc2c(=O)[nH]c(N)nc21]

then Q$^a$ is not

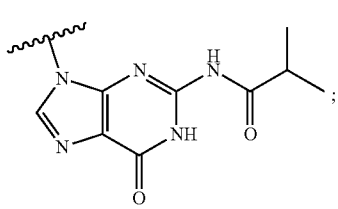 [SMILES: *n1cnc2c(=O)[nH]c(NC(=O)C(C)C)nc21]

provided that, in Formula (I), if Q$^b$ is

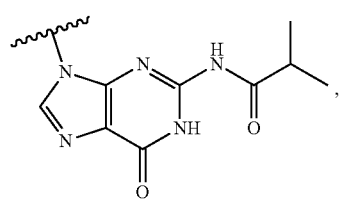 [SMILES: *n1cnc2c(=O)[nH]c(NC(=O)C(C)C)nc21]

then Q$^a$ is not

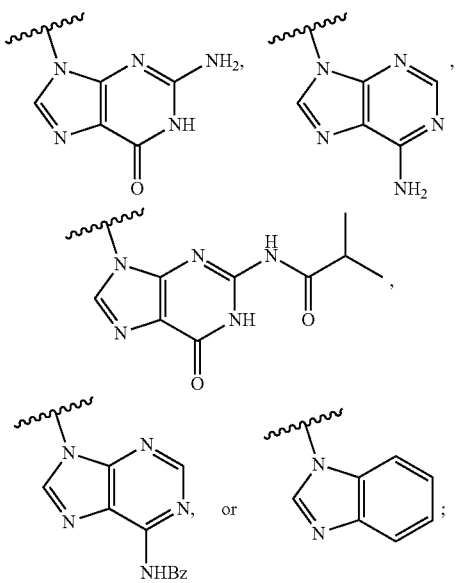

provided that, in Formula (I), if Q$^b$ is

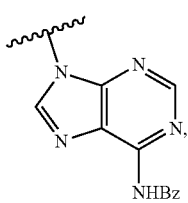

then Q$^a$ is not

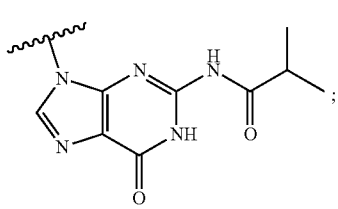 [SMILES: *n1cnc2c(=O)[nH]c(NC(=O)C(C)C)nc21]

and provided that the compound is not a compound listed in Table A or Table B.

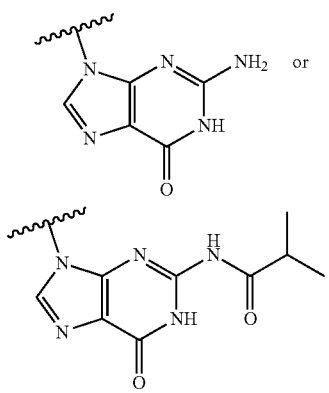

then Q$^a$ is not

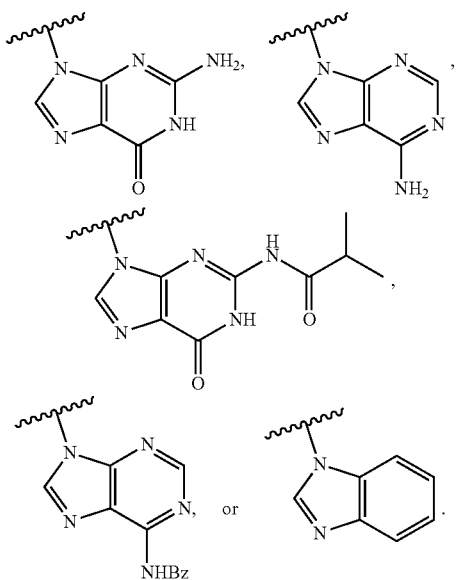

In one embodiment of the compounds of Formula (I), if Q$^b$ is

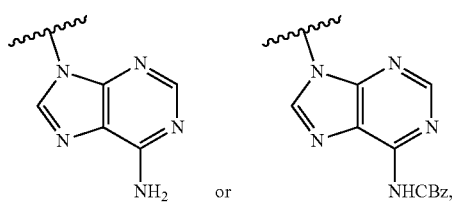

then Q$^a$ is not

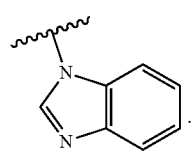

In one embodiment of the compounds of formulae (I) or (II), or a pharmaceutically acceptable salt, stereoisomer, solvate or hydrate thereof, Q$^a$ and Q$^b$ are each independently selected from:

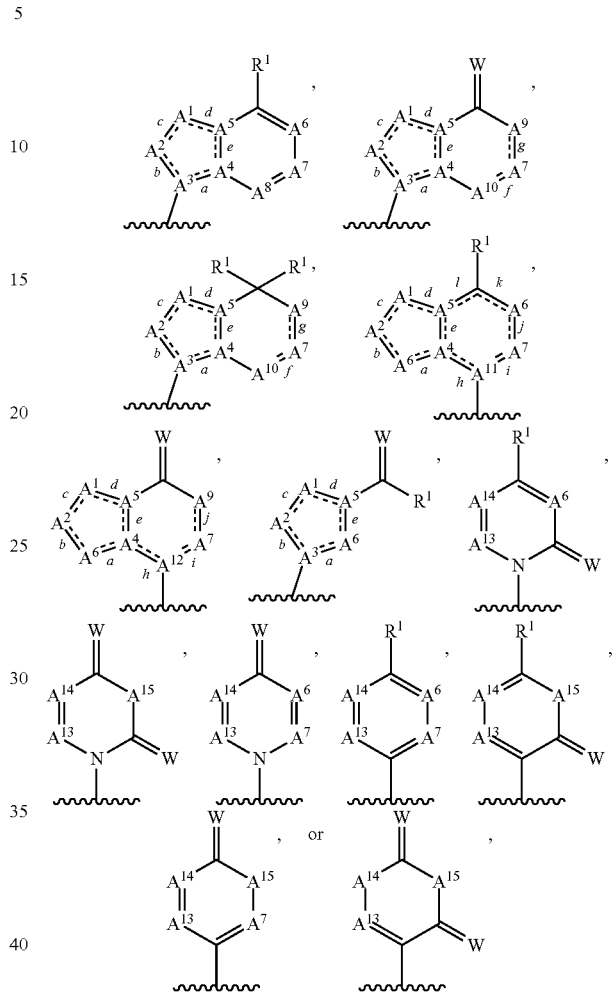

A$^1$, A$^2$, A$^6$, A$^7$, A$^8$, A$^{13}$, and A$^{14}$ are each independently CR$^1$ or N;

A$^3$, A$^4$ and A$^5$ are each independently C or N;

A$^9$ is C(R$^1$)$_2$, CR$^1$, N, or NR″;

A$^{10}$ is N, CR$^1$ or NR″;

A$^{11}$ and A$^{12}$ are each independently C or N;

A$^{15}$ is C(R$^1$)$_2$ or NR″;

W is O or S;

wherein two of bonds a, b, c, d, and e are double bonds and the remaining three bonds are single bonds, provided that none of the A$^1$, A$^2$, A$^3$, A$^4$, A$^5$ or A$^6$ has two double bonds attached to it;

wherein only one of bonds f and g is a double bond, or both bonds f and g are single bonds; and each of bonds h, i, j, k, and l can be a single bond or a double bond provided that none of the A$^4$, A$^5$, A$^6$, A$^7$, A$^9$, A$^{11}$, or A$^2$, has two double bonds attached to it.

In one embodiment of the compounds of formulae (I) or (II), or a pharmaceutically acceptable salt, stereoisomer, solvate or hydrate thereof, Q$^a$ and Q$^b$ are each independently selected from:

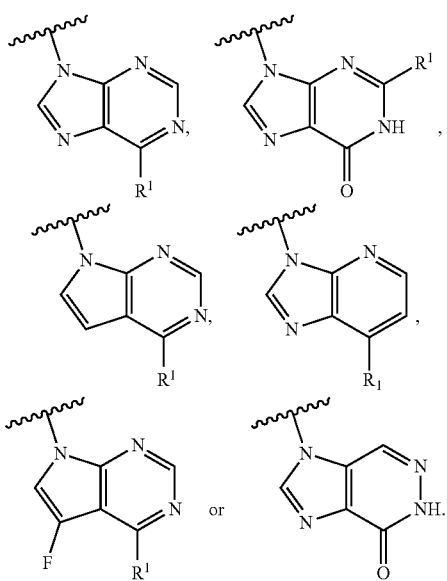

In one embodiment of the compounds of formulae (I) or (II), or a pharmaceutically acceptable salt, stereoisomer, solvate or hydrate thereof, $R^1$ is each independently hydrogen, halogen, or $-N(R^{cl})_2$, and $R^{cl}$ is each independently H, $C_{1-6}$ alkyl, $C_{3-6}$ cycloalkyl, $C_{3-6}$ cycloalkyl-$C_{1-6}$ alkyl-, 3-6 membered heterocyclyl, (3-6 membered heterocyclyl)-$C_{1-6}$ alkyl-, 5-6 membered aryl, (5-6 membered aryl)-$C_{1-6}$ alkyl-, 5-6 membered heteroaryl, or (5-6 membered heteroaryl)-$C_{1-6}$ alkyl-.

In one embodiment of the compounds of formulae (I) or (II), or a pharmaceutically acceptable salt, stereoisomer, solvate or hydrate thereof, $X^2$ and $Y^2$ are each independently SH, OH, or $BH_3^-$, wherein at least one of $X^2$ and $Y^2$ is $BH_3^-$.

In one embodiment of the compounds of formulae (I) or (II), or a pharmaceutically acceptable salt, stereoisomer, solvate or hydrate thereof, $R^{a2a}$, $R^{a2b}$, $R^{b3a}$, $R^{b3b}$, $R^{3b2a}$ and $R^{3b2b}$ are each independently selected from H, halogen, —OH, or —O($C_{1-3}$ alkyl). In one embodiment, $R^{a2a}$, $R^{a2b}$, $R^{b3a}$, $R^{b3b}$, $R^{3b2a}$ and $R^{3b2b}$ are each independently selected from H, F or OH.

In one embodiment of the compounds of formulae (I) or (II), or a pharmaceutically acceptable salt, stereoisomer, solvate or hydrate thereof, $X^3$, $X^4$, $Y^3$, and $Y^4$ are each O.

In one embodiment of the compounds of formulae (I) or (II), or a pharmaceutically acceptable salt, stereoisomer, solvate or hydrate thereof, $Z^1$ and $Z^2$ are each O.

In one embodiment of the compounds of formulae (I) or (II), the compound has the structure of Formula (I-X) or (II-X):

(I-X)

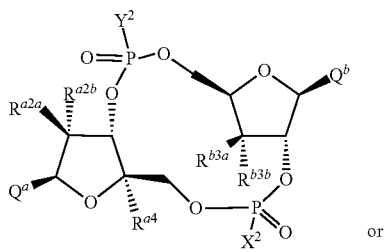

or (II-X)

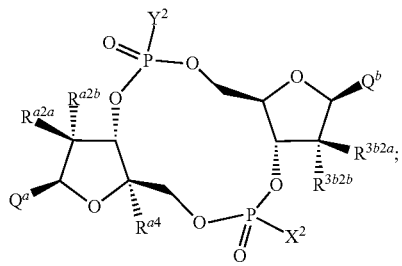

or a pharmaceutically acceptable salt, stereoisomer, solvate or hydrate thereof, wherein:

$Q^a$ and $Q^b$ are each independently selected from

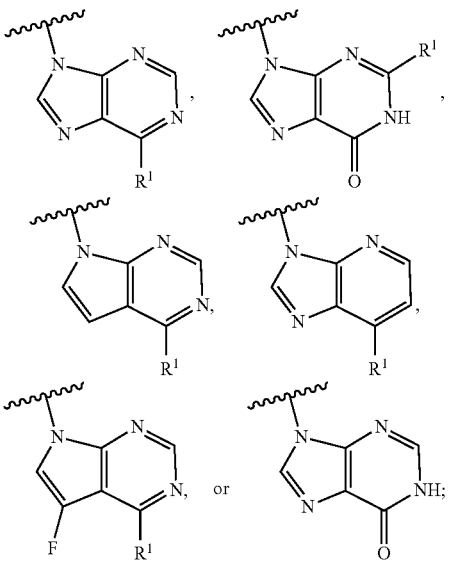

$R^1$ is hydrogen, halogen, or $-N(R^{cl})_2$;

$R^{cl}$ is H, $C_{1-6}$ alkyl, $C_{3-6}$ cycloalkyl, $C_{3-6}$ cycloalkyl-$C_{1-6}$ alkyl-, 3-6 membered heterocyclyl, (3-6 membered heterocyclyl)-$C_{1-6}$ alkyl-, 5-6 membered aryl, (5-6 membered aryl)-$C_{1-6}$ alkyl-, 5-6 membered heteroaryl, or (5-6 membered heteroaryl)-$C_{1-6}$ alkyl-;

$R^{a2a}$, $R^{a2b}$, $R^{b3a}$, $R^{b3b}$, $R^{3b2a}$ and $R^{3b2b}$ are each independently selected from H, F, OH, or OMe;

$X^2$ and $Y^2$ are each independently selected from SH, OH, or $BH_3^-$, wherein at least one of $X^2$ and $Y^2$ is $BH_3^-$; and $R^{a4}$ is H.

In one embodiment of the compounds of formula (I-X) or (II-X), one of $X^2$ and $Y^2$ is $BH_3^-$ and the other is SH or OH.

In one embodiment of the compounds of formulae (I) or (II) or subgenera thereof, $X^2$ is $BH_3^-$, and $Y^2$ is SH or OH. In one embodiment, $X^2$ is SH or OH; and $Y^2$ is $BH_3^-$.

In one embodiment of the compounds of formulae (I) or (II) or subgenera thereof, exactly one of $X^2$ and $Y^2$ is $BH_3^-$.

In one embodiment of the compounds of formulae (I) or (II) or subgenera thereof, $Q^a$ and $Q^b$ are each independently selected from

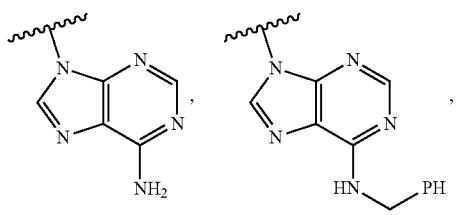

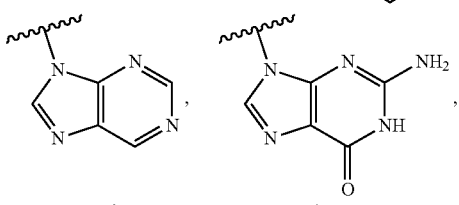

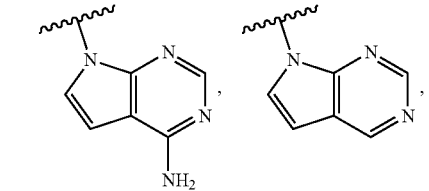

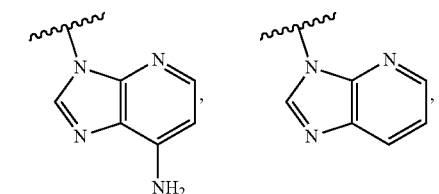

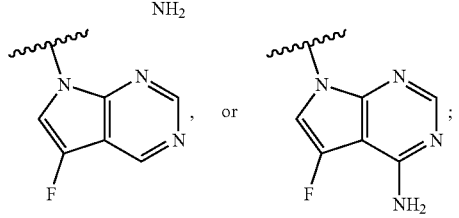

and $R^{a2a}$, $R^{a2b}$, $R^{b3a}$, $R^{b3b}$, $R^{3b2a}$ and $R^{3b2b}$ are each independently selected from H, F or OH.

In some embodiment of the compounds of formulae (I) or (II) or subgenera thereof, $Q^a$ and $Q^b$ are each independently selected from

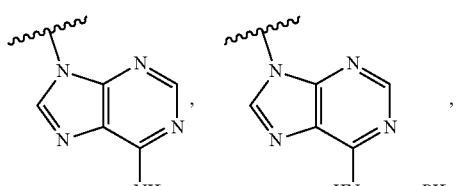

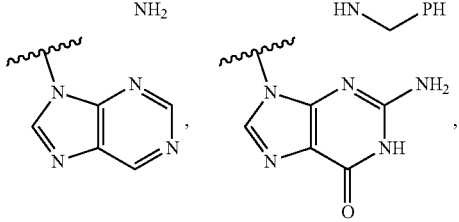

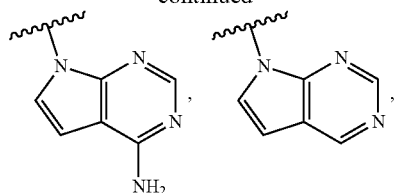

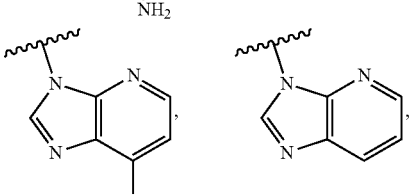

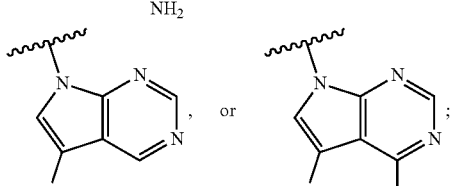

and $R^{a2a}$, $R^{a2b}$, $R^{b3a}$, $R^{b3b}$, $R^{3b2a}$ and $R^{3b2b}$ are each independently selected from H or F.

In one embodiment of the compounds of formula (I-X), $Q^a$ and $Q^b$ are each

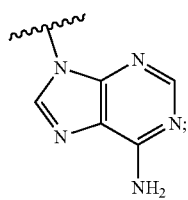 [SMILES: *n1cnc2c(N)ncnc21]

$R^{a4}$ is H;

$R^{a2a}$ and $R^{b3a}$ are each H; and $R^{a2b}$ and $R^{b3b}$ are each F.

In one embodiment of the compounds of formula (I-X), $Q^a$ and $Q^b$ are each

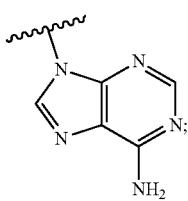 [SMILES: *n1cnc2c(N)ncnc21]

$R^{a4}$ is H;

$R^{a2a}$ and $R^{b3b}$ are each H; and $R^{a2b}$ and $R^{b3a}$ are each F.

In one embodiment of the compounds of formula (II-X), $Q^a$ and $Q^b$ are each independently selected from

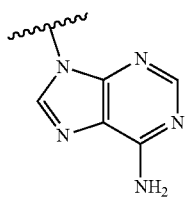 or 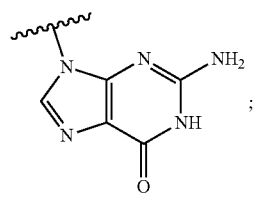 ;

$R^{a4}$ is H;
$R^{a2a}$ and $R^{3b2a}$ are each H; and
$R^{a2b}$ and $R^{3b2b}$ are each F.

In one embodiment, the compound has the structure of formula (I), or a pharmaceutically acceptable salt, stereoisomer, solvate or hydrate thereof.

In one embodiment of the compounds of formula (I), the compound has the structure of formula (I-A):

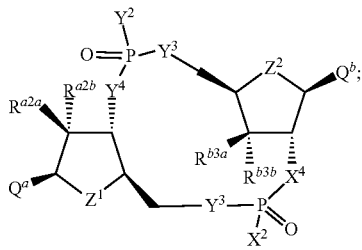
(I-A)

or a pharmaceutically acceptable salt, stereoisomer, solvate or hydrate thereof, wherein:
$R^{a2a}$, $R^{a2b}$, $R^{b3a}$, and $R^{b3b}$ are each independently H, F, or OH;
$X^2$ and $Y^2$ are each independently SH, OH, or $BH_3^-$;
$X^3$, $X^4$, $Y^3$ and $Y^4$ are each independently O or NH; and
$Z^1$ and $Z^2$ are each independently O or S.

In ne embodiment of the compounds of formula (I-A), the compound has the following structure (stereochemistry):

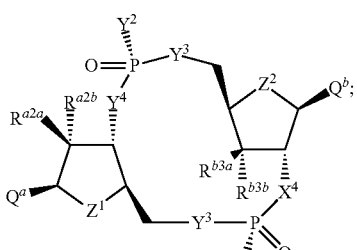
(I-A1)

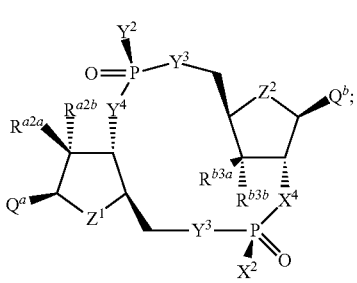
(I-A2)

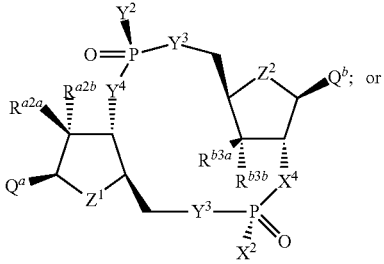
(I-A3)

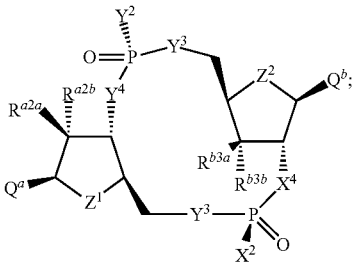
(I-A4)

or a pharmaceutically acceptable salt, solvate or hydrate thereof.

In one embodiment of the compounds of formula (I-A), $Z^1$ and $Z^2$ are each O. In one embodiment of the compounds of formula (I-A), at least one of $X^2$ and $Y^2$ is $BH_3^-$.

In one embodiment of the compounds of formula (I), the compound has the structure of formula (I-B):

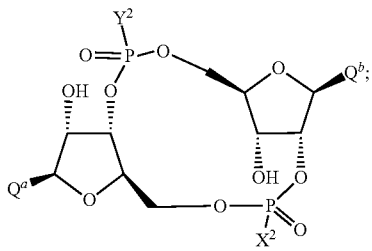
(I-B)

or a pharmaceutically acceptable salt, stereoisomer, solvate or hydrate thereof, wherein:
$X^2$ and $Y^2$ are each selected from SH, OH, or $BH_3^-$, wherein at least one of $X^2$ and $Y^2$ is $BH_3^-$.

In one embodiment of the compounds of formula (I-B), $X^2$ is $BH_3^-$ and $Y^2$ is —SH or —OH. In another embodiment, $Y^2$ is $BH_3^-$ and $X^2$ is —SH or —OH.

In one embodiment of the compounds of formulae (I), the compound has the structure of formula (I-C):

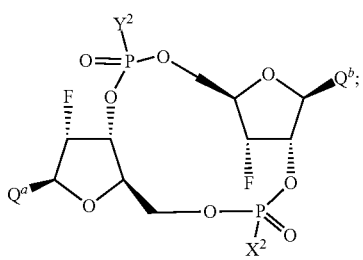
(I-C)

or a pharmaceutically acceptable salt, stereoisomer, solvate or hydrate thereof, wherein:

$X^2$ and $Y^2$ are each selected from SH, OH, or $BH_3^-$, wherein at least one of $X^2$ and $Y^2$ is $BH_3^-$.

In one embodiment of the compounds of formula (I-B), $X^2$ and $Y^2$ are each selected from SH, OH, or $BH_3^-$, wherein at least one of $X^2$ and $Y^2$ is $BH_3^-$.

In one embodiment of the compounds of formula (I-C), $X^2$ is $BH_3^-$ and $Y^2$ is —SH or —OH. In another embodiment, $Y^2$ is $BH_3^-$ and $X^2$ is —SH or —OH.

In one embodiment of the compounds of formula (I), the compound has the structure of formula (I-D):

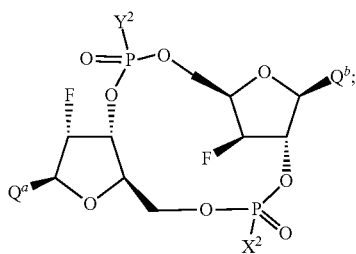

(I-D)

or a pharmaceutically acceptable salt, stereoisomer, solvate or hydrate thereof, wherein:

$X^2$ and $Y^2$ are each selected from SH, OH, or $BH_3^-$, wherein at least one of $X^2$ and $Y^2$ is $BH_3^-$.

In one embodiment of the compounds of formula (I-D), $X^2$ is $BH_3^-$ and $Y^2$ is —SH or —OH. In another embodiment, $Y^2$ is $BH_3^-$ and $X^2$ is —SH or —OH.

In one embodiment of the compounds of formulae (I), the compound has the structure of formula (I-E):

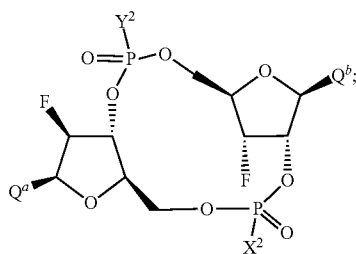

(I-E)

or a pharmaceutically acceptable salt, stereoisomer, solvate or hydrate thereof, wherein:

$X^2$ and $Y^2$ are each selected from SH, OH, or $BH_3^-$, wherein at least one of $X^2$ and $Y^2$ is $BH_3^-$.

In one embodiment of the compounds of formula (I-E), $X^2$ is $BH_3^-$ and $Y^2$ is —SH or —OH. In another embodiment, $Y^2$ is $BH_3^-$ and $X^2$ is —SH or —OH.

In one embodiment of the compounds of formulae (I), the compound has the structure of formula (I-F):

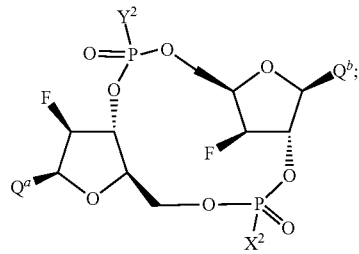

(I-F)

or a pharmaceutically acceptable salt, stereoisomer, solvate or hydrate thereof, wherein:

$X^2$ and $Y^2$ are each selected from SH, OH, or $BH_3^-$, wherein at least one of $X^2$ and $Y^2$ is $BH_3^-$.

In one embodiment of the compounds of formula (I-F), $X^2$ is $BH_3^-$ and $Y^2$ is —SH or —OH. In another embodiment, $Y^2$ is $BH_3^-$ and $X^2$ is —SH or —OH.

In one embodiment of the compounds of formula (I) or subgenera thereof, $Q^a$ and $Q^b$ are each

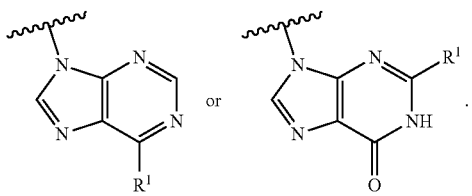

In one embodiment, $R^1$ is each independently hydrogen, halogen, or $—N(R^{c1})_2$, and $R^{c1}$ is each independently H, $C_{1-6}$ alkyl, $C_{3-6}$ cycloalkyl, $C_{3-6}$ cycloalkyl-$C_{1-6}$ alkyl-, 3-6 membered heterocyclyl, (3-6 membered heterocyclyl)-$C_{1-6}$ alkyl-, 5-6 membered aryl, (5-6 membered aryl)-$C_{1-6}$ alkyl-, 5-6 membered heteroaryl, or (5-6 membered heteroaryl)-$C_{1-6}$ alkyl-.

In one embodiment of the compounds of formula (I) or subgenera thereof, $Q^a$ and $Q^b$ are each

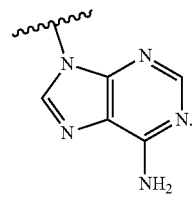 [SMILES: *n1cnc2c(N)ncnc21]

In one embodiment, the compound has the structure of formula (II), or a pharmaceutically acceptable salt, stereoisomer, solvate or hydrate thereof.

In one embodiment of the compounds of formulae (II), the compound has the structure of formula (II-A):

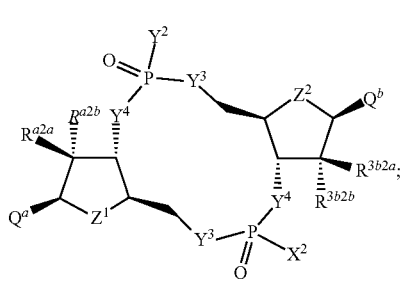

(II-A)

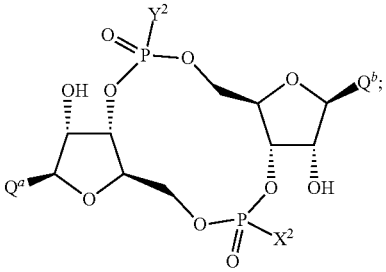

(II-B)

or a pharmaceutically acceptable salt, stereoisomer, solvate or hydrate thereof, wherein:

$R^{a2a}$, $R^{a2b}$, $R^{3b2b}$, and $R^{3b2a}$ are each independently H, F, or OH;

$X^2$ and $Y^2$ are each independently SH, OH, or $BH_3^-$;

$X^3$, $X^4$, $Y^3$ and $Y^4$ are each independently O or NH; and $Z^1$ and $Z^2$ are each independently O or S.

In one embodiment of the compounds of formula (II-A), $Z^1$ and $Z^2$ are each O. In one embodiment of the compounds of formula (II-A), at least one of $X^2$ and $Y^2$ is $BH_3^-$.

In one embodiment of the compounds of formula (II-A), the compound has the following structure (stereochemistry):

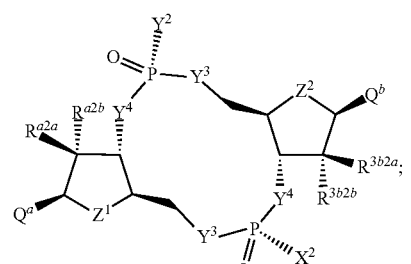

(II-A1)

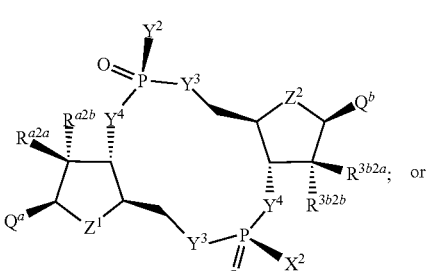

(II-A2)

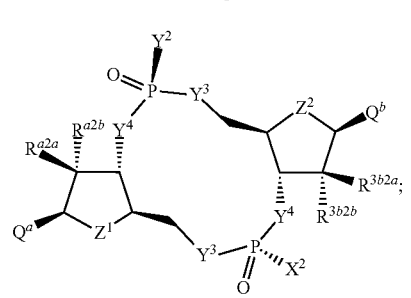

(II-A3)

or a pharmaceutically acceptable salt, solvate or hydrate thereof.

In one embodiment of the compounds of formula (II), the compound has the structure of formula (II-B):

or a pharmaceutically acceptable salt, stereoisomer, solvate or hydrate thereof, wherein:

$X^2$ and $Y^2$ are each selected from SH, OH, or $BH_3^-$, wherein at least one of $X^2$ and $Y^2$ is $BH_3^-$.

In one embodiment of the compounds of formula (II-B), $X^2$ is $BH_3^-$ and $Y^2$ is —SH or —OH. In another embodiment, $Y^2$ is $BH_3^-$ and $X^2$ is —SH or —OH.

In one embodiment of the compounds of formula (II), the compound has the structure of formula (II-C):

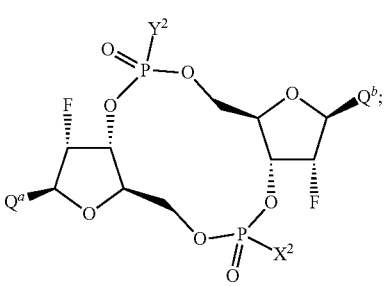

(II-C)

or a pharmaceutically acceptable salt, stereoisomer, solvate or hydrate thereof, wherein:

$X^2$ and $Y^2$ are each selected from SH, OH, or $BH_3^-$, wherein at least one of $X^2$ and $Y^2$ is $BH_3^-$.

In one embodiment of the compounds of formula (II-C), $X^2$ is $BH_3^-$ and $Y^2$ is —SH or —OH. In another embodiment, $Y^2$ is $BH_3^-$ and $X^2$ is —SH or —OH.

In one embodiment of the compounds of formula (II), the compound has the structure of formula (II-D):

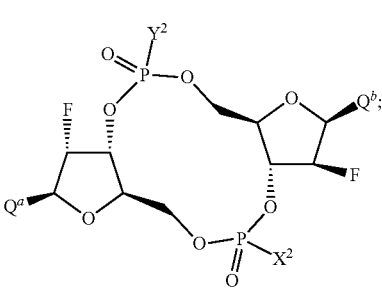

(II-D)

or a pharmaceutically acceptable salt, stereoisomer, solvate or hydrate thereof, wherein:

$X^2$ and $Y^2$ are each selected from SH, OH, or $BH_3^-$, wherein at least one of $X^2$ and $Y^2$ is $BH_3^-$.

In one embodiment of the compounds of formula (II-D), $X^2$ is $BH_3^-$ and $Y^2$ is —SH or —OH. In another embodiment, $Y^2$ is $BH_3^-$ and $X^2$ is —SH or —OH.

In one embodiment of the compounds of formula (II), the compound has the structure of formula (II-F):

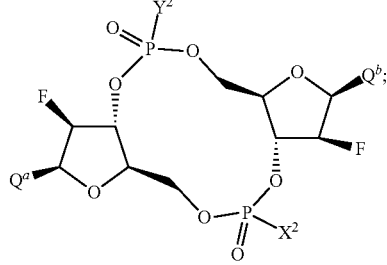
(II-F)

or a pharmaceutically acceptable salt, stereoisomer, solvate or hydrate thereof, wherein:

$X^2$ and $Y^2$ are each selected from SH, OH, or $BH_3^-$, wherein at least one of $X^2$ and $Y^2$ is $BH_3^-$.

In one embodiment of the compounds of formula (II-F), $X^2$ is $BH_3^-$ and $Y^2$ is —SH or —OH. In another embodiment, $Y^2$ is $BH_3^-$ and $X^2$ is —SH or —OH.

In one embodiment of the compounds of formula (II) or subgenera thereof, $Q^a$ and $Q^b$ are each

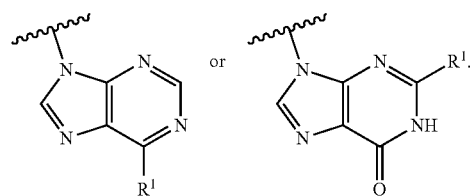

In one embodiment, $R^1$ is each independently hydrogen, halogen, or —$N(R^{c1})_2$, and $R^{c1}$ is each independently H, $C_{1-6}$ alkyl, $C_{3-6}$ cycloalkyl, $C_{3-6}$ cycloalkyl-$C_{1-6}$ alkyl-, 3-6 membered heterocyclyl, (3-6 membered heterocyclyl)-$C_{1-6}$ alkyl-, 5-6 membered aryl, (5-6 membered aryl)-$C_{1-6}$ alkyl-, 5-6 membered heteroaryl, or (5-6 membered heteroaryl)-$C_{1-6}$ alkyl-.

In one embodiment of the compounds of formula (I) or subgenera thereof, $Q^a$ and $Q^b$ are each independently selected from

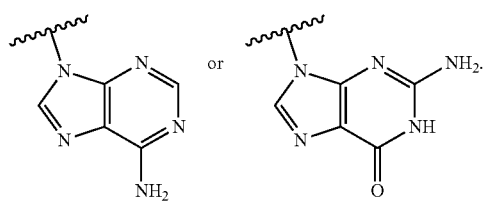 [SMILES: *n1cnc2c(N)ncnc21 ; *n1cnc2c(=O)[nH]c(N)nc21]

In one embodiment, the present disclosure relates to the compounds of formula (I-A') or (II-A'):

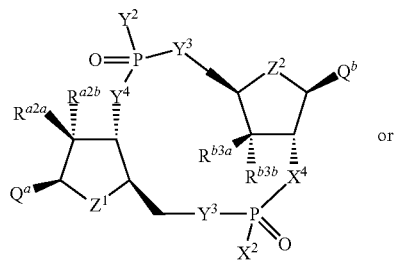
(I-A')

or

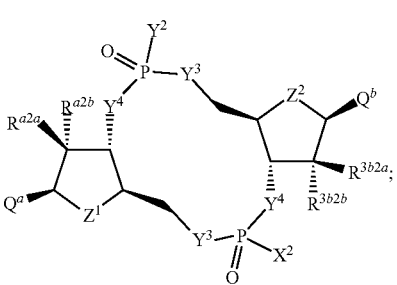
(II-A')

or a pharmaceutically acceptable salt, solvate or hydrate thereof, wherein:

$Q^a$ and $Q^b$ are each independently selected from:

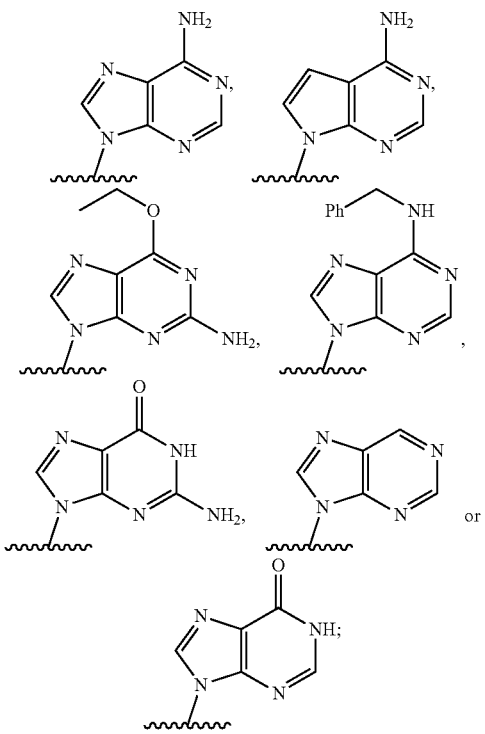

wherein, $Q^a$ and $Q^b$ can be optionally substituted with one, two, three, or four $R^1$; and $R^1$ is each independently hydrogen, F, Cl, Br, —$NO_2$, —CN, —OH, —SH, —$NH_2$, —O—$C_{1-3}$ alkyl, —O—$C_{3-6}$ cycloalkyl, —O—$CH_2$—$C_{3-6}$ cycloalkyl, —S—$C_{1-3}$ alkyl, —S—$C_{3-6}$ cycloalkyl, —S—$CH_2$—$C_{3-6}$ cycloalkyl, —NH($C_{1-3}$ alkyl), —N($C_{1-3}$ alkyl)$_2$, —NH($C_{3-6}$ cycloalkyl), —NH($CH_2$—$C_{3-6}$ cycloalkyl), —NCH₃(C₃₋₆ cycloalkyl), —NCH₃(CH₂—C₃₋₆ cycloalkyl), C₁₋₃ alkyl, —C₃₋₆ cycloalkyl, —CH₂—C₃₋₆ cycloalkyl, benzyl,

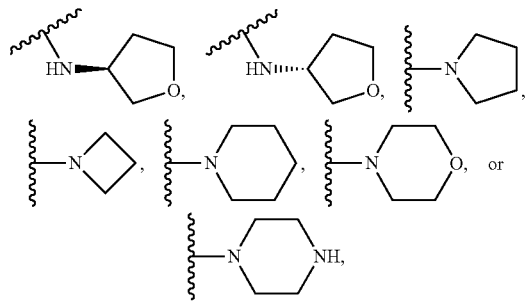

wherein, the C₁₋₃ alkyl, —C₃₋₆ cycloalkyl,

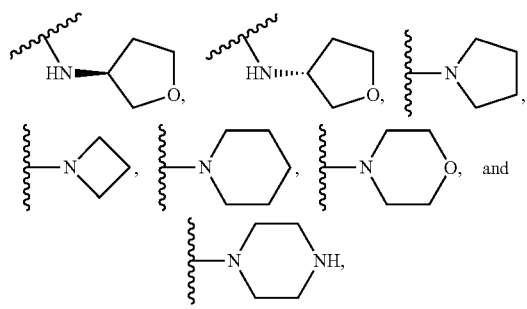

can be optionally substituted with up to 3 groups selected from F, OH, CN, NH₂, or OMe;

R$^{a2a}$, R$^{a2b}$, R$^{b3a}$, R$^{b3b}$, R$^{3b2b}$, and R$^{3b2a}$ are each independently H, F, or OH;

X² and Y² are each independently —SH, —OH, —NH₂, BH₃—, BH(OR⁷)₂⁻ or BH(R$^b$)₂⁻;

X³, X⁴, Y³ and Y⁴ are each independently O or NH; and

Z¹ and Z² are each independently O or S;

R$^b$ is each independently H, CN, carboxyl, carboxyl salts, CH₃, or CH₂CH₃;

R⁷ is each independently H or CH₃; and wherein exactly one of X² and Y² is BH₃⁻, BH(OR⁷)₂⁻ or BH(R$^b$)₂⁻;

provided that when X² is BH₃⁻, Y² is not OH and when Y² is BH₃⁻, X² is not OH.

In one embodiment, the present disclosure relates to the compounds of formula (I-A''') or (II-A'''):

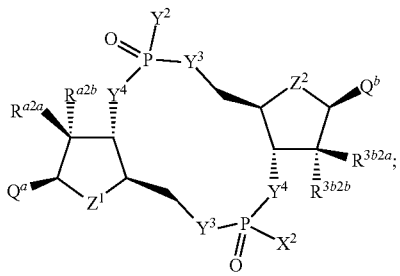
(I-A''')

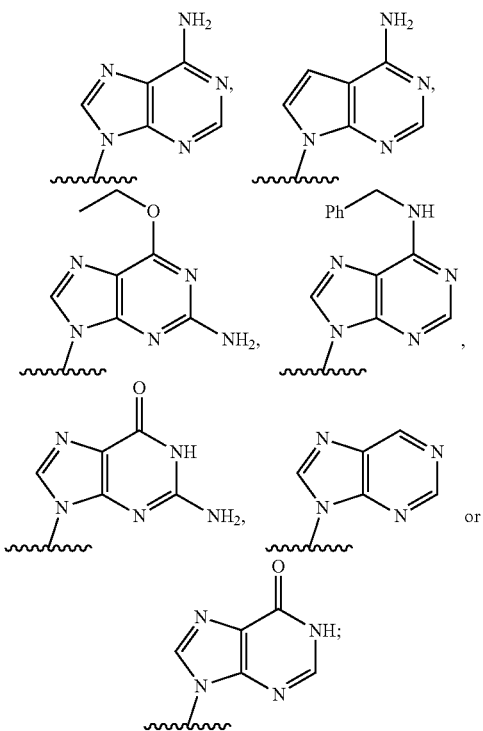
(II-A''')

or a pharmaceutically acceptable salt, solvate or hydrate thereof, wherein:

Q$^a$ and Q$^b$ are each independently selected from:

wherein, Q$^a$ and Q$^b$ can be optionally substituted with one, two, three, or four R¹; and R¹ is each independently hydrogen, F, Cl, Br, —NO₂, —CN, —OH, —SH, —NH₂, —O—C₁₋₃ alkyl, —O—C₃₋₆ cycloalkyl, —O—CH₂—C₃₋₆ cycloalkyl, —S—C₁₋₃ alkyl, —S—C₃₋₆ cycloalkyl, —S—CH₂—C₃₋₆ cycloalkyl, —NH(C₁₋₃ alkyl), —N(C₁₋₃ alkyl)₂, —NH(C₃₋₆ cycloalkyl), —NH(CH₂—C₃₋₆ cycloalkyl), —NCH₃(C₃₋₆ cycloalkyl), —NCH₃(CH₂—C₃₋₆ cycloalkyl), C₁₋₃ alkyl, —C₃₋₆ cycloalkyl, —CH₂—C₃₋₆ cycloalkyl, benzyl,

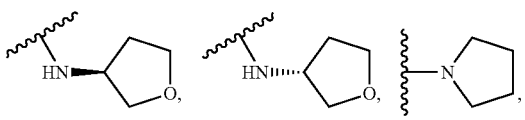

-continued

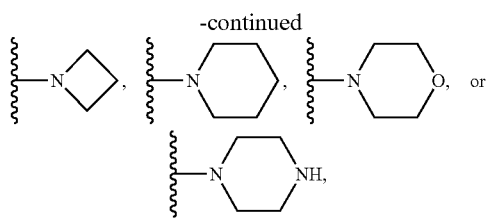

wherein, the $C_{1-3}$ alkyl, —$C_{3-6}$ cycloalkyl,

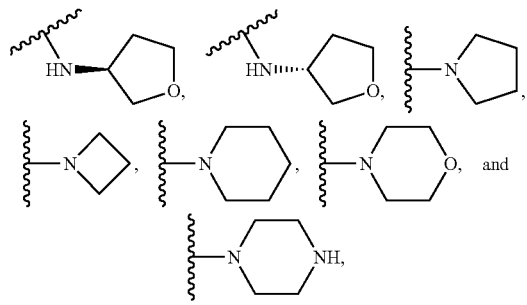

can be optionally substituted with up to 3 groups selected from F, OH, CN, $NH_2$, or OMe;

$R^{a2a}$, $R^{a2b}$, $R^{b3a}$, $R^{b3b}$, $R^{3b2b}$, and $R^{3b2a}$ are each independently H, F, or OH;

$X^2$ and $Y^2$ are each independently —SH, —OH, —$NH_2$, $BH_3^-$, $BH(OR^7)_2^-$ or $BH(R^b)_2^-$;

$X^3$, $X^4$, $Y^3$ and $Y^4$ are each independently O or NH; and $Z^1$ and $Z^2$ are each independently O or S;

$R^b$ is each independently H, CN, carboxyl, carboxyl salts, $CH_3$, or $CH_2CH_3$;

$R^7$ is each independently H or $CH_3$; and wherein at least one of $X^2$ and $Y^2$ is $BH_3^-$, $BH(OR^7)_2^-$ or $BH(R^b)_2^-$;

provided that when $R^{a2b}$, $R^{b3b}$, and $R^{3b2b}$ are each OH; $R^{a2a}$, $R^{b3a}$, and $R^{3b2a}$ are each H; $X^3$, $X^4$, $Y^3$ and $Y^4$ are each O; $Z^1$ and $Z^2$ are each O; and $X^2$ is $BH_3^-$, then $Y^2$ is not OH or $BH_3^-$; and provided that when $R^{a2b}$, $R^{b3b}$, and $R^{3b2b}$ are each OH; $R^{a2a}$, $R^{b3a}$, and $R^{3b2a}$ are each H; $X^3$, $X^4$, $Y^3$ and $Y^4$ are each O; $Z^1$ and $Z^2$ are each O; and and $Y^2$ is $BH_3^-$, then $X^2$ is not OH or $BH_3$.

In one embodiment, the present disclosure relates to the compounds of formula (I-A"):

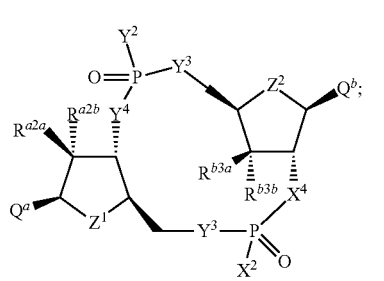

or a pharmaceutically acceptable salt, solvate or hydrate thereof, wherein:

$Q^a$ and $Q^b$ are each independently selected from:

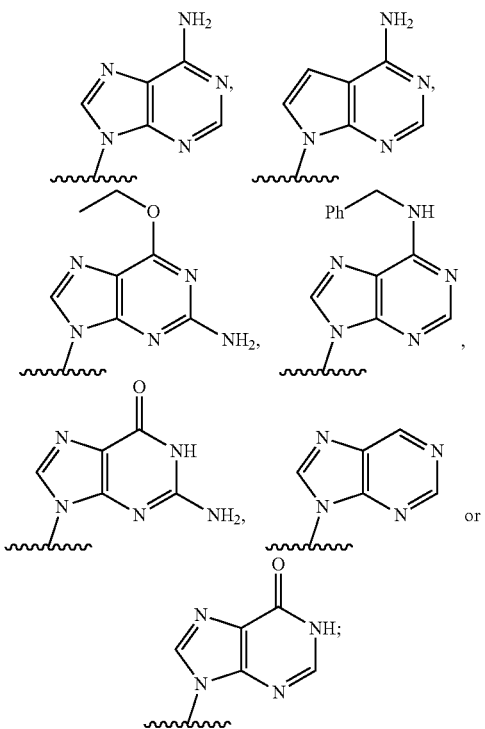

wherein, $Q^a$ and $Q^b$ can be optionally substituted with one, two, three, or four $R^1$; and $R^1$ is each independently hydrogen, F, Cl, Br, —$NO_2$, —CN, —OH, —SH, —$NH_2$, —O—$C_{1-3}$ alkyl, —O—$C_{3-6}$ cycloalkyl, —O—$CH_2$—$C_{3-6}$ cycloalkyl, —S—$C_{1-3}$ alkyl, —S—$C_{3-6}$ cycloalkyl, —S—$CH_2$—$C_{3-6}$ cycloalkyl, —NH($C_{1-3}$ alkyl), —N($C_{1-3}$ alkyl)$_2$, —NH($C_{3-6}$ cycloalkyl), —NH($CH_2$—$C_{3-6}$ cycloalkyl), —$NCH_3$($C_{3-6}$ cycloalkyl), —$NCH_3$($CH_2$—$C_{3-6}$ cycloalkyl), $C_{1-3}$ alkyl, —$C_{3-6}$ cycloalkyl, —$CH_2$—$C_{3-6}$ cycloalkyl, benzyl,

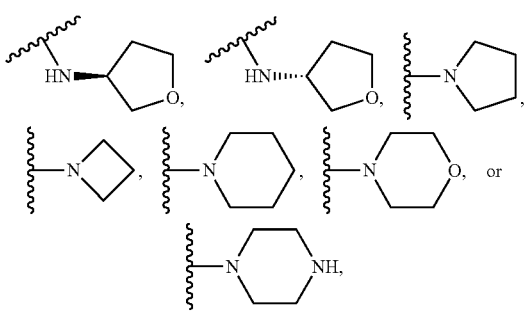

wherein, the $C_{1-3}$ alkyl, —$C_{3-6}$ cycloalkyl,

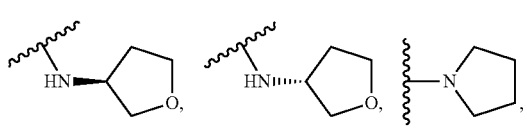

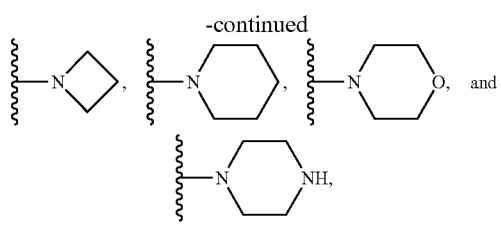

can be optionally substituted with up to 3 groups selected from F, OH, CN, NH$_2$, or OMe;

$R^{a2a}$, $R^{a2b}$, $R^{b3a}$, $R^{b3b}$, $R^{3b2b}$, and $R^{3b2a}$ are each independently H, F, or OH;

$X^2$ and $Y^2$ are each independently —SH, —OH, —NH$_2$, BH$_3^-$, BH(OR$^7$)$_2^-$ or BH(R$^b$)$_2^-$;

$X^3$, $X^4$, $Y^3$ and $Y^4$ are each independently O or NH; and $Z^1$ and $Z^2$ are each independently O or S;

R$^b$ is each independently H, CN, carboxyl, carboxyl salts, CH$_3$, or CH$_2$CH$_3$; and R$^7$ is each independently H or CH$_3$;

wherein at least one of X$^2$ and Y$^2$ is BH$_3^-$, BH(OR$^7$)$_2^-$ or BH(R$^b$)$_2^-$.

In one embodiment, the compound of the present disclosure is selected from:

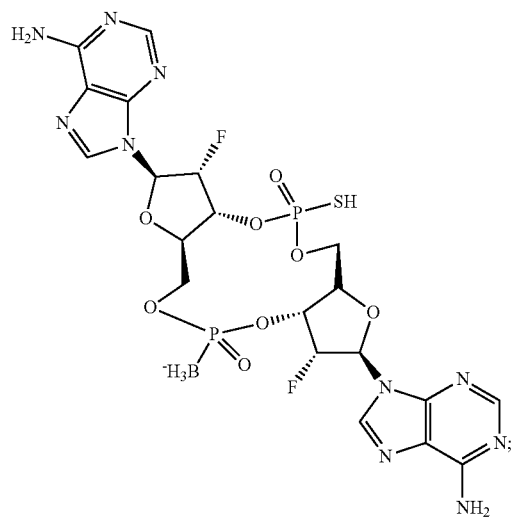

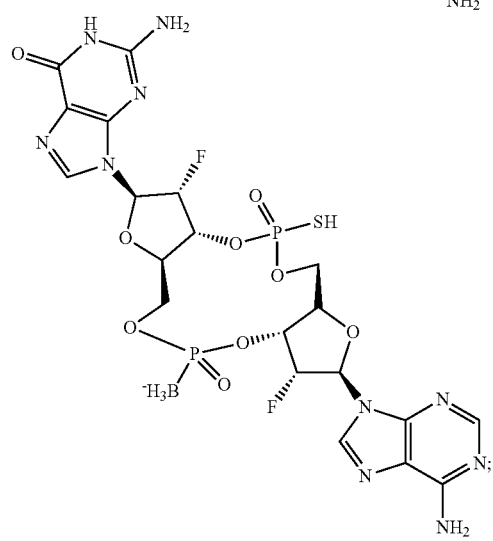

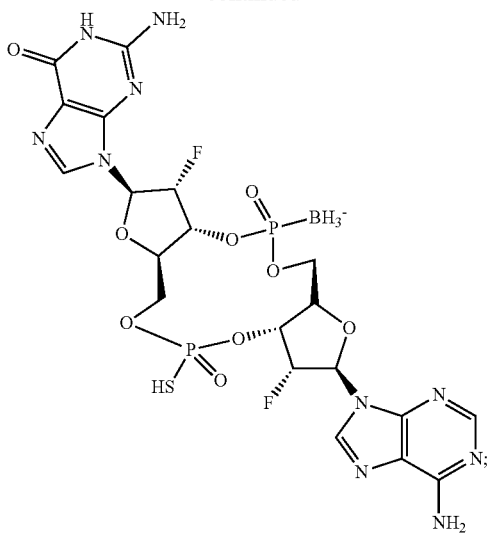

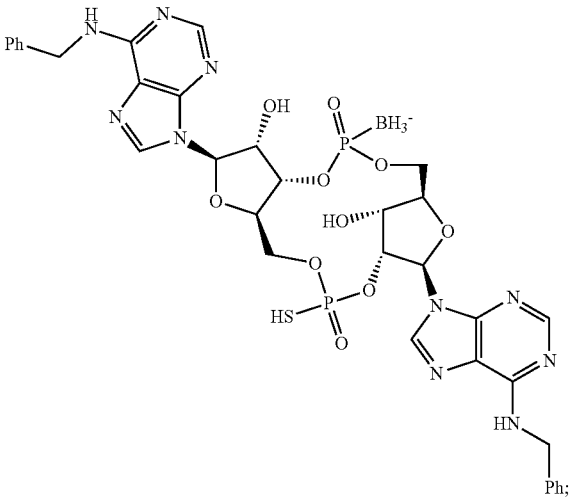

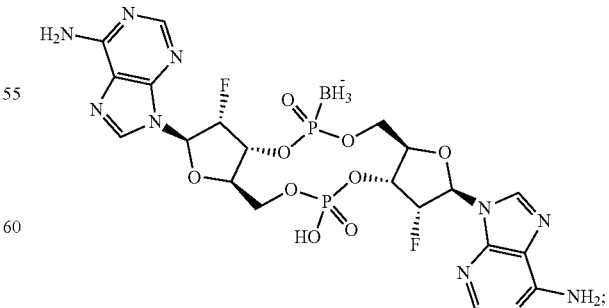

27
-continued
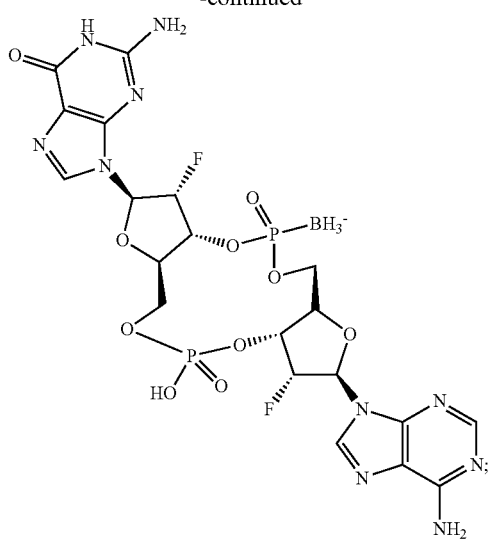
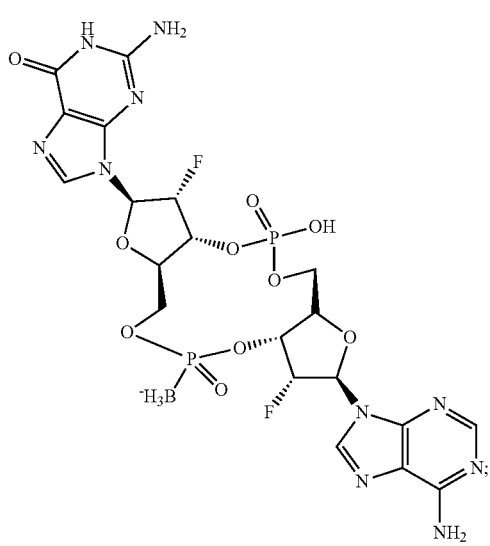
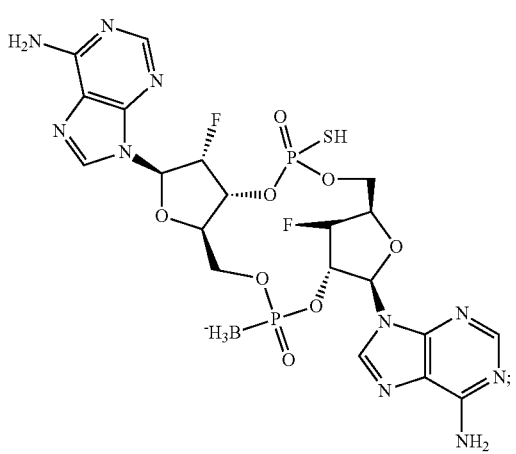
28
-continued
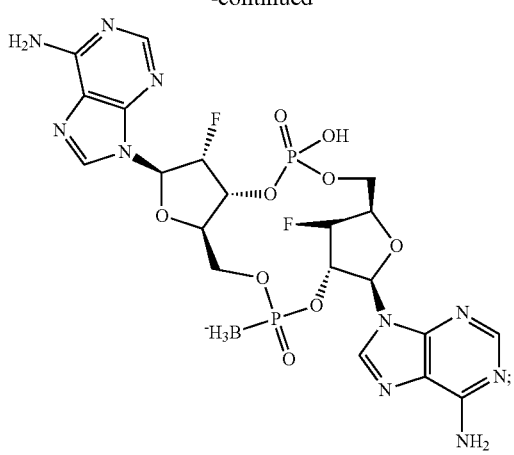
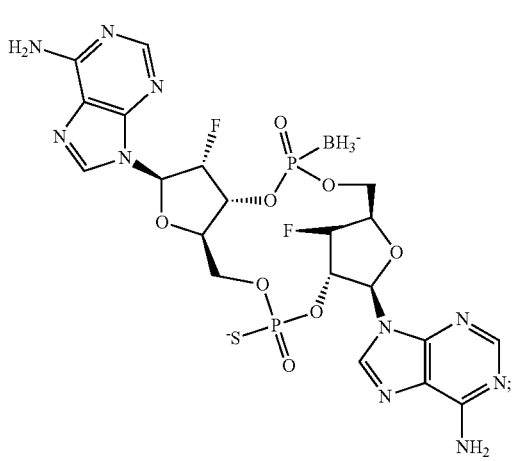
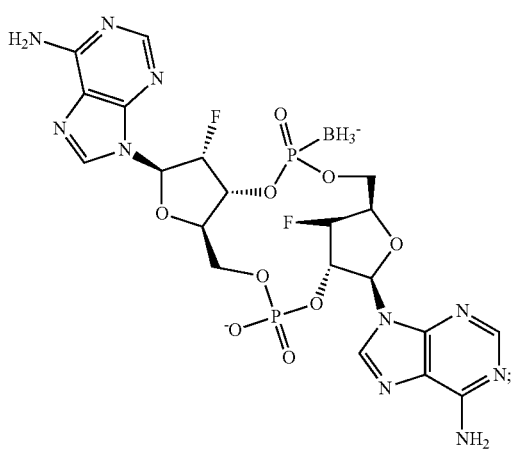

-continued

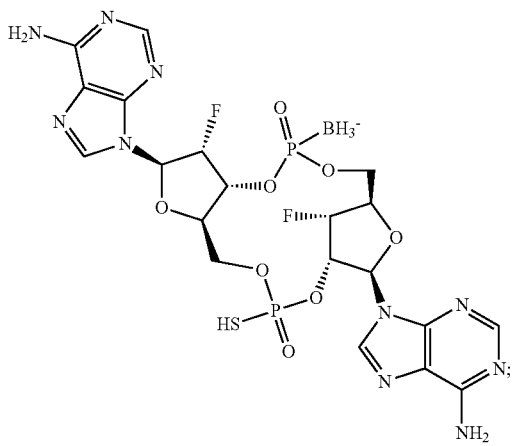

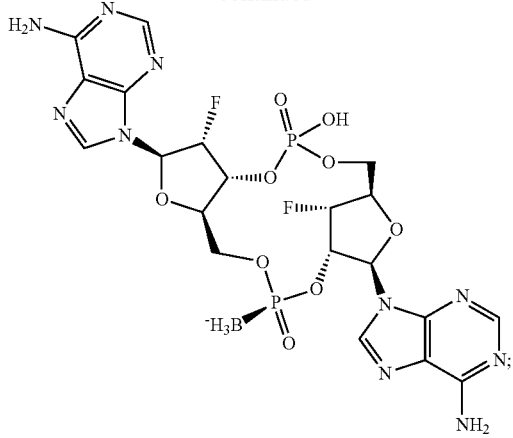

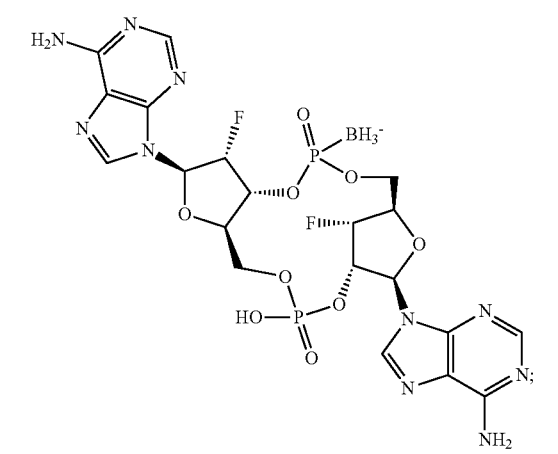

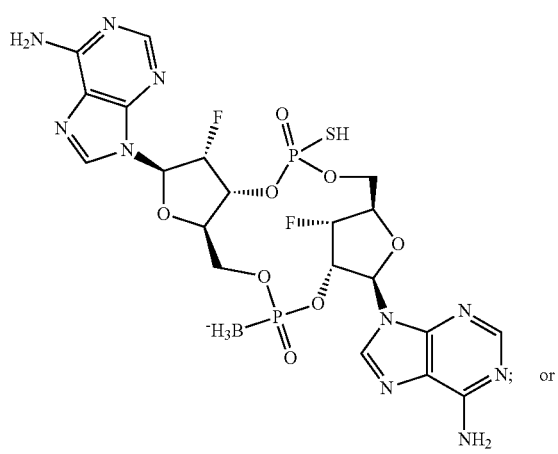

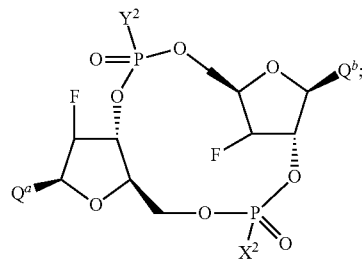

or a pharmaceutically acceptable salt, stereoisomer, solvate or hydrate thereof.

In one embodiment, the present disclosure relates to a compound of formula (A), (A)

or a pharmaceutically acceptable salt, stereoisomer, solvate or hydrate thereof, wherein:
$Q^a$ and $Q^b$ are each independently cycloalkyl, heterocyclyl, aryl, or heteroaryl, wherein the cycloalkyl, heterocyclyl, aryl, and heteroaryl can be optionally substituted with one, two, three, four, or five $R^1$;
$R^1$ is each independently hydrogen, halogen, —NO$_2$, —CN, —OR$^{cl}$, —SR$^{cl}$, —N(R$^{cl}$)$_2$, —C(O)R$^{cl}$, —CO$_2$R$^{cl}$, —C(O)C(O)R$^{cl}$, —C(O)CH$_2$C(O)R$^{cl}$, —C(O)N(R$^{cl}$)$_2$, —C(=NR$^{cl}$)N(R$^{cl}$)$_2$, —C(=NOR$^{cl}$)R$^{cl}$, —S(O)R$^{cl}$, —S(O)$_2$R$^{cl}$, —SO$_2$N(R$^{cl}$)$_2$, —OC(O)R$^{cl}$, —N(R$^{cl}$)C(O)R$^{cl}$, —NR$^{cl}$N(R$^{cl}$)$_2$, —N(R$^{cl}$)C(=NR$^{cl}$)N(R$^{cl}$)$_2$, —N(R$^{cl}$)C(O)N(R$^{cl}$)$_2$, —N(R$^{cl}$)SO$_2$N(R$^{cl}$)$_2$, —N(R$^{cl}$)SO$_2$R$^{cl}$, —N(R$^{cl}$)SO$_2$NR$^{cl}$C(=O)OR$^{cl}$, —OC(O)N(R$^{cl}$)$_2$, or R$^{cl}$;
$R^{cl}$ is each independently H, C$_{1-12}$ alkyl, C$_{2-12}$ alkenyl, C$_{2-12}$ alkynyl, C$_{3-12}$ cycloalkyl, C$_{3-12}$ cycloalkyl-C$_{1-6}$ alkyl-, heterocyclyl, heterocyclyl-C$_{1-6}$ alkyl-, aryl, aryl-C$_{1-6}$ alkyl-, heteroaryl, or heteroaryl-C$_{1-6}$ alkyl-, wherein C$_{1-12}$ alkyl, C$_{2-12}$ alkenyl, C$_{2-12}$ alkynyl, C$_{3-12}$ cycloalkyl, C$_{3-12}$ cycloalkyl-C$_{1-6}$ alkyl-, heterocyclyl, heterocyclyl-C$_{1-6}$ alkyl-, aryl, aryl-C$_{1-6}$ alkyl-, heteroaryl, and heteroaryl-C$_{1-6}$ alkyl- can be substituted one or more substituents selected from C$_{1-6}$ alkyl, halogen, C$_{1-6}$ alkoxy, —NO$_2$, —NR$^{ns}$R$^{ns}$, —OH, =O, or COOR$^{cs}$; or
$R^{ns}$ is each independently H, R$^{cs}$, R$^{cs}$—C(O)—, R$^{cs}$—S(O)$_2$—, R$^{cs}$R$^{cs}$N—C(O)—, or R$^{cs}$R$^{cs}$NS(O)$_2$—;
$R^{cs}$ is each independently H, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, or C$_2$-C$_6$ haloalkynyl; or alternatively, two $R^{cs}$ attached to the same N atom can together with the N atom form a 4-7 membered heterocyclic ring, containing up to one other heteroatom chosen from O, S, or $NR^{ns}$, wherein the 4-7 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

$X^2$ and $Y^2$ are each independently $SR^4$, $OR^4$, $NR^4R^4$, $BH(OR^7)_2^-$, or $BH(R^b)_2^-$; wherein, at least one of $X^2$ and $Y^2$ is $BH(R^b)_2^-$; and $R^b$ is each independently H, CN, carboxyl, carboxyl salts, $C_{1-6}$ alkyl, alkylaryl, aryl, alkoxycarbonyl, or alkylaminocarbonyl, wherein the $C_{1-6}$ alkyl, alkylaryl, aryl, alkoxycarbonyl and alkylaminocarbonyl is each optionally substituted with up to 3 substituents selected from OH, —P(O)(OH)$_2$, —OP(O)(OH)$_2$, CO$_2$H, or F.

In one embodiment of the compound of formula (A), $X^2$ and $Y^2$ are each selected from —OH, —SH or $BH_3^-$, wherein at least one of $X^2$ and $Y^2$ is $BH_3^-$.

In one embodiment of the compound of formula (A), $Q^a$ and $Q^b$ are each independently selected from:

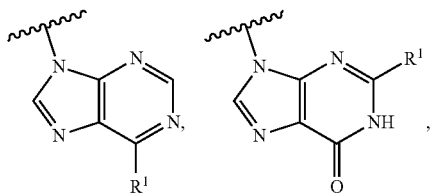

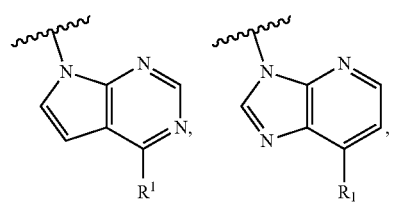

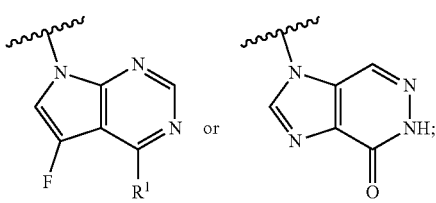

and $R^1$ is each independently hydrogen, halogen, or —N($R^{cl}$)$_2$, and $R^{cl}$ is each independently H, $C_{1-6}$ alkyl, $C_{3-6}$ cycloalkyl, $C_{3-6}$ cycloalkyl-$C_{1-6}$ alkyl-, 3-6 membered heterocyclyl, (3-6 membered heterocyclyl)-$C_{1-6}$ alkyl-, 5-6 membered aryl, (5-6 membered aryl)-$C_{1-6}$ alkyl-, 5-6 membered heteroaryl, or (5-6 membered heteroaryl)-$C_{1-6}$ alkyl-.

In one embodiment, the present disclosure relates to a compound of formula (B),

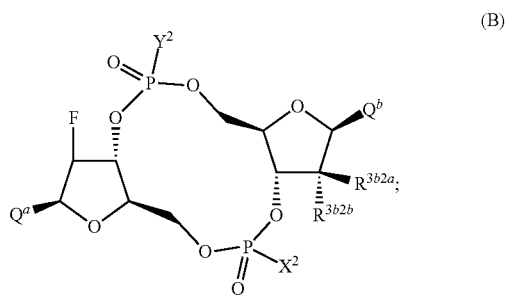

(B)

or a pharmaceutically acceptable salt, stereoisomer, solvate or hydrate thereof, wherein:

$Q^a$ and $Q^b$ are each independently cycloalkyl, heterocyclyl, aryl, or heteroaryl, wherein the cycloalkyl, heterocyclyl, aryl, and heteroaryl can be optionally substituted with one, two, three, four, or five $R^1$;

$R^1$ is each independently hydrogen, halogen, —NO$_2$, —CN, —OR$^{cl}$, —SR$^{cl}$, —N(R$^{cl}$)$_2$, —C(O)R$^{cl}$, —CO$_2$R$^{cl}$, —C(O)C(O)R$^{cl}$, —C(O)CH$_2$C(O)R$^{cl}$, —C(O)N(R$^{cl}$)$_2$, —C(=NR$^{cl}$)N(R$^{cl}$)$_2$, —C(=NOR$^{cl}$)R$^{cl}$, —S(O)R$^{cl}$, —S(O)$_2$R$^{cl}$, —SO$_2$N(R$^{cl}$)$_2$, —OC(O)R$^{cl}$, —N(R$^{cl}$)C(O)R$^{cl}$, —NR$^{cl}$N(R$^{cl}$)$_2$, —N(R$^{cl}$)C(=NR$^{cl}$)N(R$^{cl}$)$_2$, —N(R$^{cl}$)C(O)N(R$^{cl}$), —N(R$^{cl}$)SO$_2$N(R$^{cl}$)$_2$, —N(R$^{cl}$)SO$_2$R$^{cl}$, —N(R$^{cl}$)SO$_2$NR$^{cl}$C(=O)OR$^{cl}$, —OC(O)N(R$^{cl}$)$_2$, or R$^{cl}$;

$R^{cl}$ is each independently H, $C_{1-12}$ alkyl, $C_{2-12}$ alkenyl, $C_{2-12}$ alkynyl, $C_{3-12}$ cycloalkyl, $C_{3-12}$ cycloalkyl-$C_{1-6}$ alkyl-, heterocyclyl, heterocyclyl-$C_{1-6}$ alkyl-, aryl, aryl-$C_{1-6}$ alkyl-, heteroaryl, or heteroaryl-$C_{1-6}$ alkyl-, wherein $C_{1-12}$ alkyl, $C_{2-12}$ alkenyl, $C_{2-12}$ alkynyl, $C_{3-12}$ cycloalkyl, $C_{3-12}$ cycloalkyl-$C_{1-6}$ alkyl-, heterocyclyl, heterocyclyl-$C_{1-6}$ alkyl-, aryl, aryl-$C_{1-6}$ alkyl-, heteroaryl, and heteroaryl-$C_{1-6}$ alkyl- can be substituted one or more substituents selected from $C_{1-6}$ alkyl, halogen, $C_{1-6}$ alkoxy, —NO$_2$, —NR$^{cs}$R$^{cs}$, —OH, =O, or COOR$^{cs}$; or $R^{ns}$ is each independently H, $R^{cs}$, $R^{cs}$—C(O)—, $R^{cs}$—S(O)$_2$—, $R^{cs}$R$^{cs}$N—C(O)—, or $R^{cs}$R$^{cs}$NS(O)$_2$—;

$R^{cs}$ is each independently H, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, or $C_2$-$C_6$ haloalkynyl; or alternatively, two $R^{cs}$ attached to the same N atom can together with the N atom form a 4-7 membered heterocyclic ring, containing up to one other heteroatom chosen from O, S, or $NR^{ns}$, wherein the 4-7 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

$R^{3b2a}$ and $R^{3b2b}$ are each independently H, halogen, —OH, or —O($C_{1-3}$ alkyl);

$X^2$ and $Y^2$ are each independently $SR^4$, $OR^4$, $NR^4R^4$, $BH(OR^7)_2^-$, or $BH(R^b)_2^-$; wherein, at least one of $X^2$ and $Y^2$ is $BH(R^b)_2^-$; and $R^b$ is each independently H, CN, carboxyl, carboxyl salts, $C_{1-6}$ alkyl, alkylaryl, aryl, alkoxycarbonyl, or alkylaminocarbonyl, wherein the $C_{1-6}$ alkyl, alkylaryl, aryl, alkoxycarbonyl and alkylaminocarbonyl is each optionally substituted with up to 3 substituents selected from OH, —P(O)(OH)$_2$, —OP(O)(OH)$_2$, CO$_2$H, or F.

In one embodiment of the compound of formula (B), $X^2$ and $Y^2$ are each selected from —OH, —SH or $BH_3^-$, wherein at least one of $X^2$ and $Y^2$ is $BH_3^-$.

In one embodiment of the compound of formula (B), $Q^a$ and $Q^b$ are each independently selected from:

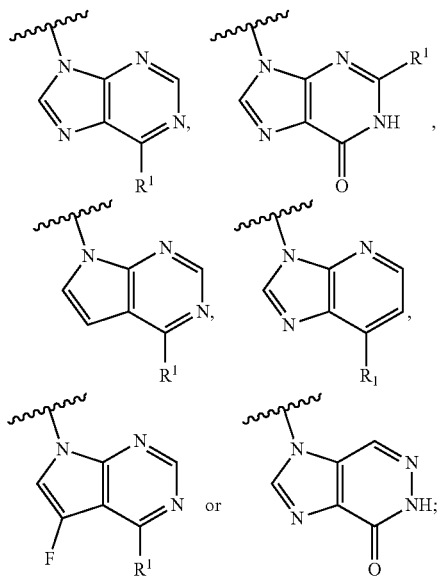

and $R^1$ is each independently hydrogen, halogen, or —N($R^{c1}$)$_2$, and $R^{c1}$ is each independently H, $C_{1-6}$ alkyl, $C_{3-6}$ cycloalkyl, $C_{3-6}$ cycloalkyl-$C_{1-6}$ alkyl-, 3-6 membered heterocyclyl, (3-6 membered heterocyclyl)-$C_{1-6}$ alkyl-, 5-6 membered aryl, (5-6 membered aryl)-$C_{1-6}$ alkyl-, 5-6 membered heteroaryl, or (5-6 membered heteroaryl)-$C_{1-6}$ alkyl-.

In one embodiment of the compound of formula (B), $R^{3b2a}$ and $R^{3b2b}$ are each independently selected from H, F or OH.

In one embodiment, the present disclosure relates to a pharmaceutical composition comprising a compound of formulae (I), (II), (A), or (B), or any subgenera thereof, or a pharmaceutically acceptable salt, stereoisomer, solvate or hydrate thereof, and one or more pharmaceutically acceptable excipients.

In one embodiment, the present disclosure relates to a method of treating a disease or a condition in which the modulation of STING is beneficial in a subject, comprising administering a therapeutically effective amount of a compound of formulae (I), (II), (A), or (B), or any subgenera thereof, or a pharmaceutically acceptable salt, stereoisomer, solvate or hydrate thereof, to the subject in need thereof.

In one embodiment, the present disclosure relates to a method modulating STING, comprising administering a therapeutically effective amount of a compound of formulae (I), (II), (A), or (B), or any subgenera thereof, or a pharmaceutically acceptable salt, stereoisomer, solvate or hydrate thereof, to the subject in need thereof.

In one embodiment, the present disclosure relates to a method of treating cancer, comprising administering a therapeutically effective amount of a compound of formulae (I), (II), (A), or (B), or any subgenera thereof, or a pharmaceutically acceptable salt, stereoisomer, solvate or hydrate thereof, to the subject in need thereof.

In one embodiment, the present disclosure relates to a method of treating a disease, comprising administering a therapeutically effective amount of a compound of formulae (I), (II), (A), or (B), or any subgenera thereof, or a pharma-ceutically acceptable salt, stereoisomer, solvate or hydrate thereof, to the subject in need thereof, wherein the disease is selected from cancer, rheumatoid arthritis, psoriasis, acute rejection of an organ transplant, allergic asthma or Crohn's disease. In one embodiment, the present disclosure relates to a compound of formulae (I), (II), (A), or (B), or any subgenera thereof, or a pharmaceutically acceptable salt, stereoisomer, solvate or hydrate thereof, for use in treating a disease or a condition in which the modulation of STING is beneficial in a subject.

In one embodiment, the present disclosure relates to compound of formulae (I), (II), (A), or (B), or any subgenera thereof, or a pharmaceutically acceptable salt, stereoisomer, solvate or hydrate thereof, for use in modulating STING.

In one embodiment, the present disclosure relates to a compound of formulae (I), (II), (A), or (B), or any subgenera thereof, or a pharmaceutically acceptable salt, stereoisomer, solvate or hydrate thereof, for use in treating cancer.

In one embodiment, the present disclosure relates to a compound of formulae (I), (II), (A), or (B), or any subgenera thereof, or a pharmaceutically acceptable salt, stereoisomer, solvate or hydrate thereof, for use in treating a disease, wherein the disease is selected from cancer, rheumatoid arthritis, psoriasis, acute rejection of an organ transplant, allergic asthma or Crohn's disease.

DETAILED DISCLOSURE

Definitions

Figure 1:
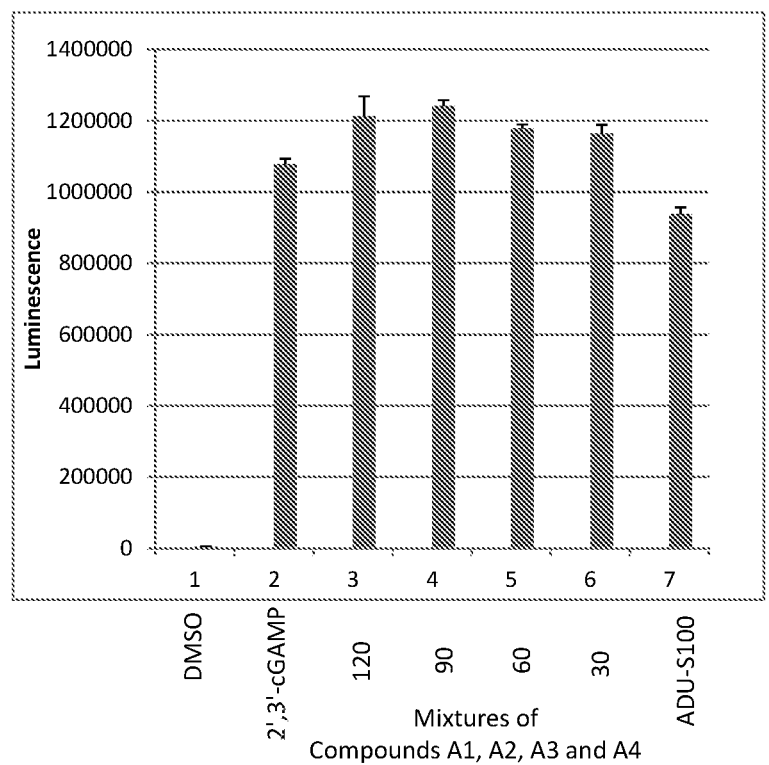
FIG. 1 is shows THP1-dual cell assay results of a mixture of Compounds A1, A2, A3 and A4.

It is to be understood that the terminology used herein is for the purpose of describing particular embodiments only and is not intended to be limiting.

Unless defined otherwise, all technical and scientific terms used herein have the same meaning as commonly understood to one of ordinary skill in the art to which the present application belongs. Although any methods and materials similar or equivalent to those described herein can be used in the practice or testing of the present application, representative methods and materials are herein described.

Following long-standing patent law convention, the terms "a", "an", and "the" refer to "one or more" when used in this application, including the claims. Thus, for example, reference to "a carrier" includes mixtures of one or more carriers, two or more carriers, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the present application.

The term "compound(s) of the present invention" or "compound(s) of the present disclosure" refers to compounds of formulae (I), (II), (III), (A), or (B), or any subgenera thereof, or a pharmaceutically acceptable salt, stereoisomer, solvate or hydrate thereof, as disclosed herein.

The compounds of the invention, or their pharmaceutically acceptable salts can contain one or more asymmetric centers and can thus give rise to enantiomers, diastereomers, and other stereoisomeric forms that can be defined, in terms of absolute stereochemistry, as (R)- or (S)- or, as (D)- or (L)- for amino acids. The present invention is meant to include all such possible isomers, as well as their racemic and optically pure forms whether or not they are specifically depicted herein. Optically active (+) and (−), (R)- and (S)-, or (D)- and (L)-isomers can be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present invention includes tautomers of any said compounds.

The terms "pharmaceutical combination," "therapeutic combination" or "combination" as used herein, refers to a single dosage form comprising at least two therapeutically active agents, or separate dosage forms comprising at least two therapeutically active agents together or separately for use in combination therapy. For example, one therapeutically active agent may be formulated into one dosage form and the other therapeutically active agent may be formulated into a single or different dosage forms. For example, one therapeutically active agent may be formulated into a solid oral dosage form whereas the second therapeutically active agent may be formulated into a solution dosage form for parenteral administration.

The chemical naming protocol and structure diagrams used herein are a modified form of the I.U.P.A.C. nomenclature system, using the ACD/Name Version 9.07 software program, ChemDraw Ultra Version 11.0.1 and/or ChemDraw Ultra Version 14.0 software naming program (CambridgeSoft). For complex chemical names employed herein, a substituent group is named before the group to which it attaches. For example, cyclopropylethyl comprises an ethyl backbone with cyclopropyl substituent. Except as described below, all bonds are identified in the chemical structure diagrams herein, except for some carbon atoms, which are assumed to be bonded to sufficient hydrogen atoms to complete the valency.

The term "composition" or "formulation" denotes one or more substance in a physical form, such as solid, liquid, gas, or a mixture thereof. One example of composition is a pharmaceutical composition, i.e., a composition related to, prepared for, or used in medical treatment.

As used herein, "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

"Salts" include derivatives of an active agent, wherein the active agent is modified by making acid or base addition salts. Preferably, the salts are pharmaceutically acceptable salts. Such salts include, but are not limited to, pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfo aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Base addition salts include but are not limited to, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine dicyclohexylamine and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Standard methods for the preparation of pharmaceutically acceptable salts and their formulations are well known in the art, and are disclosed in various references, including for example, "Remington: The Science and Practice of Pharmacy", A. Gennaro, ed., 20th edition, Lippincott, Williams & Wilkins, Philadelphia, PA.

As used herein, "solvate" means a complex formed by solvation (the combination of solvent molecules with molecules or ions of the active agent of the present invention), or an aggregate that consists of a solute ion or molecule (the active agent of the present invention) with one or more solvent molecules. In the present invention, the preferred solvate is hydrate. Examples of hydrate include, but are not limited to, hemihydrate, monohydrate, dihydrate, trihydrate, hexahydrate, etc. It should be understood by one of ordinary skill in the art that the pharmaceutically acceptable salt of the present compound may also exist in a solvate form. The solvate is typically formed via hydration which is either part of the preparation of the present compound or through natural absorption of moisture by the anhydrous compound of the present invention. Solvates including hydrates may be consisting in stoichiometric ratios, for example, with two, three, four salt molecules per solvate or per hydrate molecule. Another possibility, for example, that two salt molecules are stoichiometric related to three, five, seven solvent or hydrate molecules. Solvents used for crystallization, such as alcohols, especially methanol and ethanol; aldehydes;

ketones, especially acetone; esters, e.g. ethyl acetate; may be embedded in the crystal grating. Preferred are pharmaceutically acceptable solvents.

The terms "excipient", "carrier", and "vehicle" are used interexchangeably throughout this application and denote a substance with which a compound of the present invention is administered.

"Therapeutically effective amount" means the amount of a compound or a therapeutically active agent that, when administered to a patient for treating a disease or other undesirable medical condition, is sufficient to have a beneficial effect with respect to that disease or condition. The therapeutically effective amount will vary depending on the type of the selected compound or a therapeutically active agent, the disease or condition and its severity, and the age, weight, etc. of the patient to be treated. Determining the therapeutically effective amount of a given compound or a therapeutically active agent is within the ordinary skill of the art and requires no more than routine experimentation.

"Treating" or "treatment" as used herein covers the treatment of the disease or condition of interest in a mammal, preferably a human, having the disease or condition of interest, and includes:
  preventing the disease or condition from occurring in a mammal, in particular, when such mammal is predisposed to the condition but has not yet been diagnosed as having it;
  inhibiting the disease or condition, i.e., arresting its development;
  relieving the disease or condition, i.e., causing regression of the disease or condition; or
  relieving the symptoms resulting from the disease or condition, i.e., relieving pain without addressing the underlying disease or condition. As used herein, the terms "disease" and "condition" can be used interchangeably or can be different in that the particular malady or condition cannot have a known causative agent (so that etiology has not yet been worked out) and it is therefore not yet recognized as a disease but only as an undesirable condition or syndrome, wherein a more or less specific set of symptoms have been identified by clinicians.

The invention disclosed herein is also meant to encompass the in vivo metabolic products of the disclosed compounds. Such products can result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

As used herein, a "subject" can be a human, non-human primate, mammal, rat, mouse, cow, horse, pig, sheep, goat, dog, cat and the like. The terms "subject" and "patient" are used interchangeably herein in reference, e.g., to a mammalian subject, such as a human subject. The subject can be suspected of having or at risk for having a cancer, such as prostate cancer, breast cancer, ovarian cancer, salivary gland carcinoma, or endometrial cancer, or suspected of having or at risk for having acne, hirsutism, alopecia, benign prostatic hyperplasia, ovarian cysts, polycystic ovary disease, precocious puberty, spinal and bulbar muscular atrophy, or age-related macular degeneration. Diagnostic methods for various cancers, such as prostate cancer, breast cancer, ovarian cancer, bladder cancer, pancreatic cancer, hepatocellular cancer, salivary gland carcinoma, or endometrial cancer, and diagnostic methods for acne, hirsutism, alopecia, benign prostatic hyperplasia, ovarian cysts, polycystic ovary disease, precocious puberty, spinal and bulbar muscular atrophy, or age-related macular degeneration and the clinical delineation of cancer, such as prostate cancer, breast cancer, ovarian cancer, bladder cancer, pancreatic cancer, hepatocellular cancer, salivary gland carcinoma, or endometrial cancer, diagnoses and the clinical delineation of acne, hirsutism, alopecia, benign prostatic hyperplasia, ovarian cysts, polycystic ovary disease, precocious puberty, spinal and bulbar muscular atrophy, or age-related macular degeneration are known to those of ordinary skill in the art.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances can or cannot occur, and that the description includes instances where said event or circumstance occurs and instances in which it does not. For example, "optionally substituted aryl" means that the aryl radical can or cannot be substituted and that the description includes both substituted aryl radicals and aryl radicals having no substitution.

The terms below, as used herein, have the following meanings, unless indicated otherwise:

"Acyl" refers to —C(=O)-alkyl radical.
"Amino" refers to the —NH$_2$ radical.
"Cyano" refers to the —CN radical.
"Halo" "halide" or "halogen" refers to bromo, chloro, fluoro or iodo radical.
"Hydroxy" or "hydroxyl" refers to the —OH radical.
"Imino" refers to the =NH substituent.
"Nitro" refers to the —NO$_2$ radical.
"Oxo" refers to the =O substituent.
"Thioxo" refers to the =S substituent.
"Sulfhydryl" and "mercapto" refers to —SH radical.
"Alkyl" or "alkyl group" refers to a fully saturated, straight (linear) or branched hydrocarbon chain radical having from one to twenty carbon atoms, and which is attached to the rest of the molecule by a single bond. Alkyls comprising any number of carbon atoms from 1 to 20 are included. An alkyl comprising up to 20 carbon atoms is a $C_1$-$C_{20}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted. The term "lower alkyl" refers to a $C_1$-$C_6$ alkyl, which can be linear or branched, for example including branched $C_3$-$C_6$ alkyl.

"Alkylene", "-alkyl-" or "alkylene chain" refers to a fully saturated, straight or branched divalent hydrocarbon chain radical, and having from one to twenty carbon atoms. Non-limiting examples of $C_1$-$C_{20}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twenty carbon atoms, and having one or more carbon-carbon double bonds. Each alkenyl group is attached to the rest of the molecule by a single bond. Alkenyl group comprising any number of carbon atoms from 2 to 20 are included. An alkenyl group comprising up to 20 carbon atoms is a $C_2$-$C_{20}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or branched divalent hydrocarbon chain radical, having from two to twenty carbon atoms, and having one or more carbon-carbon double bonds. Non-limiting examples of $C_2$-$C_{20}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twenty carbon atoms, and having one or more carbon-carbon triple bonds. Each alkynyl group is attached to the rest of the molecule by a single bond. Alkynyl group comprising any number of carbon atoms from 2 to 20 are included. An alkynyl group comprising up to 20 carbon atoms is a $C_2$-$C_{20}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to twenty carbon atoms, and having one or more carbon-carbon triple bonds. Non-limiting examples of $C_2$-$C_{20}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" or "—O-alkyl" refers to a radical of the formula —$OR_a$ where $R_a$ is an alkyl, alkenyl or alknyl radical as defined above containing one to twenty carbon atoms. Unless stated otherwise specifically in the specification, an alkoxy group can be optionally substituted.

"Alkylamino" refers to a radical of the formula —$NHR_a$ or —$NR_aR_a$ where each $R_a$ is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the —$C(=O)R_a$ moiety, wherein $R_a$ is an alkyl, alkenyl or alkynyl radical as defined above. A non-limiting example of an alkyl carbonyl is the methyl carbonyl ("acetal") moiety. Alkylcarbonyl groups can also be referred to as "Cw-Cz acyl" where w and z depicts the range of the number of carbon in $R_a$, as defined above. For example, "$C_1$-$C_{10}$ acyl" refers to alkylcarbonyl group as defined above, where $R_a$ is $C_1$-$C_{10}$ alkyl, $C_1$-$C_{10}$ alkenyl, or $C_1$-$C_{10}$ alkynyl radical as defined above. Unless stated otherwise specifically in the specification, an alkyl carbonyl group can be optionally substituted.

The term "aminoalkyl" refers to an alkyl group that is substituted with one or more —$NH_2$ groups. In certain embodiments, an aminoalkyl group is substituted with one, two, three, four, five or more —$NH_2$ groups. An aminoalkyl group may optionally be substituted with one or more additional substituents as described herein.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aralkyl", "arylalkyl" or "-alkylaryl" refers to a radical of the formula —$R_b$-$R_c$ where $R_b$ is an alkylene, alkenylene or alkynylene group as defined above and $R_c$ is one or more aryl radicals as defined above, for example, benzyl, diphenylmethyl and the like. Unless stated otherwise specifically in the specification, an aralkyl group can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include aryls and cycloalkyl. Cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, bicyclo[3.1.0]hexane, octahydropentalene, bicyclo[1.1.1]pentane, cubane, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Cycloalkylalkyl" or "-alkylcycloalkyl" refers to a radical of the formula —$R_b$-$R_d$ where $R_b$ is an alkylene, alkenylene, or alkynylene group as defined above and $R_d$ is a cycloalkyl, cycloalkenyl, cycloalkynyl radical as defined above. Unless stated otherwise specifically in the specification, a cycloalkylalkyl group can be optionally substituted.

"Haloalkyl" refers to an alkyl radical, as defined above, that is substituted by one, two, three, four, five, six or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl radical, as defined above, that is substituted by one, two, three, four, five, six or more halo radicals, as defined above, e.g., 1-fluoropropenyl, 1,1-difluorobutenyl, and the like. Unless stated otherwise specifically in the specification, a haloalkenyl group can be optionally substituted.

1 "Haloalkynyl" refers to an alkynyl radical, as defined above, that is substituted by one, two, three, four, five, six or more halo radicals, as defined above, e.g., 1-fluoropropynyl, 1-fluorobutynyl, and the like. Unless stated otherwise specifically in the specification, a haloalkenyl group can be optionally substituted.

"Heterocyclyl," "heterocyclic ring" or "heterocycle" refers to a stable 3- to 20-membered non-aromatic ring radical which consists of two to twelve carbon atoms and from one to six heteroatoms selected from the group consisting of nitrogen, oxygen and sulfur. Heterocyclycl or heterocyclic rings include heteroaryls as defined below. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocyclyl group can be optionally substituted.

The term "hydroxyalkyl" or "hydroxylalkyl" refers to an alkyl group that is substituted with one or more hydroxyl (—OH) groups. In certain embodiments, a hydroxyalkyl group is substituted with one, two, three, four, five or more —OH groups. A hydroxyalkyl group may optionally be substituted with one or more additional substituents as described herein.

The term "hydrocarbyl" refers to a monovalent hydrocarbon radical, whether aliphatic, partially or fully unsaturated, acyclic, cyclic or aromatic, or any combination of the preceding. In certain embodiments, a hydrocarbyl group has 1 to 40 or more, 1 to 30 or more, 1 to 20 or more, or 1 to 10 or more, carbon atoms. The term "hydrocarbylene" refers to a divalent hydrocarbyl group. A hydrocarbyl or hydrocarbylene group may optionally be substituted with one or more substituents as described herein.

The term "heterohydrocarbyl" refers to a hydrocarbyl group in which one or more of the carbon atoms are independently replaced by a heteroatom selected from oxygen, sulfur, nitrogen and phosphorus. In certain embodiments, a heterohydrocarbyl group has 1 to 40 or more, 1 to 30 or more, 1 to 20 or more, or 1 to 10 or more, carbon atoms, and 1 to 10 or more, or 1 to 5 or more, heteroatoms. The term "heterohydrocarbylene" refers to a divalent hydrocarbyl group. Examples of heterohydrocarbyl and heterohydrocarbylene groups include without limitation ethylene glycol and polyethylene glycol moieties, such as (—$CH_2CH_2O$—)$_n$H (a monovalent heterohydrocarbyl group) and (—CH$_2$CH$_2$O—)$_n$ (a divalent heterohydrocarbylene group) where n is an integer from 1 to 12 or more, and propylene glycol and polypropylene glycol moieties, such as (—CH$_2$CH$_2$CH$_2$O—)$_n$H and (—CH$_2$CH(CH$_3$)O—)$_n$H (monovalent heterohydrocarbyl groups) and (—CH$_2$CH$_2$CH$_2$O—)$_n$ and (—CH$_2$CH(CH$_3$)O—)$_n$ (divalent heterohydrocarbylene groups) where n is an integer from 1 to 12 or more. A heterohydrocarbyl or heterohydrocarbylene group may optionally be substituted with one or more substituents as described herein.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group can be optionally substituted.

"Heterocyclylalkyl" or "-alkylheterocyclyl" refers to a radical of the formula —R$_b$-R$_c$ where R$_b$ is an alkylene, alkenylene, or alkynylene chain as defined above and R$_c$ is a heterocyclyl radical as defined above, and if the heterocyclyl is a nitrogen-containing heterocyclyl, the heterocyclyl can be attached to the alkyl, alkenyl, alkynyl radical at the nitrogen atom. Unless stated otherwise specifically in the specification, a heterocyclylalkyl group can be optionally substituted.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" or "-alkylheteroaryl" refers to a radical of the formula —R$_b$-R$_f$ where R$_b$ is an alkylene, alkenylene, or alkynylene chain as defined above and R$_f$ is a heteroaryl radical as defined above. Unless stated otherwise specifically in the specification, a heteroarylalkyl group can be optionally substituted.

"Thioalkyl" refers to a radical of the formula —SR$_a$ where R$_a$ is an alkyl, alkenyl, or alkynyl radical as defined above containing one to twelve carbon atoms. Unless stated otherwise specifically in the specification, a thioalkyl group can be optionally substituted.

The term "substituted" used herein means any of the above groups (i.e., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms with a list provided herein. If no substituent list is included, substituents can be, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with halide, cyano, nitro, hydroxyl, sulfhydryl, amino, —OR$_g$, —SR$_g$, —NR$_h$R$_i$, alkyl, alkenyl, alkynyl, haloalkyl, hydroxyalkyl, aminoalkyl, -alkylcycloalkyl, -alkylheterocyclyl, -alkylaryl, -alkylheteroaryl, cycloalkyl, heterocyclyl, aryl, heteroaryl, —C(=O)R$_g$, —C(=NR$_j$)R$_g$, —S(=O)R$_g$, —S(=O)$_2$R$_g$, —S(=O)$_2$OR$_k$, —C(=O)OR$_k$, —OC(=O)R$_g$, —C(=O)NR$_h$R$_i$, —NR$_g$C(=O)R$_g$, —S(=O)$_2$NR$_h$R$_i$, —NR$_g$S(=O)$_2$R$_g$, —OC(=O)OR$_g$, —OC(=O)NR$_h$R$_i$, —NR$_g$C(=O)OR$_g$, —NR$_g$C(=O)NR$_h$R$_i$, —NR$_g$C(=NR$_j$)NR$_h$R$_i$, —P(=O)(R$_g$)$_2$, —P(=O)(OR$_k$)R$_g$, —P(=O)(R$_k$)$_2$, —OP(=O)(R$_g$)$_2$, —OP(=O)(OR$_k$)R$_g$, and —OP(=O)(OR$_k$)$_2$, wherein: each occurrence of R$_g$ is independently selected from hydrogen, alkyl, haloalkyl, hydroxyalkyl, aminoalkyl, -alkylcycloalkyl, -alkylheterocyclyl, -alkylaryl, -alkylheteroaryl, cycloalkyl, heterocyclyl, aryl or heteroaryl; each occurrence of R$_h$ and R$_i$ is independently selected from hydrogen, alkyl, haloalkyl, hydroxyalkyl, aminoalkyl, -alkylcycloalkyl, -alkylheterocyclyl, -alkylaryl, -alkylheteroaryl, cycloalkyl, heterocyclyl, aryl or heteroaryl, or R$_h$ and R$_i$, together with the nitrogen atom to which they are attached, form a heterocyclic or heteroaryl ring; each occurrence of R$_j$ independently is hydrogen, —OR$_g$, alkyl, haloalkyl, hydroxyalkyl, aminoalkyl, -alkylcycloalkyl, -alkylheterocyclyl, -alkylaryl, -alkylheteroaryl, cycloalkyl, heterocyclyl, aryl or heteroaryl; and each occurrence of R$_k$ independently is hydrogen, W, alkyl, haloalkyl, hydroxyalkyl, aminoalkyl, -alkylcycloalkyl, -alkylheterocyclyl, -alkylaryl, -alkylheteroaryl, cycloalkyl, heterocyclyl, aryl or heteroaryl, wherein each occurrence of W independently is H$^+$, Li$^+$, Na$^+$, K$^+$, Cs$^+$, Mg$^{+2}$, Ca$^{+2}$, or —$^+$N(R$_g$)$_2$R$_h$R$_i$.

As used herein, when BH(OR$^7$)$_2$, BH(R$^b$)$_2$, or BH$_3$ group forms a single bond with a P(=O) group (e.g., X$^2$ and Y$^2$ in formulae (I), (II), or (III)), the $BH(OR^7)_2$, $BH(R^b)_2$, or $BH_3$ has one negative charge. The "—" in $BH(OR^7)_2^-$, $BH(R^b)_2^-$, and $BH_3^-$, indicates that the B group has a single negative charge.

As used herein, the symbol

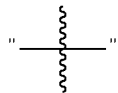

(hereinafter can be referred to as "a point of attachment bond") denotes a bond that is a point of attachment between two chemical entities, one of which is depicted as being attached to the point of attachment bond and the other of

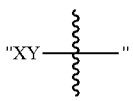

indicates that the chemical entity "XY" is bonded to another chemical entity via the point of attachment bond. Furthermore, the specific point of attachment to the non-depicted chemical entity can be specified by inference. For example, the compound $CH_3$—$R^3$, wherein $R^3$ is H or

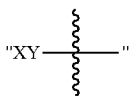

infers that when $R^3$ is "XY", the point of attachment bond is the same bond as the bond by which $R^3$ is depicted as being bonded to $CH_3$.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring can be replaced with a nitrogen atom.

Compounds

In one embodiment of the present disclosure, a compound of formulae (I), (II), (III), (A), or (B), or a pharmaceutically acceptable salt, stereoisomer, solvate or hydrate thereof, is provided.

In one embodiment, the compound of formula (I), formula (II), or formula (III):

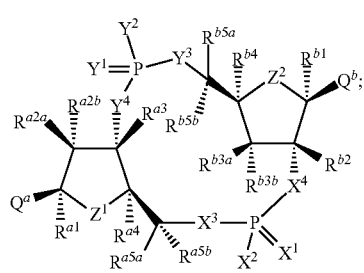
(I)

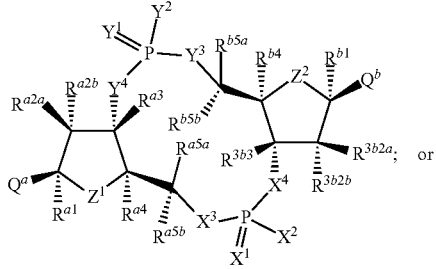
(II)

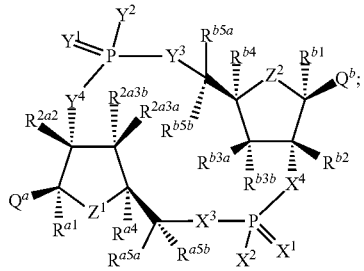
(III)

or a pharmaceutically acceptable salt, stereoisomer, solvate or hydrate thereof, wherein:

$Q^a$ and $Q^b$ are each independently cycloalkyl, heterocyclyl, aryl, or heteroaryl, wherein the cycloalkyl, heterocyclyl, aryl, and heteroaryl can be optionally substituted with one, two, three, four, or five $R^1$;

$R^1$ is each independently hydrogen, halogen, $-NO_2$, $-CN$, $-OR^{cl}$, $-SR^{cl}$, $-N(R^{cl})_2$, $-C(O)R^{cl}$, $-CO_2R^{cl}$, $-C(O)C(O)R^{cl}$, $-C(O)CH_2C(O)R^{cl}$, $-C(O)N(R^{cl})_2$, $-C(=NR^{cl})N(R^{cl})_2$, $-C(=NOR^{cl})R^{cl}$, $-S(O)R^{cl}$, $-S(O)_2R^{cl}$, $-SO_2N(R^{cl})_2$, $-OC(O)R^{cl}$, $-N(R^{cl})C(O)R^{cl}$, $-NR^{cl}N(R^{cl})_2$, $-N(R^{cl})C(=NR^{cl})N(R^{cl})_2$, $-N(R^{cl})C(O)N(R^{cl})_2$, $-N(R^{cl})SO_2N(R^{cl})_2$, $-N(R^{cl})SO_2R^{cl}$, $-N(R^{cl})SO_2NR^{cl}C(=O)OR^{cl}$, $-OC(O)N(R^{cl})_2$, or $R^{cl}$;

$R^{cl}$ is each independently H, $C_{1-12}$ alkyl, $C_{2-12}$ alkenyl, $C_{2-12}$ alkynyl, $C_{3-12}$ cycloalkyl, $C_{3-12}$ cycloalkyl-$C_{1-6}$ alkyl-, heterocyclyl, heterocyclyl-$C_{1-6}$ alkyl-, aryl, aryl-$C_{1-6}$ alkyl-, heteroaryl, or heteroaryl-$C_{1-6}$ alkyl-, wherein $C_{1-12}$ alkyl, $C_{2-12}$ alkenyl, $C_{2-12}$ alkynyl, $C_{3-12}$ cycloalkyl, $C_{3-12}$ cycloalkyl-$C_{1-6}$ alkyl-, heterocyclyl, heterocyclyl-$C_{1-6}$ alkyl-, aryl, aryl-$C_{1-6}$ alkyl-, heteroaryl, and heteroaryl-$C_{1-6}$ alkyl- can be substituted one or more substituents selected from $C_{1-6}$ alkyl, halogen, $C_{1-6}$ alkoxy, $-NO_2$, $-NR^{ns}R^{ns}$, $-OH$, $=O$, or $COOR^{cs}$; or alternatively, two $R^{cl}$ attached to the same N atom can together with the N atom form a 4-7 membered heterocyclic ring, containing up to one other heteroatom selected from O, S, or $NR^{ns}$, and wherein the 4-7 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

$R^{ns}$ is each independently H, $R^{cs}$, $R^{cs}$—C(O)—, $R^{cs}$—S(O)$_2$—, $R^{cs}R^{cs}N$—C(O)—, or $R^{cs}R^{cs}NS(O)_2$—;

$R^{cs}$ is each independently H, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, or $C_2$-$C_6$ haloalkynyl; or alternatively, two $R^{cs}$ attached to the same N atom can together with the N atom form a 4-7 membered heterocyclic ring, containing up to one other heteroatom chosen from O, S, or $NR^{ns}$, wherein the 4-7 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

$R^{a1}$ and $R^{b1}$ are each independently H, CN, $C_{3-6}$ cycloakyl, $R^{cs}$, —$OR^{cs}$, —$SR^{cs}$, —$CH_2N_3$, —$CH_2NR^{cs}R^{cs}$ or —$CH_2OR^{cs}$, wherein $C_{3-6}$ cycloakyl and $R^{cs}$ is optionally substituted with one, two or three substituents selected from halogen, OH, OMe, $NMe_2$, CN or $N_3$;

$R^{a4}$ and $R^{b4}$ are each independently selected from the group consisting of H, halogen, OH, CN, $N_3$, $R^{cs}$, —$CH_2OR^{cs}$, —$CH_2SR^{cs}$, —$CH_2N_3$, —$CH_2NR^{cs}R^{cs}$, —$CO_2R^{cs}$, —$SR^{cs}$, and —$OR^{cs}$, where said $R^{cs}$ is substituted by 0-3 substituents selected from the group consisting of halogen, OH, OMe, $NMe_2$, CN and $N_3$;

$R^{a2a}$, $R^{a2b}$, $R^{b3a}$, $R^{b3b}$, $R^{3b2a}$, $R^{3b2b}$, $R^{2a3a}$ and $R^{2a3b}$ are each independently H, halogen, CN, $N_3$, —$CH_2N_3$, —$CH_2NR^{cs}R^{cs}$, —$CO_2R^{cs}$, —$CH_2OR^{cs}$, —$CH_2SR^{cs}$, —$C_{3-6}$ cycloakyl, $R^{cs}$, —$NR''R''$, —$OCH_2CO_2R^{cs}$, or —$OR^0$, wherein the —$R^{cs}$ and the $R^{cs}$ in —$CH_2NR^{cs}R^{cs}$, —$CO_2R^{cs}$, —$CH_2OR^{cs}$, —$CH_2SR^{cs}$, and —$OCH_2CO_2R^{cs}$, the $R''$ in —$NR''R''$, and the $R^0$ in —$OR^0$ can be optionally substituted with up to three substituents selected from halogen, CN, —$NMe_2$, $C_{1-6}$ alkoxy, —$NO_2$, —$NR''^sR''^s$, —OH, OMe, =O, or $COOR^{cs}$; or alternatively, $R^{a2b}$ and $R^{a4}$, or $R^{3b2b}$ and $R^{b4}$, can be taken together with the cyclic ring to which they are attached, form a bridged 7-9 membered heterobicyclic ring, containing up to one other heteroatom selected from O, S, or $NR^{ns}$, and wherein the bridged 7-9 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, $NMe_2$, cyano or halo; or alternatively, $R^{a2a}$ and $R^{a2b}$, $R^{b3a}$ and $R^{b3b}$, $R^{3b2a}$ and $R^{3b2b}$, or $R^{2a3a}$ and $R^{2a3b}$, can be taken together with the carbon atom to which they are attached, form a 4-6 membered heterocyclic ring, containing up to one other heteroatom chosen from O, S, or $NR^{ns}$, and wherein the 4-6 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, $NMe_2$, cyano or halo;

$R^0$ is hydrogen, $R^{cl}$, or $R^{cl}$—C(O)—;

$R^{a3}$, $R^{b2}$, $R^{3b3}$ and $R^{2a2}$ are each independently H, halogen, CN, $N_3$, —P(=O)($OR^{cs}$)$_2$, $C_{3-6}$ cycloakyl, $R^{cs}$, —C≡C—Cl, —$CH_2N_3$, —$CH_2NR^{cs}R^{cs}$, —$CO_2R^{cs}$, —$CH_2OR^{cs}$ or —$CH_2SR^{cs}$; wherein the $C_{3-6}$ cycloakyl and $R^{cs}$ is optionally substituted with one, two, or three substituents selected from halogen, OH, OMe, oxo, $NMe_2$, CN or $N_3$;

$R^{a5a}$, $R^{a5b}$, $R^{b5a}$ and $R^{b5b}$ are each independently H, F, $R^{cs}$, wherein the $R^{cs}$ is optionally substituted with one, two, or three substituents selected from halogen, OH, OMe, $NMe_2$, CN or $N_3$;

$R''$ is independently hydrogen, $R^{cl}$, $R^{cl}$—C(=O)—, $R^{cl}$—S(=O)$_2$—, $R^{cl}R^{cl}$N—C(=O)—, $R^{cl}$O—C(=O)—, $R^{cl}R^{cl}$N—S(=O)$_2$—, or $R^{cl}$OC(=O)$NR^{cl}$—S(=O)$_2$—, wherein, two $R^{cl}$ attached to the same N atom can together with the N atom form a 4-7 membered heterocyclic ring, containing up to one other heteroatom selected from O, S, or $NR^{cs}$, wherein the 4-7 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo; or alternatively, two $R''$ attached to the same N atom can together with the N atom form a 4-7 membered heterocyclic ring, containing up to one other heteroatom chosen from O, S, or $NR^{ns}$, wherein the 4-7 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

$X^1$ and $Y^1$ are each independently O or S;

$X^2$ and $Y^2$ are each independently $SR^4$, $OR^4$, $NR^4R^4$, $BH(OR^7)_2^-$, or $BH(R^b)_2^-$;

$R^b$ is each independently H, CN, carboxyl, carboxyl salts, $C_{1-6}$ alkyl, alkylaryl, aryl, alkoxycarbonyl, or alkylaminocarbonyl, wherein the $C_{1-6}$ alkyl, alkylaryl, aryl, alkoxycarbonyl and alkylaminocarbonyl is each optionally substituted with up to 3 substituents selected from OH, —P(O)(OH)$_2$, —OP(O)(OH)$_2$, $CO_2H$, or F; or alternatively, two $R^b$ taken together with the B atom to which they are both attached, form a 4-7 membered heterocyclic ring, containing up to one other heteroatom selected from O, S, or $NR^{ns}$, wherein the 4-7 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano, $CO_2H$, —P(O)(OH)$_2$, —OP(O)(OH)$_2$, or halo;

$R^4$ is each independently H, $R^{cl}$, $C_{1-20}$ alkyl, $CH_2COOR^5$, $CH_2OC(O)R^5$, $CH_2OCO_2R^5$, $CH_2CH_2SC(O)R^5$,

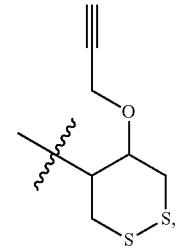 [SMILES: *C1CSSCC1OCC#C]

or $CH_2CH_2SSCH_2R^5$;

$R^5$ is each independently $R^{cl}$, $C_{1-20}$ alkyl, $C_{1-20}$ alkenyl, or $C_{1-20}$ alkynyl, wherein the $R^{cl}$, $C_{1-20}$ alkyl, $C_{1-20}$ alkenyl and $C_{1-20}$ alkynyl is each optionally substituted with 1 to 5 substituents independently selected from OH, —P(O)(OH)$_2$, —OP(O)(OH)$_2$, $CO_2H$, aryl, cycloalkyl, hydroxy or fluorine;

$R^6$ is selected from the group consisting of H, $R''$, and $R^4$;

$R^7$ is H, $R^{cl}$, or $R^4$; or alternatively, two $R^7$ taken together with the —O—B(H)—O— group to which they are both attached, form a 5-7 membered heterocyclic ring, containing up to one other heteroatom selected from O, S, or $NR^{ns}$, wherein the 5-7 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano, $CO_2H$, $-P(O)(OH)_2$, $-OP(O)(OH)_2$, $CO_2H$, or halo;

$X^3$, $X^4$, $Y^3$ and $Y^4$ are each independently selected from the group consisting of O, S and $NR^6$; and $Z^1$ and $Z^2$ are independently selected from O, S, S(O), $SO_2$, $NR^{ns}$, $CH_2$, CHF, $CF_2$, $CH_2O$, $OCH_2$, $CH_2CH_2$, CHFCHF, or CH=CH.

In one embodiment, the compounds of formulae (I), (II), (III), (A), or (B), excludes compounds exemplified in WO2014/179335, US2014/341976A1, WO2014/093936A1, WO2014/189805A1, WO2015/185565A1, WO2016/120305A1, WO2016/145102A1, WO2017/027645, WO2017/027646, WO2017/075477A1, WO2017/093933, WO2016/096174A1, WO2017/106740, WO2017/123657, WO2017/123669, WO2009/133560, WO2005/030186, WO2015/074145, WO2016/096577, WO2005/005450, and US2005/0203051. In one embodiment, the compounds of formulae (I), (II), (III), (A), or (B), excludes compounds exemplified in WO2018/138685, WO2018/138684, WO2018/118665, WO2018/100558, WO2018/098203, WO2018/065360, WO2018/060323, WO2018/045204, WO2018/009466, and WO2017/161349.

In one embodiment, the present disclosure relates to the compound of formula (I) or formula (II):

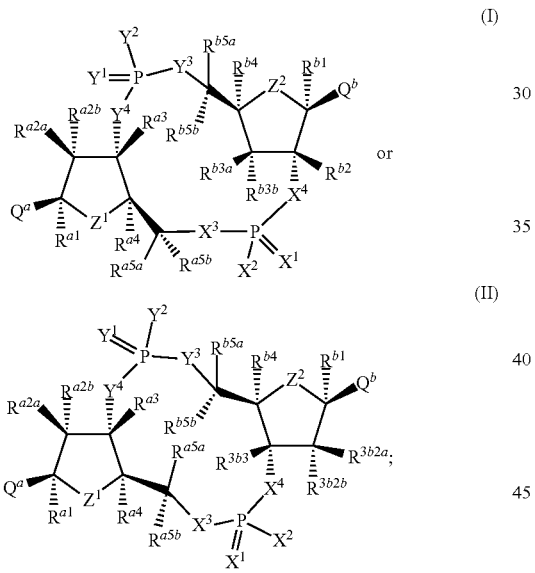

or a pharmaceutically acceptable salt, stereoisomer, solvate or hydrate thereof, wherein:

$Q^a$ and $Q^b$ are each independently cycloalkyl, heterocyclyl, aryl, or heteroaryl, wherein the cycloalkyl, heterocyclyl, aryl, and heteroaryl can be optionally substituted with one, two, three, four, or five $R^1$;

$R^1$ is each independently hydrogen, halogen, $-NO_2$, $-CN$, $-OR^{cl}$, $-SR^{cl}$, $-N(R^{cl})_2$, $-C(O)R^{cl}$, $-CO_2R^{cl}$, $-C(O)C(O)R^{cl}$, $-C(O)CH_2C(O)R^{cl}$, $-C(O)N(R^{cl})_2$, $-C(=NR^{cl})N(R^{cl})_2$, $-C(=NOR^{cl})R^{cl}$, $-S(O)R^{cl}$, $-S(O)_2R^{cl}$, $-SO_2N(R^{cl})_2$, $-OC(O)R^{cl}$, $-N(R^{cl})C(O)R^{cl}$, $-NR^{cl}N(R^{cl})_2$, $-N(R^{cl})C(=NR^{cl})N(R^{cl})_2$, $-N(R^{cl})C(O)N(R^{cl})_2$, $-N(R^{cl})SO_2N(R^{cl})_2$, $-N(R^{cl})SO_2R^{cl}$, $-N(R^{cl})SO_2NR^{cl}C(=O)OR^{cl}$, $-OC(O)N(R^{cl})_2$, or $R^{cl}$;

$R^{cl}$ is each independently H, $C_{1-12}$ alkyl, $C_{2-12}$ alkenyl, $C_{2-12}$ alkynyl, $C_{3-12}$ cycloalkyl, $C_{3-12}$ cycloalkyl-$C_{1-6}$ alkyl-, heterocyclyl, heterocyclyl-$C_{1-6}$ alkyl-, aryl, aryl-$C_{1-6}$ alkyl-, $C_{1-6}$ alkyl-, heteroaryl, or heteroaryl-$C_{1-6}$ alkyl-, wherein $C_{1-12}$ alkyl, $C_{2-12}$ alkenyl, $C_{2-12}$ alkynyl, $C_{3-12}$ cycloalkyl, $C_{3-12}$ cycloalkyl-$C_{1-6}$ alkyl-, heterocyclyl, heterocyclyl-$C_{1-6}$ alkyl-, aryl, aryl-$C_{1-6}$ alkyl-, heteroaryl, and heteroaryl-$C_{1-6}$ alkyl- can be substituted one or more substituents selected from $C_{1-6}$ alkyl, halogen, $C_{1-6}$ alkoxy, $-NO_2$, $-NR^{ns}R^{ns}$, $-OH$, =O, or $COOR^{cs}$; or alternatively, two $R^{cl}$ attached to the same N atom can together with the N atom form a 4-7 membered heterocyclic ring, containing up to one other heteroatom selected from O, S, or $NR^{ns}$, and wherein the 4-7 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

$R^{cs}$ is each independently H, $R^{cs}$, $R^{cs}$—C(O)—, $R^{cs}$—S(O)_2—, $R^{cs}R^{cs}N$—C(O)—, or $R^{cs}R^{cs}NS(O)_2$—;

$R^{cs}$ is each independently H, $C_1-C_6$ alkyl, $C_2-C_6$ alkenyl, $C_2-C_6$ alkynyl, $C_1-C_6$ haloalkyl, $C_2-C_6$ haloalkenyl, or $C_2-C_6$ haloalkynyl; or alternatively, two $R^{cs}$ attached to the same N atom can together with the N atom form a 4-7 membered heterocyclic ring, containing up to one other heteroatom chosen from O, S, or $NR^{ns}$, wherein the 4-7 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

$R^{a1}$ and $R^{b1}$ are each independently H, CN, $C_{3-6}$ cycloalkyl, $R^{cs}$, $-OR^{cs}$, $-SR^{cs}$, $-CH_2N_3$, $-CH_2NR^{cs}R^{cs}$ or $-CH_2OR^{cs}$, wherein $C_{3-6}$ cycloalkyl and $R^{cs}$ is optionally substituted with one, two or three substituents selected from halogen, OH, OMe, $NMe_2$, CN or $N_3$;

$R^{a4}$ and $R^{b4}$ are each independently selected from the group consisting of H, halogen, OH, CN, $N_3$, $R^{cs}$, $-CH_2OR^{cs}$, $-CH_2SR^{cs}$, $-CH_2N_3$, $-CH_2NR^{cs}R^{cs}$, $-CO_2R^{cs}$, $-SR^{cs}$, and $-OR^{cs}$, where said $R^{cs}$ is substituted by 0-3 substituents selected from the group consisting of halogen, OH, OMe, $NMe_2$, CN and $N_3$;

$R^{a2a}$, $R^{a2b}$, $R^{b3a}$, $R^{b3b}$, $R^{3b2a}$, $R^{3b2b}$, $R^{2a3a}$ and $R^{2a3b}$ are each independently H, halogen, CN, $N_3$, $-CH_2N_3$, $-CH_2NR^{cs}R^{cs}$, $-CO_2R^{cs}$, $-CH_2OR^{cs}$, $-CH_2SR^{cs}$, $-C_{3-6}$ cycloalkyl, $-R^{cs}$, $-NR''R''$, $-OCH_2CO_2R^{cs}$, or $-OR^O$, wherein the $-R^{cs}$ and the $R^{cs}$ in $-CH_2NR^{cs}R^{cs}$, $-CO_2R^{cs}$, $-CH_2OR^{cs}$, $-CH_2SR^{cs}$, and $-OCH_2CO_2R^{cs}$, the $R''$ in $-NR''R''$, and the $R^O$ in $-OR^O$ can be optionally substituted with up to three substituents selected from halogen, CN, $-NMe_2$, $C_{1-6}$ alkoxy, $-NO_2$, $-NR^{ns}R^{ns}$, $-OH$, OMe, =O, or $COOR^{cs}$; or alternatively, $R^{a2a}$ and $R^{a2b}$, $R^{b3a}$ and $R^{b3b}$, $R^{3b2a}$ and $R^{3b2b}$, or $R^{2a3a}$ and $R^{2a3b}$, can be taken together with the carbon atom to which they are attached, form a 4-6 membered heterocyclic ring, containing up to one other heteroatom chosen from O, S, or $NR^{ns}$, and wherein the 4-6 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, $NMe_2$, cyano or halo;

$R^O$ is hydrogen, $R^{cl}$, or $R^{cl}$—C(O)—;

$R^{a3}$, $R^{b2}$, $R^{3b3}$ and $R^{2a2}$ are each independently H, halogen, CN, $N_3$, $-P(=O)(OR^{cs})_2$, $C_{3-6}$ cycloalkyl, $R^{cs}$, $-C\equiv C$—Cl, $-CH_2N_3$, $-CH_2NR^{cs}R^{cs}$, $-CO_2R^{cs}$, —CH$_2$OR$^{cs}$ or —CH$_2$SR$^{cs}$; wherein the C$_{3-6}$ cycloakyl and R$^{cs}$ is optionally substituted with one, two, or three substituents selected from halogen, OH, OMe, oxo, NMe$_2$, CN or N$_3$;

R$^{a5a}$, R$^{a5b}$, R$^{b5a}$ and R$^{b5b}$ are each independently H, F, R$^{cs}$, wherein the R$^{cs}$ is optionally substituted with one, two, or three substituents selected from halogen, OH, OMe, NMe$_2$, CN or N$_3$;

R$^n$ is independently hydrogen, R$^{cl}$, R$^{cl}$—C(=O)—, R$^{cl}$—S(=O)$_2$—, R$^{cl}$R$^{cl}$N—C(=O)—, R$^{cl}$O—C(=O)—, R$^{cl}$R$^{cl}$N—S(=O)$_2$—, or R$^{cl}$OC(=O)NR$^{cl}$—S(=O)$_2$—, wherein, two R$^{cl}$ attached to the same N atom can together with the N atom form a 4-7 membered heterocyclic ring, containing up to one other heteroatom selected from O, S, or NR$^{ns}$, wherein the 4-7 membered heterocyclic ring is optionally substituted with up to three substituents selected from hydroxyl, C$_{1-6}$ alkoxy, C$_{1-6}$ hydroxyalkyl, C$_{1-6}$ alkoxy-C$_{1-6}$ alkyl, C$_{1-6}$ alkoxy-C$_{1-6}$ alkoxy, C$_{2-6}$ hydroxyalkoxy, oxo, thiono, cyano or halo; or alternatively, two R$^n$ attached to the same N atom can together with the N atom form a 4-7 membered heterocyclic ring, containing up to one other heteroatom chosen from O, S, or NR$^{ns}$, wherein the 4-7 membered heterocyclic ring is optionally substituted with up to three substituents selected from hydroxyl, C$_{1-6}$ alkoxy, C$_{1-6}$ hydroxyalkyl, C$_{1-6}$ alkoxy-C$_{1-6}$ alkyl, C$_{1-6}$ alkoxy-C$_{1-6}$ alkoxy, C$_{2-6}$ hydroxyalkoxy, oxo, thiono, cyano or halo;

X$^1$ and Y$^1$ are each independently O or S;

X$^2$ and Y$^2$ are each independently SR$^4$, OR$^4$, NR$^4$R$^4$, BH(OR$^7$)$_2^-$, or BH(R$^b$)$_2^-$; wherein, at least one of X$^2$ and Y$^2$ is BH(R$^b$)$_2^-$;

R$^b$ is each independently H, CN, carboxyl, carboxyl salts, C$_{1-6}$ alkyl, alkylaryl, aryl, alkoxycarbonyl, or alkylaminocarbonyl, wherein the C$_{1-6}$ alkyl, alkylaryl, aryl, alkoxycarbonyl and alkylaminocarbonyl is each optionally substituted with up to 3 substituents selected from OH, —P(O)(OH)$_2$, —OP(O)(OH)$_2$, CO$_2$H, or F; or alternatively, two R$^b$ taken together with the B atom to which they are both attached, form a 4-7 membered heterocyclic ring, containing up to one other heteroatom selected from O, S, or NR$^{ns}$, wherein the 4-7 membered heterocyclic ring is optionally substituted with up to three substituents selected from hydroxyl, C$_{1-6}$ alkoxy, C$_{1-6}$ hydroxyalkyl, C$_{1-6}$ alkoxy-C$_{1-6}$ alkyl, C$_{1-6}$ alkoxy-C$_{1-6}$ alkoxy, C$_{2-6}$ hydroxyalkoxy, oxo, thiono, cyano, CO$_2$H, —P(O)(OH)$_2$, —OP(O)(OH)$_2$, or halo;

R$^4$ is each independently H, R$^{cl}$, C$_{1-20}$ alkyl, CH$_2$COOR$^5$, CH$_2$OC(O)R$^5$, CH$_2$OCO$_2$R$^5$, CH$_2$CH$_2$SC(O)R$^5$,

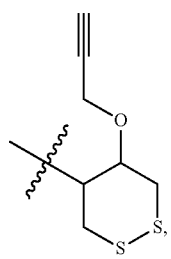 [SMILES: *C1CSSCC1OCC#C]

or CH$_2$CH$_2$SSCH$_2$R$^5$;

R$^5$ is each independently R$^{cl}$, C$_{1-20}$ alkyl, C$_{1-20}$ alkenyl, or C$_{1-20}$ alkynyl, wherein the R$^{cl}$, C$_{1-20}$alkyl, C$_{1-20}$ alkenyl and C$_{1-20}$ alkynyl is each optionally substituted with 1 to 5 substituents independently selected from OH, —P(O)(OH)$_2$, —OP(O)(OH)$_2$, CO$_2$H, aryl, cycloalkyl, hydroxy or fluorine;

R$^6$ is selected from the group consisting of H, R$^n$, and R$^4$;

R$^7$ is H, R$^{cl}$, or R$^4$; or alternatively, two R$^7$ taken together with the —O—B(H)—O— group to which they are both attached, form a 5-7 membered heterocyclic ring, containing up to one other heteroatom selected from O, S, or NR$^{ns}$, wherein the 5-7 membered heterocyclic ring is optionally substituted with up to three substituents selected from hydroxyl, C$_{1-6}$ alkoxy, C$_{1-6}$ hydroxyalkyl, C$_{1-6}$ alkoxy-C$_{1-6}$ alkyl, C$_{1-6}$ alkoxy-C$_{1-6}$ alkoxy, C$_{2-6}$ hydroxyalkoxy, oxo, thiono, cyano, CO$_2$H, —P(O)(OH)$_2$, —OP(O)(OH)$_2$, CO$_2$H, or halo;

X$^3$, X$^4$, Y$^3$ and Y$^4$ are each independently selected from the group consisting of O, S and NR$^6$; and Z$^1$ and Z$^2$ are independently selected from O, S, S(O), SO$_2$, NR$^{ns}$, CH$_2$, CHF, CF$_2$, CH$_2$O, OCH$_2$, CH$_2$CH$_2$, CHFCHF, or CH=CH;

provided that, in Formula (I), if Q$^b$ is

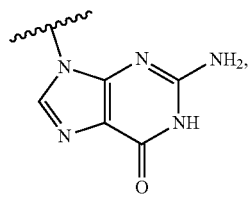 [SMILES: *n1cnc2c(=O)[nH]c(N)nc21]

then Q$^a$ is not

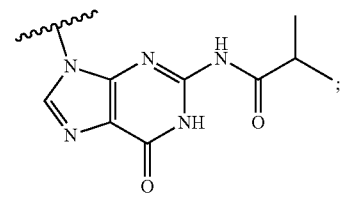 [SMILES: *n1cnc2c(=O)[nH]c(NC(=O)C(C)C)nc21]

provided that, in Formula (I), if Q$^b$ is

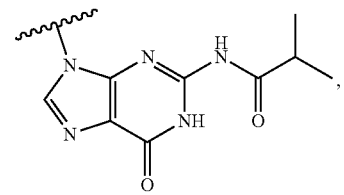 [SMILES: *n1cnc2c(=O)[nH]c(NC(=O)C(C)C)nc21]

then Q$^a$ is not

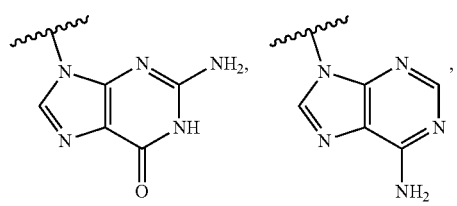

-continued
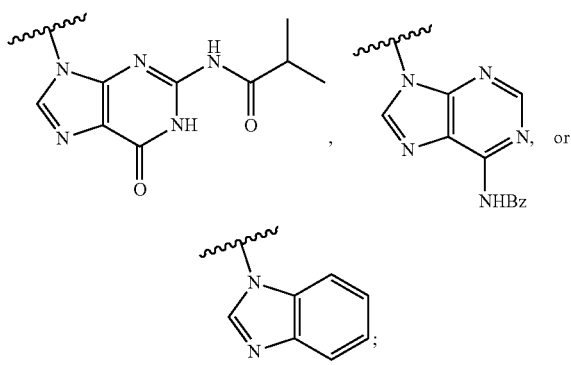
provided that, in Formula (I), if $Q^b$ is
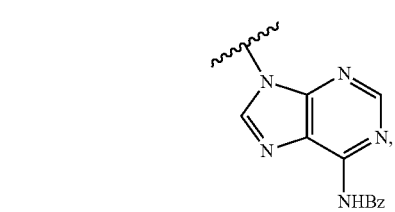
then $Q^a$ is not
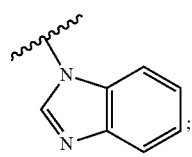 [SMILES: *n1cnc2ccccc21]
and
provided that the compound is not a compound listed in Table A or Table B.
Table A
TABLE A
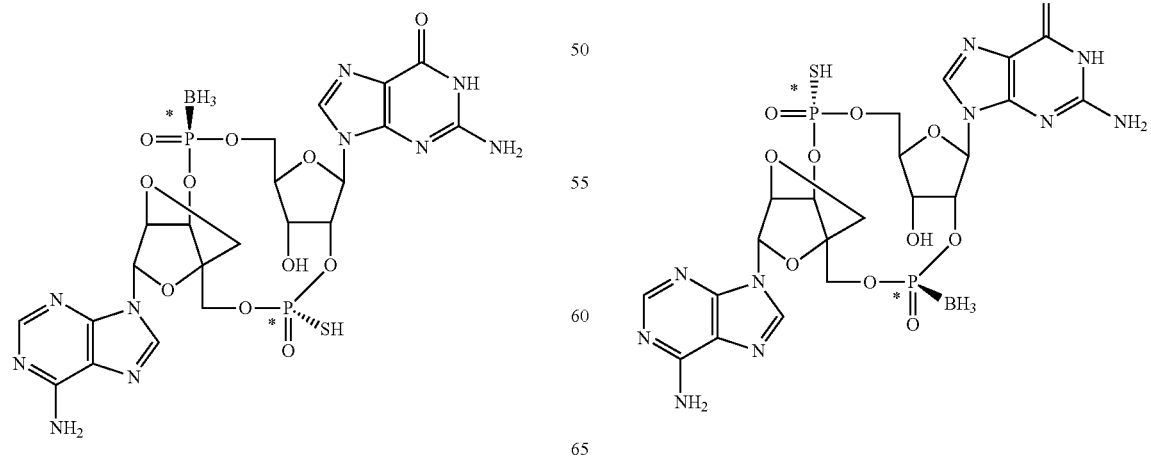
TABLE A-continued
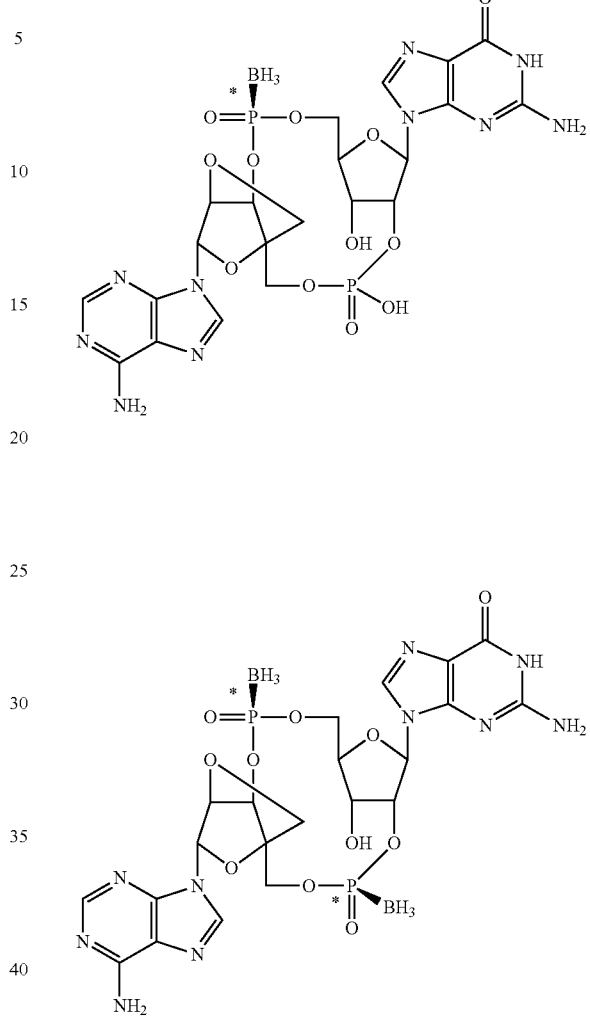

TABLE A-continued
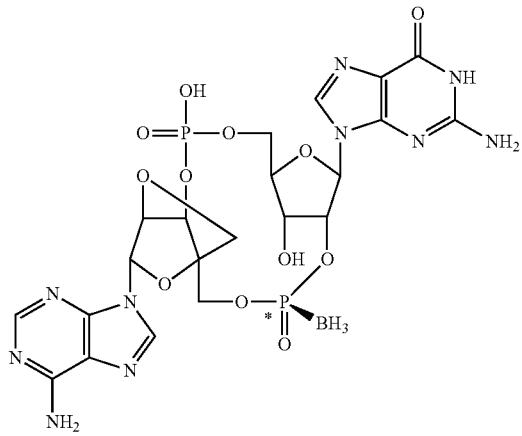
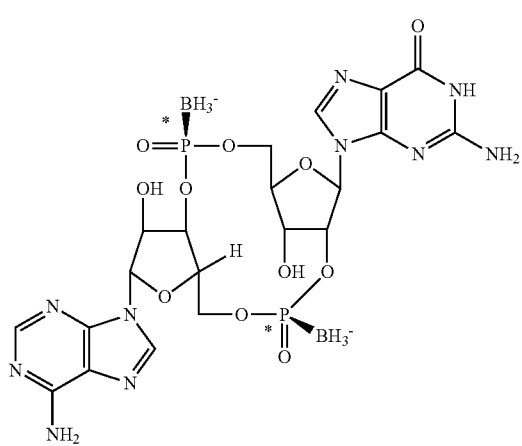
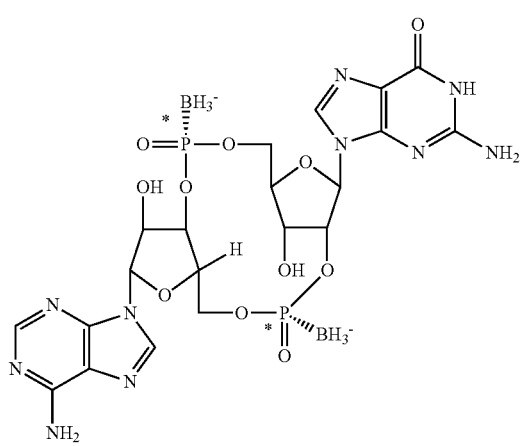
TABLE A-continued
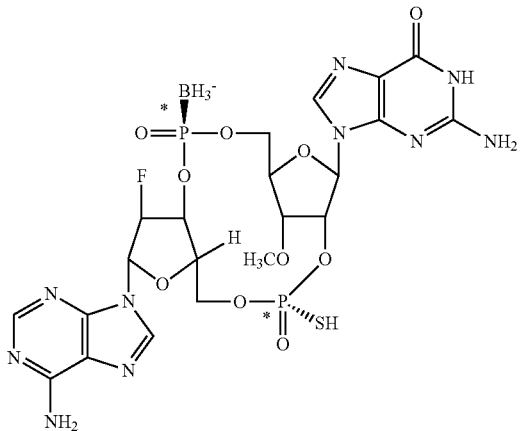
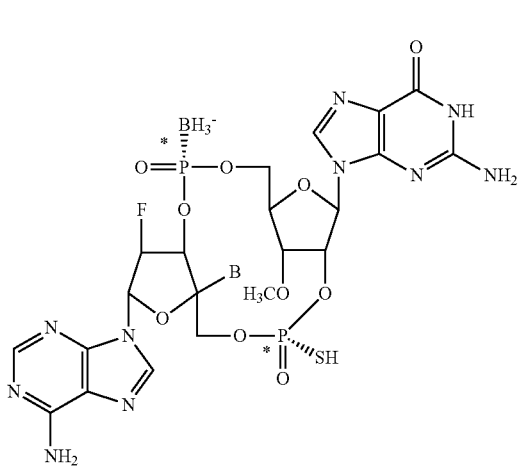
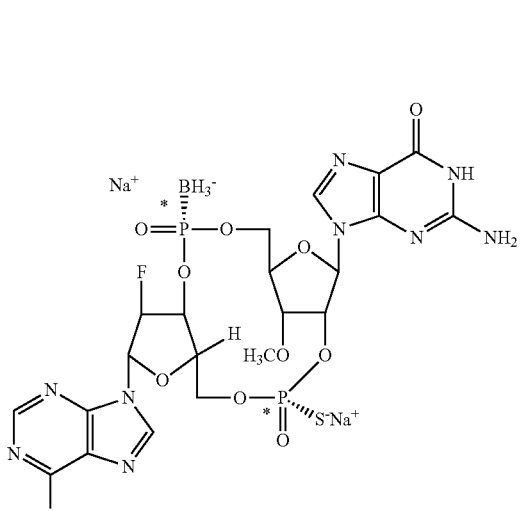

TABLE A-continued
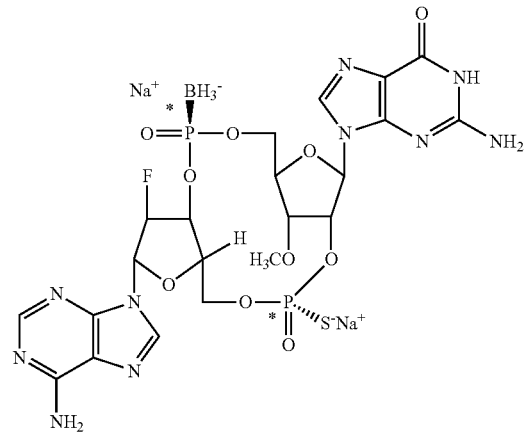
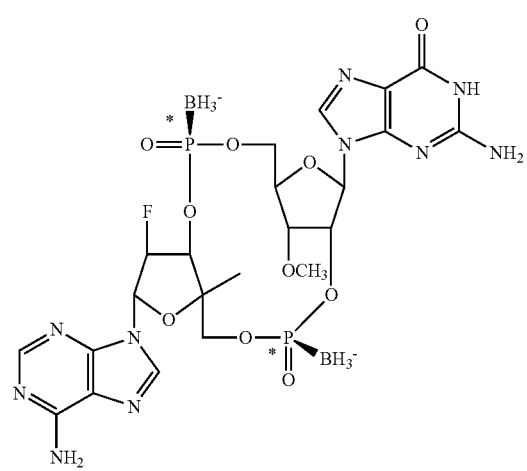
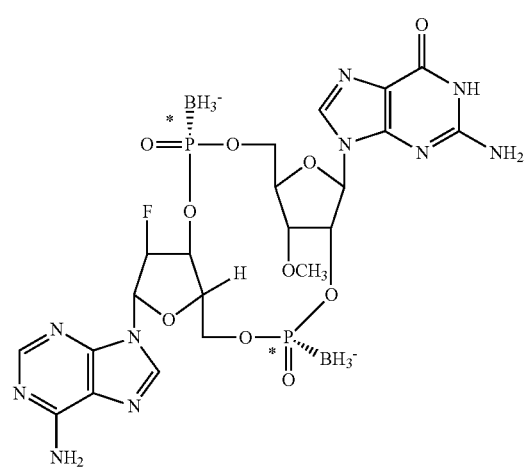
TABLE A-continued
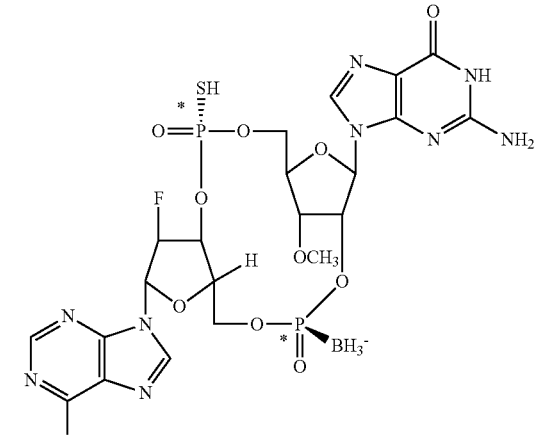
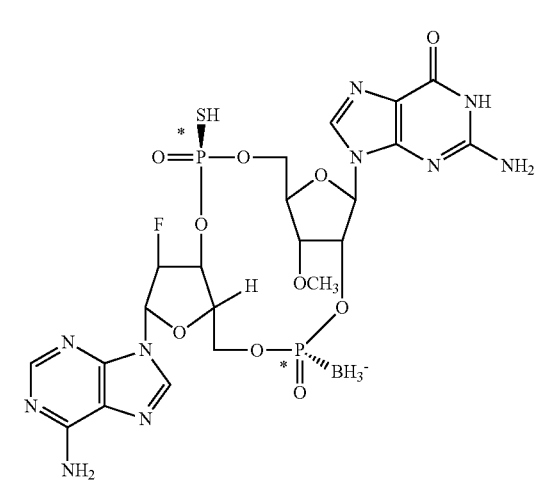
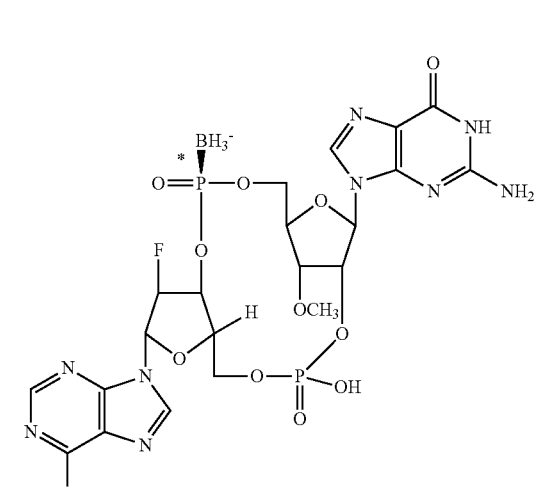

TABLE A-continued
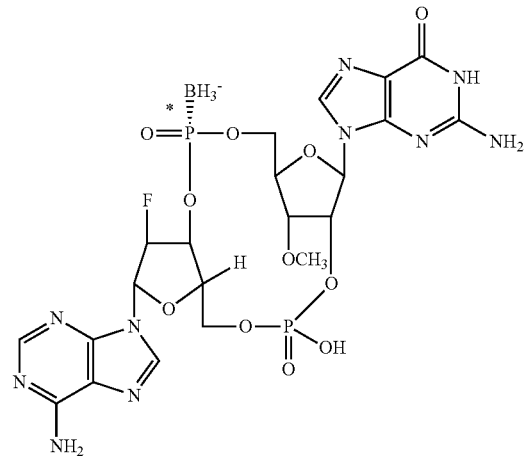
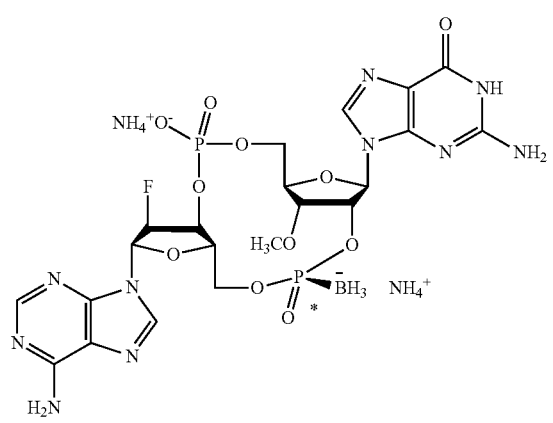
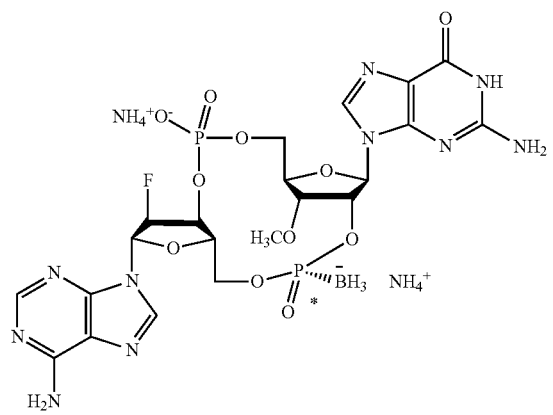
TABLE A-continued
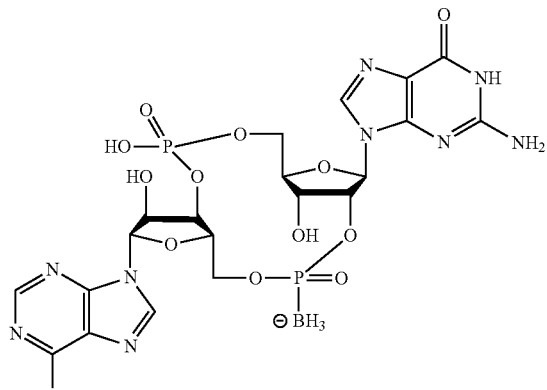
isomer 1
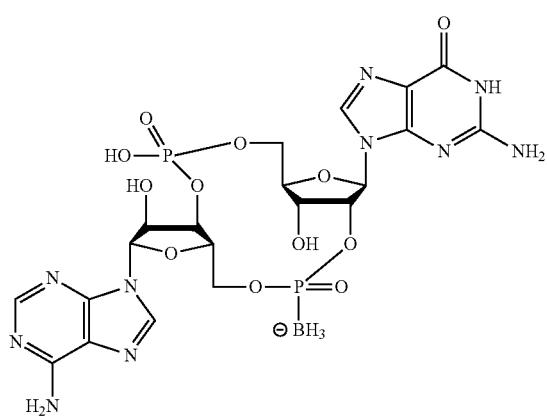
isomer 2
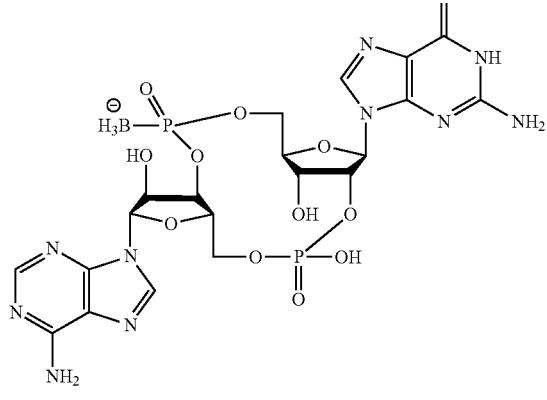

| 61 | 62 |
|---|---|
| TABLE A-continued | TABLE A-continued |
| 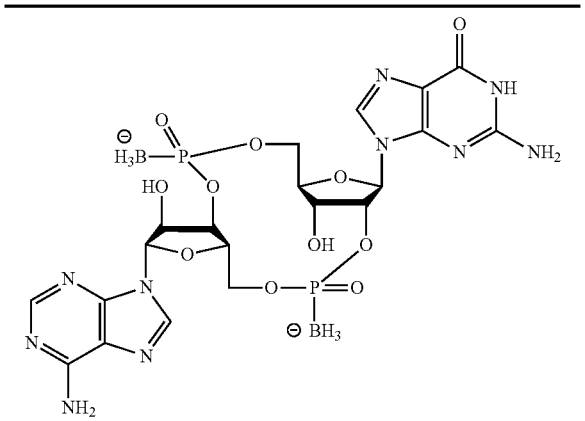 | 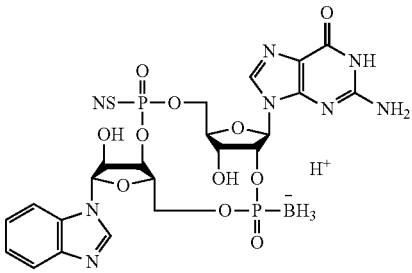 |
| 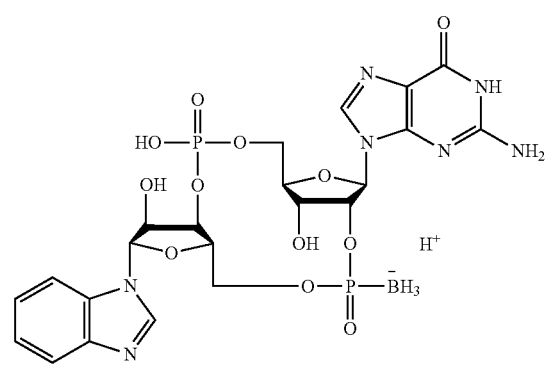 | 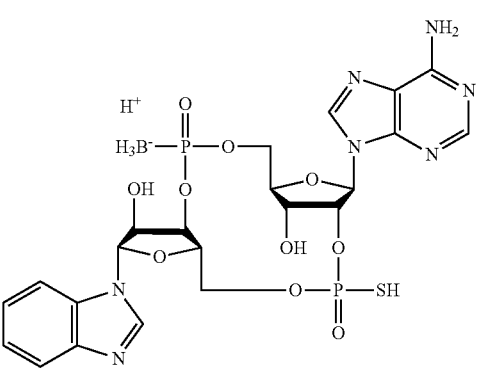 |
TABLE B
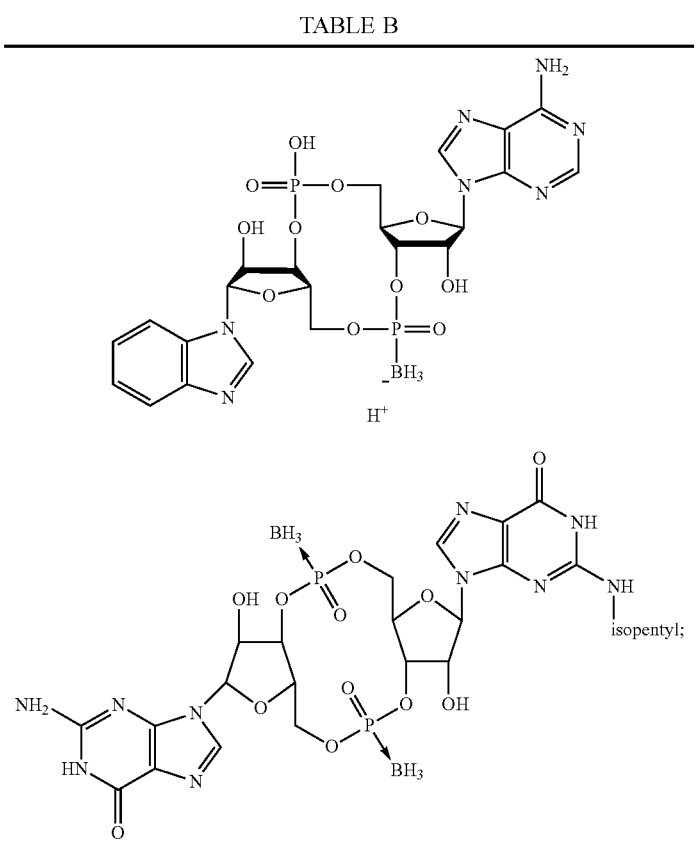

TABLE B-continued
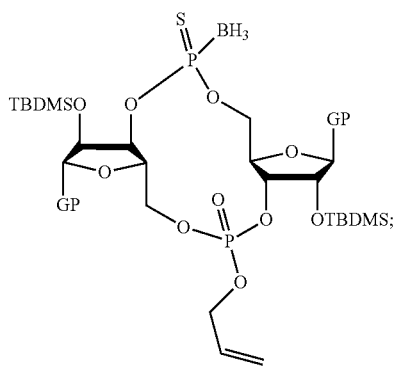
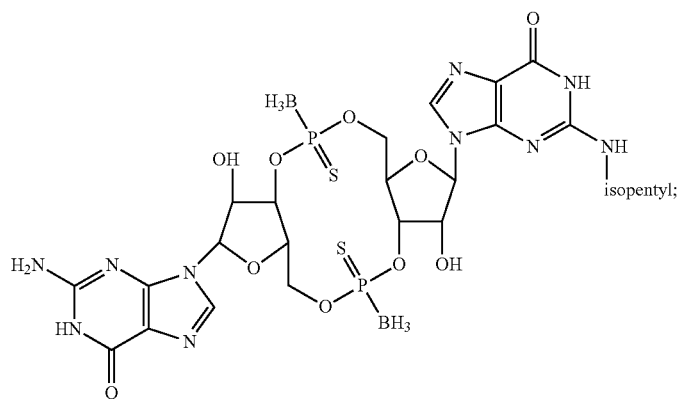
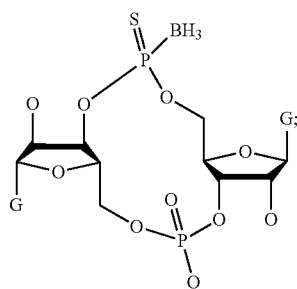
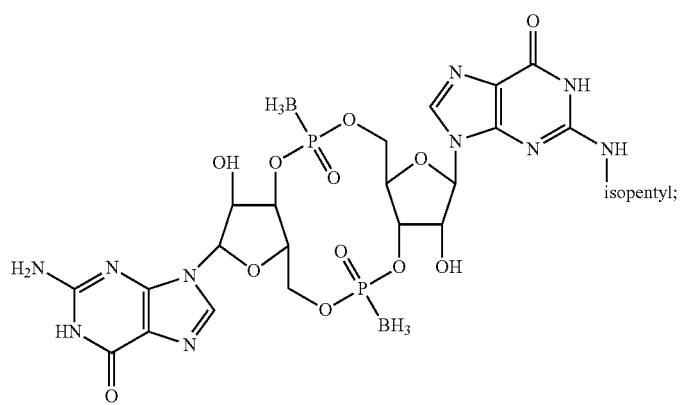

TABLE B-continued
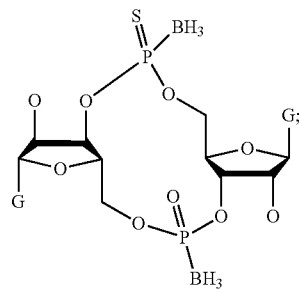
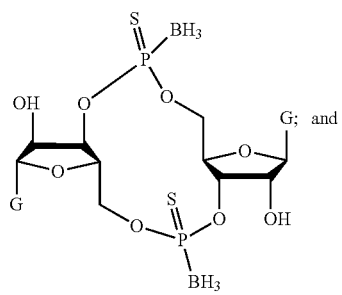
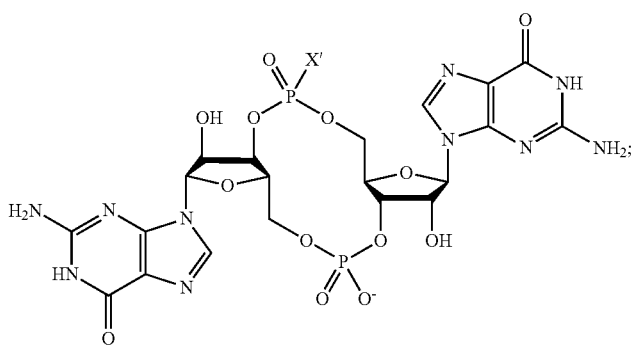
wherein GP is
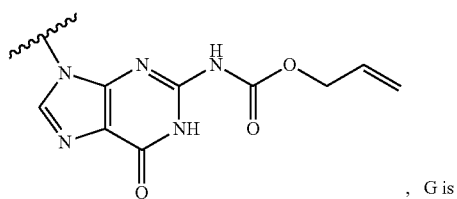 [SMILES: *n1cnc2c(=O)[nH]c(NC(=O)OCC=C)nc21]
, G is
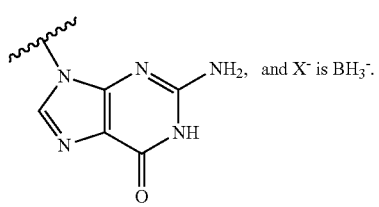
NH$_2$, and X$^-$ is BH$_3^-$.

In one embodiment of the compounds of Formula (I), if $Q^b$ is

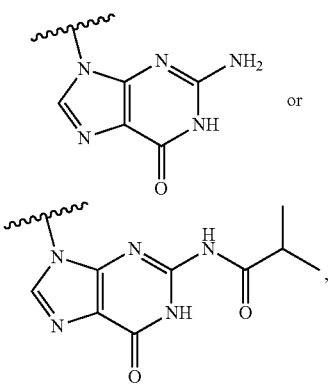

then $Q^a$ is not

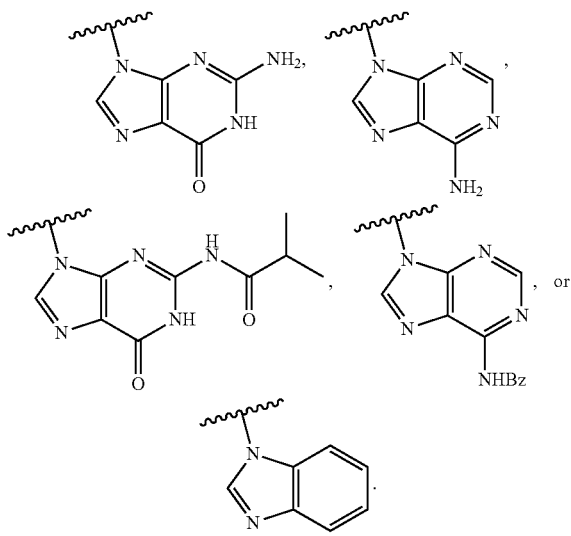

In one embodiment of the compounds of Formula (I), if $Q^b$ is

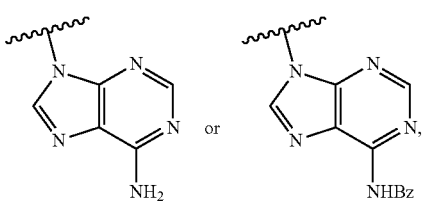

then $Q^a$ is not

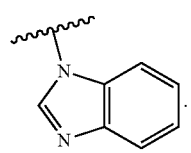 [SMILES: *n1cnc2ccccc21]

In one embodiment, the compounds of formulae (I), (II), or (III), or a pharmaceutically acceptable salt, stereoisomer, solvate or hydrate thereof comprise:

$Q^a$ and $Q^b$ are each independently selected from:

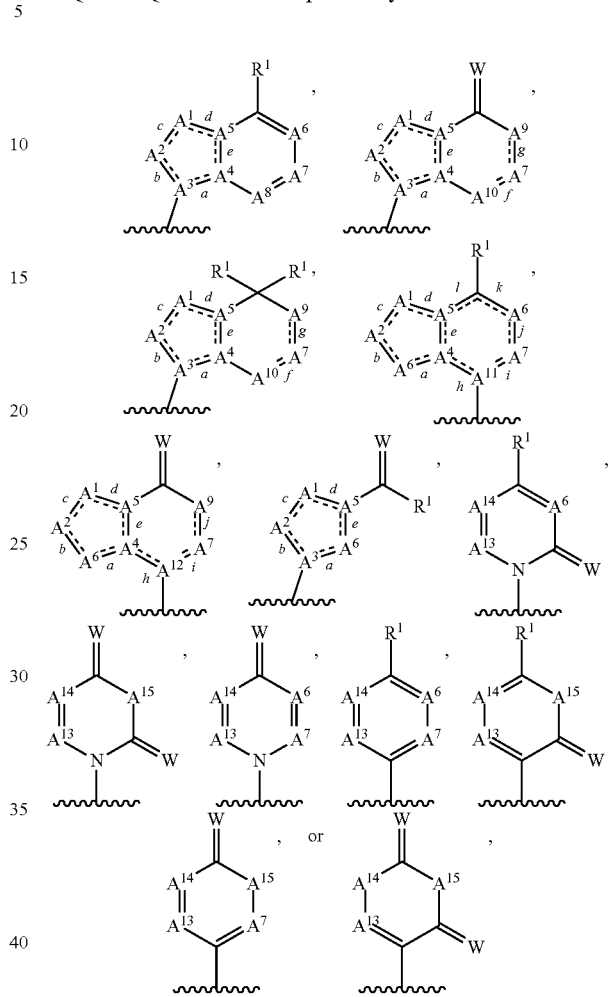

$A^1, A^2, A^6, A^7, A^8, A^{13}$, and $A^{14}$ are each independently $CR^1$ or N;

$A^3, A^4$ and $A^5$ are each independently C or N;

$A^9$ is $C(R^1)_2$, $CR^1$, N, or $NR^n$;

$A^{10}$ is N, $CR^1$ or $NR^n$;

$A^{11}$ and $A^{12}$ are each independently C or N;

$A^{15}$ is $C(R^1)_2$ or $NR^n$;

W is O or S;

wherein two of bonds a, b, c, d, and e are double bonds and the remaining three bonds are single bonds, provided that none of the $A^1, A^2, A^3, A^4, A^5$ or $A^6$ has two double bonds attached to it;

wherein only one of bonds f and g is a double bond, or both bonds f and g are single bonds; and each of bonds h, i, j, k, and l can be a single bond or a double bond provided that none of the $A^4, A^5, A^6, A^7, A^9, A^{11}$, or $A^{12}$, has two double bonds attached to it.

In one embodiment of the compounds of formulae (I) or (II), or a pharmaceutically acceptable salt, stereoisomer, solvate or hydrate thereof, $Q^a$ and $Q^b$ are each independently selected from:

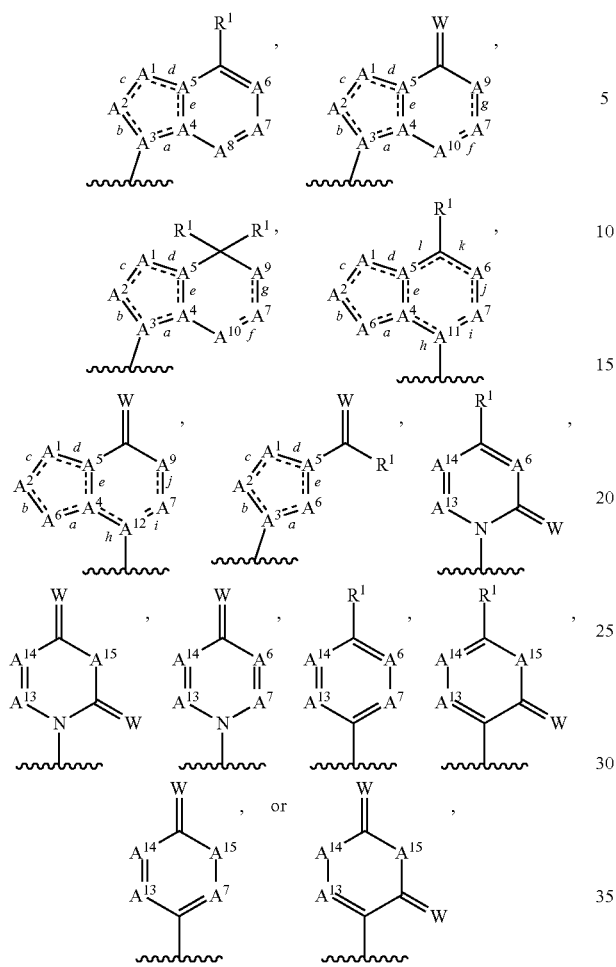

$A^1$, $A^2$, $A^6$, $A^7$, $A^8$, $A^{13}$, and $A^{14}$ are each independently $CR^1$ or N;

$A^3$, $A^4$ and $A^5$ are each independently C or N;

$A^9$ is $C(R^1)_2$, $CR^1$, N, or $NR''$;

$A^{10}$ is N, $CR^1$ or $NR''$;

$A^{10}$ and $A^{12}$ are each independently C or N;

$A^{15}$ is $C(R^1)_2$ or $NR''$;

W is O or S;

wherein two of bonds a, b, c, d, and e are double bonds and the remaining three bonds are single bonds, provided that none of the $A^1$, $A^2$, $A^3$, $A^4$, $A^5$ or $A^6$ has two double bonds attached to it;

wherein only one of bonds f and g is a double bond, or both bonds f and g are single bonds; and each of bonds h, i, j, k, and l can be a single bond or a double bond provided that none of the $A^4$, $A^5$, $A^6$, $A^7$, $A^9$, $A^{11}$, or $A^{12}$, has two double bonds attached to it.

In one embodiment, the compounds of formulae (I), (II), or (III), or a pharmaceutically acceptable salt, stereoisomer, solvate or hydrate thereof comprise:

$Q^a$ and $Q^b$ are each independently selected from:

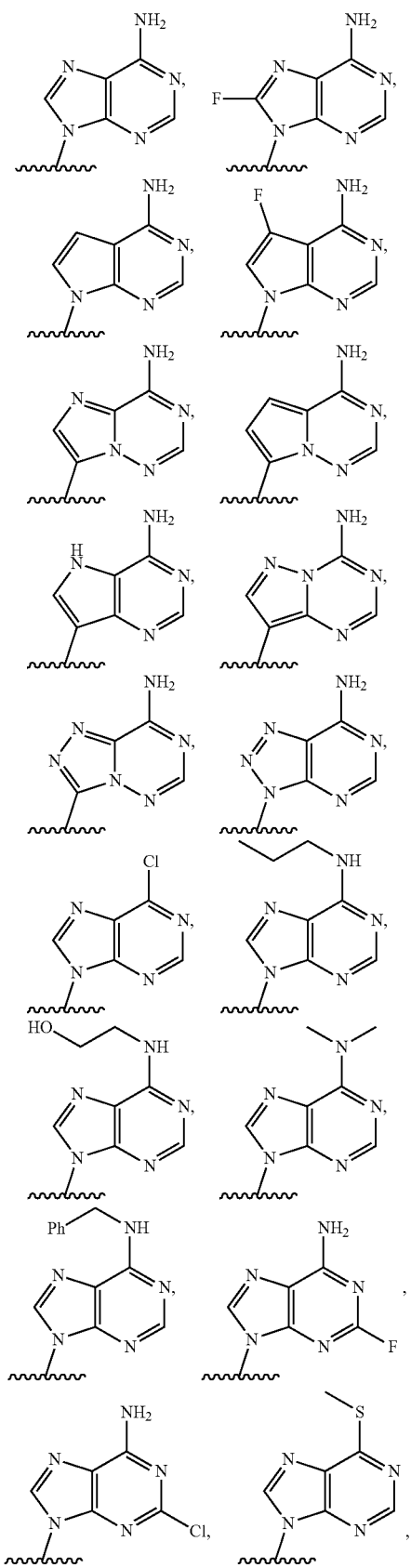

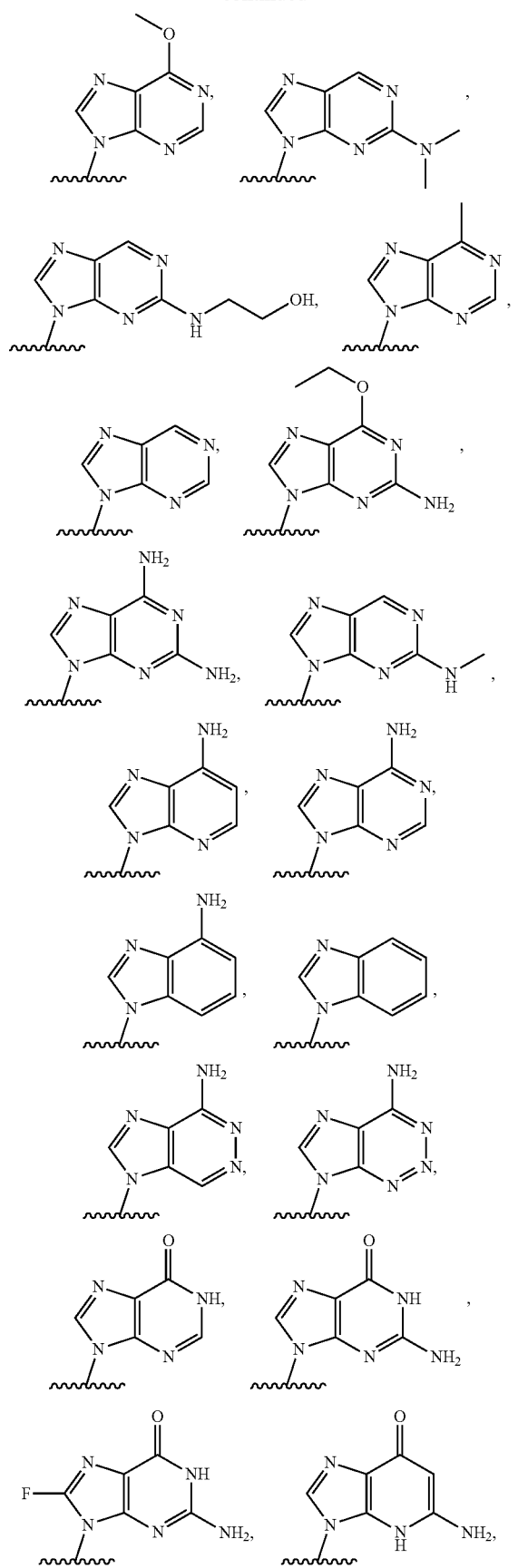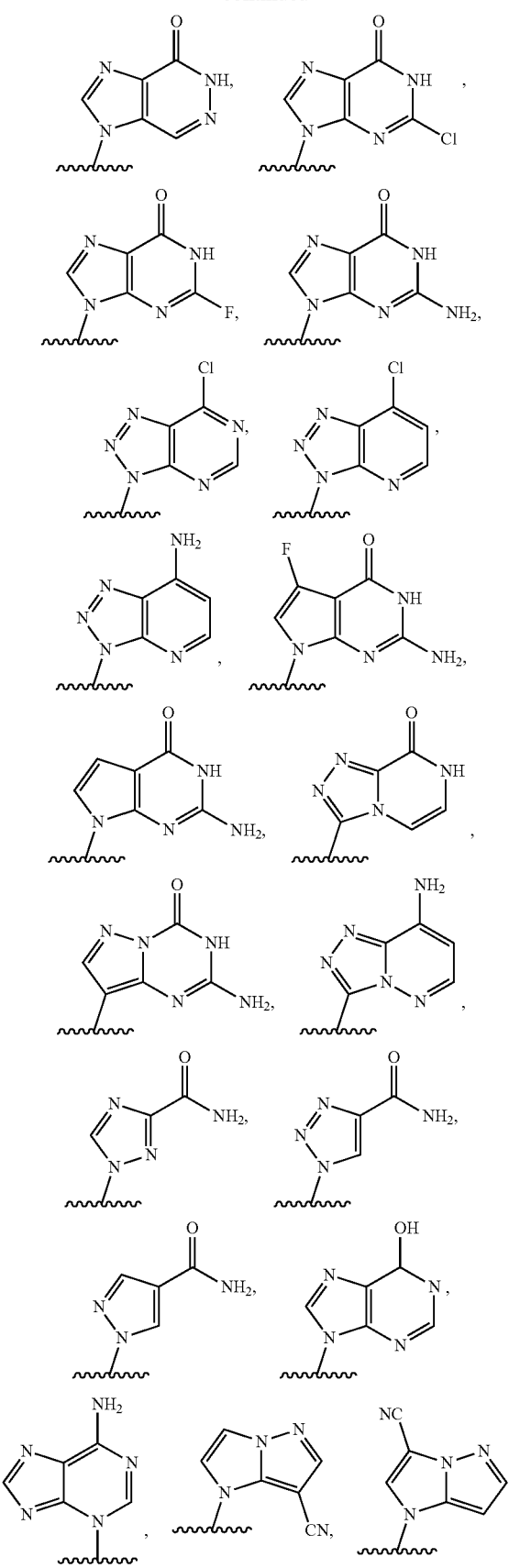

-continued

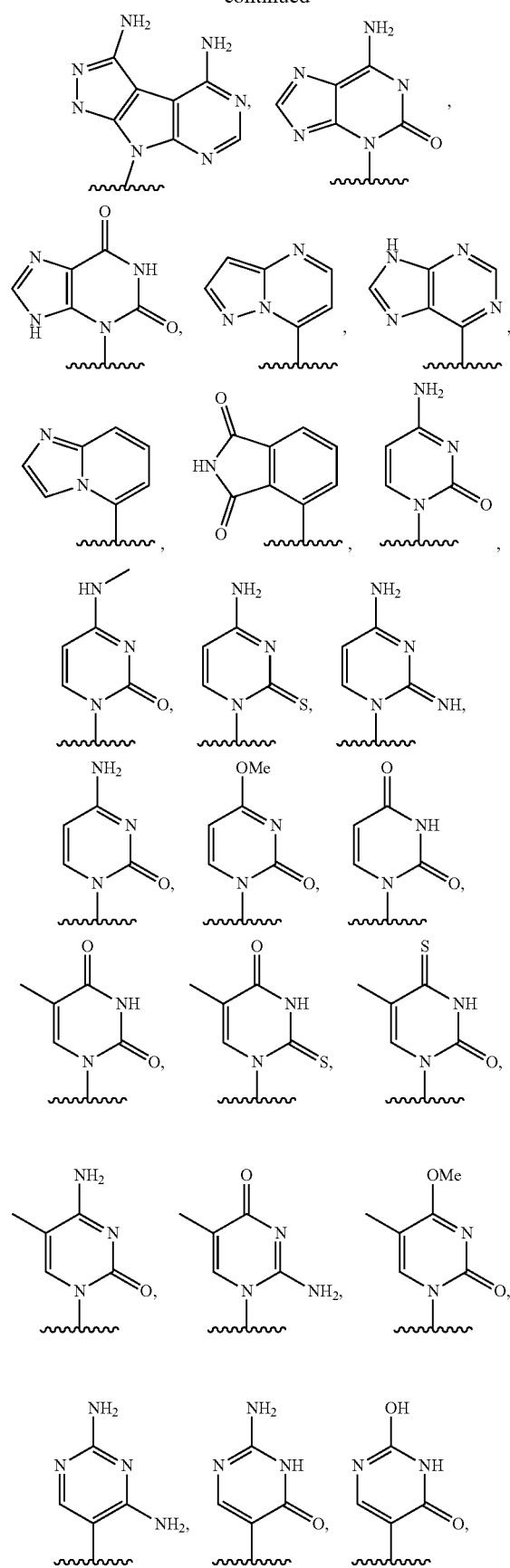

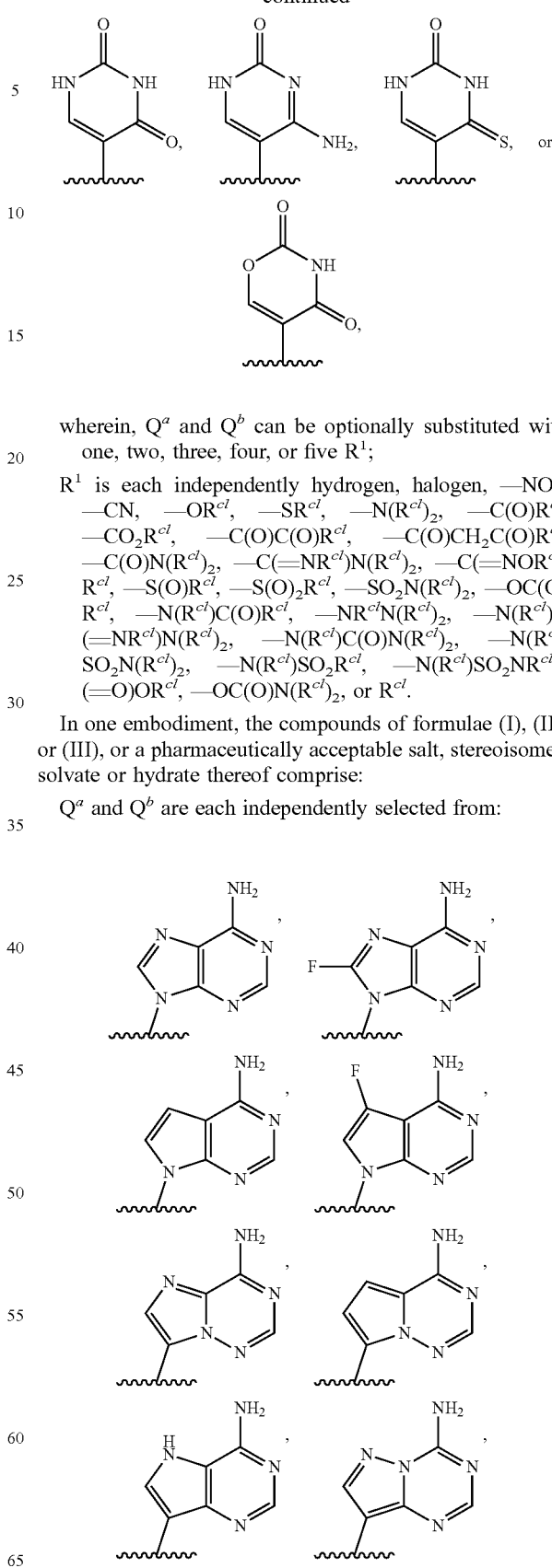

wherein, $Q^a$ and $Q^b$ can be optionally substituted with one, two, three, four, or five $R^1$;

$R^1$ is each independently hydrogen, halogen, —NO$_2$, —CN, —OR$^{c1}$, —SR$^{c1}$, —N(R$^{c1}$)$_2$, —C(O)R$^{c1}$, —CO$_2$R$^{c1}$, —C(O)C(O)R$^{c1}$, —C(O)CH$_2$C(O)R$^{c1}$, —C(O)N(R$^{c1}$)$_2$, —C(=NR$^{c1}$)N(R$^{c1}$)$_2$, —C(=NOR$^{c1}$)R$^{c1}$, —S(O)R$^{c1}$, —S(O)$_2$R$^{c1}$, —SO$_2$N(R$^{c1}$)$_2$, —OC(O)R$^{c1}$, —N(R$^{c1}$)C(O)R$^{c1}$, —NR$^{c1}$N(R$^{c1}$)$_2$, —N(R$^{c1}$)C(=NR$^{c1}$)N(R$^{c1}$)$_2$, —N(R$^{c1}$)C(O)N(R$^{c1}$)$_2$, —N(R$^{c1}$)SO$_2$N(R$^{c1}$)$_2$, —N(R$^{c1}$)SO$_2$R$^{c1}$, —N(R$^{c1}$)SO$_2$NR$^{c1}$C(=O)OR$^{c1}$, —OC(O)N(R$^{c1}$)$_2$, or R$^{c1}$.

In one embodiment, the compounds of formulae (I), (II), or (III), or a pharmaceutically acceptable salt, stereoisomer, solvate or hydrate thereof comprise:

$Q^a$ and $Q^b$ are each independently selected from:

-continued

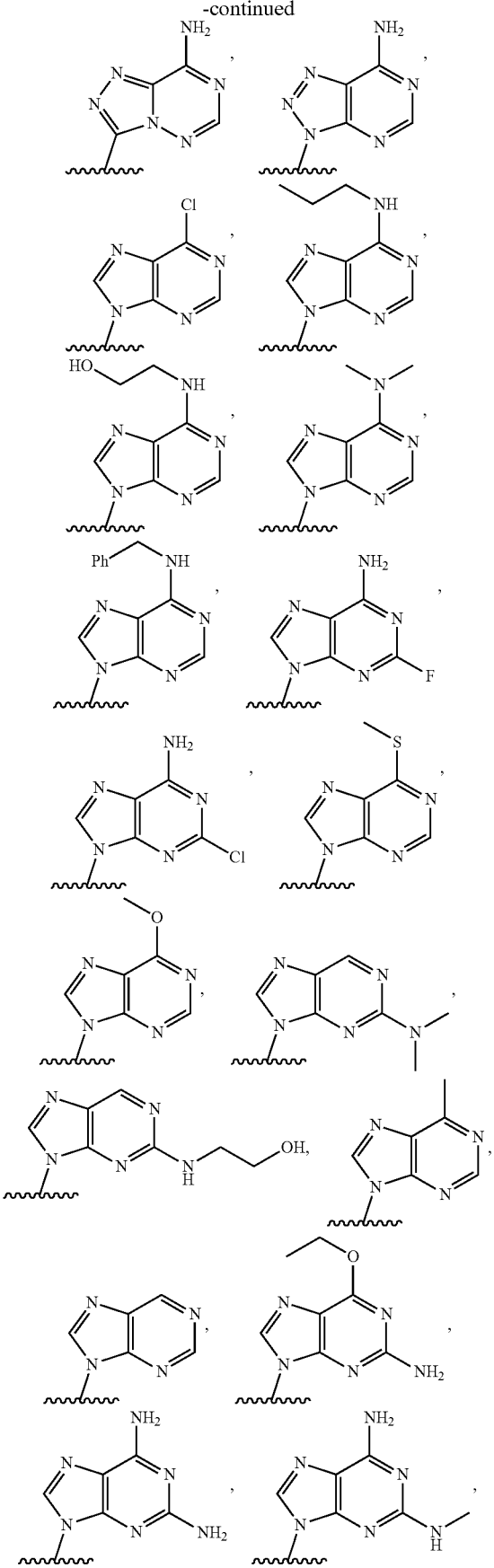

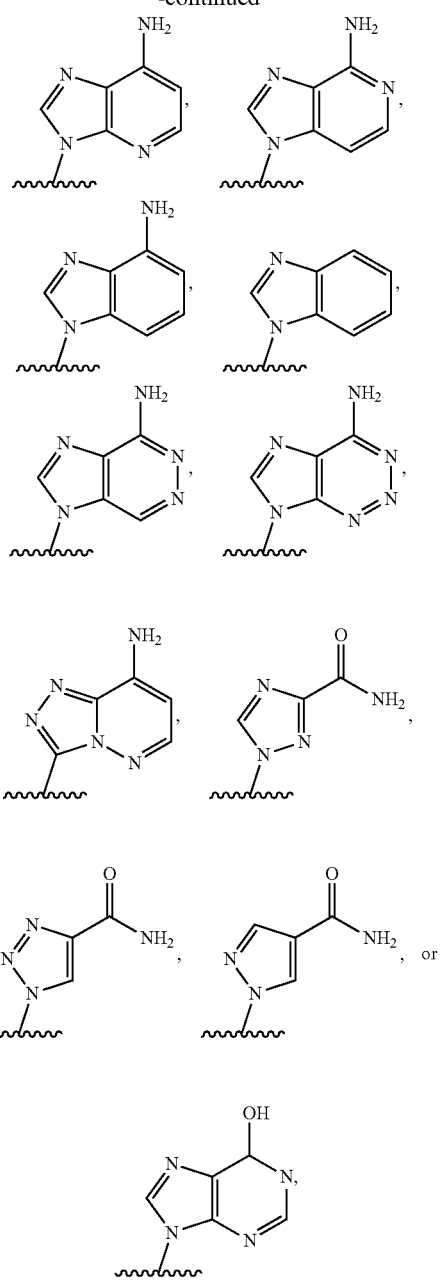

wherein, $Q^a$ and $Q^b$ can be optionally substituted with one, two, three, four, or five $R^1$; and $R^1$ is each independently selected from the group consisting of hydrogen, halogen, —$NO_2$, —CN, —$OR^{cl}$, —$SR^{cl}$, —$N(R^{cl})_2$, —$C(O)R^{cl}$, —$CO_2R_{cl}$, —$C(O)C(O)R^{cl}$, —$C(O)CH_2C(O)R^{cl}$, —$C(O)N(R^{cl})_2$, —$C(=NR^{cl})N(R^{cl})_2$, —$C(=NOR^{cl})R^{cl}$, —$S(O)R^{cl}$, —$S(O)_2R^{cl}$, —$SO_2N(R^{cl})_2$, —$OC(O)R^{cl}$, —$N(R^{cl})C(O)R^{cl}$, —$NR^{cl}N(R^{cl})_2$, —$N(R^{cl})C(=NR^{cl})N(R^{cl})_2$, —$N(R^{cl})C(O)N(R^{cl})_2$, —$N(R^{cl})SO_2N(R^{cl})_2$, —$N(R^{cl})SO_2R^{cl}$, —$N(R^{cl})SO_2NR^{cl}C(=O)OR^{cl}$, —$OC(O)N(R^{cl})_2$, or $R^{cl}$.

In one embodiment, the compounds of formulae (I), (II), or (III), or a pharmaceutically acceptable salt, stereoisomer, solvate or hydrate thereof comprise:

$Q^a$ and $Q^b$ are each independently selected from:

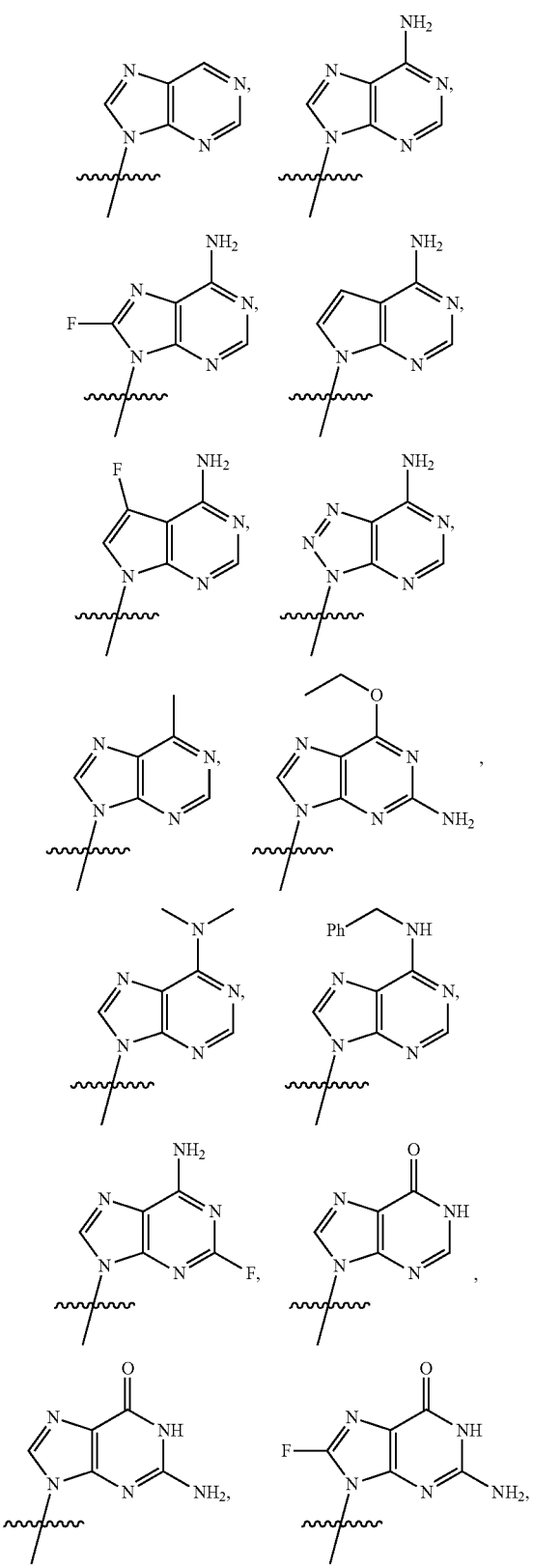

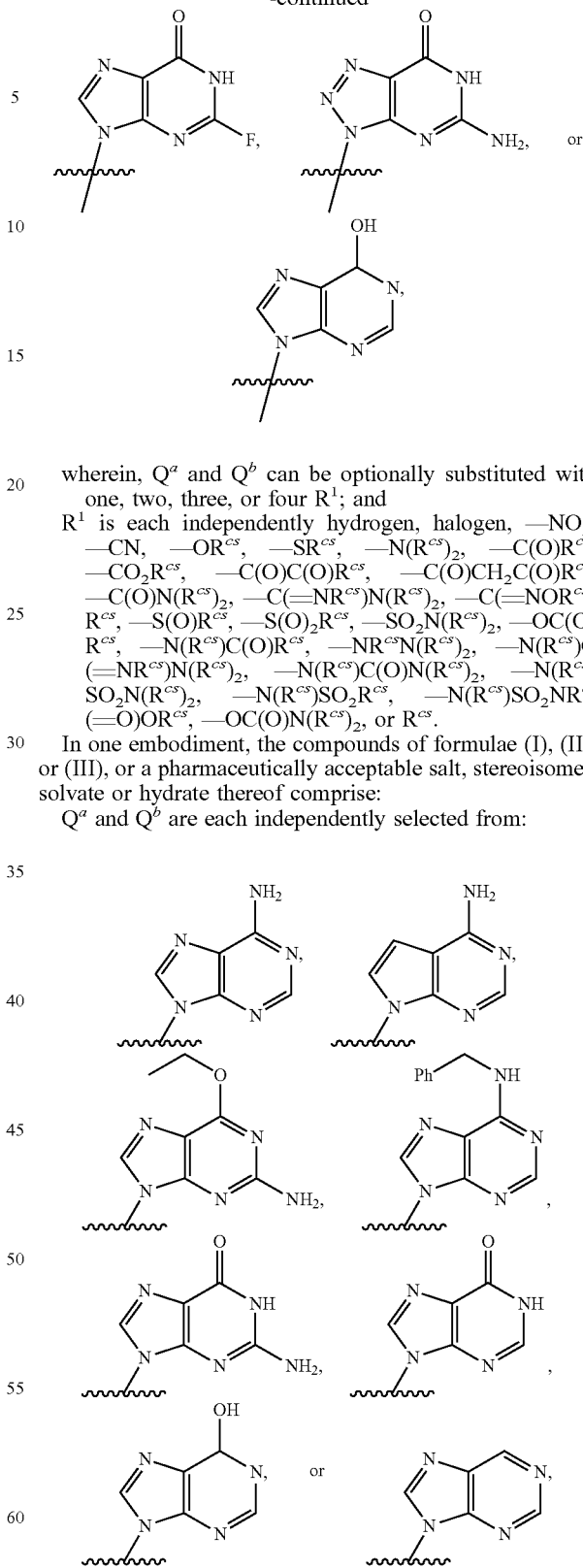

wherein, $Q^a$ and $Q^b$ can be optionally substituted with one, two, three, or four $R^1$; and $R^1$ is each independently hydrogen, halogen, —NO$_2$, —CN, —OR$^{cs}$, —SR$^{cs}$, —N(R$^{cs}$)$_2$, —C(O)R$^{cs}$, —CO$_2$R$^{cs}$, —C(O)C(O)R$^{cs}$, —C(O)CH$_2$C(O)R$^{cs}$, —C(O)N(R$^{cs}$)$_2$, —C(=NR$^{cs}$)N(R$^{cs}$)$_2$, —C(=NOR$^{cs}$)R$^{cs}$, —S(O)R$^{cs}$, —S(O)$_2$R$^{cs}$, —SO$_2$N(R$^{cs}$)$_2$, —OC(O)R$^{cs}$, —N(R$^{cs}$)C(O)R$^{cs}$, —NR$^{cs}$N(R$^{cs}$)$_2$, —N(R$^{cs}$)C(=NR$^{cs}$)N(R$^{cs}$)$_2$, —N(R$^{cs}$)C(O)N(R$^{cs}$)$_2$, —N(R$^{cs}$)SO$_2$N(R$^{cs}$)$_2$, —N(R$^{cs}$)SO$_2$R$^{cs}$, —N(R$^{cs}$)SO$_2$NR$^{cs}$(=O)OR$^{cs}$, —OC(O)N(R$^{cs}$)$_2$, or R$^{cs}$.

In one embodiment, the compounds of formulae (I), (II), or (III), or a pharmaceutically acceptable salt, stereoisomer, solvate or hydrate thereof comprise:

$Q^a$ and $Q^b$ are each independently selected from:

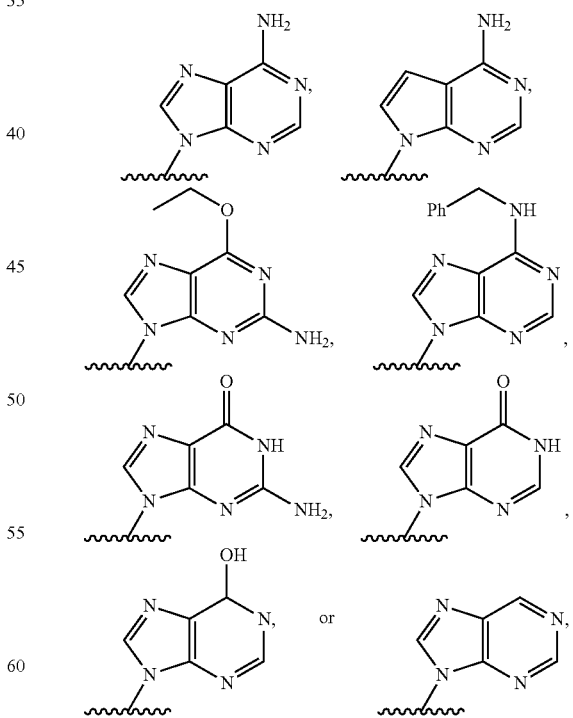

wherein, $Q^a$ and $Q^b$ can be optionally substituted with one, two, three, or four $R^1$; and $R^1$ is each independently hydrogen, F, Cl, Br, —NO$_2$, —CN, —OH, —SH, —NH$_2$, —O—C$_{1-3}$ alkyl, —O—C$_{3-6}$ cycloalkyl, —O—CH$_2$—C$_{3-6}$ cycloalkyl, —S—C$_{1-3}$ alkyl, —S—C$_{3-6}$ cycloalkyl, —S—CH$_2$—C$_{3-6}$ cycloalkyl, —NH(C$_{1-3}$ alkyl), —N(C$_{1-3}$ alkyl)$_2$, —NH(C$_{3-6}$ cycloalkyl), —NH(CH$_2$—C$_{3-6}$ cycloalkyl), —NCH$_3$(C$_{3-6}$ cycloalkyl), —NCH$_3$(CH$_2$—C$_{3-6}$ cycloalkyl), C$_{1-3}$ alkyl, —C$_{3-6}$ cycloalkyl, —CH$_2$—C$_{3-6}$ cycloalkyl, benzyl,

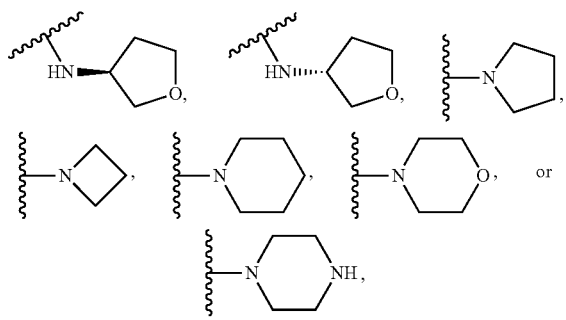

wherein, the C$_{1-3}$ alkyl, —C$_{3-6}$ cycloalkyl,

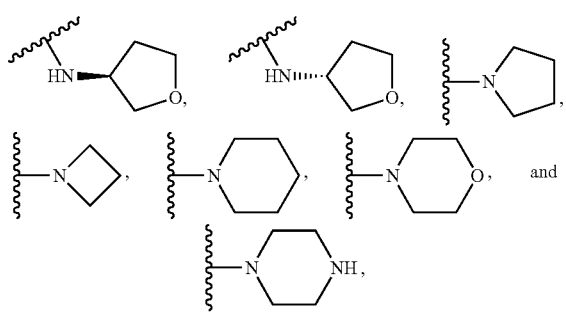

can be optionally substituted with up to 3 groups selected from F, OH, CN, NH$_2$, or OMe;

In one embodiment of the compounds of formulae (I), (II), or (II), or a pharmaceutically acceptable salt, stereoisomer, solvate or hydrate thereof, Q$^a$ and Q$^b$ are each bicyclic heterocyclyl or bicyclic heteroaryl. In another embodiment, Q$^a$ and Q$^b$ are each fused bicyclic heterocyclyl or fused bicyclic heteroaryl.

In one embodiment of the compounds of formulae (I), (II), or (III), or a pharmaceutically acceptable salt, stereoisomer, solvate or hydrate thereof, Q$^a$ and Q$^b$ are each

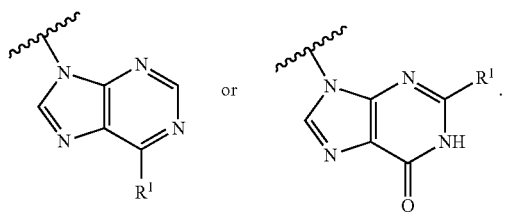

In one embodiment of the compounds of formulae (I) or (II), or a pharmaceutically acceptable salt, stereoisomer, solvate or hydrate thereof, Q$^a$ and Q$^b$ are each independently selected from:

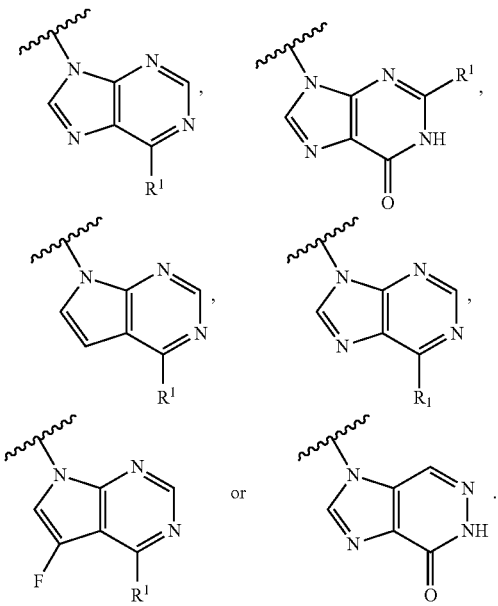

In one embodiment of the compounds of formulae (I) or (II), or a pharmaceutically acceptable salt, stereoisomer, solvate or hydrate thereof, R$^1$ is each independently hydrogen, halogen, or —N(R$^{c1}$)$_2$, and R$^{c1}$ is each independently H, C$_{1-6}$ alkyl, C$_{3-6}$ cycloalkyl, C$_{3-6}$ cycloalkyl-C$_{1-6}$ alkyl-, 3-6 membered heterocyclyl, (3-6 membered heterocyclyl)-C$_{1-6}$ alkyl-, 5-6 membered aryl, (5-6 membered aryl)-C$_{1-6}$ alkyl-, 5-6 membered heteroaryl, or (5-6 membered heteroaryl)-C$_{1-6}$ alkyl-.

In one embodiment of the compounds of formulae (I) or (II), or a pharmaceutically acceptable salt, stereoisomer, solvate or hydrate thereof, X$^2$ and Y$^2$ are each independently SH, OH, or BH$_3^-$, wherein at least one of X$^2$ and Y$^2$ is BH$_3^-$.

In one embodiment of the compounds of formulae (I) or (II), or a pharmaceutically acceptable salt, stereoisomer, solvate or hydrate thereof, R$^{a2a}$, R$^{a2b}$, R$^{b3a}$, R$^{b3b}$, R$^{3b2a}$ and R$^{3b2b}$ are each independently selected from H, halogen, —OH, or —O(C$_{1-3}$ alkyl). In one embodiment, R$^{a2a}$, R$^{a2b}$, R$^{b3a}$, R$^{b3b}$, R$^{3b2a}$ and R$^{3b2b}$ are each independently selected from H, F or OH.

In one embodiment of the compounds of formulae (I) or (II), or a pharmaceutically acceptable salt, stereoisomer, solvate or hydrate thereof, X$^3$, X$^4$, Y$^3$, and Y$^4$ are each O.

In one embodiment of the compounds of formulae (I) or (II), or a pharmaceutically acceptable salt, stereoisomer, solvate or hydrate thereof, Z$^1$ and Z$^2$ are each O.

In one embodiment of the compounds of formulae (I) or (II), the compound has the structure of Formula (I-X) or (II-X):

(I-X)

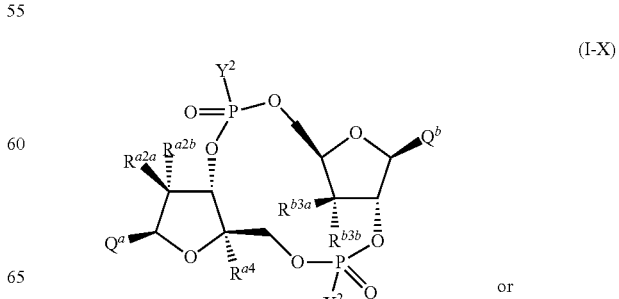

or

-continued (II-X)

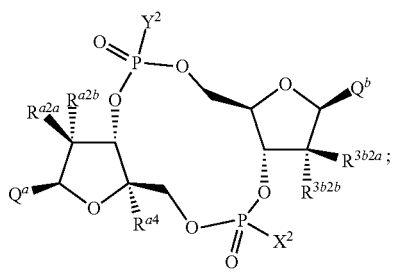

or a pharmaceutically acceptable salt, stereoisomer, solvate or hydrate thereof, wherein:

$Q^a$ and $Q^b$ are each independently selected from

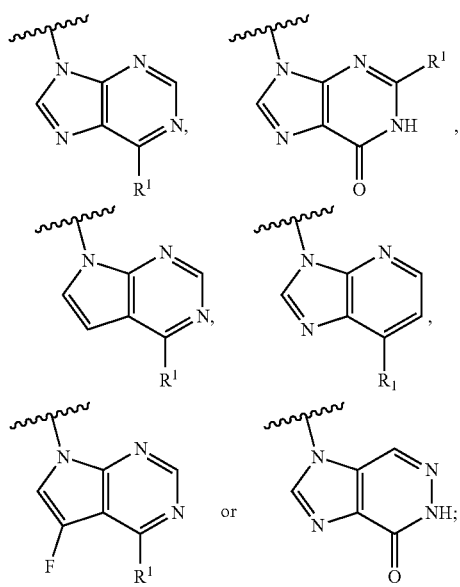

R[1] is hydrogen, halogen, or —N(R[c1])$_2$;

R[c1] is H, C$_{1-6}$ alkyl, C$_{3-6}$ cycloalkyl, C$_{3-6}$ cycloalkyl-C$_{1-6}$ alkyl-, 3-6 membered heterocyclyl, (3-6 membered heterocyclyl)-C$_{1-6}$ alkyl-, 5-6 membered aryl, (5-6 membered aryl)-C$_{1-6}$ alkyl-, 5-6 membered heteroaryl, or (5-6 membered heteroaryl)-C$_{1-6}$ alkyl-;

$R^{a2a}$, $R^{a2b}$, $R^{b3a}$, $R^{b3b}$, $R^{3b2a}$ and $R^{3b2b}$ are each independently selected from H, F, OH, or OMe;

$X^2$ and $Y^2$ are each independently selected from SH, OH, or BH$_3^-$, wherein at least one of $X^2$ and $Y^2$ is BH$_3$; and $R^{a4}$ is H.

In one embodiment of the compounds of formula (I-X) or (II-X), one of $X^2$ and $Y^2$ is BH$_3^-$ and the other is SH or OH.

In one embodiment of the compounds of formulae (I) or (II) or subgenera thereof, $X^2$ is BH$_3^-$, and $Y^2$ is SH or OH. In one embodiment, $X^2$ is SH or OH; and $Y^2$ is BH$_3^-$.

In one embodiment of the compounds of formulae (I) or (II) or subgenera thereof, exactly one of $X^2$ and $Y^2$ is BH$_3^-$.

In one embodiment of the compounds of formulae (I) or (II) or subgenera thereof, $Q^a$ and $Q^b$ are each independently selected from

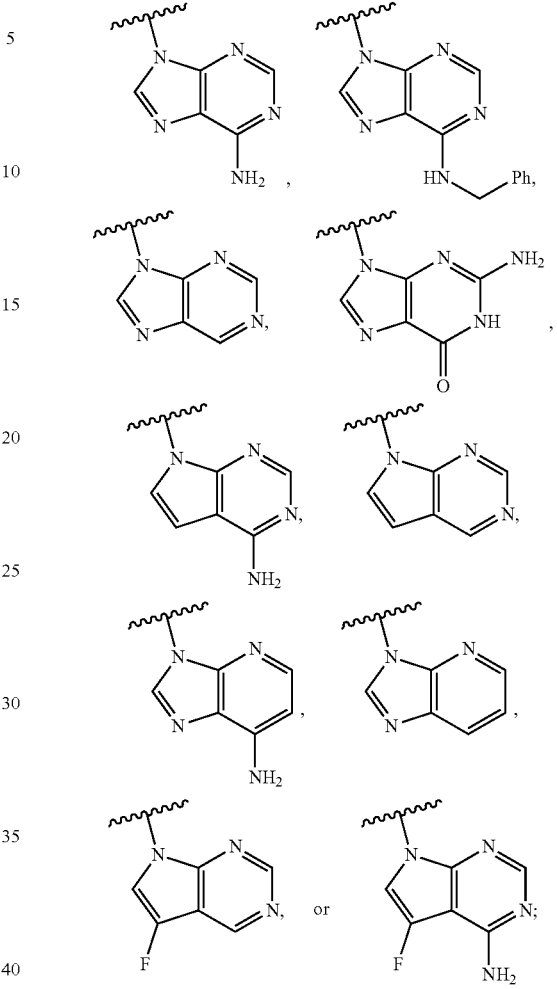

and $R^{a2a}$, $R^{a2b}$, $R^{b3a}$, $R^{b3b}$, $R^{3b2a}$ and $R^{3b2b}$ are each independently selected from H, F or OH.

In one embodiment of the compounds of formula (I-X), $Q^a$ and $Q^b$ are each

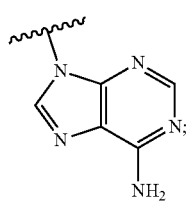 [SMILES: *n1cnc2c(N)ncnc21]

$R^{a4}$ is H;

$R^{a2a}$ and $R^{b3a}$ are each H; and $R^{a2b}$ and $R^{b3b}$ are each F.

In one embodiment of the compounds of formula (I-X), $Q^a$ and $Q^b$ are each

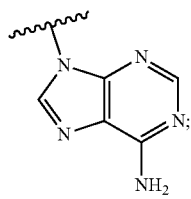 [SMILES: *n1cnc2c(N)ncnc21]

$R^{a4}$ is H;
$R^{a2a}$ and $R^{b3b}$ are each H; and
$R^{a2b}$ and $R^{b3a}$ are each F.

In one embodiment of the compounds of formula (II-X), $Q^a$ and $Q^b$ are each independently selected from

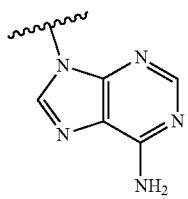 or 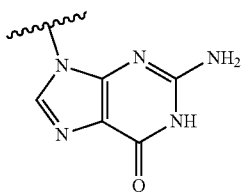 ;

$R^{a4}$ is H;
$R^{a2a}$ and $R^{3b2a}$ are each H;
$R^{a2b}$ and $R^{3b2b}$ are each F.

In one embodiment, the compound has the structure of formula (I), or a pharmaceutically acceptable salt, stereoisomer, solvate or hydrate thereof.

In one embodiment of the compounds of formulae (I), (II), or (III), or a pharmaceutically acceptable salt, stereoisomer, solvate or hydrate thereof, $R^1$ is each independently hydrogen, halogen, or —N($R^{c1}$)$_2$, and $R^1$ is each independently H, $C_{1-6}$ alkyl, $C_{3-6}$ cycloalkyl, $C_{3-6}$ cycloalkyl-$C_{1-6}$ alkyl-, 3-6 membered heterocyclyl, (3-6 membered heterocyclyl)-$C_{1-6}$ alkyl-, 5-6 membered aryl, (5-6 membered aryl)-$C_{1-6}$ alkyl-, 5-6 membered heteroaryl, or (5-6 membered heteroaryl)-$C_{1-6}$ alkyl-. In some embodiments, $R^1$ is hydrogen, F, Cl, Br, —OH, —SH, —NH$_2$, —NH($C_{1-3}$ alkyl)-aryl; or —N($C_{1-3}$ alkyl)$C_{1-3}$ alkyl-aryl. In other embodiments, $R^1$ is hydrogen, F, Cl, Br, —OH, —SH, —NH$_2$, —NH($C_{1-3}$ alkyl-phenyl); or —N($C_{1-3}$ alkyl)($C_{1-3}$ alkyl-phenyl). In one embodiment, $R^1$ is hydrogen, F, Cl, Br, —OH, —SH, —NH$_2$, —NHCH$_2$-phenyl; or —N(CH$_3$)CH$_2$-phenyl.

In one embodiment of the compounds of formulae (I), (II), or (III), or a pharmaceutically acceptable salt, stereoisomer, solvate or hydrate thereof, $Q^a$ and $Q^b$ are each nucleobase optionally substituted with one, two, or three $R^1$. In some embodiments, $Q^a$ and $Q^b$ are each independently nucleobase selected from adenine, guanine, thymine, uracil, or cytosine, each of which are optionally substituted with one, two, or three $R^1$. In one embodiment, $Q^a$ and $Q^b$ are each independently nucleobase selected from adenine or guanine, each of which are optionally substituted with one, two, or three $R^1$. In one embodiment, $Q^a$ and $Q^b$ are each independently nucleobase selected from adenine or guanine, each of which are optionally substituted with one or two R at the amino nitrogen. In one embodiment, $Q^a$ and $Q^b$ are each independently nucleobase selected from adenine or guanine, each of which are optionally substituted with one, two, or three $R^1$, wherein the nucleobase is attached to the rest of the molecule by a nitrogen atom on the imidazole ring of the nucleobase.

In one embodiment of the compounds of formulae (I), (II), or (III), or a pharmaceutically acceptable salt, stereoisomer, solvate or hydrate thereof,
$R^{a1}$ and $R^{b1}$ are each independently H, CN, Me, CF$_3$, —C≡CH, —C≡CCl, —CH=CH$_2$, —OMe, —OCF$_3$, —SMe, —CH$_2$N$_3$, —CH$_2$NHMe, —CH$_2$NMe$_2$, —CH$_2$OH, —CH$_2$OMe, or —CH$_2$OCF$_3$;
$R^{a2a}$, $R^{a2b}$, $R^{b3a}$, $R^{b3b}$, $R^{3b2a}$, $R^{3b2b}$, $R^{2a3a}$ and $R^{2a3b}$ are each independently H, F, Cl, OH, CN, N$_3$, Me, CF$_3$, —C≡CH, —C≡CCl, —CH=CH$_2$, —CH$_2$N$_3$, —CH$_2$NHMe, —CH$_2$NMe$_2$, —CH$_2$OH, —CH$_2$OMe, —CH$_2$OCF$_3$, —CO$_2$Me, —CH$_2$SH, —CH$_2$SMe, —OMe, —OCF$_3$, —SMe, —NMe$_2$, —NHMe, -cyclopropyl, —CH$_2$-cyclopropyl,

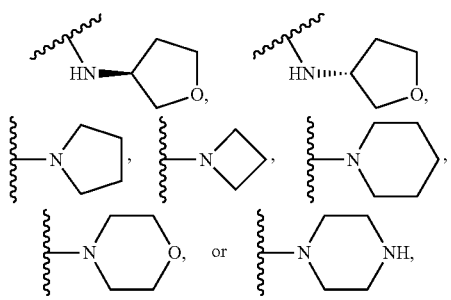

wherein, the -cyclopropyl and the cyclopropyl in —CH$_2$-cyclopropyl,

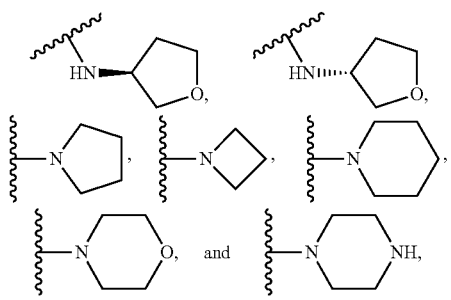

can be each optionally substituted with up to 3 groups selected from F, OH, CN, NH$_2$, —NMe$_2$, —NO$_2$, oxo, or OMe;
$R^{a4}$ and $R^{b4}$ are each independently selected from the group consisting of H, F, Cl, OH, CN, N$_3$, Me, CF$_3$, —C≡CH, —C≡CCl, —CH=CH$_2$, —CH$_2$N$_3$, —CH$_2$NHMe, —CH$_2$NMe$_2$, —CH$_2$OH, —CH$_2$OMe, —CH$_2$OCF$_3$, —SMe, —CO$_2$Me, —CH$_2$SH, —CH$_2$SMe —OMe, —OCF$_3$; or
alternatively, $R^{a2b}$ and $R^{a4}$, or $R^{3b2b}$ and $R^{b4}$, independently taken together with the cyclic ring to which they are both attached, form a bridged 7-membered heterobicyclic ring, containing up to one other heteroatom selected from O, S, NH, NMe, NC(O)Me, or NSO$_2$Me, wherein the bridged 7-membered heterocyclic ring is optionally substituted with up to three substituents selected from hydroxyl, oxo, NH$_2$, NMe$_2$, cyano or F; or alternatively, $R^{a2a}$ and $R^{a2b}$, $R^{b3a}$ and $R^{b3b}$, $R^{3b2a}$ and $R^{3b2b}$, or $R^{2a3a}$ and $R^{2a2b}$, can be taken together with the carbon atom to which they are attached, form a 4-5 membered heterocyclic ring, containing up to one other heteroatom selected from O, S, NH, NMe, N—C(O)Me, or NSO$_2$Me, wherein the 4-5 membered heterocyclic ring is optionally substituted with up to three substituents selected from hydroxyl, OMe, oxo, NH$_2$, NMe$_2$, cyano or F;

$R^{a3}$, $R^{b2}$, $R^{3b3}$ and $R^{2a2}$ are each independently H, F, CN, N$_3$, Me, CF$_3$, —C≡CH, —C≡CCl, —CH=CH$_2$, —CH$_2$N$_3$, —CH$_2$NHMe, —CH$_2$NMe$_2$, —CO$_2$Me, —CH$_2$OH, —CH$_2$OMe, —CH$_2$OCF$_3$, —CH$_2$SH, or —CH$_2$SMe;

$R^{a5a}$, $R^{a5b}$, $R^{b5a}$ and $R^{b5b}$ are each independently H, F, CH$_3$, or CF$_3$;

$X^1$ and $Y^1$ are each independently O or S;

$X^2$ and $Y^2$ are each independently SR$^4$, OR$^4$, NR$^4$R$^4$, BH(OR$^7$)$_2^-$, or BH(R$^b$)$_2^-$; or $R^b$ is each independently H, CN, carboxyl, carboxyl salts, CH$_3$, or CH$_2$CH$_3$; or alternatively, two $R^b$ taken together with the B atom to which they are both attached, form a 4-7 membered heterocyclic ring, containing up to one other heteroatom chosen from O, S, NH, NMe, N—C(O)Me, or NSO$_2$Me, wherein the 4-7 membered heterocyclic ring is optionally substituted with up to three substituents selected from hydroxyl, OMe, oxo, cyano, or F;

$R^4$ is each independently H or CH$_3$;

$R^7$ is H or CH$_3$; or alternatively, two $R^7$ taken together with the —O—B(H)—O— group to which they are both attached, form a heterocyclic ring of 5-7 members, containing up to one other heteroatom chosen from O, S, NH, NMe, N—C(O)Me, or NSO$_2$Me, and the heterocyclic ring is optionally substituted with up to three substituents chosen from hydroxyl, OMe, oxo, cyano, or F;

$X^3$, $X^4$, $Y^3$ and $Y^4$ are each independently O, S or NR$^6$;

$R^6$ is H or CH$_3$; and $Z^1$ and $Z^2$ are each independently O or S.

In one embodiment of the compounds of formulae (I), (II), or (III), or a pharmaceutically acceptable salt, stereoisomer, solvate or hydrate thereof, $R^{a1}$ and $R^{b1}$ are each independently H, CN, Me, —C—CH, —CH$_2$N$_3$, —CH$_2$OH, or —CH$_2$OMe;

$R^{a2a}$, $R^{a2b}$, $R^{b3a}$, $R^{b3b}$, $R^{3b2a}$, $R^{3b2b}$, $R^{2a3a}$ and $R^{2a3b}$ are each independently H, F, OH, CN, N$_3$, Me, —C≡CH, —CH$_2$N$_3$, —CH$_2$OH, —CH$_2$OMe, —OMe, —NMe$_2$, or —NHMe;

$R^{a3}$, $R^{b2}$, $R^{3b3}$ and $R^{2a2}$ are each independently H, F, CN, N$_3$, Me, —C≡CH, —CH$_2$N$_3$, —CH$_2$OH, or —CH$_2$OMe;

$R^{a4}$ and $R^{b4}$ are each independently H, F, Cl, OH, CN, N$_3$, Me, —C≡H, —CH$_2$N$_3$, —CH$_2$OH, —CH$_2$OMe, or —OMe;

$R^{a5a}$, $R^{a5b}$, $R^{b5a}$ and $R^{b5b}$ are each independently H or F;

$X^1$ and $Y^1$ are each independently O or S;

$X^2$ and $Y^2$ are each independently SR$^4$, OR$^4$, NR$^4$R$^4$, BH(OR$^7$)$_2^-$, or BH(R$^b$)$_2^-$;

$X^3$, $X^4$, $Y^3$ and $Y^4$ are each independently O, S or NR$^6$;

$R^4$ is each independently H or CH$_3$;

$R^6$ is H or CH$_3$;

$R^7$ is each independently H or CH$_3$;

$R^b$ is each independently H, CN, or CH$_3$; and $Z^1$ and $Z^2$ are each independently O, or S.

In one embodiment of the compounds of formulae (I), (II), or (III), or a pharmaceutically acceptable salt, stereoisomer, solvate or hydrate thereof, $X^2$ is SR$^4$, OR$^4$, BH(OR$^7$)$_2^-$, or BH(R$^b$)$_2^-$. In another embodiment, $X^2$ is BH(OR$^7$)$_2^-$ or BH(R$^b$)$_2^-$. In some embodiments, $X^2$ is BH(R$^b$)$_2^-$.

In one embodiment of the compounds of formulae (I), (II), or (III), or a pharmaceutically acceptable salt, stereoisomer, solvate or hydrate thereof, $Y^2$ is SR$^4$, OR$^4$, BH(OR$^7$)$_2^-$, or BH(R$^b$)$_2^-$. In another embodiment, $Y^2$ is BH(OR$^7$)$_2^-$ or BH(R$^b$)$_2^-$. In some embodiments, $Y^2$ is BH(R$^b$)$_2^-$.

In one embodiment of the compounds of formulae (I), (II), or (III), or a pharmaceutically acceptable salt, stereoisomer, solvate or hydrate thereof, $X^2$ is BH(R$^b$)$_2^-$; and $Y^2$ is SR$^4$ or OR$^4$.

In one embodiment of the compounds of formulae (I), (II), or (III), or a pharmaceutically acceptable salt, stereoisomer, solvate or hydrate thereof, $X^2$ is SR$^4$ or OR$^4$; and $Y^2$ is BH(R$^b$)$_2^-$.

In one embodiment of the compounds of formulae (I), (II), or (III), or a pharmaceutically acceptable salt, stereoisomer, solvate or hydrate thereof, $X^2$ and $Y^2$ are each BH(R$^b$)$_2^-$.

In another embodiment of the compounds of formulae (I), (II), or (III), or a pharmaceutically acceptable salt, stereoisomer, solvate or hydrate thereof, both $X^2$ and $Y^2$ are BH$_3$, or at least one of $X^2$ and $Y^2$ is BH$_3^-$, and the other is —OH, —SH, or —NH$_2$.

In another embodiment of the compounds of formulae (I), (II), or (III), or a pharmaceutically acceptable salt, stereoisomer, solvate or hydrate thereof, $X^2$ is BH$_3^-$ and $Y^2$ is —SH. In another embodiment, $Y^2$ is BH$_3^-$ and $X^2$ is —SH.

In another embodiment of the compounds of formulae (I), (II), or (III), or a pharmaceutically acceptable salt, stereoisomer, solvate or hydrate thereof, wherein:

$X^2$ and $Y^2$ are each independently —SH, —OH, —NH$_2$, BH$_3^-$, BH(OR$^7$)$_2^-$ or BH(R$^b$)$_2^-$; and wherein exactly one of $X^2$ and $Y^2$ is BH$_3^-$, BH(OR$^7$)$_2^-$ or BH(R$^b$)$_2^-$;

provided that when $X^2$ is BH$_3^-$, $Y^2$ is not OH and when $Y^2$ is BH$_3^-$, $X^2$ is not OH.

In one embodiment of the compounds of formulae (I), (II), or (III), or a pharmaceutically acceptable salt, stereoisomer, solvate or hydrate thereof, $X^3$ is O. In one embodiment of the compounds of formulae (I), (II), or (III), or a pharmaceutically acceptable salt, stereoisomer, solvate or hydrate thereof, $X^3$ and $Y^3$ are each O. In one embodiment of the compounds of formulae (I), (II), or (III), or a pharmaceutically acceptable salt, stereoisomer, solvate or hydrate thereof, $X^3$, $X^4$, and $Y^3$ are each O. In one embodiment of the compounds of formulae (I), (II), or (III), or a pharmaceutically acceptable salt, stereoisomer, solvate or hydrate thereof, $X^3$, $X^4$, $Y^3$, and $Y^4$ are each O.

In one embodiment of the compounds of formulae (I), (II), or (III), or a pharmaceutically acceptable salt, stereoisomer, solvate or hydrate thereof, $X^4$ is —NR$^6$. In one embodiment of the compounds of formulae (I), (II), or (III), or a pharmaceutically acceptable salt, stereoisomer, solvate or hydrate thereof, $X^4$ and $Y^4$ are each —NR$^6$.

In one embodiment of the compounds of formulae (I), (II), or (I), or a pharmaceutically acceptable salt, stereoisomer, solvate or hydrate thereof, $Z^1$ is O. In one embodiment of the compounds of formulae (I), (II), or (III), or a pharmaceutically acceptable salt, stereoisomer, solvate or hydrate thereof, $Z^1$ and $Z^2$ are each O.

In one embodiment of the compounds of formulae (I), (II), or (III), or a pharmaceutically acceptable salt, stereoisomer, solvate or hydrate thereof, $Z^1$ is S. In one embodiment of the compounds of formulae (I), (II), or (III), or a pharmaceutically acceptable salt, stereoisomer, solvate or hydrate thereof, $Z^1$ is S; and $Z^2$ is O.

In one embodiment of the compounds of formulae (I), (II), or (III), or a pharmaceutically acceptable salt, stereoisomer, solvate or hydrate thereof, $Z^2$ is S. In one embodiment of the compounds of formulae (I), (II), or (III), or a pharmaceutically acceptable salt, stereoisomer, solvate or hydrate thereof, Z' is O; and $Z^2$ is S.

In one embodiment of the compounds of formulae (I) or (II), or a pharmaceutically acceptable salt, stereoisomer, solvate or hydrate thereof, $Q^a$ and $Q^b$ are each independently selected from:

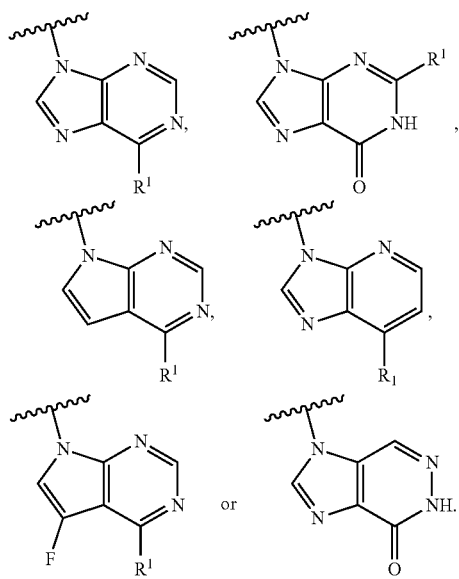

In one embodiment of the compounds of formulae (I) or (II), or a pharmaceutically acceptable salt, stereoisomer, solvate or hydrate thereof, $R^1$ is each independently hydrogen, halogen, or —N($R^{c1}$)$_2$, and $R^0$ is each independently H, $C_{1-6}$ alkyl, $C_{3-6}$ cycloalkyl, $C_{3-6}$ cycloalkyl-$C_{1-6}$ alkyl-, 3-6 membered heterocyclyl, (3-6 membered heterocyclyl)-$C_{1-6}$ alkyl-, 5-6 membered aryl, (5-6 membered aryl)-$C_{1-6}$ alkyl-, 5-6 membered heteroaryl, or (5-6 membered heteroaryl)-$C_{1-6}$ alkyl-.

In one embodiment of the compounds of formulae (I) or (II), or a pharmaceutically acceptable salt, stereoisomer, solvate or hydrate thereof, $X^2$ and $Y^2$ are each independently SH, OH, or $BH_3^-$, wherein at least one of $X^2$ and $Y^2$ is $BH_3^-$.

In one embodiment of the compounds of formulae (I) or (II), or a pharmaceutically acceptable salt, stereoisomer, solvate or hydrate thereof, $R^{a2a}$, $R^{a2b}$, $R^{b3a}$, $R^{b3b}$, $R^{3b2a}$ and $R^{3b2b}$ are each independently selected from H, halogen, —OH, or —O($C_{1-3}$ alkyl). In one embodiment, $R^{a2a}$, $R^{a2b}$, $R^{b3a}$, $R^{b3b}$, $R^{3b2a}$ and $R^{3b2b}$ are each independently selected from H, F or OH.

In one embodiment of the compounds of formulae (I) or (II), or a pharmaceutically acceptable salt, stereoisomer, solvate or hydrate thereof, $R^{a4}$ is H.

In one embodiment of the compounds of formulae (I) or (II), or a pharmaceutically acceptable salt, stereoisomer, solvate or hydrate thereof, $X^3$, $X^4$, $Y^3$, and $Y^4$ are each O.

In one embodiment of the compounds of formulae (I) or (II), or a pharmaceutically acceptable salt, stereoisomer, solvate or hydrate thereof, $Z^1$ and $Z^2$ are each O.

In one embodiment the present disclosure relates to the compounds of formula (I), or a pharmaceutically acceptable salt, stereoisomer, solvate or hydrate thereof.

In one embodiment of the compounds of formula (I), the compound has the structure of formula (I-A):

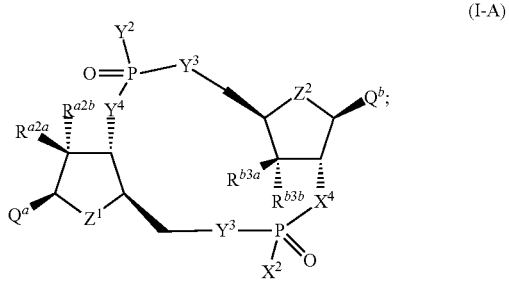

(I-A)

or a pharmaceutically acceptable salt, stereoisomer, solvate or hydrate thereof, wherein:

$R^{a2a}$, $R^{a2b}$, $R^{b3a}$, and $R^{b3b}$ are each independently H, F, or OH;

$X^2$ and $Y^2$ are each independently —SH, —OH, —NH$_2$, or $BH_3^-$;

$X^3$, $X^4$, $Y^3$ and $Y^4$ are each independently O or NH; and $Z^1$ and $Z^2$ are each independently O or S.

In one embodiment of the compounds of formula (I-A), $X^2$ and $Y^2$ are each independently —SH, —OH, or $BH_3^-$.

In one embodiment of the compounds of formula (I-A), $Z^1$ and $Z^2$ are each O.

In one embodiment of the compounds of formula (I-A), $X^2$ and $Y^2$ are each $BH_3^-$.

In ne embodiment of the compounds of formula (I-A), the compound has the following structure (stereochemistry):

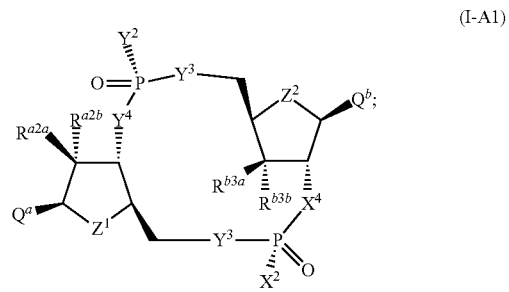

(I-A1)

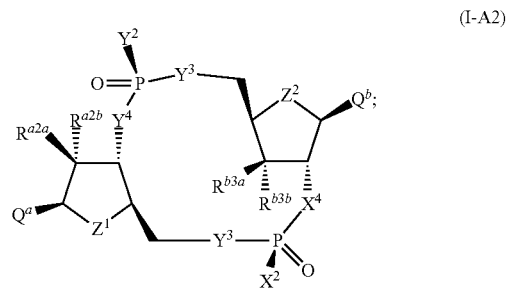

(I-A2)

(I-A3)

(I-A4)

or a pharmaceutically acceptable salt, solvate or hydrate thereof.

In one embodiment of the compounds of formula (I), the compound has the structure of formula (I-B):

(I-B)

or a pharmaceutically acceptable salt, stereoisomer, solvate or hydrate thereof, wherein:
both $X^2$ and $Y^2$ are $BH_3^-$; or
at least one of $X^2$ and $Y^2$ is $BH_3^-$, and the other is —OH, —SH, or —NH$_2$.

In one embodiment of the compounds of formula (I-B), $X^2$ and $Y^2$ are each selected from SH, OH, or $BH_3^-$, wherein at least one of $X^2$ and $Y^2$ is $BH_3^-$. In one embodiment of the compounds of formula (I-B), at least one of $X^2$ and $Y^2$ is $BH_3^-$, and the other is —OH or —SH.

In one embodiment of the compounds of formula (I), the compound has the structure of formula (I-C):

(I-C)

or a pharmaceutically acceptable salt, stereoisomer, solvate or hydrate thereof, wherein:
both $X^2$ and $Y^2$ are $BH_3^-$; or
at least one of $X^2$ and $Y^2$ is $BH_3^-$, and the other is —OH, —SH, or —NH$_2$.

In one embodiment of the compounds of formula (I-C), $X^2$ and $Y^2$ are each selected from SH, OH, or $BH_3^-$, wherein at least one of $X^2$ and $Y^2$ is $BH_3^-$. In one embodiment of the compounds of formula (I-C), at least one of $X^2$ and $Y^2$ is $BH_3^-$, and the other is —OH or —SH.

In one embodiment of the compounds of formula (I), the compound has the structure of formula (I-D):

(I-D)

or a pharmaceutically acceptable salt, stereoisomer, solvate or hydrate thereof, wherein:
both $X^2$ and $Y^2$ are $BH_3^-$; or
at least one of $X^2$ and $Y^2$ is $BH_3^-$, and the other is —OH, —SH, or —NH$_2$.

In one embodiment of the compounds of formula (I-D), $X^2$ and $Y^2$ are each selected from SH, OH, or $BH_3^-$, wherein at least one of $X^2$ and $Y^2$ is $BH_3^-$. In one embodiment of the compounds of formula (I-D), at least one of $X^2$ and $Y^2$ is $BH_3^-$, and the other is —OH or -SH.

In one embodiment of the compounds of formula (I), the compound has the structure of formula (I-E):

(I-E)

or a pharmaceutically acceptable salt, stereoisomer, solvate or hydrate thereof, wherein:
both $X^2$ and $Y^2$ are $BH_3^-$; or
at least one of $X^2$ and $Y^2$ is $BH_3^-$, and the other is —OH, —SH, or —NH$_2$.

In one embodiment of the compounds of formula (I-E), $X^2$ and $Y^2$ are each selected from SH, OH, or $BH_3^-$, wherein at least one of $X^2$ and $Y^2$ is $BH_3^-$. In one embodiment of the compounds of formula (I-E), at least one of $X^2$ and $Y^2$ is $BH_3^-$, and the other is —OH or —SH.

In one embodiment of the compounds of formula (I), the compound has the structure of formula (I-F):

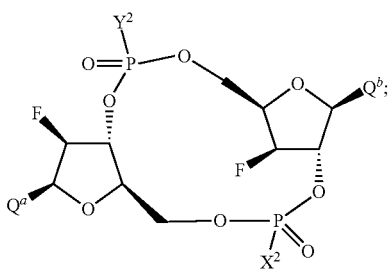

(I-F)

or a pharmaceutically acceptable salt, stereoisomer, solvate or hydrate thereof, wherein:

both $X^2$ and $Y^2$ are $BH_3^-$; or at least one of $X^2$ and $Y^2$ is $BH_3$, and the other is —OH, —SH, or —NH$_2$.

In one embodiment of the compounds of formula (I-F), $X^2$ and $Y^2$ are each selected from SH, OH, or $BH_3^-$, wherein at least one of $X^2$ and $Y^2$ is $BH_3^-$. In one embodiment of the compounds of formula (I-F), at least one of $X^2$ and $Y^2$ is $BH_3^-$, and the other is —OH or —SH.

In one embodiment of the compounds of formulae (I-A), (I-B), (I-C), (I-D), (I-E), or (I-F), or a pharmaceutically acceptable salt, stereoisomer, solvate or hydrate thereof, $X^2$ is $BH_3^-$ and $Y^2$ is —SH or —OH. In another embodiment, $Y^2$ is $BH_3^-$ and $X^2$ is —SH or —OH. In one embodiment, $X^2$ and $Y^2$ are each $BH_3^-$.

In one embodiment of the compounds of formulae (I-A), (I-B), (I-C), (I-D), (I-E), or (I-F), or a pharmaceutically acceptable salt, stereoisomer, solvate or hydrate thereof, $Y^2$ is $BH_3^-$; and $X^2$ is —OH, —SH, or —NH$_2$. In another embodiment, $Y^2$ is $BH_3^-$; and $X^2$ is SH or OH.

In one embodiment of the compounds of formulae (I-A), (I-B), (I-C), (I-D), (I-E), or (I-F), or a pharmaceutically acceptable salt, stereoisomer, solvate or hydrate thereof, $X^2$ is $BH_3^-$; and $Y^2$ is —OH, —SH, or —NH$_2$. In another embodiment, $X^2$ is $BH_3$; and $Y^2$ is SH or OH.

In one embodiment of the compounds of formulae (I-A), (I-B), (I-C), (I-D), (I-E), or (I-F), or a pharmaceutically acceptable salt, stereoisomer, solvate or hydrate thereof, $X^2$ and $Y^2$ are each $BH_3^-$.

In one embodiment of the compounds of formula (I) or any subgenera thereof (including formulae (I-A), (I-B), (I-C), (I-D), (I-E), or (I-F)), or a pharmaceutically acceptable salt, stereoisomer, solvate or hydrate thereof, $Q^a$ and $Q^b$ are each

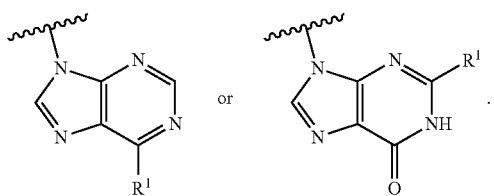

or

In one embodiment $Q^a$ and $Q^b$ are each

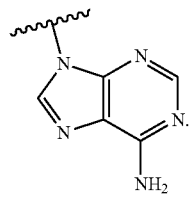 [SMILES: *n1cnc2c(N)ncnc21]

In one embodiment of the compounds of formula (I) or any subgenera thereof (including formulae (I-A), (I-B), (I-C), (I-D), (I-E), or (I-F)), or a pharmaceutically acceptable salt, stereoisomer, solvate or hydrate thereof, $R^1$ is each independently hydrogen, halogen, or —N($R^{ci}$)$_2$, and $R^{ci}$ is each independently H, $C_{1-6}$ alkyl, $C_{3-6}$ cycloalkyl, $C_{3-6}$ cycloalkyl-$C_{1-6}$ alkyl-, 3-6 membered heterocyclyl, (3-6 membered heterocyclyl)-$C_{1-6}$ alkyl-, 5-6 membered aryl, (5-6 membered aryl)-$C_{1-6}$ alkyl-, 5-6 membered heteroaryl, or (5-6 membered heteroaryl)-$C_{1-6}$ alkyl-.

In one embodiment, formulae (I-A), (I-B), (I-C), (I-D), (I-E), or (I-F) are subgenera of formula (I). In some embodiments, various embodiments disclosed herein for formulae (I-A), (I-B), (I-C), (I-D), (I-E), or (I-F) can apply to formula (I). In another embodiment, various embodiments disclosed herein for formula (I) can be applied for formulae (I-A), (I-B), (I-C), (I-D), (I-E), or (I-F), where appropriate.

In one embodiment the present disclosure relates to the compounds of formula (II), or a pharmaceutically acceptable salt, stereoisomer, solvate or hydrate thereof.

In one embodiment of the compounds of formula (II), the compound has the structure of formula (II-A):

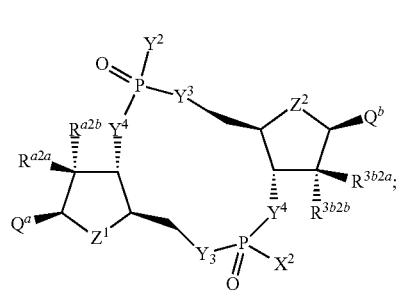

(II-A)

or a pharmaceutically acceptable salt, stereoisomer, solvate or hydrate thereof, wherein:

$R^{a2a}$, $R^{a2b}$, $R^{3b2b}$, and $R^{3b2a}$ are each independently H, F, or —OH;

$X^2$ and $Y^2$ are each independently —SH, —OH, —NH$_2$, or $BH_3^-$;

$X^3$, $X^4$, $Y^3$ and $Y^4$ are each independently O or NH; and $Z^1$ and $Z^2$ are each independently O or S.

In one embodiment of the compounds of formula (II-A), $Z^1$ and $Z^2$ are each O.

In one embodiment, of the compounds of formula (II-A), $X^2$ and $Y^2$ are each independently —SH, —OH, or $BH_3^-$. In one embodiment of the compounds of formula (II-A), $X^2$ and $Y^2$ are each $BH_3^-$.

In one embodiment of the compounds of formula (II-A), the compound has the following structure (stereochemistry):

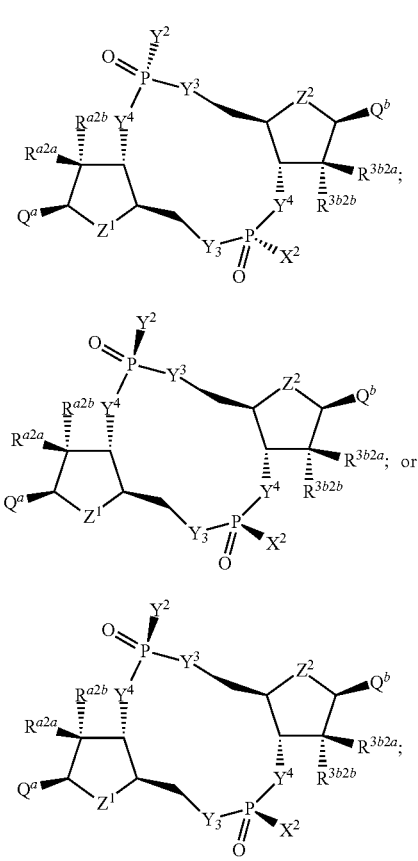

(II-A1)

(II-A2)

(II-A3)

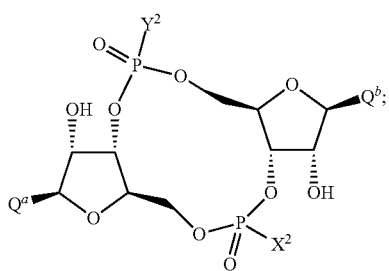

or a pharmaceutically acceptable salt, solvate or hydrate thereof.

In one embodiment of the compounds of formula (II), the compound has the structure of formula (II-B):

(II-B)

or a pharmaceutically acceptable salt, stereoisomer, solvate or hydrate thereof, wherein:

both $X^2$ and $Y^2$ are $BH_3^-$; or at least one of $X^2$ and $Y^2$ is $BH_3^-$, and the other is —OH, —SH, or —NH$_2$.

In one embodiment of the compounds of formula (II-B), $X^2$ and $Y^2$ are each selected from SH, OH, or $BH_3^-$, wherein at least one of $X^2$ and $Y^2$ is $BH_3^-$. In one embodiment, of the compounds of formula (II-B), at least one of $X^2$ and $Y^2$ is $BH_3^-$, and the other is —OH or —SH.

In one embodiment of the compounds of formula (II), the compound has the structure of formula (II-C):

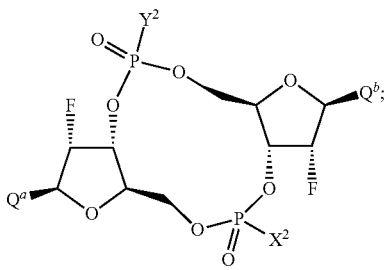

(II-C)

or a pharmaceutically acceptable salt, stereoisomer, solvate or hydrate thereof, wherein:

both $X^2$ and $Y^2$ are $BH_3^-$; or at least one of $X^2$ and $Y^2$ is $BH_3^-$, and the other is —OH, —SH, or —NH$_2$.

In one embodiment of the compounds of formula (II-C), $X^2$ and $Y^2$ are each selected from SH, OH, or $BH_3^-$, wherein at least one of $X^2$ and $Y^2$ is $BH_3^-$. In one embodiment, of the compounds of formula (II-C), at least one of $X^2$ and $Y^2$ is $BH_3^-$, and the other is —OH or —SH.

In one embodiment of the compounds of formula (II), the compound has the structure of formula (II-D):

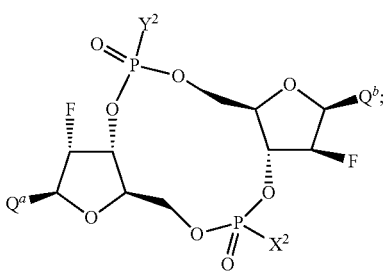

(II-D)

or a pharmaceutically acceptable salt, stereoisomer, solvate or hydrate thereof, wherein:

both $X^2$ and $Y^2$ are $BH_3^-$; or at least one of $X^2$ and $Y^2$ is $BH_3^-$, and the other is —OH, —SH, or —NH$_2$.

In one embodiment of the compounds of formula (II-D), $X^2$ and $Y^2$ are each selected from SH, OH, or $BH_3$, wherein at least one of $X^2$ and $Y^2$ is $BH_3^-$. In one embodiment, of the compounds of formula (II-D), at least one of $X^2$ and $Y^2$ is $BH_3^-$, and the other is —OH or —SH.

In one embodiment of the compounds of formula (II), the compound has the structure of formula (II-E):

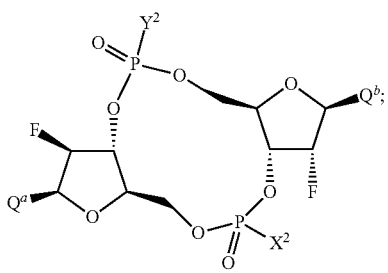

(II-E)

or a pharmaceutically acceptable salt, stereoisomer, solvate or hydrate thereof, wherein:

both $X^2$ and $Y^2$ are $BH_3^-$; or at least one of $X^2$ and $Y^2$ is $BH_3^-$, and the other is —OH, —SH, or —NH$_2$.

In one embodiment of the compounds of formula (II-E), $X^2$ and $Y^2$ are each selected from SH, OH, or $BH_3^-$, wherein at least one of $X^2$ and $Y^2$ is $BH_3$. In one embodiment of the compounds of formula (II), the compound has the structure of formula (II-F):

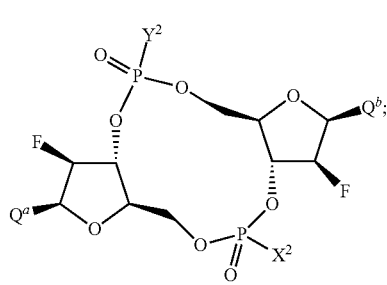

(II-F)

or a pharmaceutically acceptable salt, stereoisomer, solvate or hydrate thereof, wherein:

both $X^2$ and $Y^2$ are $BH_3^-$; or at least one of $X^2$ and $Y^2$ is $BH_3^-$, and the other is —OH, —SH, or —NH$_2$.

In one embodiment of the compounds of formula (II-F), $X^2$ and $Y^2$ are each selected from SH, OH, or $BH_3^-$, wherein at least one of $X^2$ and $Y^2$ is $BH_3^-$. In one embodiment, of the compounds of formula (II-F), at least one of $X^2$ and $Y^2$ is $BH_3^-$, and the other is —OH or —SH.

In one embodiment of the compounds of formulae (II-A), (II-B), (II-C), (II-D), (II-E), or (II-F), or a pharmaceutically acceptable salt, stereoisomer, solvate or hydrate thereof, $X^2$ is $BH_3^-$ and $Y^2$ is —SH or —OH. In another embodiment, $Y^2$ is $BH_3^-$ and $X^2$ is —SH or —OH. In one embodiment, $X^2$ and $Y^2$ are each $BH_3^-$.

In one embodiment of the compounds of formulae (II-A), (II-B), (II-C), (II-D), (II-E), or (II-F), or a pharmaceutically acceptable salt, stereoisomer, solvate or hydrate thereof, $Y^2$ is $BH_3^-$; and $X^2$ is —OH, —SH, or —NH$_2$. In another embodiment, $Y^2$ is $BH_3^-$; and $X^2$ is SH or OH.

In one embodiment of the compounds of formulae (II-A), (II-B), (II-C), (II-D), (II-E), or (II-F), or a pharmaceutically acceptable salt, stereoisomer, solvate or hydrate thereof, $X^2$ is $BH_3^-$; and $Y^2$ is —OH, —SH, or —NH$_2$. In another embodiment, $X^2$ is $BH_3^-$; and $Y^2$ is SH or OH.

In one embodiment of the compounds of formulae (II-A), (II-B), (II-C), (II-D), (II-E), or (II-F), or a pharmaceutically acceptable salt, stereoisomer, solvate or hydrate thereof, $X^2$ and $Y^2$ are each $BH_3^-$.

In one embodiment of the compounds of formula (II) or any subgenera thereof (including formulae (II-A), (II-B), (II-C), (II-D), (II-E), or (II-F)), or a pharmaceutically acceptable salt, stereoisomer, solvate or hydrate thereof, $Q^a$ and $Q^b$ are each

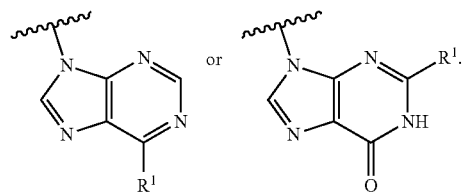

In one embodiment $Q^a$ and $Q^b$ are each independently selected from

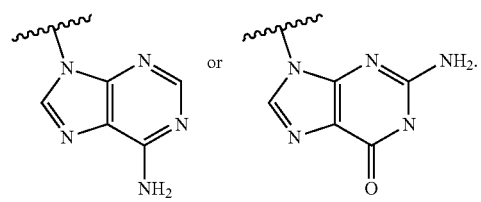 [SMILES: *n1cnc2c(N)ncnc21 ; *n1cnc2c(=O)[nH]c(N)nc21]

In one embodiment of the compounds of formula (II) or any subgenera thereof (including formulae (II-A), (II-B), (II-C), (II-D), (II-E), or (II-F)) or a pharmaceutically acceptable salt, stereoisomer, solvate or hydrate thereof, $R^1$ is each independently hydrogen, halogen, or —N($R^{c1}$)$_2$, and $R^{c1}$ is each independently H, $C_{1-6}$ alkyl, $C_{3-6}$ cycloalkyl, $C_{3-6}$ cycloalkyl-$C_{1-6}$ alkyl-, 3-6 membered heterocyclyl, (3-6 membered heterocyclyl)-$C_{16}$ alkyl-, 5-6 membered aryl, (5-6 membered aryl)-$C_{1-6}$ alkyl-, 5-6 membered heteroaryl, or (5-6 membered heteroaryl)-$C_{1-6}$ alkyl-.

In one embodiment, formulae (II-A), (II-B), (II-C), (II-D), (II-E), or (II-F) are subgenera of formula (II). In some embodiments, various embodiments disclosed herein for formulae (II-A), (II-B), (II-C), (II-D), (II-E), or (II-F) can apply to formula (II). In another embodiment, various embodiments disclosed herein for formula (II) can be applied for formulae (II-A), (II-B), (II-C), (II-D), (II-E), or (II-F), where appropriate.

In one embodiment the present disclosure relates to the compounds of formula (III), or a pharmaceutically acceptable salt, stereoisomer, solvate or hydrate thereof.

In one embodiment, the present disclosure relates to the compounds of formula (I-A') or (II-A'):

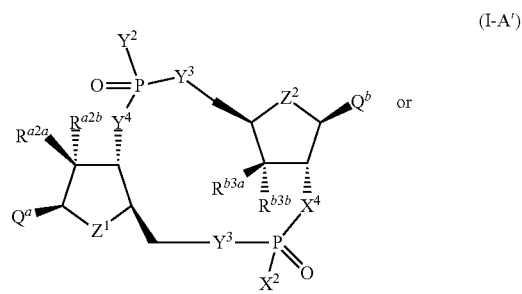

(I-A')

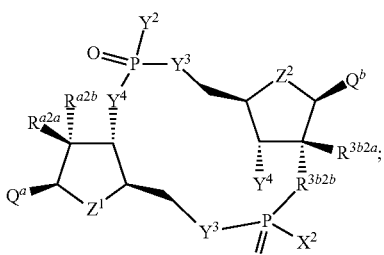
(II-A')

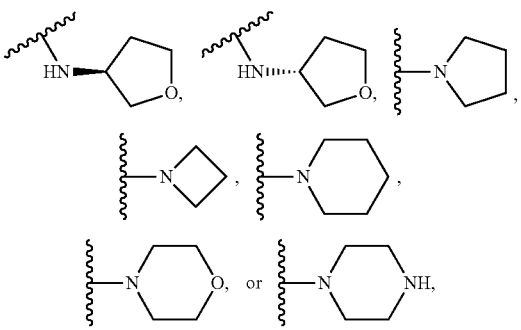

or a pharmaceutically acceptable salt, stereoisomer, solvate or hydrate thereof, wherein:

$Q^a$ and $Q^b$ are each independently selected from:

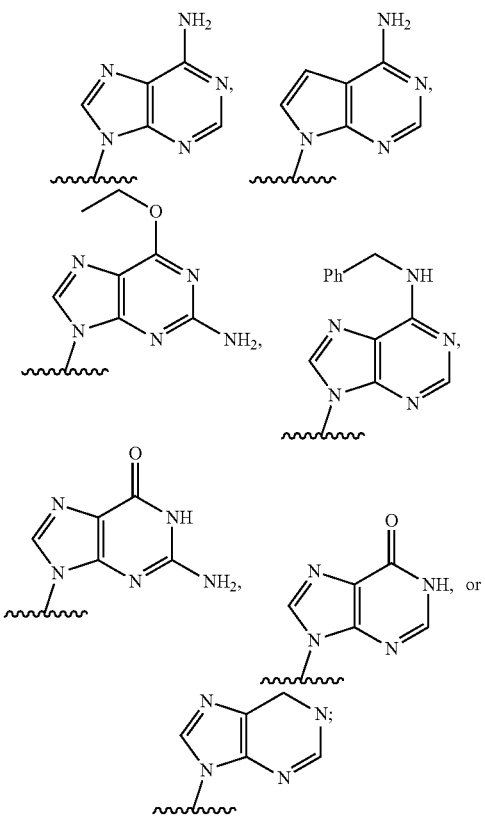

wherein, $Q^a$ and $Q^b$ can be optionally substituted with one, two, three, or four $R^1$; and $R^1$ is each independently hydrogen, F, Cl, Br, —$NO_2$, —CN, —OH, —SH, —$NH_2$, —O—$C_{1-3}$ alkyl, —O—$C_{3-6}$ cycloalkyl, —O—$CH_2$—$C_{3-6}$ cycloalkyl, —S—$C_{1-3}$ alkyl, —S—$C_{3-6}$ cycloalkyl, —S—$CH_2$—$C_{3-6}$ cycloalkyl, —NH($C_{1-3}$ alkyl), —N($C_{1-3}$ alkyl)$_2$, —NH($C_{3-6}$ cycloalkyl), —NH($CH_2$—$C_{3-6}$ cycloalkyl), —$NCH_3$($C_{3-6}$ cycloalkyl), —$NCH_3$($CH_2$—$C_{3-6}$ cycloalkyl), $C_{1-3}$ alkyl, —$C_{3-6}$ cycloalkyl, —$CH_2$—$C_{3-6}$ cycloalkyl, benzyl,

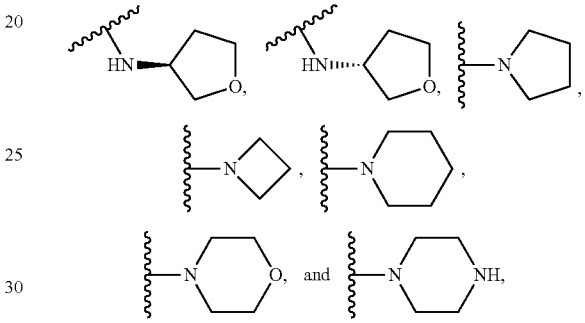

wherein, the $C_{1-3}$ alkyl, —$C_{3-6}$ cycloalkyl,

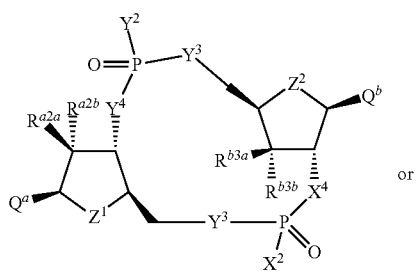

can be optionally substituted with up to 3 groups selected from F, OH, CN, $NH_2$, or OMe;

$R^{a2a}$, $R^{a2b}$, $R^{b3a}$, $R^{b3b}$, $R^{3b2b}$, and $R^{3b2a}$ are each independently H, F, or OH;

$X^2$ and $Y^2$ are each independently —SH, —OH, —$NH_2$, $BH_3^-$, $BH(OR^7)_2^-$ or $BH(R^b)_2^-$;

$X^3$, $X^4$, $Y^3$ and $Y^4$ are each independently O or NH; and $Z^1$ and $Z^2$ are each independently O or S;

$R^b$ is each independently H, CN, carboxyl, carboxyl salts, $CH_3$, or $CH_2CH_3$;

$R^7$ is each independently H or $CH_3$; and wherein exactly one of $X^2$ and $Y^2$ is $BH_3$, $BH(OR^7)_2$ or $BH(R^b)_2^-$;

provided that when $X^2$ is $BH_3^-$, $Y^2$ is not OH and when $Y^2$ is $BH_3^-$, $X^2$ is not OH.

In one embodiment, the present disclosure relates to the compounds of formula (I-A''') or (II-A'''):

(I-A''')

or

-continued

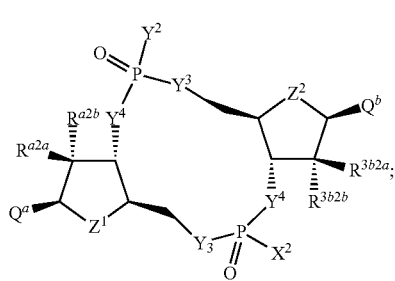
(II-A''')

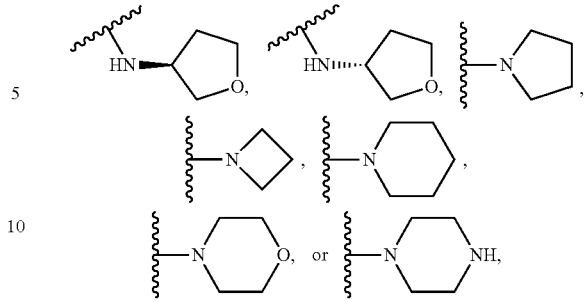

wherein, the $C_{1-3}$ alkyl, $—C_{3-6}$ cycloalkyl,

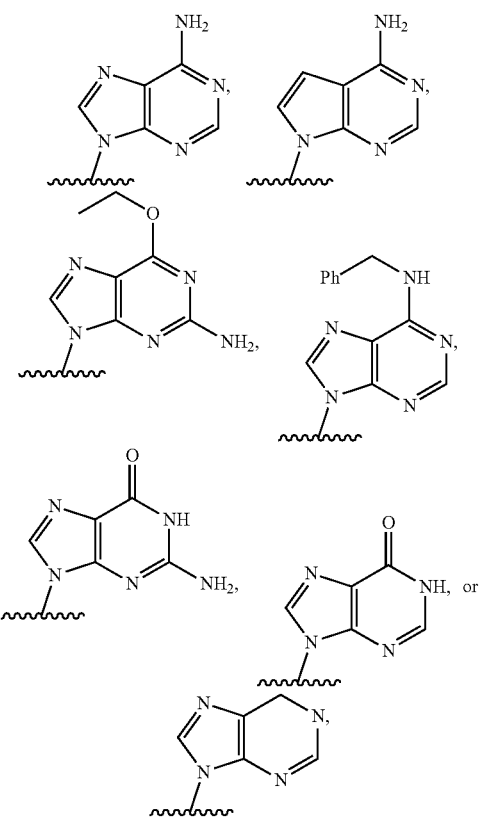

or a pharmaceutically acceptable salt, stereoisomer, solvate or hydrate thereof, wherein:

$Q^a$ and $Q^b$ are each independently selected from:

wherein, $Q^a$ and $Q^b$ can be optionally substituted with one, two, three, or four $R^1$; and $R^1$ is each independently hydrogen, F, Cl, Br, —NO$_2$, —CN, —OH, —SH, —NH$_2$, —O—$C_{1-3}$ alkyl, —O—$C_{3-6}$ cycloalkyl, —O—CH$_2$—$C_{3-6}$ cycloalkyl, —S—$C_{1-3}$ alkyl, —S—$C_{3-6}$ cycloalkyl, —S—CH$_2$—$C_{3-6}$ cycloalkyl, —NH($C_{1-3}$ alkyl), —N($C_{1-3}$ alkyl)$_2$, —NH($C_{3-6}$ cycloalkyl), —NH(CH$_2$—$C_{3-6}$ cycloalkyl), —NCH$_3$($C_{3-6}$ cycloalkyl), —NCH$_3$(CH$_2$—$C_{3-6}$ cycloalkyl), $C_{1-3}$ alkyl, —$C_{3-6}$ cycloalkyl, —CH$_2$—$C_{3-6}$ cycloalkyl, benzyl, can be optionally substituted with up to 3 groups selected from F, OH, CN, NH$_2$, or OMe;

$R^{a2a}$, $R^{a2b}$, $R^{b3a}$, $R^{b3b}$, $R^{3b2b}$, and $R^{3b2a}$ are each independently H, F, or OH;

$X^2$ and $Y^2$ are each independently —SH, —OH, —NH$_2$, BH$_3^-$, BH(OR$^7$)$_2^-$ or BH(R$^b$)$_2^-$;

$X^3$, $X^4$, $Y^3$ and $Y^4$ are each independently O or NH; and $Z^1$ and $Z^2$ are each independently O or S;

$R^b$ is each independently H, CN, carboxyl, carboxyl salts, CH$_3$, or CH$_2$CH$_3$;

$R^7$ is each independently H or CH$_3$; and wherein at least one of $X^2$ and $Y^2$ is BH$_3$, BH(OR$^7$)$_2^-$ or BH(R$^b$)$_2^-$;

provided that when $R^{a2b}$, $R^{b3b}$, and $R^{3b2b}$ are each OH; $R^{a2a}$, $R^{b3a}$, and $R^{3b2a}$ are each H; $X^3$, $X^4$, $Y^3$ and $Y^4$ are each O; $Z^1$ and $Z^2$ are each O; and $X^2$ is BH$_3^-$, then $Y^2$ is not OH or BH$_3^-$; and provided that when $R^{a2b}$, $R^{b3b}$, and $R^{3b2b}$ are each OH; $R^{a2a}$, $R^{b3a}$, and $R^{3b2a}$ are each H; $X^3$, $X^4$, $Y^3$ and $Y^4$ are each O; $Z^1$ and $Z^2$ are each O; and $Y^2$ is BH$_3^-$, then $X^2$ is not OH or BH$_3^-$.

In one embodiment, the present disclosure relates to the compounds of formula (I-A"):

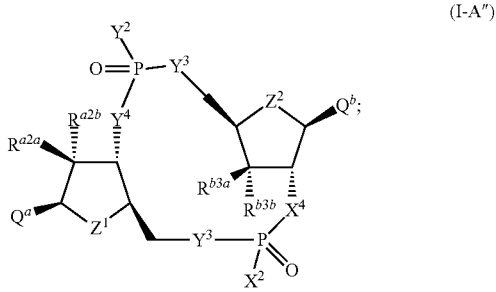
(I-A")

or a pharmaceutically acceptable salt, stereoisomer, solvate or hydrate thereof, wherein:

$Q^a$ and $Q^b$ are each independently selected from:

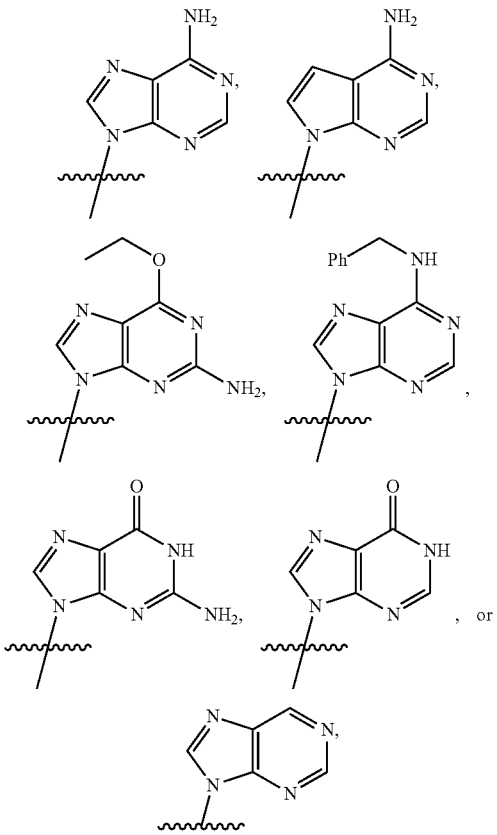

wherein, $Q^a$ and $Q^b$ can be optionally substituted with one, two, three, or four $R^1$; and $R^1$ is each independently hydrogen, F, Cl, Br, —NO$_2$, —CN, —OH, —SH, —NH$_2$, —O—C$_{1-3}$ alkyl, —O—C$_{3-6}$ cycloalkyl, —O—CH$_2$—C$_{3-6}$ cycloalkyl, —S—C$_{1-3}$ alkyl, —S—C$_{3-6}$ cycloalkyl, —S—CH$_2$—C$_{3-6}$ cycloalkyl, —NH(C$_{1-3}$ alkyl), —N(C$_{1-3}$ alkyl)$_2$, —NH(C$_{3-6}$ cycloalkyl), —NH(CH$_2$—C$_{3-6}$ cycloalkyl), —NCH$_3$(C$_{3-6}$ cycloalkyl), —NCH$_3$(CH$_2$—C$_{3-6}$ cycloalkyl), C$_{1-3}$ alkyl, —C$_{3-6}$ cycloalkyl, —CH$_2$—C$_{3-6}$ cycloalkyl, benzyl,

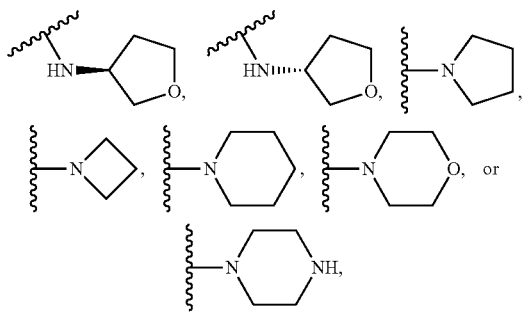

wherein, the C$_{1-3}$ alkyl, —C$_{3-6}$ cycloalkyl,

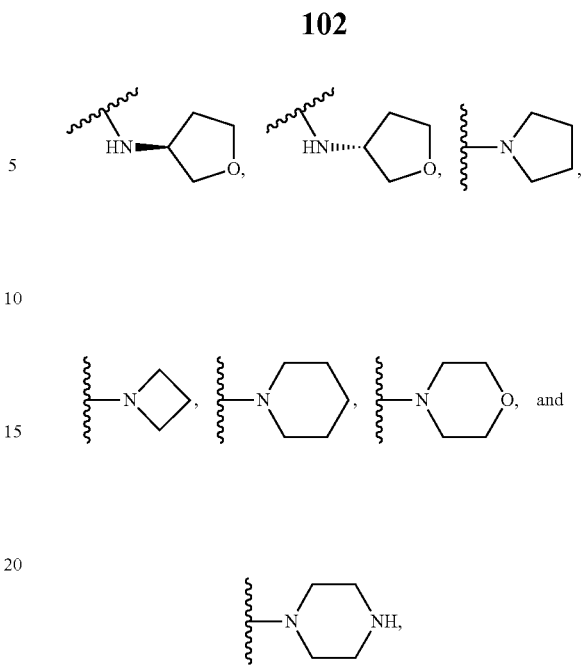

can be optionally substituted with up to 3 groups selected from F, OH, CN, NH$_2$, or OMe;

$R^{a2a}$, $R^{a2b}$, $R^{b3a}$, $R^{b3b}$, $R^{3b2b}$, and $R^{3b2a}$ are each independently H, F, or OH;

$X^2$ and $Y^2$ are each independently —SH, —OH, —NH$_2$, BH$_3^-$, BH(OR$^7$)$_2^-$ or BH(R$^b$)$_2^-$;

$X^3$, $X^4$, $Y^3$ and $Y^4$ are each independently O or NH; and $Z^1$ and $Z^2$ are each independently O or S;

$R^b$ is each independently H, CN, carboxyl, carboxyl salts, CH$_3$, or CH$_2$CH$_3$; and $R^7$ is each independently H or CH$_3$;

wherein at least one of $X^2$ and $Y^2$ is BH$_3^-$, BH(OR$^7$)$_2^-$ or BH(R$^b$)$_2^-$.

In one embodiment, the compound of the present disclosure is selected from:

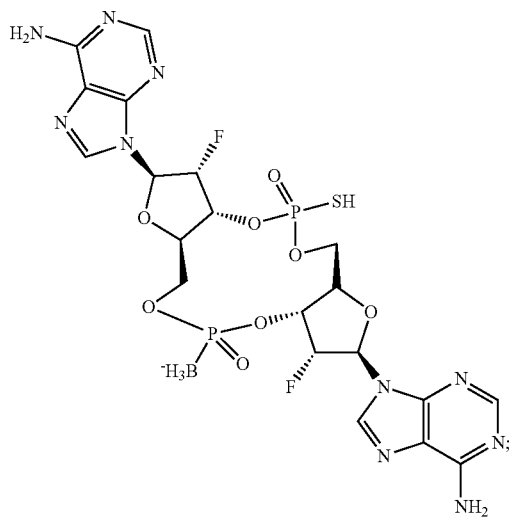

103
-continued
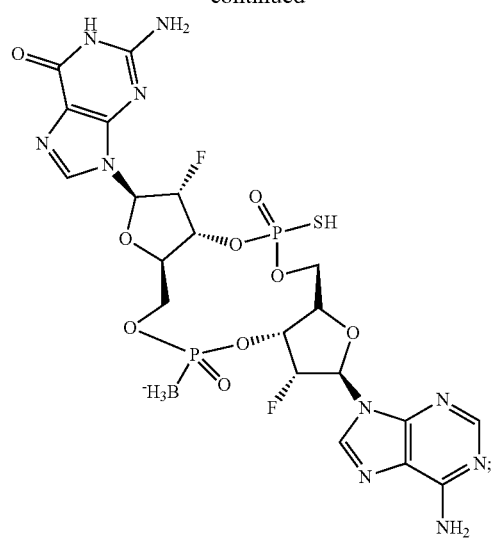
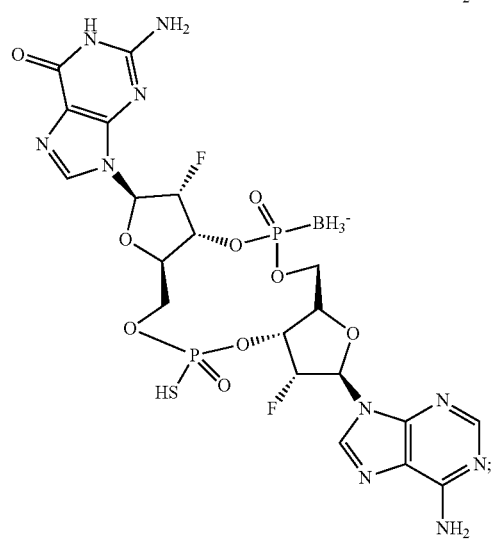
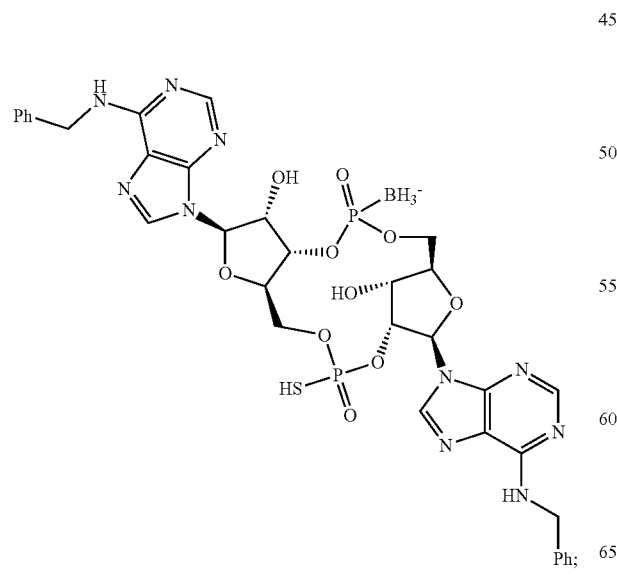
104
-continued
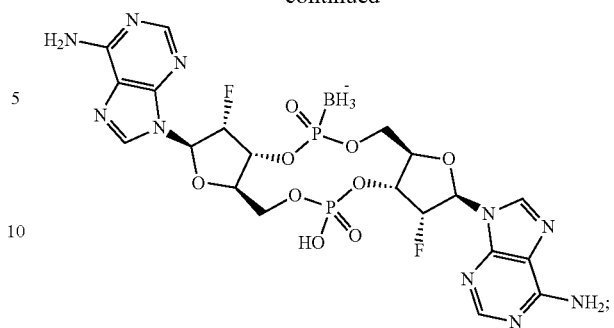
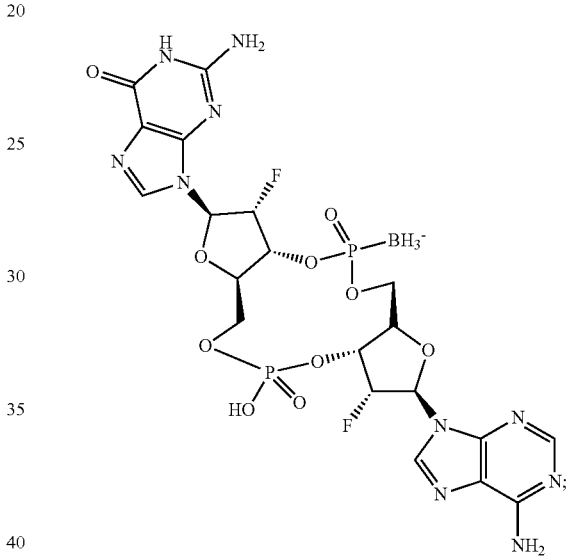
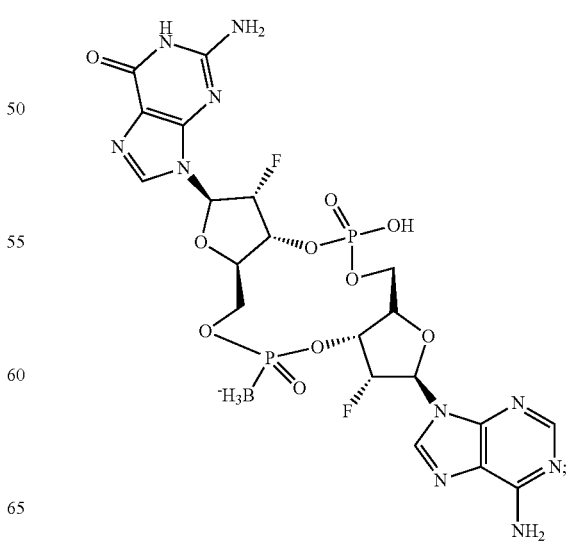

105
-continued
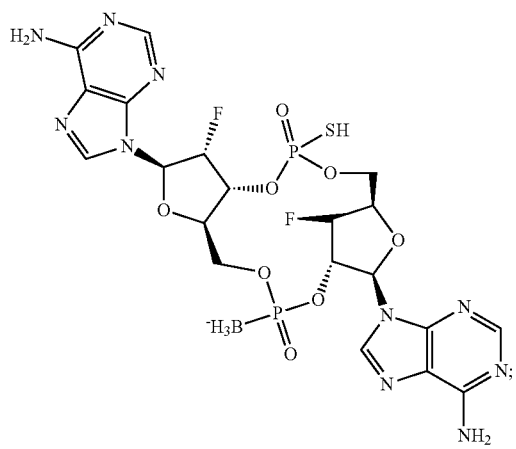
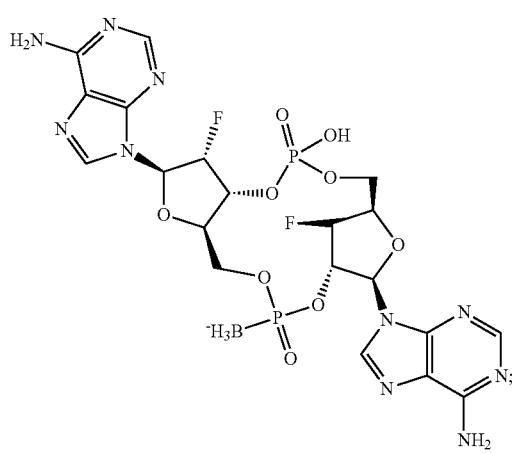
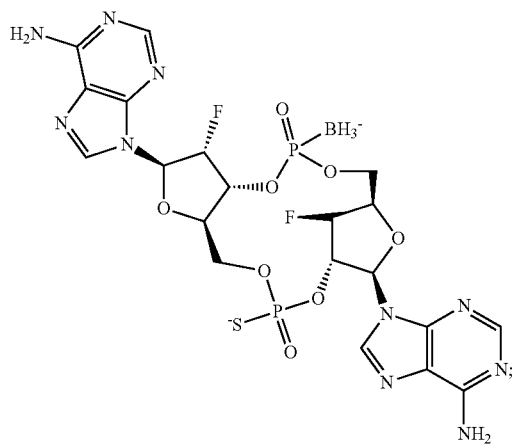
106
-continued
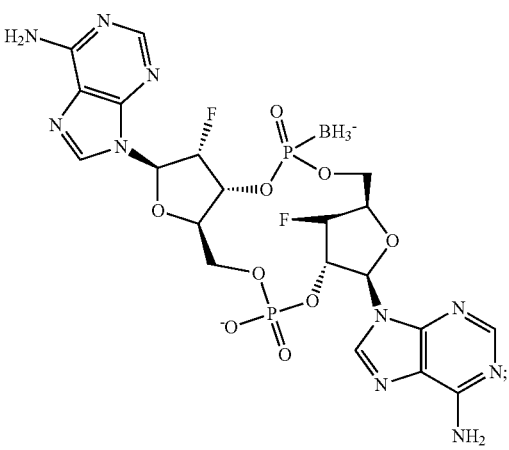
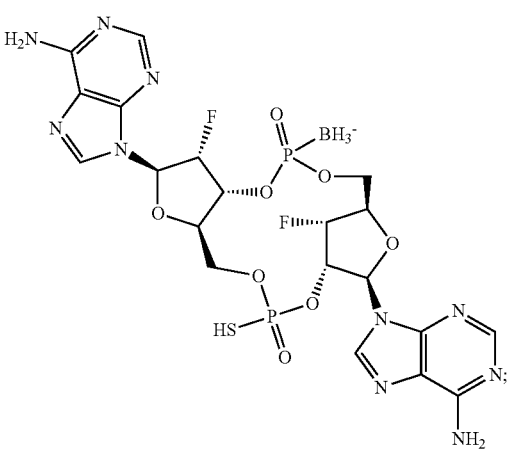
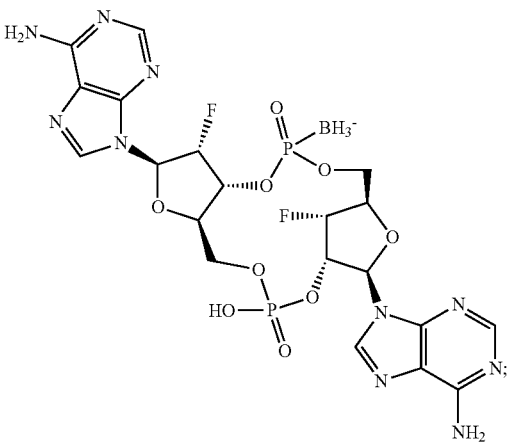

107
-continued
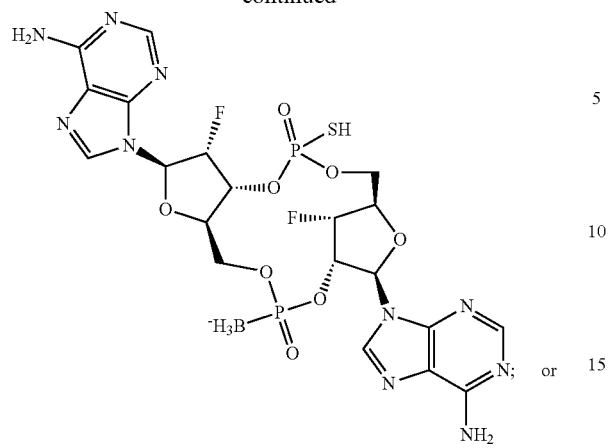
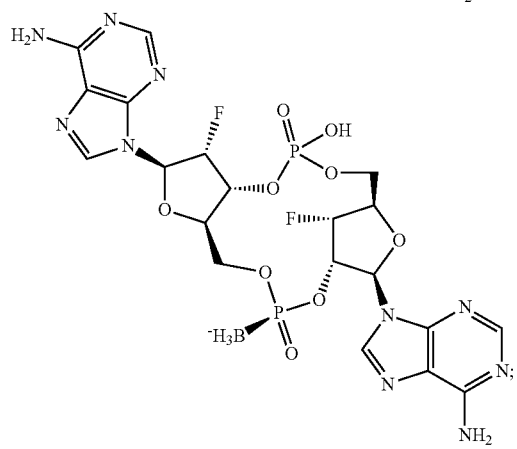
or a pharmaceutically acceptable salt, stereoisomer, solvate or hydrate thereof.
In one embodiment, the compound of the present disclosure is selected from:
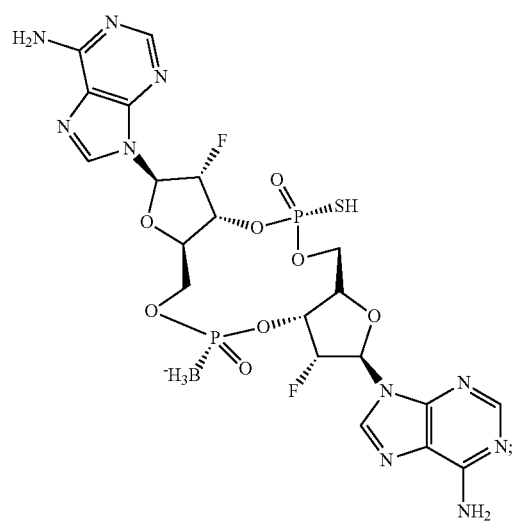
108
-continued
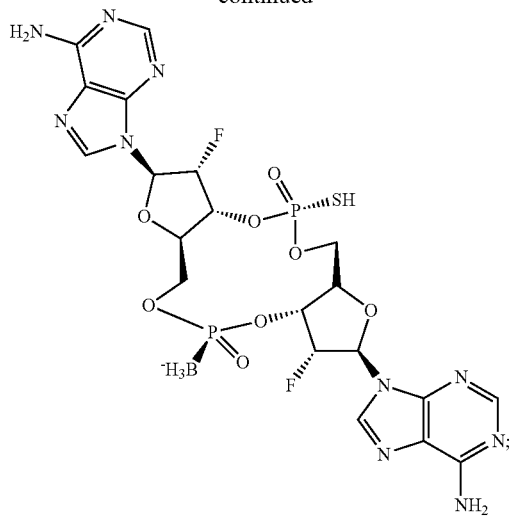
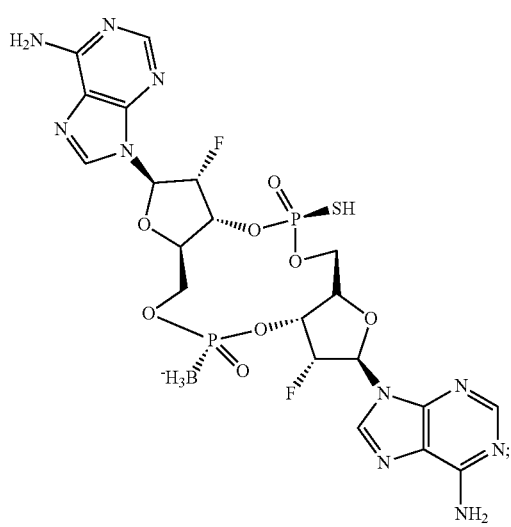
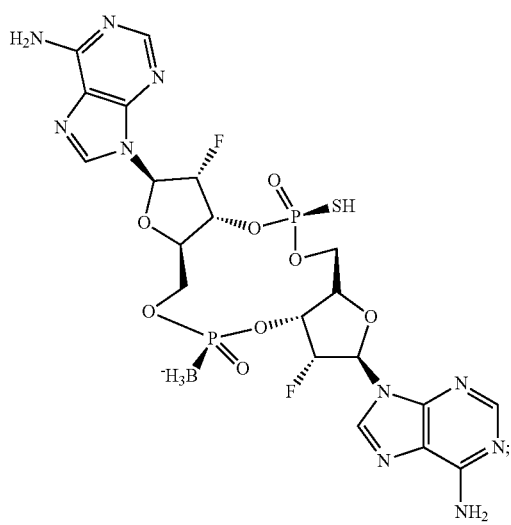

109
-continued
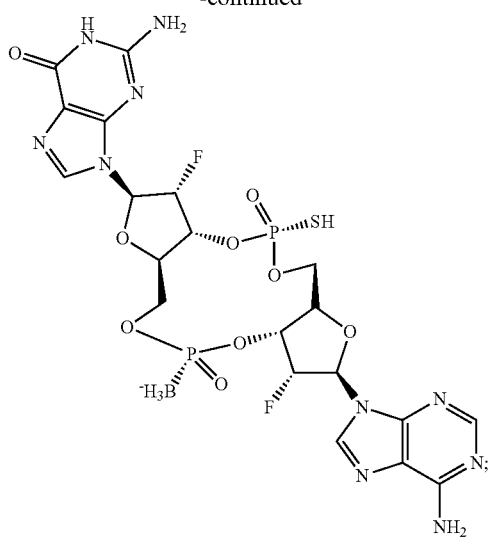
110
-continued
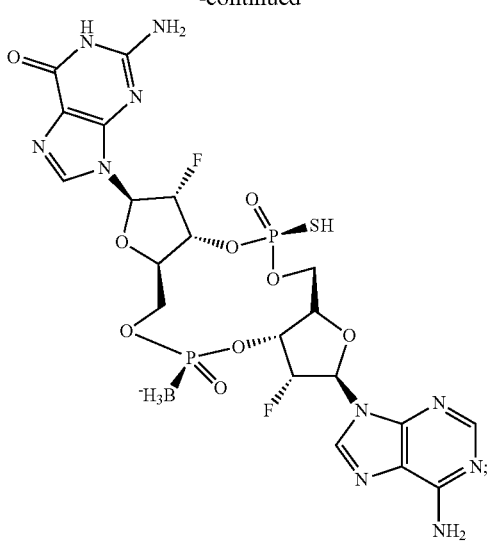
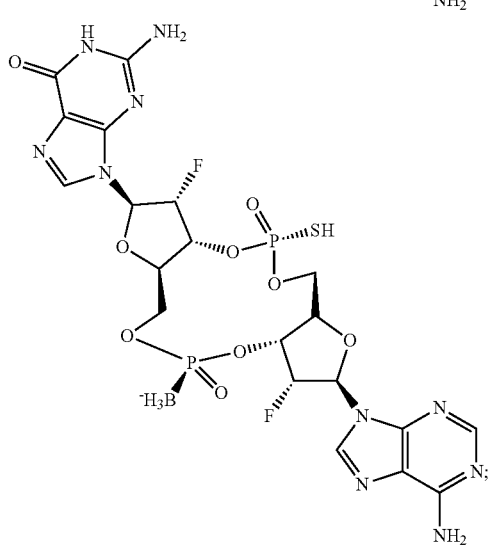
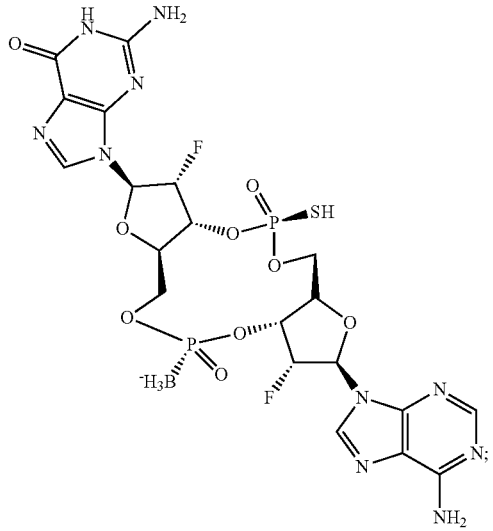
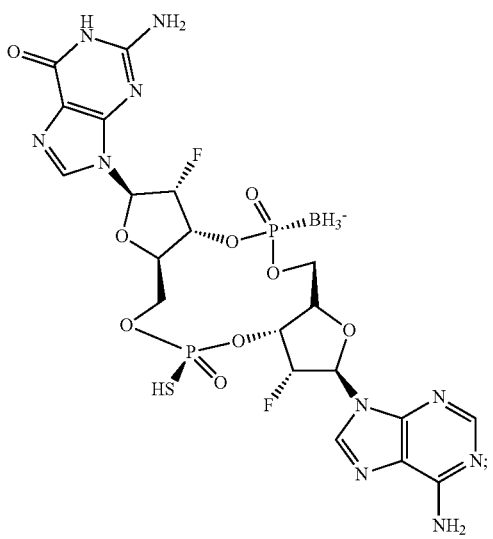

111
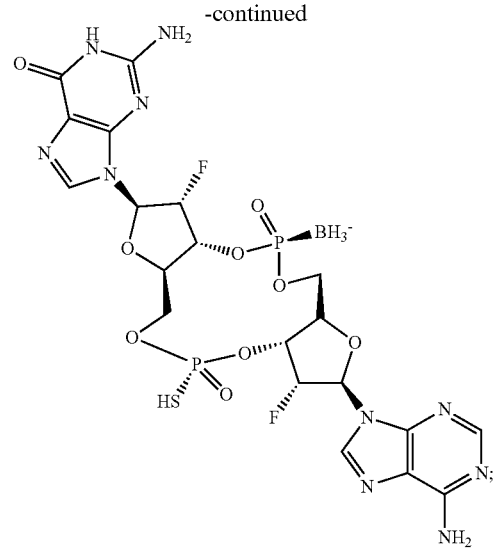
112
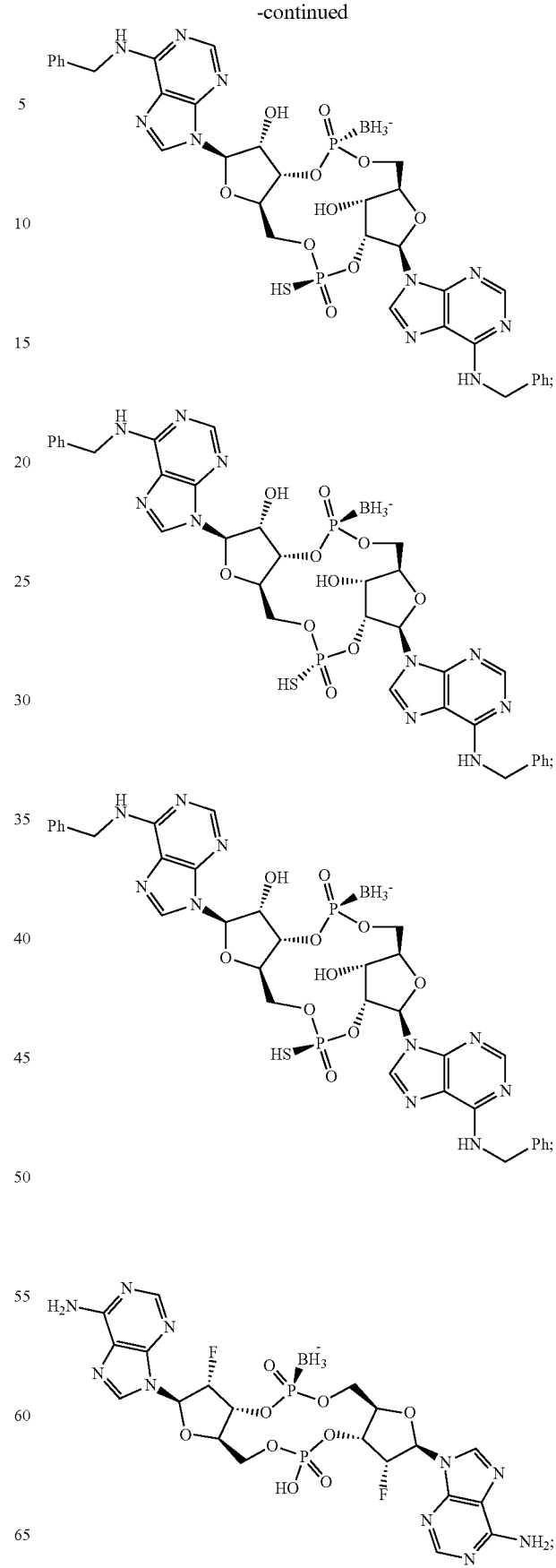

113
-continued
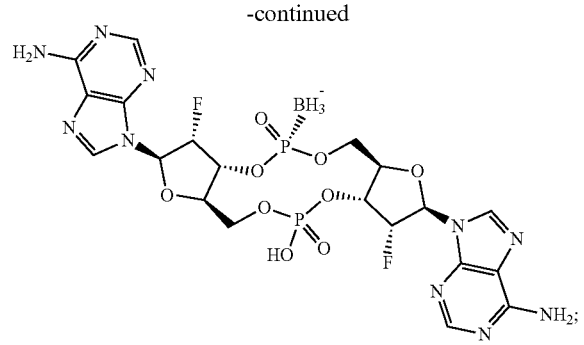
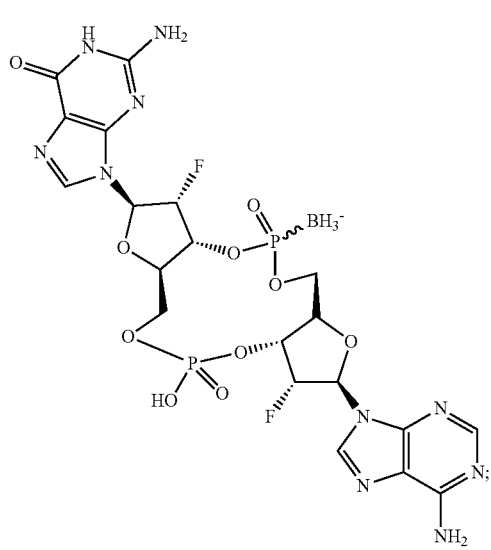
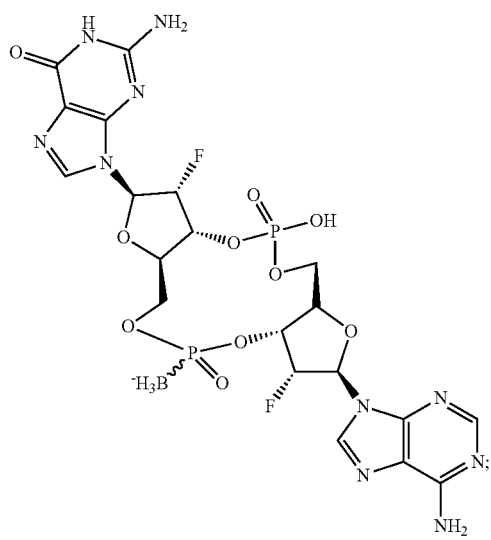
114
-continued
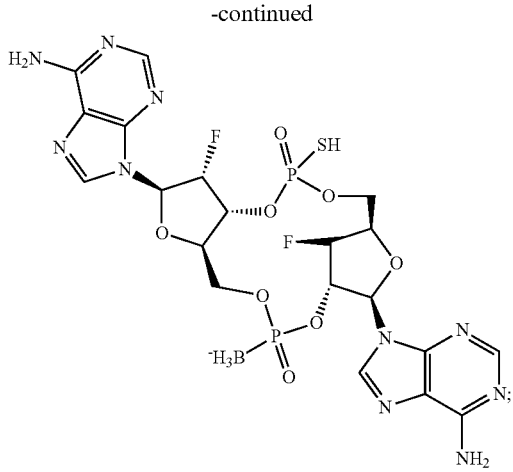
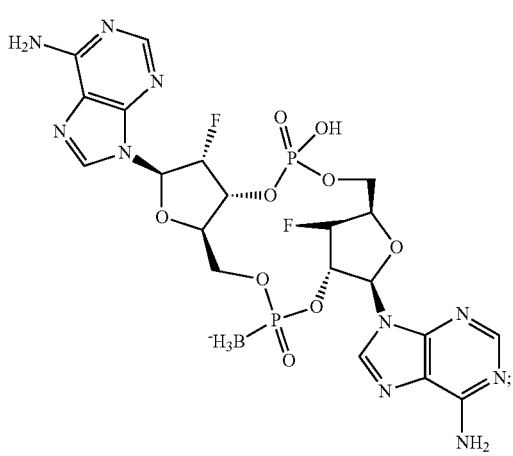
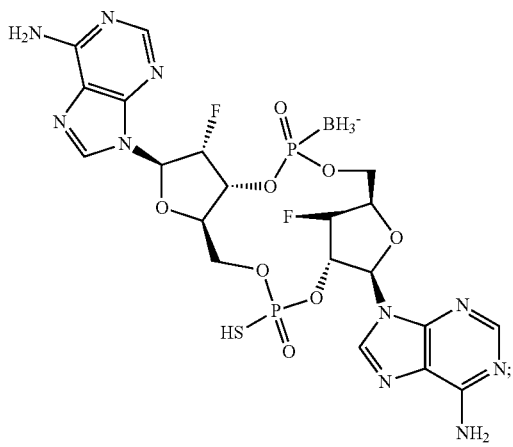

115
-continued
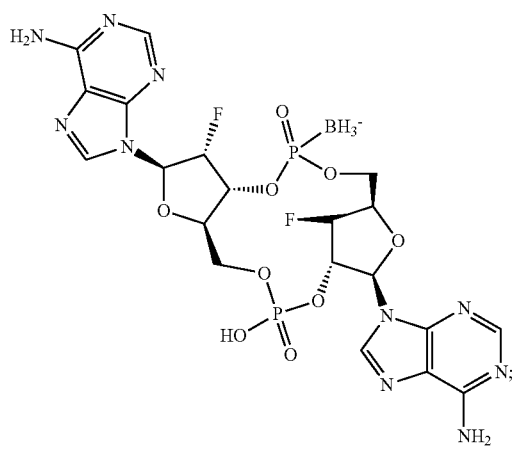
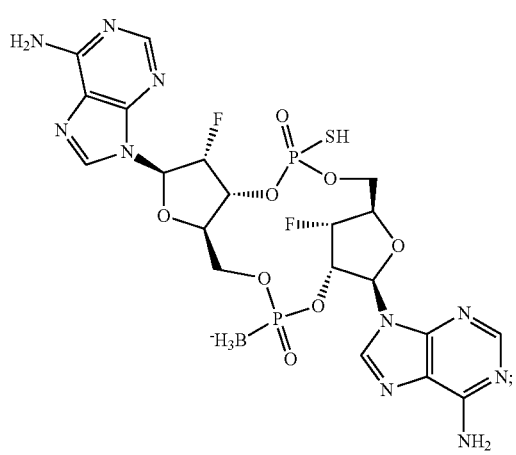
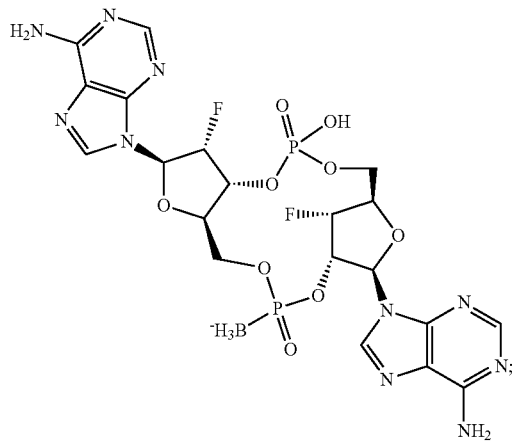
116
-continued
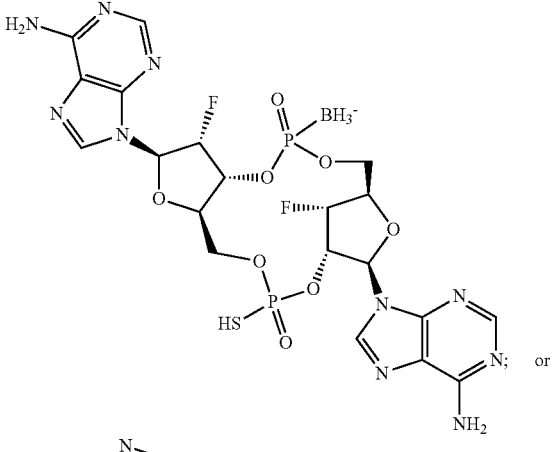
or a pharmaceutically acceptable salt, solvate or hydrate thereof.
In one embodiment of the compounds of formula (I) or (II), the compound has the structure of formula (I-G) or (II-G):
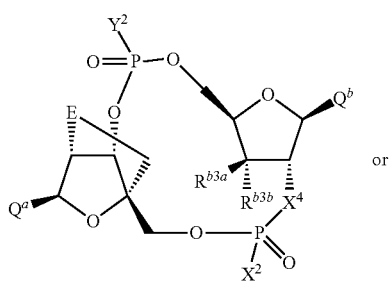
(I-G)
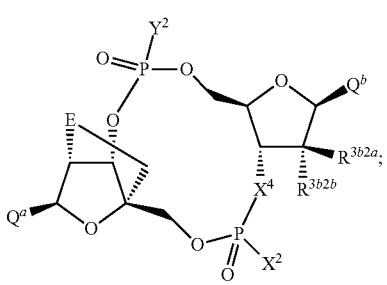
(II-G)

or a pharmaceutically acceptable salt, stereoisomer, solvate or hydrate thereof; wherein:

E is O or S;

$R^{b3a}$, $R^{b3b}$, $R^{3b2a}$, and $R^{3b2b}$ are each independently H, F, or OH;

$X^2$ and $Y^2$ are each independently SH, OH, $NH_2$, or $BH_3^-$; and $X^4$ is O or NH.

In one embodiment of the compounds of formula (I-G) or (II-G), $X^2$ and $Y^2$ are each independently SH, OH, or $BH_3^-$.

In one embodiment of the compounds of formula (I-G) or (II-G), both $X^2$ and $Y^2$ are $BH_3^-$; or at least one of $X^2$ and $Y^2$ is $BH_3^-$, and the other is —OH, —SH, or —$NH_2$;

$R^{b3a}$ and $R^{3b2a}$ are each H; and $R^{b3b}$ and $R^{3b2b}$ are each independently F or OH.

In one embodiment of the compounds of formula (I-G) or (II-G), one of $X^2$ and $Y^2$ is $BH_3^-$, and the other is —OH or —SH. In one embodiment of the compounds of formula (I-G) or (II-G), $X^2$ is $BH_3^-$; and $Y^2$ is —OH or —SH.

In one embodiment, formula (I-G) is a subgenus of formula (I). In some embodiments, various embodiments disclosed herein for formula (I-G) can apply to formula (I). In another embodiment, various embodiments disclosed herein for formula (I) can be applied for formula (I-G), where appropriate.

In one embodiment, formula (II-G) is a subgenus of formula (II). In some embodiments, various embodiments disclosed herein for formula (II-G) can apply to formula (II). In another embodiment, various embodiments disclosed herein for formula (II) can be applied to formula (II-G), where appropriate.

In one embodiment, the present disclosure relates to a compound of formula (A),

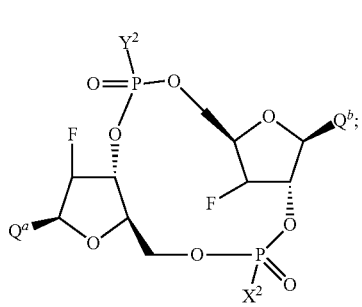

(A)

or a pharmaceutically acceptable salt, stereoisomer, solvate or hydrate thereof, wherein:

$Q^a$ and $Q^b$ are each independently cycloalkyl, heterocyclyl, aryl, or heteroaryl, wherein the cycloalkyl, heterocyclyl, aryl, and heteroaryl can be optionally substituted with one, two, three, four, or five $R^1$;

$R^1$ is each independently hydrogen, halogen, —$NO_2$, —CN, —$OR^{cl}$, —$SR^{cl}$, —$N(R^{cl})_2$, —$C(O)R^{cl}$, —$CO_2R^{cl}$, —$C(O)C(O)R^{cl}$, —$C(O)CH_2C(O)R^{cl}$, —$C(O)N(R^{cl})_2$, —$C(=NR^{cl})N(R^{cl})_2$, —$C(=NOR^{cl})R^{cl}$, —$S(O)R^{cl}$, —$S(O)_2R^{cl}$, —$SO_2N(R^{cl})_2$, —$OC(O)R^{cl}$, —$N(R^{cl})C(O)R^{cl}$, —$NR^{cl}N(R^{cl})_2$, —$N(R^{cl})C(=NR^c)N(R^{cl})_2$, —$N(R^{cl})C(O)N(R^{cl})_2$, —$N(R^{cl})SO_2N(R^{cl})_2$, —$N(R^{cl})SO_2R^{cl}$, —$N(R^{cl})SO_2NR^{cl}C(=O)OR^{cl}$, —$OC(O)N(R^{cl})_2$, or $R^{cl}$;

$R^{cl}$ is each independently H, $C_{1-12}$ alkyl, $C_{2-12}$ alkenyl, $C_{2-12}$ alkynyl, $C_{3-12}$ cycloalkyl, $C_{3-12}$ cycloalkyl-$C_{1-6}$ alkyl-, heterocyclyl, heterocyclyl-$C_{1-6}$ alkyl-, aryl, aryl-$C_{1-6}$ alkyl-, heteroaryl, or heteroaryl-$C_{1-6}$ alkyl-, wherein $C_{1-12}$ alkyl, $C_{2-12}$ alkenyl, $C_{2-12}$ alkynyl, $C_{3-12}$ cycloalkyl, $C_{3-12}$ cycloalkyl-$C_{1-6}$ alkyl-, heterocyclyl, heterocyclyl-$C_{1-6}$ alkyl-, aryl, aryl-$C_{1-6}$ alkyl-, heteroaryl, and heteroaryl-$C_{1-6}$ alkyl- can be substituted one or more substituents selected from $C_{1-6}$ alkyl, halogen, $C_{1-6}$ alkoxy, —$NO_2$, —$NR^{ns}R^{ns}$, —OH, =O, or $COOR^{cs}$; or $R^{ns}$ is each independently H, $R^{cs}$, $R^{cs}$—C(O)—, $R^{cs}$—S(O)_2—, $R^{cs}R^{cs}N$—C(O)—, or $R^{cs}R^{cs}NS(O)_2$—;

$R^{cs}$ is each independently H, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, or $C_2$-$C_6$ haloalkynyl; or alternatively, two $R^{cs}$ attached to the same N atom can together with the N atom form a 4-7 membered heterocyclic ring, containing up to one other heteroatom chosen from O, S, or $NR^{ns}$, wherein the 4-7 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

$X^2$ and $Y^2$ are each independently $SR^4$, $OR^4$, $NR^4R^4$, $BH(OR^7)_2$—, or $BH(R^b)_2^-$; wherein, at least one of $X^2$ and $Y^2$ is $BH(R^b)_2^-$; and $R^b$ is each independently H, CN, carboxyl, carboxyl salts, $C_{1-6}$ alkyl, alkylaryl, aryl, alkoxycarbonyl, or alkylaminocarbonyl, wherein the $C_{1-6}$ alkyl, alkylaryl, aryl, alkoxycarbonyl and alkylaminocarbonyl is each optionally substituted with up to 3 substituents selected from OH, —$P(O)(OH)_2$, —$OP(O)(OH)_2$, $CO_2H$, or F.

In one embodiment of the compound of formula (A), $X^2$ and $Y^2$ are $BH_3$; or at least one of $X^2$ and $Y^2$ is $BH_3^-$, and the other is —OH or —SH.

In one embodiment of the compound of formula (A), $Q^a$ and $Q^b$ are each independently selected from:

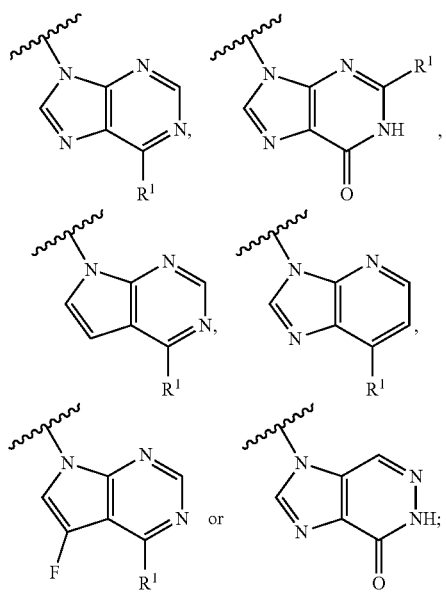

and $R^1$ is each independently hydrogen, halogen, or —$N(R^{cl})_2$, and $R^c$ is each independently H, $C_{1-6}$ alkyl, $C_{3-6}$ cycloalkyl, $C_{3-6}$ cycloalkyl-$C_{1-6}$ alkyl-, 3-6 membered heterocyclyl, (3-6 membered heterocyclyl)-$C_{1-6}$ alkyl-, 5-6 membered aryl, (5-6 membered aryl)-$C_{1-6}$ alkyl-, 5-6 membered heteroaryl, or (5-6 membered heteroaryl)-$C_{1-6}$ alkyl-.

In one embodiment, various embodiments disclosed herein for formula (I), (I-A), (I-B), (I-C), (I-D), (I-E), (I-F), (I-G), (I-X), (I-A'), (I-A''), (I-A'''), (I-A1), (I-A2), (I-A3), or (I-A4), can apply to formula (A). In another embodiment, various embodiments disclosed herein for formula (I) or any subgenera thereof can be applied for formula (A), where appropriate. In one embodiment, formulae (I-A), (I-B), (I-C), (I-D), (I-E), (I-F), (I-G), (I-X), (I-A'), (I-A''), (I-A'''), (I-A1), (I-A2), (I-A3), or (I-A4), are each a subgenus of formula (I).

In one embodiment, the present disclosure relates to a compound of formula (B),

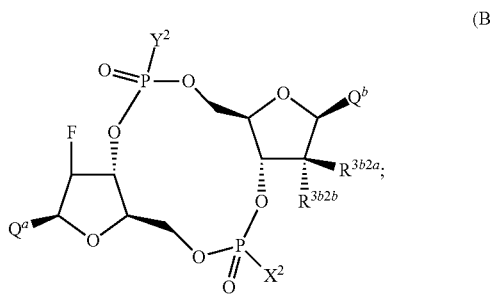

(B)

or a pharmaceutically acceptable salt, stereoisomer, solvate or hydrate thereof, wherein:

$Q^a$ and $Q^b$ are each independently cycloalkyl, heterocyclyl, aryl, or heteroaryl, wherein the cycloalkyl, heterocyclyl, aryl, and heteroaryl can be optionally substituted with one, two, three, four, or five $R^1$;

$R^1$ is each independently hydrogen, halogen, $-NO_2$, $-CN$, $-OR^{cl}$, $-SRl$, $-N(R^{cl})_2$, $-C(O)R^{cl}$, $-CO_2R^{cl}$, $-C(O)C(O)R^{cl}$, $-C(O)CH_2C(O)R^{cl}$, $-C(O)N(R^{cl})_2$, $-C(=NR^{cl})N(R^{cl})_2$, $-C(=NOR^{cl})R^{cl}$, $-S(O)R^{cl}$, $-S(O)_2R^{cl}$, $-SO_2N(R^{cl})_2$, $-OC(O)R^{cl}$, $-N(R^{cl})C(O)R^{cl}$, $-NR^{cl}N(R^{cl})_2$, $-N(R^{cl})C(=NR^{cl})N(R^{cl})_2$, $-N(R^{cl})C(O)N(R^{cl})_2$, $-N(R^{cl})SO_2N(R^{cl})_2$, $-N(R^{cl})SO_2R^{cl}$, $-N(R^{cl})SO_2NR^{cl}C(=O)OR^{cl}$, $-OC(O)N(R^{cl})_2$, or $R^{cl}$;

$R^{cl}$ is each independently H, $C_{1-12}$ alkyl, $C_{2-12}$ alkenyl, $C_{2-12}$ alkynyl, $C_{3-12}$ cycloalkyl, $C_{3-12}$ cycloalkyl-$C_{1-6}$ alkyl-, heterocyclyl, heterocyclyl-$C_{1-6}$ alkyl-, aryl, aryl-$C_{1-6}$ alkyl-, heteroaryl, or heteroaryl-$C_{1-6}$ alkyl-, wherein $C_{1-12}$ alkyl, $C_{2-12}$ alkenyl, $C_{2-12}$ alkynyl, $C_{3-12}$ cycloalkyl, $C_{3-12}$ cycloalkyl-$C_{1-6}$ alkyl-, heterocyclyl, heterocyclyl-$C_{1-6}$ alkyl-, aryl, aryl-$C_{1-6}$ alkyl-, heteroaryl, and heteroaryl-$C_{1-6}$ alkyl- can be substituted one or more substituents selected from $C_{1-6}$ alkyl, halogen, $C_{1-6}$ alkoxy, $-NO_2$, $-NR^{ns}R^{ns}$, $-OH$, $=O$, or $COOR^{cs}$; or $R^{ns}$ is each independently H, $R^{cs}$, $R^{cs}-C(O)-$, $R^{cs}-S(O)_2-$, $R^{cs}R^{cs}N-C(O)-$, or $R^{cs}R^{cs}NS(O)_2-$;

$R^{cs}$ is each independently H, $C_1-C_6$ alkyl, $C_2-C_6$ alkenyl, $C_2-C_6$ alkynyl, $C_1-C_6$ haloalkyl, $C_2-C_6$ haloalkenyl, or $C_2-C_6$ haloalkynyl; or alternatively, two $R^{cs}$ attached to the same N atom can together with the N atom form a 4-7 membered heterocyclic ring, containing up to one other heteroatom chosen from O, S, or $NR^{ns}$, wherein the 4-7 membered heterocyclic ring is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

$R^{3b2a}$ and $R^{3b2b}$ are each independently H, halogen, $-OH$, or $-O(C_{1-3}$ alkyl);

$X^2$ and $Y^2$ are each independently $SR^4$, $OR^4$, $NR^4R^4$, $BH(OR^7)_2^-$, or $BH(R^b)_2^-$; wherein, at least one of $X^2$ and $Y^2$ is $BH(R^b)_2^-$; and $R^b$ is each independently H, CN, carboxyl, carboxyl salts, $C_{1-6}$ alkyl, alkylaryl, aryl, alkoxycarbonyl, or alkylaminocarbonyl, wherein the $C_{1-6}$ alkyl, alkylaryl, aryl, alkoxycarbonyl and alkylaminocarbonyl is each optionally substituted with up to 3 substituents selected from OH, $-P(O)(OH)_2$, $-OP(O)(OH)_2$, $CO_2H$, or F.

In one embodiment of the compound of formula (B), $X^2$ and $Y^2$ are $BH_3^-$; or at least one of $X^2$ and $Y^2$ is $BH_3^-$, and the other is $-OH$ or $-SH$.

In one embodiment of the compound of formula (B), $Q^a$ and $Q^b$ are each independently selected from:

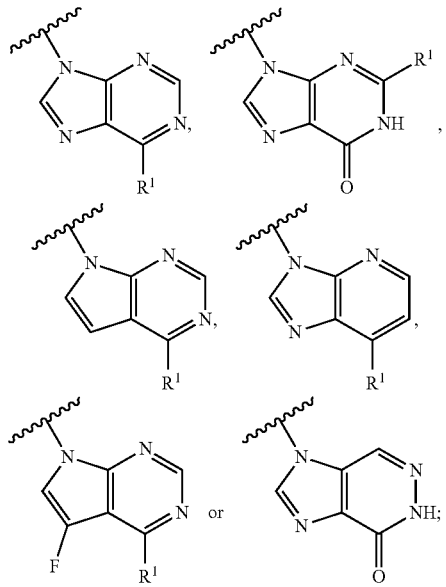

$R^1$ is each independently hydrogen, halogen, or $-N(R^{cl})_2$, and $R^{cl}$ is each independently H, $C_{1-6}$ alkyl, $C_{3-6}$ cycloalkyl, $C_{3-6}$ cycloalkyl-$C_{1-6}$ alkyl-, 3-6 membered heterocyclyl, (3-6 membered heterocyclyl)-$C_{1-6}$ alkyl-, 5-6 membered aryl, (5-6 membered aryl)-$C_{1-6}$ alkyl-, 5-6 membered heteroaryl, or (5-6 membered heteroaryl)-$C_{1-6}$ alkyl-.

In one embodiment of the compound of formula (B), $R^{3b2a}$ and $R^{3b2b}$ are each independently selected from H, F or OH.

In one embodiment, various embodiments disclosed herein for formula (II), (II-A), (II-B), (II-C), (II-D), (II-E), (II-F), (II-G), (II-X), (II-A'), (II-A''), (II-A'''), (II-A1), (II-A2), or (II-A3), can apply to formula (B). In another embodiment, various embodiments disclosed herein for formula (II) or any subgenera thereof can be applied for formula (B), where appropriate. In some embodiments, formulae (II-A), (II-B), (II-C), (II-D), (II-E), (II-F), (II-G), (II-X), (II-A'), (II-A''), (II-A'''), (II-A1), (II-A2), or (II-A3), are each a subgenus of formula (II).

In one embodiment of the present disclosure, a compound of formulae (I), (II), (III), (A), or (B), or a pharmaceutically acceptable salt, stereoisomer, solvate or hydrate thereof, excludes:

2H,7H-Difuro[3,2-d:3',2'-j][1,3,7,9,2,8] tetraoxadiborano-phosphacyclododecin 3'-N²-isopentyl guanylic acid;

2H,7H-Difuro[3,2-d:3',2'-j][1,3,7,9,2,8] tetraoxa diborano-monophosphorothioate cyclododecin 3'-N²-isopentyl-guanylic acid;

2H,7H-Difuro[3,2-d:3',2'-j][1,3,7,9,2,8) tetraoxadiborano-phosphoro dithioate-cyclododecin 3'-N²-isopentyl-guanylic acid; and compounds listed in Tables A and B.

Pharmaceutical Compositions and Formulations

In one embodiment, the present disclosure relates to a pharmaceutical composition comprising a compound of formulae (I), (II), (III), (A), or (B), or any subgenera thereof, or a pharmaceutically acceptable salt, stereoisomer, solvate or hydrate thereof, and one or more pharmaceutically acceptable excipients.

The pharmaceutically acceptable excipients and adjuvants are added to the composition or formulation for a variety of purposes. In another embodiment, a pharmaceutical composition comprising one or more compounds of formulae (I), (II), (III), (A), or (B), or any subgenera thereof, or a pharmaceutically acceptable salt, stereoisomer, solvate or hydrate thereof, further comprises a pharmaceutically acceptable carrier. In one embodiment, a pharmaceutically acceptable carrier includes a pharmaceutically acceptable excipient, binder, and/or diluent. In one embodiment, suitable pharmaceutically acceptable excipients include, but are not limited to, water, salt solutions, alcohol, polyethylene glycols, gelatin, lactose, amylase, magnesium stearate, talc, silicic acid, viscous paraffin, hydroxymethylcellulose and polyvinylpyrrolidone.

In one embodiment, excipients can be used to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

In certain embodiments, the pharmaceutical compositions of the present disclosure may additionally contain other adjunct components conventionally found in pharmaceutical compositions, at their art-established usage levels. Thus, for example, the pharmaceutical compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents.

Liquid formulations may also be prepared by the reconstitution of a solid.

The compounds of the present invention may also be used in fast-dissolving, fast-disintegrating dosage forms such as those described in Expert Opinion in Therapeutic Patents, 11 (6), 981986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colorants, flavoring agents, preservatives and taste-masking agents.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

The foregoing formulations for the various types of administration discussed herein may be in an immediate and/or modified release formulation. Modified release formulations include delayed-, sustained-, pulsed-, controlled-, targeted and programmed release. Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

The solubility of compounds of the present disclosure used in the preparation of parenteral solutions may be increased by the use of appropriate formulation techniques, such as the incorporation of solubility-enhancing agents.

Formulations for parenteral administration may be in an immediate and/or modified release formulation. Thus, compounds of the invention may be formulated as a solid, semi-solid, or thixotropic liquid for administration as an implanted depot providing modified release of the active compound. Examples of such formulations include drug-coated stents and poly (glycolideco-dl-lactide) or PGLA microspheres.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gammacyclodextrins, examples of which may be found in International Patent Applications WO 91/11172, WO 94/02518 and WO 98/55148.

Because of their potential use in medicine, the salts of the compounds of this invention are preferably pharmaceutically acceptable. In one embodiment, the salt of the compounds of the present disclosure in a pharmaceutical formulation or a pharmaceutical composition is a pharmaceutically acceptable salt. Suitable pharmaceutically acceptable salts include, but are not limited to, those described by P. Heinrich Stahl and Camille G. Wermuth in Handbook of Pharmaceutical Salts: Properties, Selection, and Use, 2nd ed. (Wiley-VCH: 2011) and also Remington's Pharmaceutical Sciences, 18th ed. (Mack Publishing, Easton PA: 1990) and also Remington: The Science and Practice of Pharmacy, 19th ed. (Mack Publishing, Easton PA: 1995). Salt encompassed within the term "pharmaceutically acceptable salts" refer to non-toxic salts of the compounds in this invention.

Salts of the compounds of this invention containing a basic amine or other basic functional group may be prepared by any suitable method known in the art, including treatment of the free bases with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, formic acid, alginic acid, pyruvic acid, oxalic acid, glycolic acid, salicylic acid, pyranosildyl acid, such as glucuronic acid or galacturonic acid, alphahydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, glycolate, resinate, lactates, camsylates, tartrates, mandelates, and sulfonates, such as xylenesulfonates, methanesulfonates, propanesulfonates, naphthalene-1-sulfonates and naphthalene-2-sulfonates.

Salts of the compounds of this invention can be prepared by reacting with a suitable base. Pharmaceutically acceptable salts include, but are not limited to: alkali metal salts (especially sodium and potassium), alkaline earth metal salts (especially calcium and magnesium), aluminum salts and ammonium salts, zinc, as well as salts made from physiologically acceptable organic bases such as diethylamine, isopropylamine, olamine, benzathine, benethamine, tromethamine (2-amino-2-(hydroxymethyl)propane-1,3-diol), morpholine, epolamine, piperidine, piperazine, picoline, dicyclohexylamine, N,N'-dibenzylethylenediamine, 2-hydroxyethylamine, tri-(2-hydroxyethyl)amine, chloroprocaine, choline, deanol, imidazole, diethanolamine, ethylenediamine, meglumine (N-methylglucamine), procaine, dibenzylpiperidine, dehydroabietylamine, glucamine, collidine, quinine, quinolone, erbumine and basic amino acids such as lysine and arginine. Additional pharmaceutically acceptable salts are known to those skilled in the art.

Therapeutic Use

In some embodiments, the present invention relates to therapeutic methods in the treatment of diseases and conditions in which modulation of STING (Stimulator of Interferon Genes) is beneficial. In one embodiment, the present disclosure relates to a method of treating a disease or a condition in which the modulation of STING is beneficial in a subject, comprising administering a therapeutically effective amount of a compound of formulae (I), (II), (III), (A), or (B), or any subgenera thereof, or a pharmaceutically acceptable salt, stereoisomer, solvate or hydrate thereof, to the subject in need thereof. In one embodiment, the present disclosure relates to a compound of formulae (I), (II), (A), or (B), or any subgenera thereof, or a pharmaceutically acceptable salt, stereoisomer, solvate or hydrate thereof, for use in treating a disease or a condition in which the modulation of STING is beneficial in a subject.

In one embodiment, the present disclosure relates to a method modulating STING, comprising administering a therapeutically effective amount of a compound of formulae (I), (II), (III), (A), or (B), or any subgenera thereof, or a pharmaceutically acceptable salt, stereoisomer, solvate or hydrate thereof, to the subject in need thereof. In one embodiment, the present disclosure relates to compound of formulae (I), (II), (A), or (B), or any subgenera thereof, or a pharmaceutically acceptable salt, stereoisomer, solvate or hydrate thereof, for use in modulating STING.

In certain embodiment, the present invention relates to a method for inducing, modifying or stimulating an appropriate immune response in a mammal comprising administering to the mammal a therapeutically effective amount of a compound of the invention, or pharmaceutically acceptable salt thereof. In one embodiment, the present disclosure relates to compound of formulae (I), (II), (A), or (B), or any subgenera thereof, or a pharmaceutically acceptable salt, stereoisomer, solvate or hydrate thereof, for use in inducing, modifying or stimulating an appropriate immune response in a mammal. The immune response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression.

In certain embodiments, the compounds of the present disclosure induce STING-dependent type I interferon production in a subject (e.g., a human).

In some embodiments, the diseases or conditions in which modulation of STING is beneficial is cancer.

In some embodiments, the compounds of the present disclosure can be useful in the treatment of cancer. In one embodiment, the present disclosure relates to a method of treating cancer, comprising administering a therapeutically effective amount of a compound of formulae (I), (II), (III), (A), or (B), or any subgenera thereof, or a pharmaceutically acceptable salt, stereoisomer, solvate or hydrate thereof, to the subject in need thereof. In one embodiment, the present disclosure relates to a compound of formulae (I), (II), (A), or (B), or any subgenera thereof, or a pharmaceutically acceptable salt, stereoisomer, solvate or hydrate thereof, for use in treating cancer. Non-limiting examples of cancer include, colorectal cancer, an aero-digestive squamous cancer, a lung cancer, a brain cancer, a liver cancer, a stomach cancer, a bladder cancer, a thyroid cancer, an adrenal cancer, a gastrointestinal cancer, an oropharyngeal cancer, an esophageal cancer, a head and neck cancer, an ovarian cancer, a uterine cancer, a cervical cancer, an endometrial cancer, a breast cancer, a melanoma, a prostate cancer, a pancreatic carcinoma, a renal carcinoma, a sarcoma, a leukemia, a lymphoma and a multiple myeloma.

In one embodiment, the present disclosure relates to a method of treating a disease, comprising administering a therapeutically effective amount of a compound of formulae (I), (II), (III), (A), or (B), or any subgenera thereof, or a pharmaceutically acceptable salt, stereoisomer, solvate or hydrate thereof, to the subject in need thereof, wherein the disease is selected from cancer, rheumatoid arthritis, psoriasis, acute rejection of an organ transplant, allergic asthma or Crohn's disease. In one embodiment, the present disclosure relates to a compound of formulae (I), (II), (A), or (B), or any subgenera thereof, or a pharmaceutically acceptable salt, stereoisomer, solvate or hydrate thereof, for use in treating a disease, wherein the disease is selected from cancer, rheumatoid arthritis, psoriasis, acute rejection of an organ transplant, allergic asthma or Crohn's disease.

In one embodiment, the diseases or conditions in which modulation of STING is beneficial are neurological disorders. In some embodiments, the compounds of the present disclosure can be useful in the treatment of a neurological disorder, which includes, but is not limited to, disorders that involve the central nervous system (brain, brainstem and cerebellum), the peripheral nervous system (including cranial nerves), and the autonomic nervous system (parts of which are located in both central and peripheral nervous system). Non-limiting examples of cancer include acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Alzheimer's disease; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telegiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; Dandy-Walker syndrome; Dawson disease; De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Kearns-Sayre syndrome; Kennedy disease Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease;

Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; milti-infarct dementia; multifocal motor neuropathy; multiple sclerosis and other demyelinating disorders; multiple system atrophy with postural hypotension; p muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocal leukoencephalopathy; progressive sclerosing poliodystrophy; progressive supranuclear palsy; pseudotumor cerebri; Ramsay-Hunt syndrome (types I and II); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjögren's syndrome; sleep apnea; Soto's syndrome; spasticity; *spina bifida*; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildon's disease; and Zellweger syndrome.

In one embodiment, the diseases or conditions in which modulation of STING is beneficial are autoimmune diseases and disorders. In some embodiments, the compounds of the present disclosure can be useful in the treatment of an autoimmune disease. Non-limiting examples include rheumatoid arthritis, systemic lupus erythematosus, multiple sclerosis, inflammatory bowel diseases (IBDs) comprising Crohn disease (CD) and ulcerative colitis (UC), which are chronic inflammatory conditions with polygenic susceptibility. In certain embodiments, the condition is an inflammatory bowel disease. In certain embodiments, the condition is Crohn's disease, autoimmune colitis, iatrogenic autoimmune colitis, ulcerative colitis, colitis induced by one or more chemotherapeutic agents, colitis induced by treatment with adoptive cell therapy, colitis associated by one or more alloimmune diseases (such as graft-vs-host disease, e.g., acute graft vs. host disease and chronic graft vs. host disease), radiation enteritis, collagenous colitis, lymphocytic colitis, microscopic colitis, and radiation enteritis. In certain of these embodiments, the condition is alloimmune disease (such as graft-vs-host disease, e.g., acute graft vs. host disease and chronic graft vs. host disease), celiac disease, irritable bowel syndrome, rheumatoid arthritis, lupus, scleroderma, psoriasis, cutaneous T-cell lymphoma, uveitis, and mucositis (e.g., oral mucositis, esophageal mucositis or intestinal mucositis).

In one embodiment, the present disclosure relates to modulation of the immune system by STING comprising administering a therapeutically effective amount of the compounds of the present disclosure. In some embodiments, modulation of the immune system by STING provides for the treatment of diseases, such as diseases caused by foreign agents. Exemplary infections by foreign agents which may be treated and/or prevented by the method of the present invention include an infection by a bacterium (e.g., a Gram-positive or Gram-negative bacterium), an infection by a fungus, an infection by a parasite, and an infection by a virus. In one embodiment of the present invention, the infection is a bacterial infection (e.g., infection by *E. coli, Klebsiella pneumoniae, Pseudomonas aeruginosa, Salmonella* spp., *Staphylococcus aureus, Streptococcus* spp., or vancomycin-resistant *enterococcus*). In another embodiment, the infection is a fungal infection (e.g. infection by a mold, an yeast, or a higher fungus). In still another embodiment, the infection is a parasitic infection (e.g., infection by a single-celled or multicellular parasite, including *Giardia duodenalis, Cryptosporidium parvum, Cyclospora cayetanensis*, and *Toxoplasma* gondiz). In yet another embodiment, the infection is a viral infection (e.g., infection by a virus associated with AIDS, avian flu, chickenpox, cold sores, common cold, gastroenteritis, glandular fever, influenza, measles, mumps, pharyngitis, pneumonia, rubella, SARS, and lower or upper respiratory tract infection (e.g., respiratory syncytial virus).

In one embodiment, the disease or condition in which modulation of STING is beneficial is hepatitis B. In some embodiments, the compounds of the present disclosure can be useful in the treatment of hepatitis B (see, e.g., WO 2015/061294).

In one embodiment, the disease or condition in which modulation of STING is beneficial is mucositis. In some embodiments, the compounds of the present disclosure can be useful in the treatment of mucositis, also known as stomatitits, which can occur as a result of chemotherapy or radiation therapy, either alone or in combination as well as damage caused by exposure to radiation outside of the context of radiation therapy.

In one embodiment, the disease or condition in which modulation of STING is beneficial is uveitis. In some embodiments, the compounds of the present disclosure can be useful in the treatment of uveitis, which is inflammation of the uvea (e.g., anterior uveitis, e.g., iridocyclitis or iritis; intermediate uveitis (also known as pars planitis); posterior uveitis; or chorioretinitis, e.g., pan-uveitis).

Combination Therapy

In some embodiments, the methods described herein can further comprise administering one or more additional therapies (e.g., one or more additional therapeutic agents and/or one or more therapeutic regimens) in combination with administration of the compounds of the present disclosure.

The compounds or pharmaceutical compositions of the present disclosure may be co-administered with one or more therapeutically active agent. The term "co-administration" or "coadministration" refers to administration of (a) compound of formula (I), (II), (III), (A), or (B), or any subgenera thereof, or a pharmaceutically acceptable salt, stereoisomer, solvate, or hydrate thereof, and (b) at least one additional therapeutically active agent, together in a coordinated fashion. For example, the co-administration can be simultaneous administration, sequential administration, overlapping administration, interval administration, continuous administration, or a combination thereof. In one embodiment, the compound of the present disclosure and at least one additional therapeutically active agent are formulated into a single dosage form. In another embodiment, the compound of the present disclosure and at least one additional therapeutically active agent are provided in a separate dosage forms.

In certain embodiment, the one or more additional therapeutic agent is selected from the group consisting of an immune checkpoint inhibitor (e.g. CTLA-4, PD-1, Tim-3, Vista, BTLA, LAG-3 and TIGIT pathway antagonists; PD-1 pathway blocking agents; PD-L1 inhibitors; including without limitation anti-PD-1 antibodies nivolumab, pembrolizumab or pidilizumab; PD-1 inhibitor AMP-224; anti-CTLA-4 antibody ipilimumab; and anti-PD-L1 antibodies BMS-936559, MPDL3280A, MED14736, or avelumab); a TLR agonist (e.g. CpG or monophosphoryl lipid A); an inactivated or attenuated bacteria which induce innate immunity (e.g., inactivated or attenuated *Listeria monocytogenes*); a composition that mediates innate immune activation via Toll-like Receptors (TLRs), via (NOD)-like receptors (NLRs), via Retinoic acid inducible gene-based (RIG)-I-like receptors (RLRs), via C-type lectin receptors (CLRs), or via pathogen-associated molecular patterns (PAMPs); and a chemotherapeutic agent.

In certain embodiment, the compound of the present invention can be used in combination with a Toll like receptor agonist. The term "Toll like receptor" (or "TLR") as used herein refers to a member of the Toll-like receptor family of proteins or a fragment thereof that senses a microbial product and/or initiates an adaptive immune response. In one embodiment, a TLR activates a dendritic cell (DC). Toll like receptors (TLRs) are a family of pattern recognition receptors that were initially identified as sensors of the innate immune system that recognize microbial pathogens. TLRs comprise a family of conserved membrane spanning molecules containing an ectodomain of leucine-rich repeats, a transmembrane domain and an intracellular TIR (Toll/IL-1R) domain. TLRs recognize distinct structures in microbes, often referred to as "PAMPs" (pathogen associated molecular patterns). Ligand binding to TLRs invokes a cascade of intra-cellular signaling pathways that induce the production of factors involved in inflammation and immunity. TLR agonists known in the art and finding use in the present invention include, but are not limited to, the following: Pam3Cys, a TLR-1/2 agonist; CFA, a TLR-2 agonist; MALP2, a TLR-2 agonist; Pam2Cys, a TLR-2 agonist; FSL-1, a TLR-2 agonist; Hib-OMPC, a TLR-2 agonist; polyribosinic:polyribocytidic acid (Poly I:C), a TLR-3 agonist; polyadenosine-polyuridylic acid (poly AU), a TLR-3 agonist; Polyinosinic-Polycytidylic acid stabilized with poly-L-lysine and carboxymethylcellulose (Hiltonol®), a TLR-3 agonist; monophosphoryl lipid A (MPL), a TLR-4 agonist; LPS, a TLR-4 agonist; bacterial flagellin, a TLR-5 agonist; sialyl-Tn (STn), a carbohydrate associated with the MUC1 mucin on a number of human cancer cells and a TLR-4 agonist; imiquimod, a TLR-7 agonist; resiquimod, a TLR-7/8 agonist; loxoribine, a TLR-7/8 agonist; and unmethylated CpG dinucleotide (CpG-ODN), a TLR-9 agonist.

In certain embodiment, the compound of the present invention can be used in combination with therapeutic antibodies. In some embodiments, the mechanism of action of the therapeutic antibody is Antibody-Dependent Cell-Mediated Cytotoxicity (ADCC). ADCC is a mechanism of cell-mediated immune defense whereby an effector cell of the immune system actively lyses a target cell, whose membrane-surface antigens have been bound by specific antibodies. It is one of the mechanisms through which antibodies, as part of the humoral immune response, can act to limit and contain infection. Classical ADCC is mediated by natural killer (NK) cells; macrophages, neutrophils and eosinophils can also mediate ADCC. ADCC is an important mechanism of action of therapeutic monoclonal antibodies, including trastuzumab and rituximab, against tumors. Compounds of the present invention may act to potentiate ADCC. The following are an exemplary list of antibodies which may be used together with the compounds of the present invention. Muromonab-CD3 is used to prevent acute rejection of organ, e.g., kidney transplants. The humanized versions show promise in inhibiting the autoimmune destruction of beta cells in Type 1 diabetes mellitus; Infliximab (Remicade®) and adalimumab (Humira®), which bind to tumor necrosis factor-alpha (TNF-a) and is used in some inflammatory diseases such as rheumatoid arthritis, psoriasis, Crohn's disease; Omalizumab (Xolair®), which binds to IgE thus preventing IgE from binding to mast cells and is used against allergic asthma; Daclizumab (Zenapax®), which binds to part of the IL-2 receptor exposed at the surface of activated T cells and is used to prevent acute rejection of transplanted kidneys; Rituximab (trade name=Rituxan®), which binds to the CD20 molecule found on most B-cells and is used to treat B-cell lymphomas; Ibritumomab (trade name=Zevalin®) is a monoclonal antibody against the CD20 molecule on B cells (and lymphomas) conjugated to isotopes and is given to the lymphoma patient supplemented with Rituxan; Tositumomab (Bexxar®), which is a conjugate of a monoclonal antibody against CD20 and the radioactive isotope iodine-131 (131I); Cetuximab (Erbitux®), which blocks HER1, a receptor for epidermal growth factor (EGF) that is found on some tumor cells (some breast cancers, lymphomas); Trastuzumab (Herceptin®), which blocks HER2, a growth factor receptor over-expressed in some 20% of breast cancers; Adcetris®, which is a conjugate of a monoclonal antibody that binds CD30, a cell-surface molecule expressed by the cells of some lymphomas but not found on the normal stem cells needed to repopulate the bone marrow; Alemtuzumab (Campath-1H®), which binds to CD52, a molecule found on lymphocytes and depletes both T cells and B cells, has produced complete remission of chronic lymphocytic leukemia and shows promise in preventing rejection of kidney transplants; Lym-1 (Oncolym®), which binds to the HLA-DR-encoded histocompatibility antigen that can be expressed at high levels on lymphoma cells; Ipilimumab (Yervoy®), which acts to enhance the body's own immune response to tumors; Vitaxin Binds to a vascular integrin (alpha-v/beta-3) found on the blood vessels of tumors but not on the blood vessels supplying normal tissues; Bevacizumab (Avastin®), which binds to vascular endothelial growth factor (VEGF) preventing it from binding to its receptor and is used for the treatment of colorectal cancers; Abciximab (ReoPro®), which inhibits the clumping of platelets by binding the receptors on their surface that normally are linked by fibrinogen.

Additional therapeutic antibodies that may be used in combination with the compounds of the present invention as described herein include a prolactin receptor (PRLR) inhibitor, e.g. as disclosed in U.S. Pat. No. 7,867,493, a HER3 inhibitor, e.g. as disclosed in PCT Publication No. WO2012/022814, an EGFR2 and/or EGFR4 inhibitor, e.g. as disclosed in PCT Publication No. WO2014/160160, an M-CSF inhibitor, e.g. as disclosed in PCT Publication No. WO2004/045532, an anti-APRIL antibody, e.g. as disclosed in U.S. Pat. No. 8,895,705, or an anti-SIRPα or anti-CD47 antibody, e.g. as disclosed in U.S. Pat. Nos. 8,728,476 and 8,562,997.

In certain embodiment, the compounds of the present invention as described herein can be used in combination with an immune checkpoint inhibitor, such as an immune checkpoint inhibitor selected from the group consisting of a CTLA-4 pathway antagonist, a PD-1 pathway antagonist, a Tim-3 pathway antagonist, a Vista pathway antagonist, a BTLA pathway antagonist, a LAG-3 pathway antagonist, and a TIGIT pathway antagonist.

In certain embodiment, the compounds of the present invention are used in combination with chemotherapeutic agents (e.g. small molecule pharmaceutical compounds). Thus, the methods of the present disclosure further involve administering to the subject an effective amount of one or more chemotherapeutic agents as an additional treatment or a combination treatment. In certain embodiments the one or more chemotherapeutic agents is selected from the group consisting of sotrastaurin, nilotinib, 5-(2,4-dihydroxy-5-isopropylphenyl)-N-ethyl-4-(4-(morpholinomethyl)phenyl) isoxazole-3-carboxamide, dactolisib, 8-(6-Methoxy-pyridin-3-yl)-3-methyl-1-(4-piperazin-1-yl-3-trifluoromethyl-phenyl)-1,3-dihydro-imidazo[4,5-c]quinolin-2-one, 3-(2,6-dichloro-3,5-dimethoxyphenyl)-1-(6-((4-(4-ethylpiperazin-1-yl)phenyl)amino)pyrimidin-4-yl)-1-methylurea, buparlisib, 8-(2,6-difluoro-3,5-dimethoxyphenyl)-N-(4-((dimethylamino)methyl)-1H-imidazol-2-yl)quinoxaline-5-carboxamide, (S)-N1-(4-methyl-5-(2-(1,1,1-trifluoro-2-methylpropan-2-yl)pyridin-4-yl)thiazol-2-yl)pyrrolidine-1,2-dicarboxamide, (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one, deferasirox, letrozole, (4S,5R)-3-(2'-amino-2-morpholino-4'-(trifluoromethyl)-[4,5'-bipyrimidin]-6-yl)-4-(hydroxymethyl)-5-methyloxazolidin-2-one, (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one, 4-((2-(((1R,2R)-2-hydroxycyclohexyl)amino)benzo[d]thiazol-6-yl)oxy)-N-methylpicolinamide, imatinib mesylate, 2-fluoro-N-methyl-4-(7-(quinolin-6-ylmethyl)imidazo[1,2-b][1,2,4]triazin-2-yl)benzamide, ruxolitinib, panobinostat, osilodrostat, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide, sonidegib phosphate, ceritinib, 7-cyclopentyl-N,N-dimethyl-2-((5-(piperazin-1-yl)pyridin-2-yl)amino)-7H-pyrrolo[2,3-d]pyrimidine-6-carboxamide, N-(4-((1R,3S,5S)-3-amino-5-methylcyclohexyl)pyridin-3-yl)-6-(2,6-difluorophenyl)-5-fluoropicolinamide, 2-(2',3-dimethyl-[2,4'-bipyridin]-5-yl)-N-(5-(pyrazin-2-yl)pyridin-2-yl)acetamide, encorafenib, 7-cyclopentyl-N,N-dimethyl-2-((5-(((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide, binimetinib, midostaurin, everolimus, 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine, pasireotide diaspartate, dovitinib, (R,E)-N-(7-chloro-1-(1-(4-(dimethylamino)but-2-enoyl)azepan-3-yl)-1H-benzo[d]imidazol-2-yl)-2-methylisonicotinamide, N6-(2-isopropoxy-5-methyl-4-(1-methylpiperidin-4-yl)phenyl)-N4-(2-(isopropylsulfonyl)phenyl)-1H-pyrazolo[3,4-d]pyrimidine-4,6-diamine, 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide, 5-chloro-N2-(2-fluoro-5-methyl-4-(1-(tetrahydro-2H-pyran-4-yl)piperidin-4-yl)phenyl)-N4-(5-methyl-1H-pyrazol-3-yl)pyrimidine-2,4-diamine, 5-chloro-N2-(4-(1-ethylpiperidin-4-yl)-2-fluoro-5-methylphenyl)-N4-(5-methyl-1H-pyrazol-3-yl)pyrimidine-2,4-diamine, valspodar, and vatalanib succinate.

In certain embodiment, the compounds of the present invention are administered in conjunction with one or more vaccines intended to stimulate an immune response to one or more predetermined antigens. Examples of target antigens that may find use in the invention include, but are not limited to, tumor antigens: mesothelin, Wilms' tumor-1 associated protein, including isoform A; isoform B, isoform C; isoform D, stratum corneum chymotryptic enzyme and variants et al, MHC class I chain-related protein A and MHC class I chain-related protein B, CCK-B, glypican-3, coactosin-like protein, prostate stem cell antigen, PAP, PSA, PSM, PSMA, STEAP, PCTA-1, PTI-1, prostase, proteinase 3, cancer testis antigens etc. This list is not meant to be limiting.

Administration and Dosages

Administration of the compounds of the present invention may be effected by any method that enables delivery of the compounds to the site of action. These methods includes a variety of means including, but are not limited to, non-parenterally, parenterally, inhalation spray, topically, or rectally in formulations containing pharmaceutically acceptable carriers, adjuvants and vehicles. "Non-parenteral administration" encompasses oral, buccal, sublingual, topical, transdermal, ophthalmic, otic, nasal, rectal, cervical, pulmonary, mucosal, and vaginal routes. The term parenteral as used here includes but is not limited to subcutaneous, intravenous, intramuscular, intraarterial, intradermal, intrathecal and epidural injections with a variety of infusion techniques. Intraarterial and intravenous injection as used herein includes administration through catheters. Administration via intracoronary stents and intracoronary reservoirs is also contemplated. Intra-tumoral (directly into the tumor mass) or peri-tumoral (around the tumor mass) administration of the compounds of the present invention may directly activate locally infiltrating DC, directly promote tumor cell apoptosis or sensitize tumor cells to cytotoxic agents.

In one embodiment, the compounds of the present invention may be administered orally. Oral administration may involve swallowing, so that the compound enters the gastrointestinal tract, or buccal or sublingual administration may be employed by which the compound enters the blood stream directly from the mouth.

The compounds of the present invention may also be administered directly into the blood stream, into muscle, into an internal organ or into a tumor. Suitable means for parenteral administration include intravenous, intraarterial, intraperitoneal, intrathecal, intraventricular, intraurethral, intrasternal, intracranial, intramuscular, intra-tumoral (directly into the tumor mass), peri-tumoral (around the tumor mass) and subcutaneous. Suitable devices for parenteral administration include needle (including microneedle) injectors, needle-free injectors and infusion techniques.

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Method of Making

Compounds of the invention and intermediates thereof can be prepared in a number of ways known to one of ordinary skill in the art of organic synthesis. Non-limiting examples are illustrated below. It is understood by one skilled in the art that these methods are representative, and are not limiting. Some of the compounds described herein can be synthesized by methods described in US2015/0056224, WO2017/027645 or WO2017/027646, the contents of each of which are hereby incorporated by reference in their entirety. Starting materials and intermediates can be purchased from commercial sources or can be made from known procedures. The skilled artisan will also recognize that conditions and reagents described herein can be interchanged with alternative art-recognized equivalents.

The variations of the examples provided below within the scope of the claims are within the purview of one skilled in the art and are considered to fall within the scope of the invention as described and claimed herein. The reader will recognize that the skilled artisan, provided with the present disclosure will able to prepare and use the invention without exhaustive examples.

General Synthesis of Boranophosphates

The general synthetic methods for boranophosphates can be found in Chem. Rev. 2007, 107, 4746-4796, which is hereby incorporated by reference. The synthesis of boranophosphate through phosphoramidite is well documented. One of example is outlined as Scheme 1.

Reaction of 5'-DMTr-nucleoside phosphoramidite with a free 5'-OH nucleoside in the presence of 1H-tetrazole can result in the formation of an intermediate, phosphite triester, which can then converted to the dinucleoside boranophosphate (boranophosphotriester) by oxidation with dimethyl sulfide-borane.

Scheme 1. Synthesis of Dinucleoside Boranophosphate

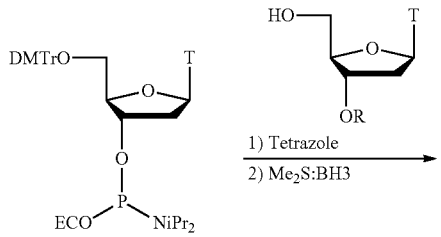

-continued

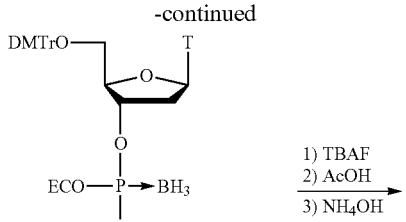

Jin, Y.; Just, G. *Tetrahedron Lett.* 1998, 39, 6429 (Scheme 1).

Boranophosphates can also be synthesized through H-phosphonate. As illustrated in Schemes 2A and 2B, conversion of the H-phosphonate diester to an activated phosphite triester can be achieved by silylation with BSA, In situ boronation with excessive DIPEA: $BH_3$ or $BH_3 \cdot SMe_2$ can result in the formation of boranophosphotriester. The desired dinucleoside boranophosphate diester can be obtained after the removal of protection groups by $NH_4OH$.

Scheme 2A. Synthesis of Dinucleoside Boranophosphate via H-phosphonate

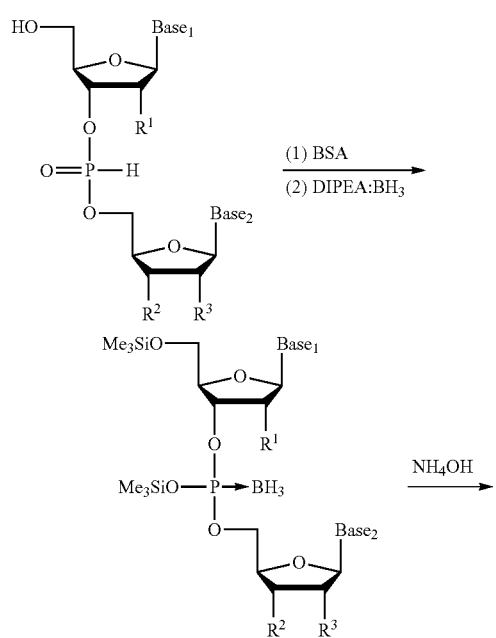

-continued

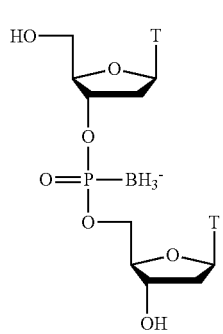

| Dimer | Base₁ | Base₂ | R¹ | R² | R³ | R⁴ | R⁵ |
|---|---|---|---|---|---|---|---|
| a: $T^b_pT$ | T | T | H | OAc | H | H | H |
| b: $U^b_pU$ | U | U | OBTDMS | OBz | OBz | OH | OH |
| c: $U^b_pA$ | U | A | OBTDMS | OAc | OAc | OH | OH |

He, K. Z.; Sergueev, D. S.; Sergueeva, Z. A.; Shaw, B. R. *Tetrahedron Lett.* 1999, 40, 4601. (Scheme 2A)

Scheme 2B. Synthesis of Dinucleoside Boranophosphate via H-phosphonate

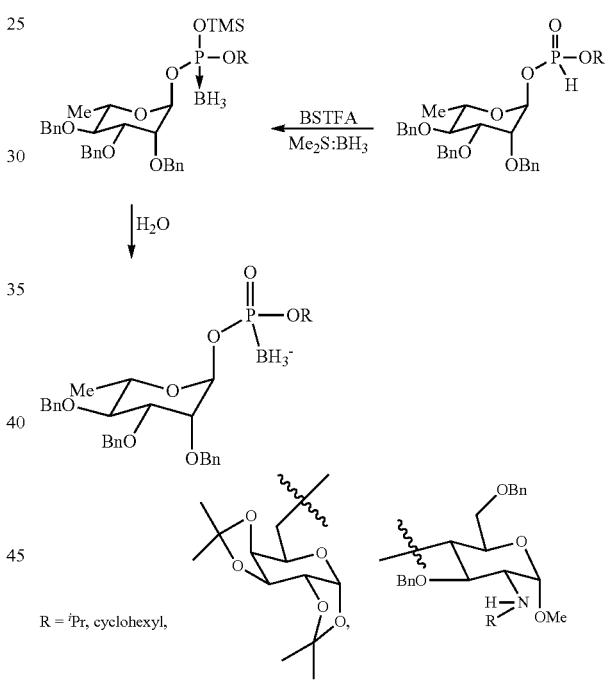

Prosperi, D.; Panza, L.; Poletti, L.; Lay, L. *Tetrahedron* 2000, 56, 4811. (Scheme 2B).

Based on literature as mentioned above, the general synthetic routes for boranophosphates containing (2'-5')(3'-5') phosphodiester internucleotidic linkage (denoted as 2',3') are shown below (Schemes 3-8). If the 2'-5' linkage of 2',3'-cyclic dinucleotide is boranophosphate, the proposed synthetic route is shown in Scheme 3 or Scheme 4, while in the case of boranophosphate as 3'-5' linkage of 2',3'-cyclic dinucleotide, the proposed synthetic route is shown in Scheme 5 or Scheme 6, each synthetic route can provide four isomers. The cyclic nucleotides bearing two boranophosphates internucleotidic linkages can also be achieved as outlined in Scheme 7 and Scheme 8.

The general synthetic routes for 3',3'-cyclic dinucleotide boranophosphates are shown in Schemes 9-12. The cyclic nucleotides containing one boranophosphate internucleotidic linkage are obtained through the synthetic routes as illustrated in Scheme 9 or Scheme 10, in the case of two boranophosphates, the synthetic method is detailed in Scheme 11 and Scheme 12. Cyclic dinucleotide boranophosphates which include an amino linkage bonded to the 3' or 5' position of ribose moiety are synthesized as depicted in Schemes 13, 14 and 15 respectively.

The general synthetic routes for 2',2'-cyclic dinucleotide boranophosphates are shown in Scheme 16 and Scheme 17.

The synthetic methods of cyclic dinucleotide thiophosphates or phosphates are shown in Schemes 18, 19 and 20.

In Schemes 3-20, where appropriate, the following definitions apply:

$Z_1$ and $Z_2$ are independently selected from O, S and C;

CE is $CH_2CH_2CN$;

$Q^a$, $Q^b$=nucleobases; and $Q^{ap}$ stands for protected nucleobase $Q^a$ and $Q^{bp}$ stands for protected nucleobase $Q^b$.

Method 1

One method for the preparation the compounds of the present disclosure is outline in Scheme 3. The sequence starts with modified ribo-nucleoside or thio-nucleoside with a nucleobase of which amino group (if available) is appropriately protected with an alkyl or phenyl carbonyl group, a phosphoramidite functionality at 2'-O position, and DMTr ether at 5'-O position. The 2-phosphoramidite can be reacted with 5'-hydroxyl of second modified ribo-nucleoside or thio-nucleoside to give a phosphite triester, which is can then be converted to the dinucleoside boranophosphate (boranophosphotriester) by oxidation with dimethyl sulfide-borane or $BH(R^b)_2$. After removal of DMTr under acidic condition, the cyclization can be achieved in the presence of 3-((bis (diisopropylamino)phosphanyl)oxy)propanenitrile. The cyclized product can be immediately oxidized either by DDTT or tert-butyl peroxide. Treatment with tert-butyl amine and methyl amine or ammonium hydroxide can provide the cyclic dinucleotides.

Scheme 3. Synthesis of Cyclic Dinucleotides

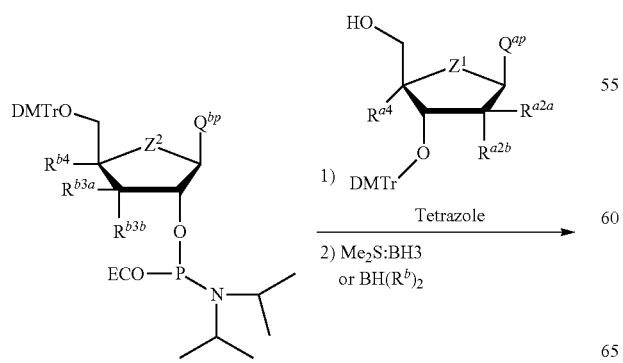

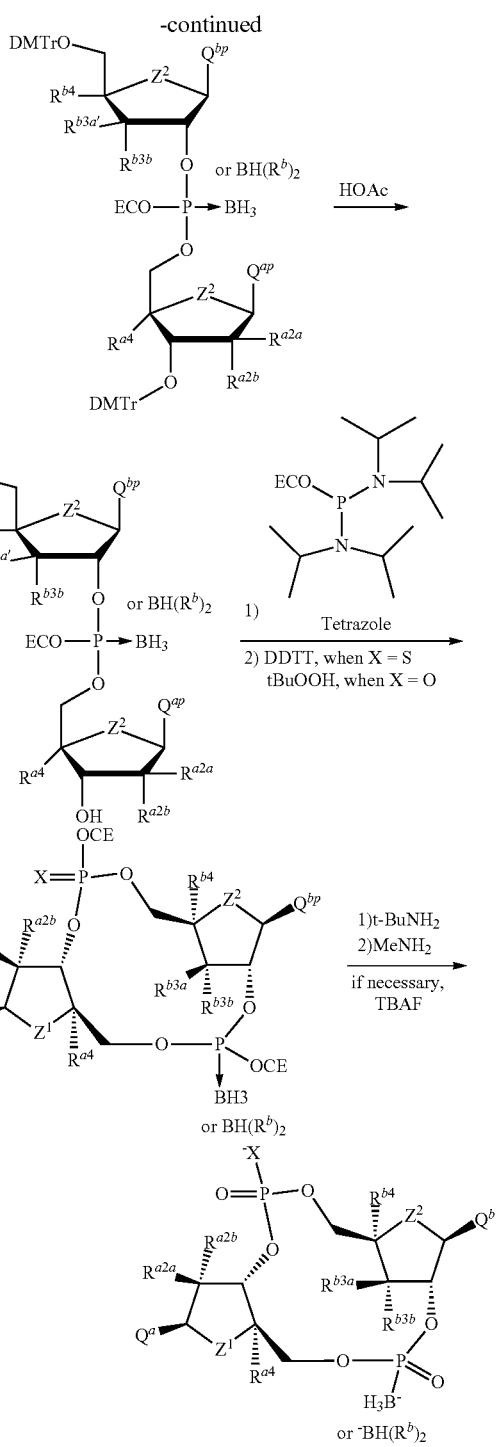

Method 2

Another way to prepare above compound is detailed in Scheme 4. The 3-phosphoramidite of fully protected ribo-nucleoside or thio-nucleoside can be reacted with 5'-hydroxyl of second modified ribo-nucleoside or thio-nucleoside to give a phosphite triester, which is can then be oxidized with DDTT or tert-butyl peroxide. After removal of DMTr under acidic condition, the cyclization can be achieved in the presence of 3-((bis(diisopropylamino)phosphanyl)oxy)propanenitrile. The cyclized product is can be reacted with dimethyl sulfide-borane or $BH(R^b)_2$. Treatment with tert-butyl amine and methyl amine or ammonium hydroxide can provide the cyclic dinucleotides.

Scheme 4. Synthesis of Cyclic Dinucleotides

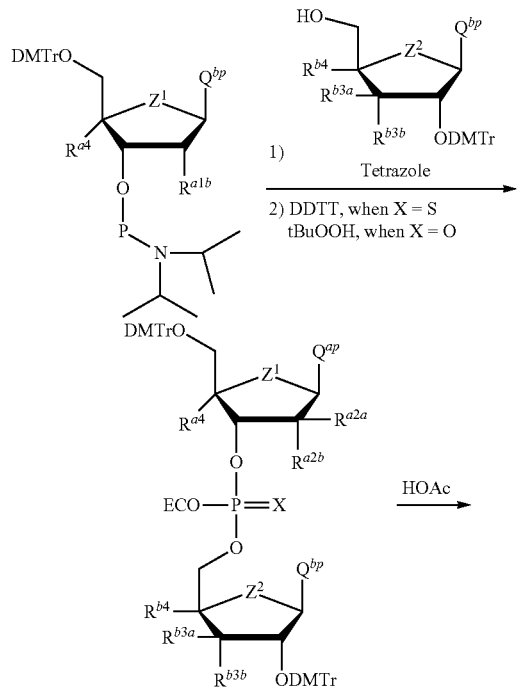

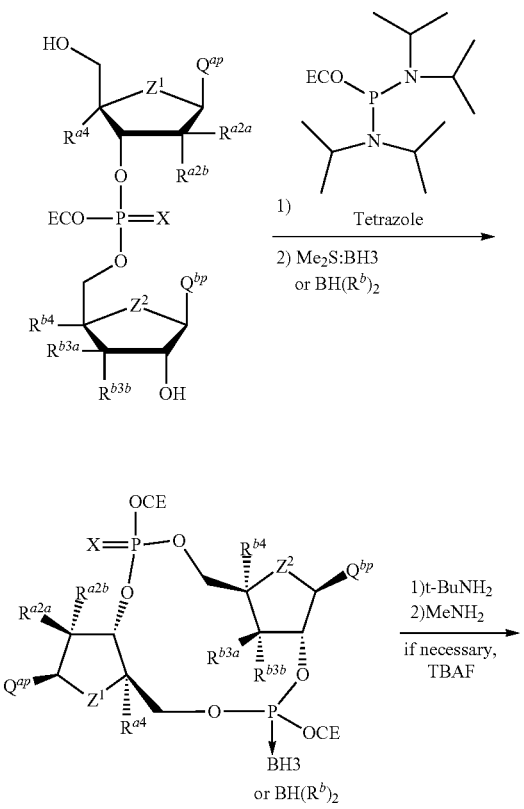

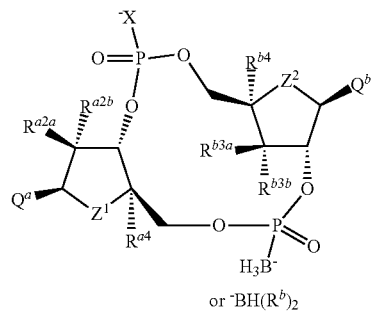

Method 3

One example for the preparation of compounds of the disclosure is detailed in Scheme 5. The sequence starts with modified ribo-nucleoside or thio-nucleoside with a nucleobase of which amino group (if available) is appropriately protected with an alkyl or phenyl carbonyl group, a phosphoramidite functionality at 2'-O position, and DMTr ether at 5'-O position. The 2-phosphoramidite of fully protected ribo-nucleoside can be reacted with 5'-hydroxyl of second modified ribo-nucleoside or thio-nucleoside to give a phosphite triester, which is can then be oxidized with DDTT or tert-butyl peroxide. After removal of DMTr under acidic condition, the cyclization can be achieved in the presence of 3-((bis(diisopropylamino)phosphanyl)oxy)propanenitrile.

The cyclized product is can be reacted with dimethyl sulfide-borane or $BH(R^b)_2$. Treatment with tert-butyl amine and methyl amine or ammonium hydroxide can provide the cyclic dinucleotides.

Scheme 5. Synthesis of Cyclic Dinucleotides

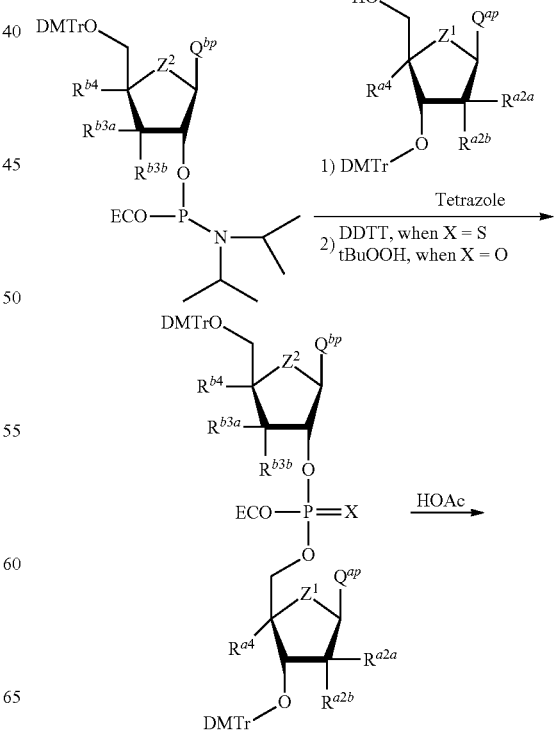

-continued

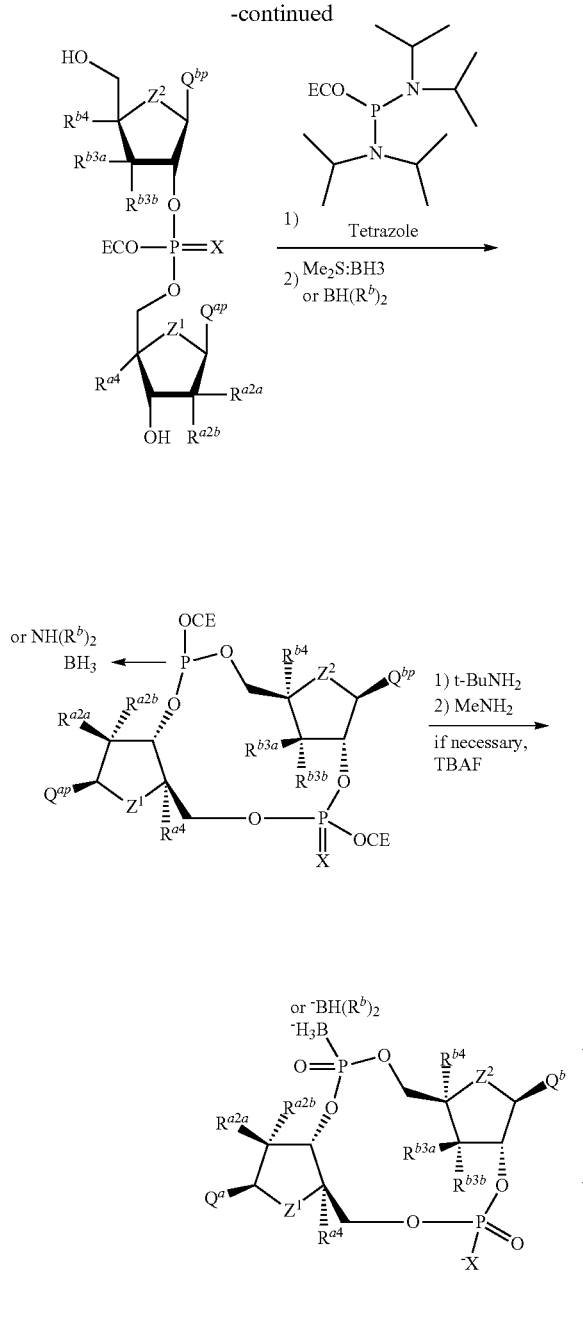

Scheme 6. Synthesis of Cyclic Dinucleotides

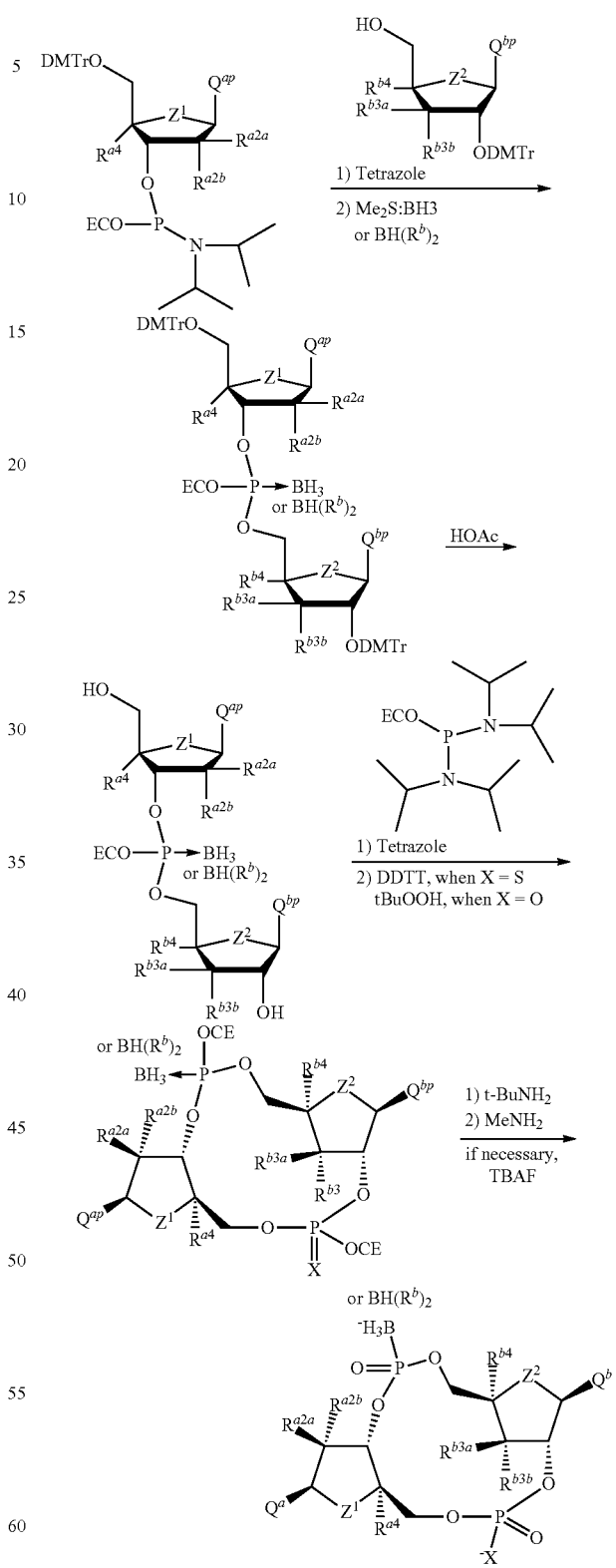

Method 4

Another way to prepare above compound is detailed in Scheme 6. The 3-phosphoramidite of fully protected ribonucleoside or thio-nucleoside can be reacted with 5'-hydroxyl of second modified ribo-nucleoside or thio-nucleoside to give a phosphite triester, which can then be oxidized with dimethyl sulfide-borane or $BH(R^b)_2$. After removal of DMTr under acidic condition, the cyclization can be achieved in the presence of 3-((bis(diisopropylamino)phosphanyl)oxy)propanenitrile. The cyclized product is then reacted with DDTT or tert-butyl peroxide. Treatment with tert-butyl amine and methyl amine or ammonium hydroxide can provide the cyclic dinucleotides.

Method 5

One example for the preparation of the compounds of the disclosure is detailed in Scheme 7. The dinucleotide intermediate, which can be synthesized as shown in Scheme 3, can be cyclized in the presence of 3-((bis(diisopropylamino)phosphanyl)oxy)propanenitrile. The cyclized product can be reacted with dimethyl sulfide-borane or $BH(R^b)_2$. Treatment with tert-butyl amine and methyl amine or ammonium hydroxide can provide the cyclic dinucleotides.

Scheme 7. Synthesis of Cyclic Dinucleotides

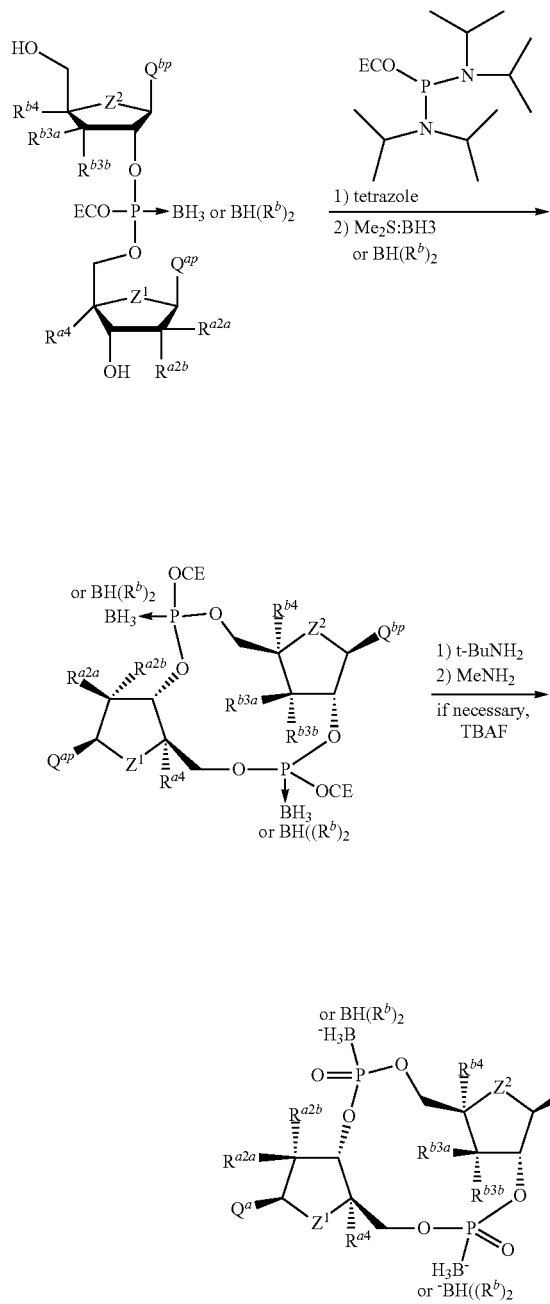

Method 6

Another way to prepare above compound is detailed in Scheme 8. The dinucleotide, which can be synthesized as shown in Scheme 6, can follow the same synthetic scheme as shown in Scheme 7 to prepare the cyclic dinucleotides.

Scheme 8. Synthesis of Cyclic Dinucleotides

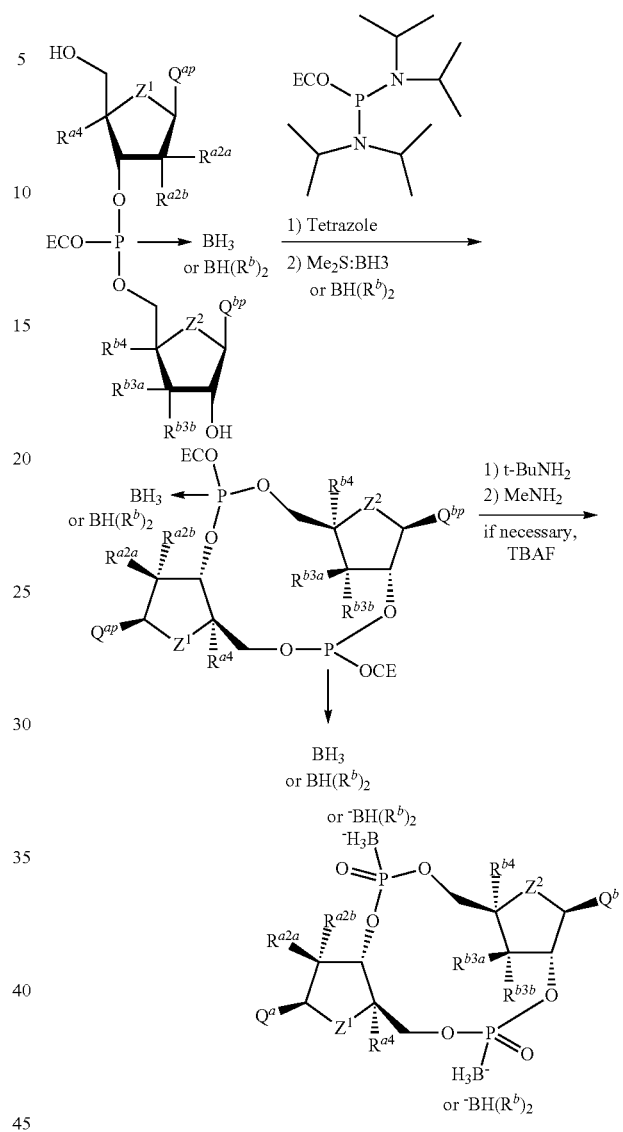

Method 7

One example for the preparation of the compounds of the disclosure is detailed in Scheme 9. The sequence starts with modified ribo-nucleoside or thio-nucleoside with a nucleobase of which amino group (if available) is appropriately protected with an alkyl or phenyl carbonyl group, a phosphoramidite functionality at 3'-O position, and DMTr ether at 5'-O position. The 3-phosphoramidite of fully protected ribo-nucleoside can be reacted with 5'-hydroxyl of second modified ribo-nucleoside or thio-nucleoside to give a phosphite triester, which is can then be oxidized with DDTT or tert-butyl peroxide. After removal of DMTr under acidic condition, the cyclization can be achieved in the presence of 3-((bis(diisopropylamino)phosphanyl)oxy)propanenitrile.

The cyclized product can be reacted with dimethyl sulfide-borane or $BH(R^b)_2$. Treatment with tert-butyl amine and methyl amine or ammonium hydroxide can provide the cyclic dinucleotides.

Scheme 9. Synthesis of Cyclic Dinucleotides

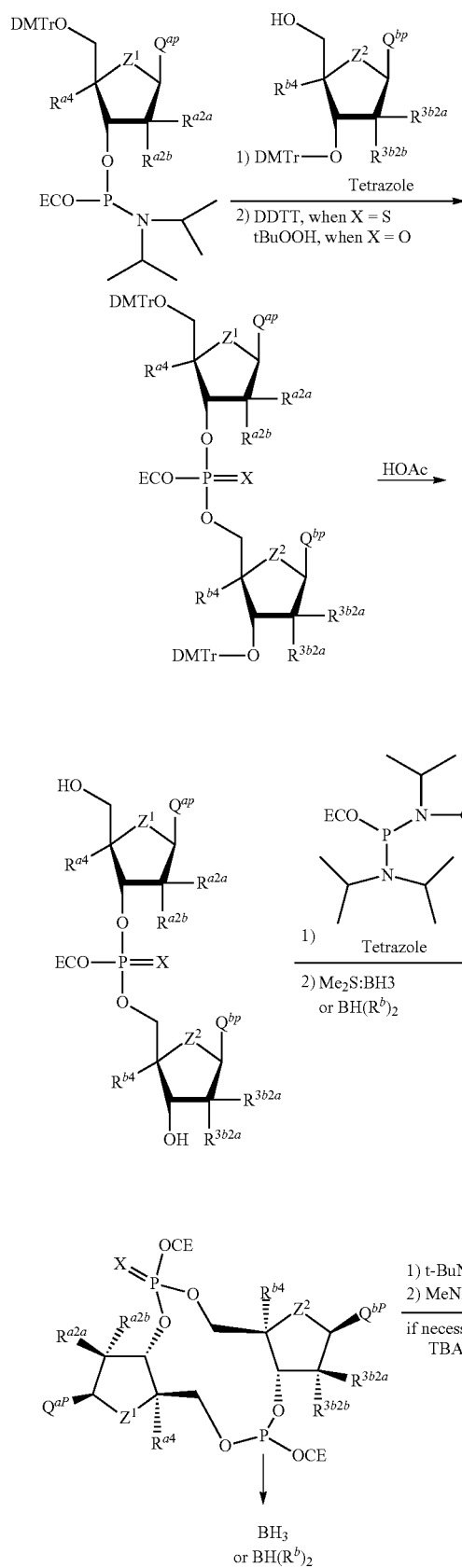

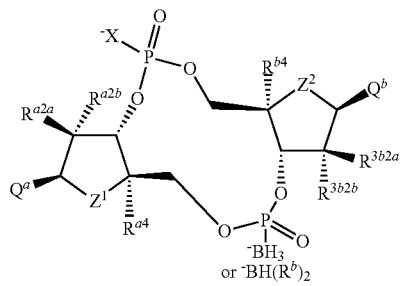

Method 8

Another way to prepare above compound is detailed in Scheme 10. The 3-phosphoramidite of fully protected ribo-nucleoside or thio-nucleoside can be reacted with 5'-hydroxyl of second modified ribo-nucleoside or thio-nucleoside to give a phosphite triester, which is then oxidized with dimethyl sulfide-borane or $BH(R^b)_2$. After removal of DMTr under acidic condition, the cyclization can be achieved in the presence of 3-((bis(diisopropylamino)phosphanyl)oxy)propanenitrile. The cyclized product can be reacted with DDTT or tert-butyl peroxide. Treatment with tert-butyl amine and methyl amine or ammonium hydroxide can provide the cyclic dinucleotides.

Scheme 10. Synthesis of Cyclic Dinucleotides

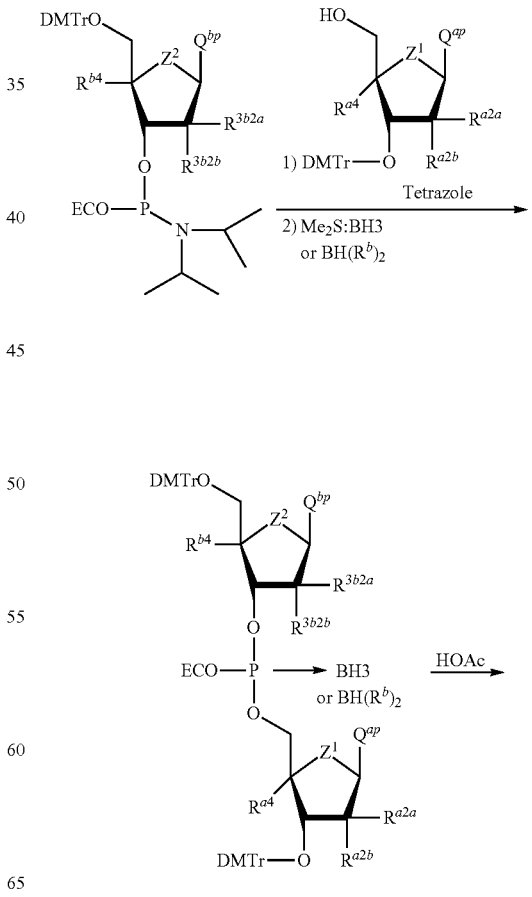

-continued

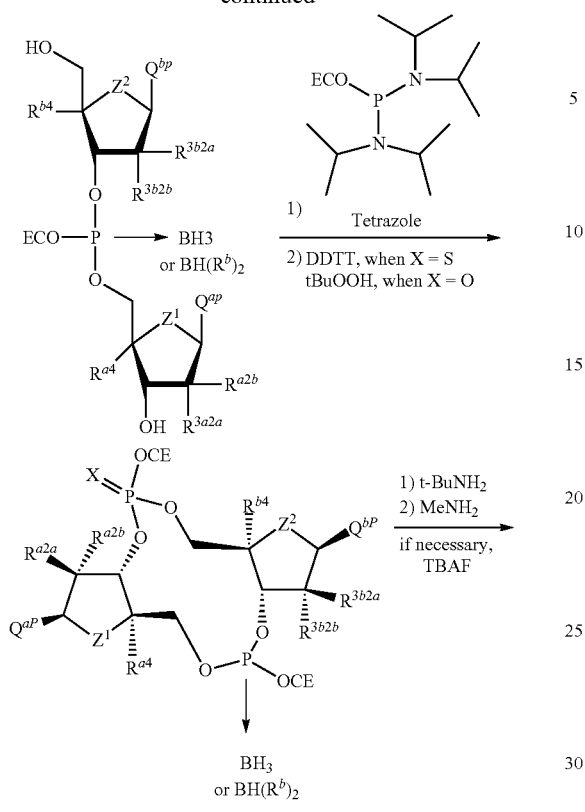

Scheme 11. Synthesis of Cyclic Dinucleotides

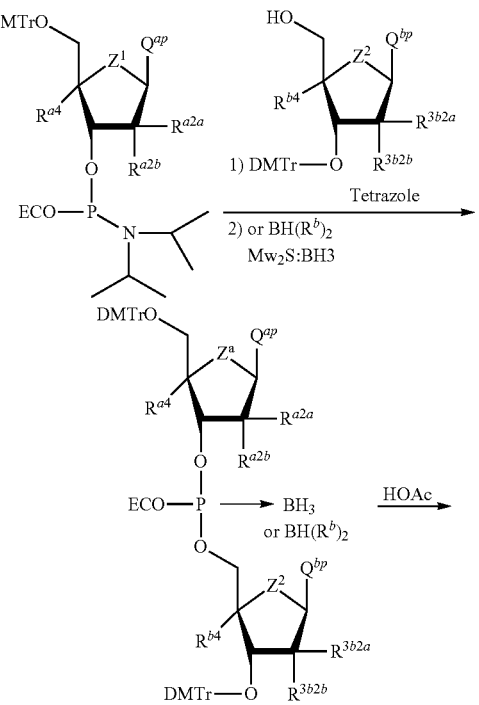

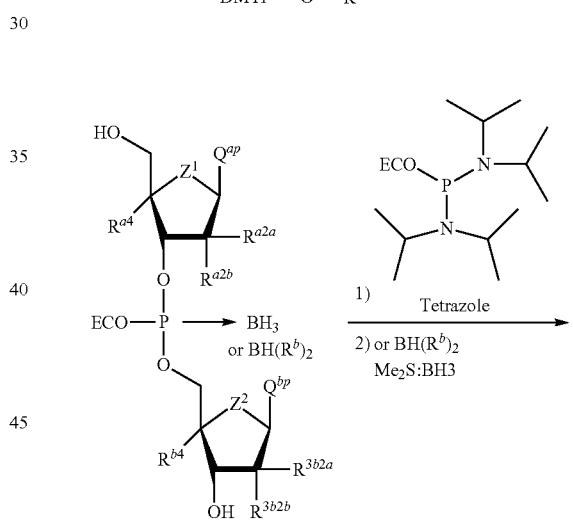

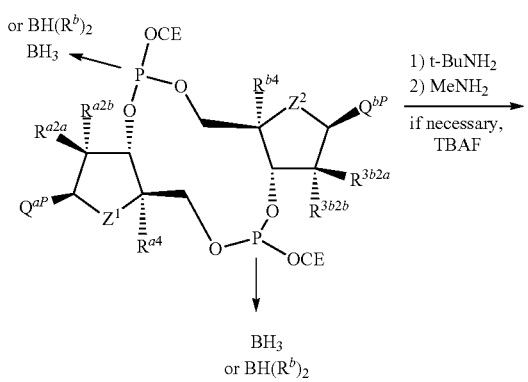

Method 9

One example for the preparation of compounds of the disclosure is detailed in Scheme 11. The sequence starts with modified ribo-nucleoside or thio-nucleoside with a nucleobase of which amino group is appropriately protected with an alkyl or phenyl carbonyl group, a phosphoramidite functionality at 3'-O position, and DMTr ether at 5'-O position. The 3-phosphoramidite of fully protected ribo-nucleoside can be reacted with 5'-hydroxyl of second modified ribo-nucleoside or thio-nucleoside to give a phosphite triester, which can then be oxidized with dimethyl sulfide-borane or $BH(R^b)_2$. After removal of DMTr under acidic condition, the cyclization can be achieved in the presence of 3-((bis(diisopropylamino)phosphanyl)oxy)propanenitrile. The cyclized product can be reacted with dimethyl sulfide-borane or $BH(R^b)_2$. Treatment with tert-butyl amine and methyl amine or ammonium hydroxide can provide the cyclic dinucleotides.

149
-continued

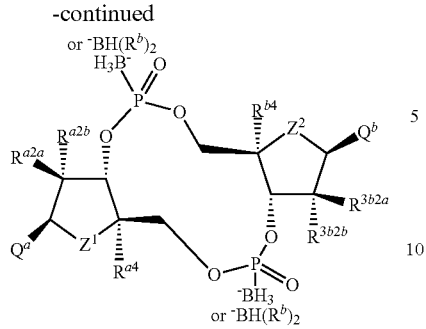

150
-continued

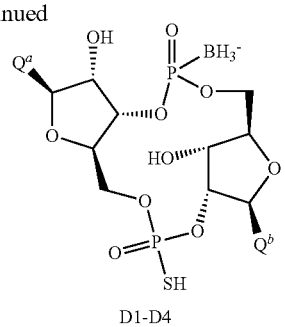

D1-D4

Method 10

Another way to make 2',3'-boranophosphates is illustrated as in Scheme 12. G1 was prepared as reported in WO2014/189805A1. The H-phosphonate diester can be converted to an activated phosphite triester by silylation with BSA. In situ boronation with $BH_3 \cdot SMe_2$ can result in the formation of boranophosphotriester, and treatment with $NH_4OH$ followed by fluorine anion can provided dinucleoside boranophosphate diesters.

$Q^{ap}$, $Q^{bp}$=protected nucleobases of which amino group is appropriately protected with an alkyl or phenyl carbonyl group.

$Q^a$, $Q^b$=nucleobases of which amino group is substituted with alkyl or benzyl.

Method 11

Scheme 13 depicts an example of synthesizing cyclic dinucleotide boranophosphates as disclosed herein that include an amino linkage bonded to the 3' position of ribose moiety. The sequence can be initiated with the treatment of compound S1 with 3-((bis(diisopropylamino)phosphanyl)oxy)propanenitrile in the presence of pyridine trifluoroacetate to furnish phosphoramidite S2. Subsequent water or hydrogen sulfide treatment can result in phosphonate S3a or phosphonothioate S3b, respectively. Compound S4 can then be combined with either of compounds S3a or S3b in the presence of triethylamine in carbon tetrachloride to generate either phosphoramidate S5a or phosphoramidothioate S5b, respectively. After removal of DMTr under acidic condition, the cyclization can be achieved in the presence of 3-((bis(diisopropylamino)phosphanyl)oxy)propanenitrile. The cyclized product can then be reacted with dimethyl sulfide-borane. Treatment with methyl amine and triethylamine-hydrogen fluoride complex can provide the cyclic dinucleotides.

Scheme 12. Synthesis of Cyclic Dinucleotides

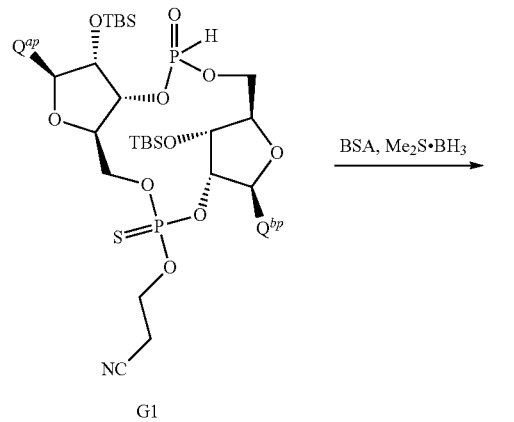

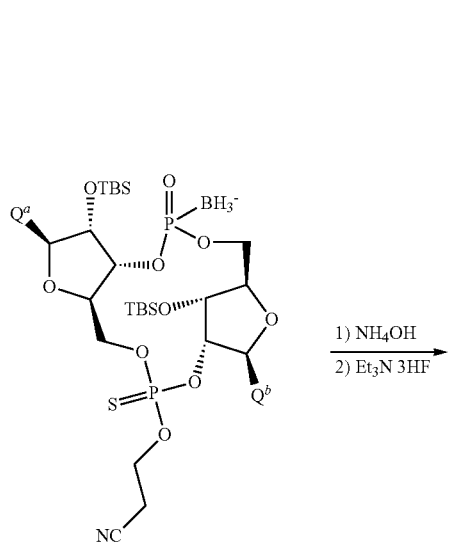

Scheme 13. Synthesis of Cyclic Dinucleotides

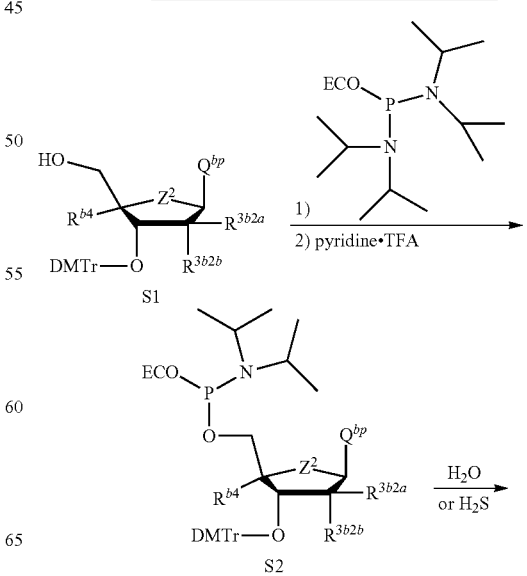

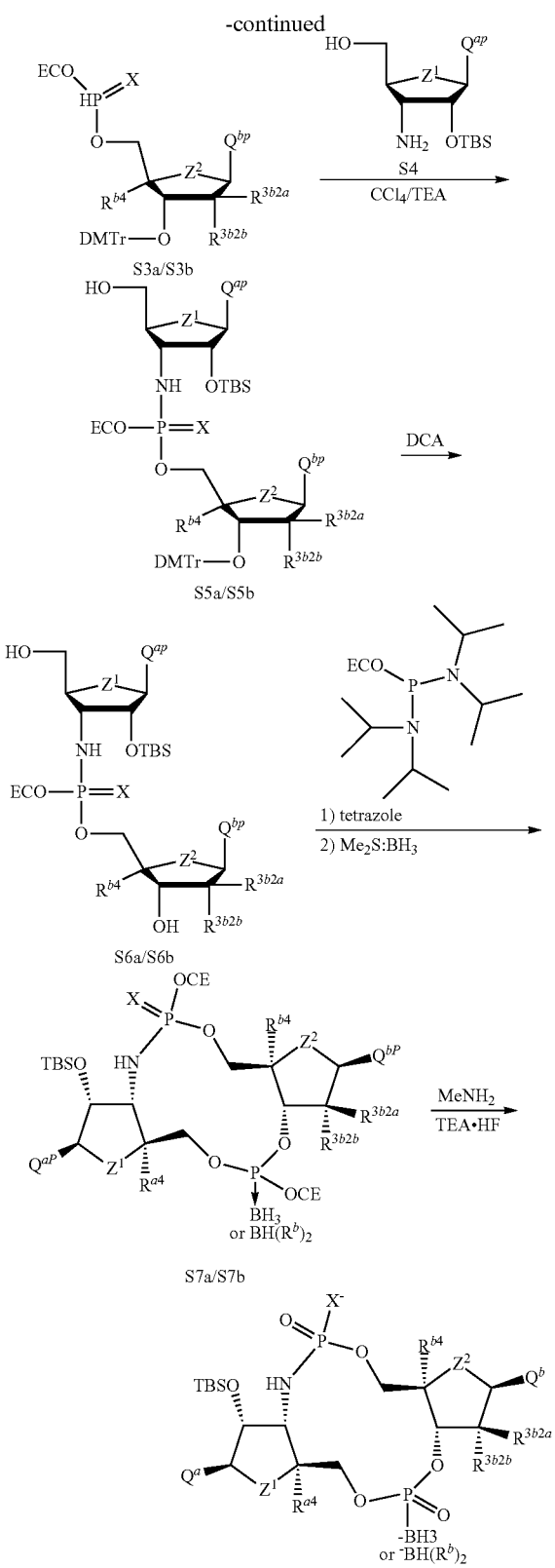

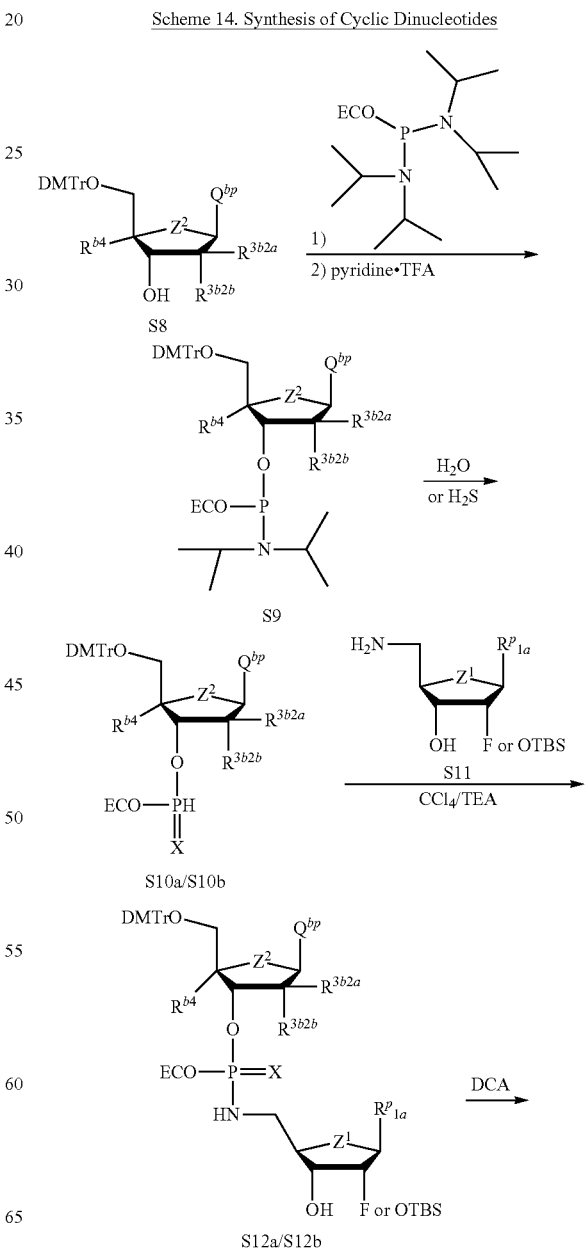

Scheme 14. Synthesis of Cyclic Dinucleotides compound S8 with 3-((bis(diisopropylamino)phosphanyl)oxy)propanenitrile in the presence of pyridine trifluoroacetate to furnish phosphoramidite S9. Subsequent water or hydrogen sulfide treatment can result in phosphonate S10a or phosphonothioate S10b, respectively. Compound S11, which can be synthesized as reported in WO2017/123669, can then be combined with either of compounds S1Ga or S10b in the presence of triethylamine in carbon tetrachloride to generate either phosphoramidate S12a or phosphoramidothioate S12b, respectively. After removal of DMTr under acidic condition, the cyclization can be achieved in the presence of 3-((bis(diisopropylamino)phosphanyl)oxy)propanenitrile. The cyclized product can then be reacted with dimethyl sulfide-borane. Treatment with methyl amine and triethylamine-hydrogen fluoride complex can provide the cyclic dinucleotides.

Method 12

Scheme 14 depicts an example for synthesizing cyclic dinucleotide boranophosphates as disclosed herein that include an amino linkage bonded to the 5' position of ribose moiety. The sequence can be initiated with the treatment of

153

-continued

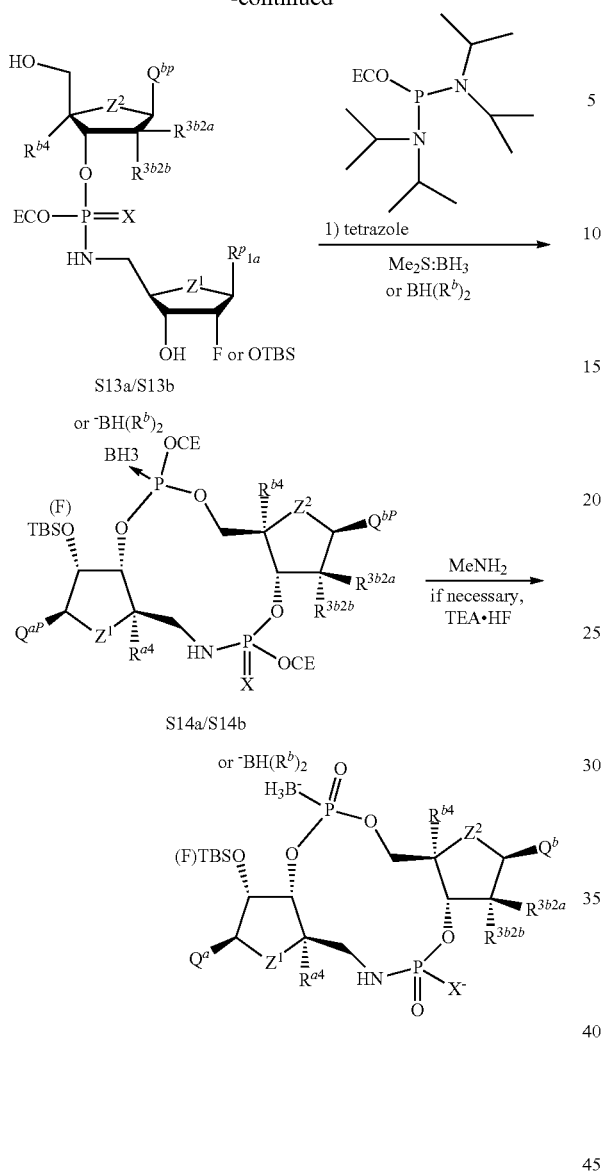

S13a/S13b

S14a/S14b

Method 13

Scheme 15 depicts an example of synthesizing cyclic dinucleotide boranophosphates as disclosed herein that include an amino linkage bonded to the 3' position of ribose moiety. The sequence can be initiated with the treatment of compound S15 with 3-((bis(diisopropylamino)phosphanyl)oxy)propanenitrile in the presence of pyridine trifluoroacetate to furnish phosphoramidite S16. Subsequent water or hydrogen sulfide treatment can result in phosphonate S17a or phosphonothioate S17b, respectively. Compound S4 can then be combined with either of compounds S17a or S17b in the presence of triethylamine in carbon tetrachloride to generate either phosphoramidate S18a or phosphoramidothioate S18b, respectively. After removal of DMTr under acidic condition, the cyclization can be achieved in the presence of 3-((bis(diisopropylamino)phosphanyl)oxy)propanenitrile. The cyclized product can then be reacted with dimethyl sulfide-borane. Treatment with methyl amine and triethylamine-hydrogen fluoride complex can provide the cyclic dinucleotides.

154

Scheme 15. Synthesis of Cyclic Dinucleotides

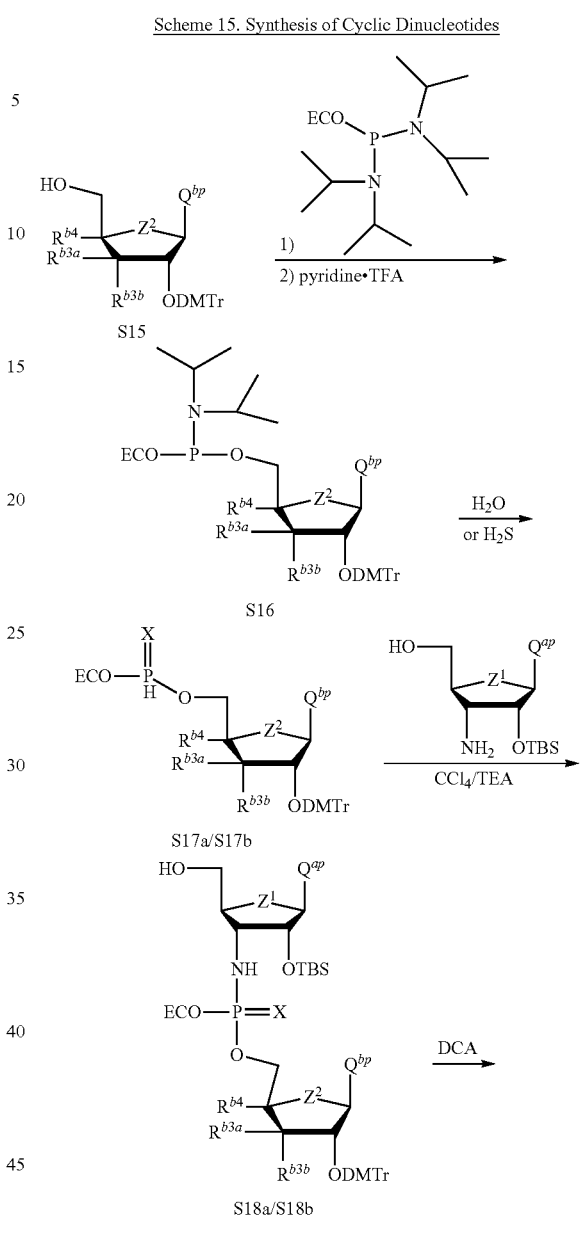

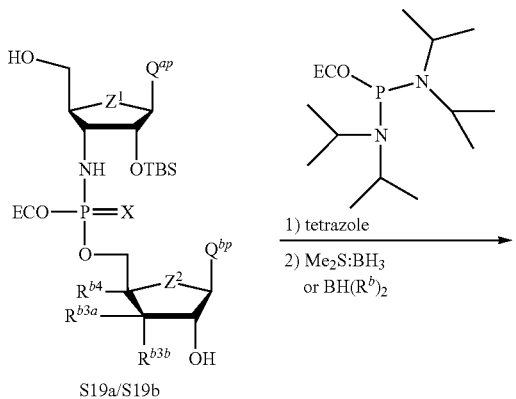

-continued

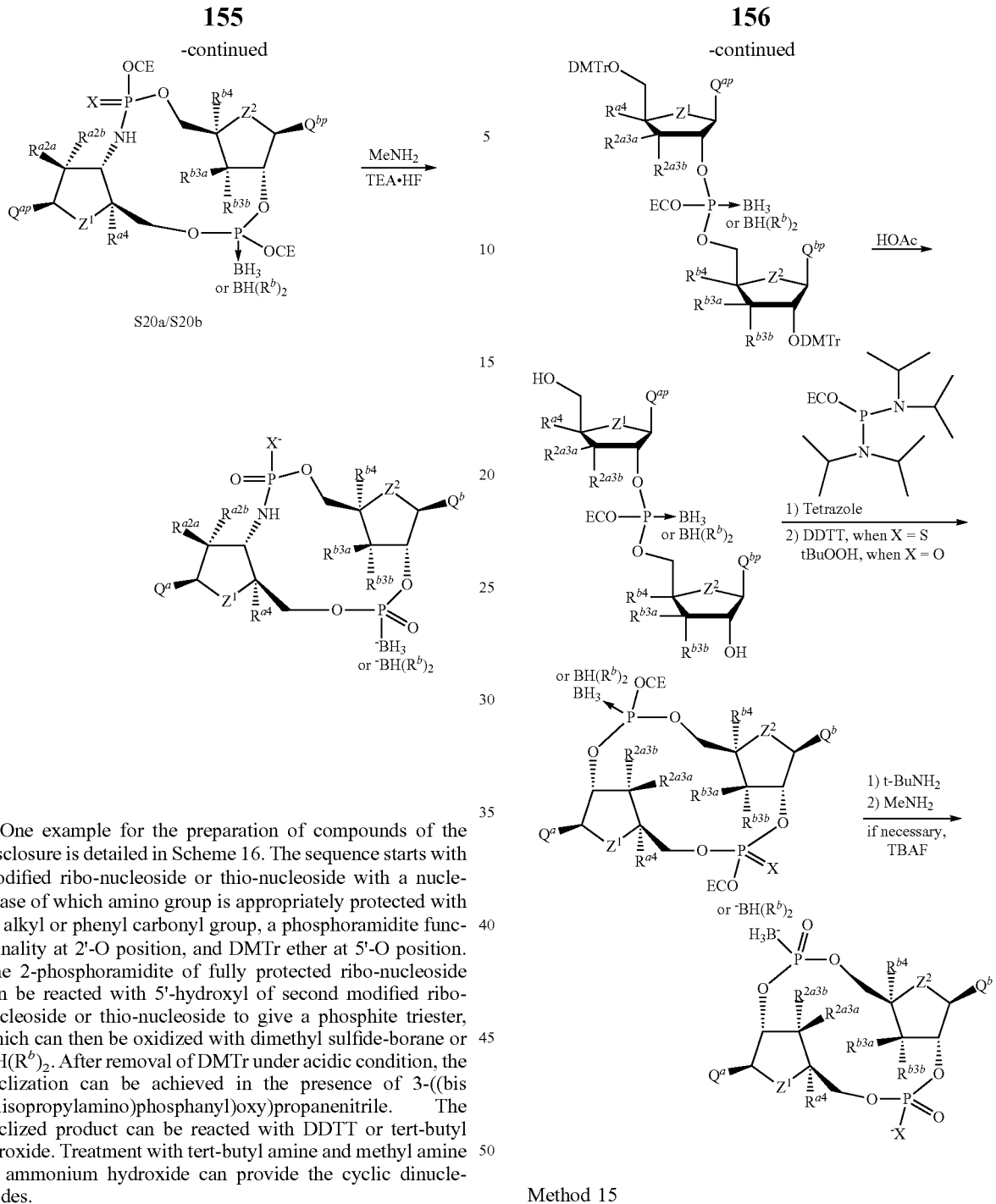

One example for the preparation of compounds of the disclosure is detailed in Scheme 16. The sequence starts with modified ribo-nucleoside or thio-nucleoside with a nucleobase of which amino group is appropriately protected with an alkyl or phenyl carbonyl group, a phosphoramidite functionality at 2'-O position, and DMTr ether at 5'-O position. The 2-phosphoramidite of fully protected ribo-nucleoside can be reacted with 5'-hydroxyl of second modified ribo-nucleoside or thio-nucleoside to give a phosphite triester, which can then be oxidized with dimethyl sulfide-borane or $BH(R^b)_2$. After removal of DMTr under acidic condition, the cyclization can be achieved in the presence of 3-((bis(diisopropylamino)phosphanyl)oxy)propanenitrile. The cyclized product can be reacted with DDTT or tert-butyl peroxide. Treatment with tert-butyl amine and methyl amine or ammonium hydroxide can provide the cyclic dinucleotides.

Scheme 16. Synthesis of Cyclic Dinucleotides

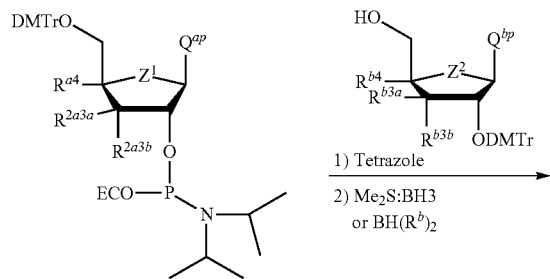

Method 15

One method for the preparation of examples of the disclosure is detailed in Scheme 17. The sequence starts with modified ribo-nucleoside or thio-nucleoside with a nucleobase of which amino group is appropriately protected with an alkyl or phenyl carbonyl group, a phosphoramidite functionality at 2'-O position, and DMTr ether at 5'-O position. The 2-phosphoramidite of fully protected ribo-nucleoside can be reacted with 5'-hydroxyl of second modified ribo-nucleoside or thio-nucleoside to give a phosphite triester, which can then be oxidized with dimethyl sulfide-borane or $BH(R^b)_2$. After removal of DMTr under acidic condition, the cyclization can be achieved in the presence of 3-((bis(diisopropylamino)phosphanyl)oxy)propanenitrile. The cyclized product can be reacted with dimethyl sulfide-borane or BH($R^b$)$_2$. Treatment with tert-butyl amine and methyl amine or ammonium hydroxide can provide the cyclic dinucleotides.

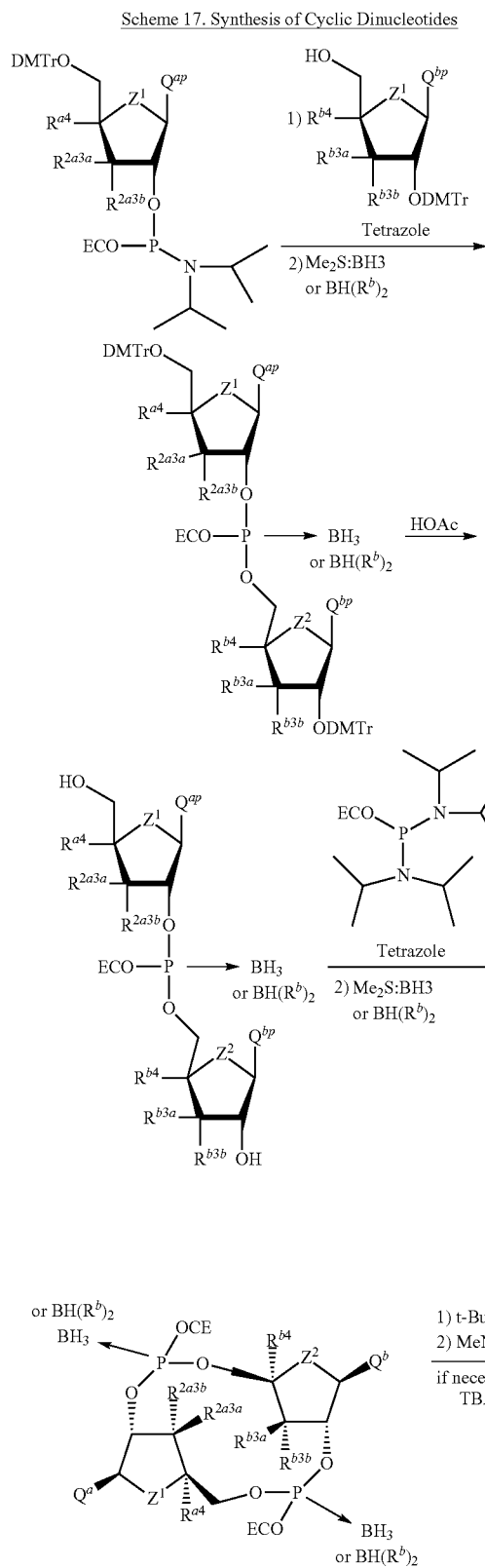

Scheme 17. Synthesis of Cyclic Dinucleotides

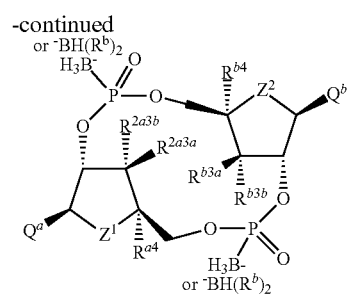

Method 16

One examples for the preparation of the compounds of the disclosure is detailed in Scheme 18. The sequence starts with modified ribo-nucleoside with a nucleobase of which amino group is appropriately protected with an alkyl or phenyl carbonyl group, a phosphoramidite functionality at 3'-O position, and DMTr ether at 5'-O position. The 3-phosphoramidite of fully protected ribo-nucleoside can be reacted with 5'-hydroxyl of second modified ribo-nucleoside or thio-nucleoside containing 2'-H-phosphonate to give a phosphite triester, which is can then be oxidized by DDTT or tert-butyl peroxide. After removal of DMTr under acidic condition, the cyclization can be achieved in the presence of 2-chloro-5,5-dimethyl-1,3,2-dioxaphosphinane 2-oxide. The cyclized product can then be immediately reacted with 3H-benzo[c][1,2]dithiol-3-one or aqueous iodine. Treatment with t-butylamine and methylamine plus fluoride anion in case silyl protection is used can provide the desired cyclic dinucleotides.

Scheme 18. Synthesis of Cyclic Dinucleotides

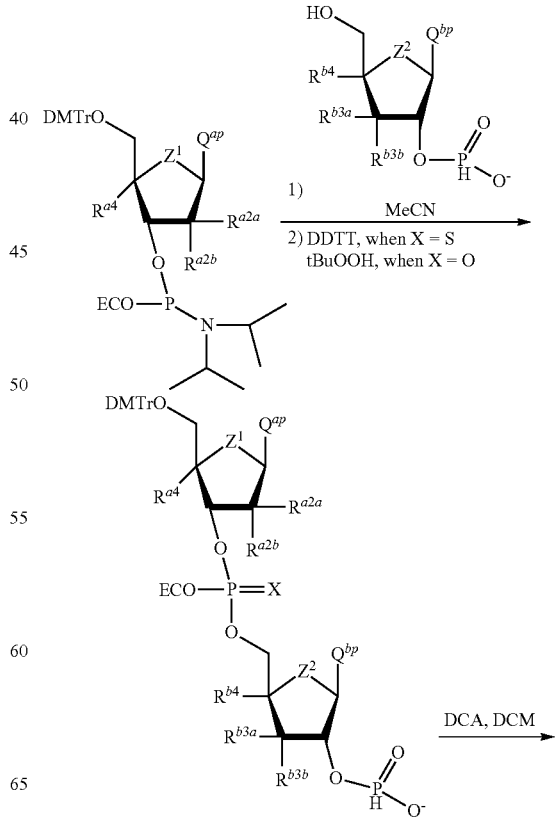

-continued

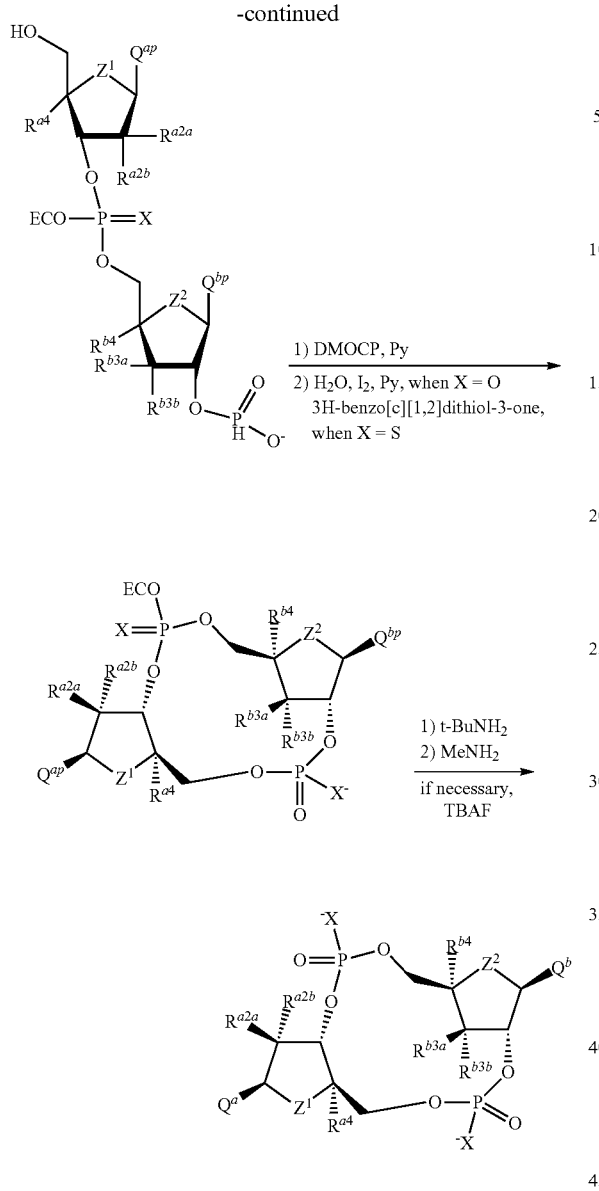

Scheme 19. Synthesis of Cyclic Dinucleotides

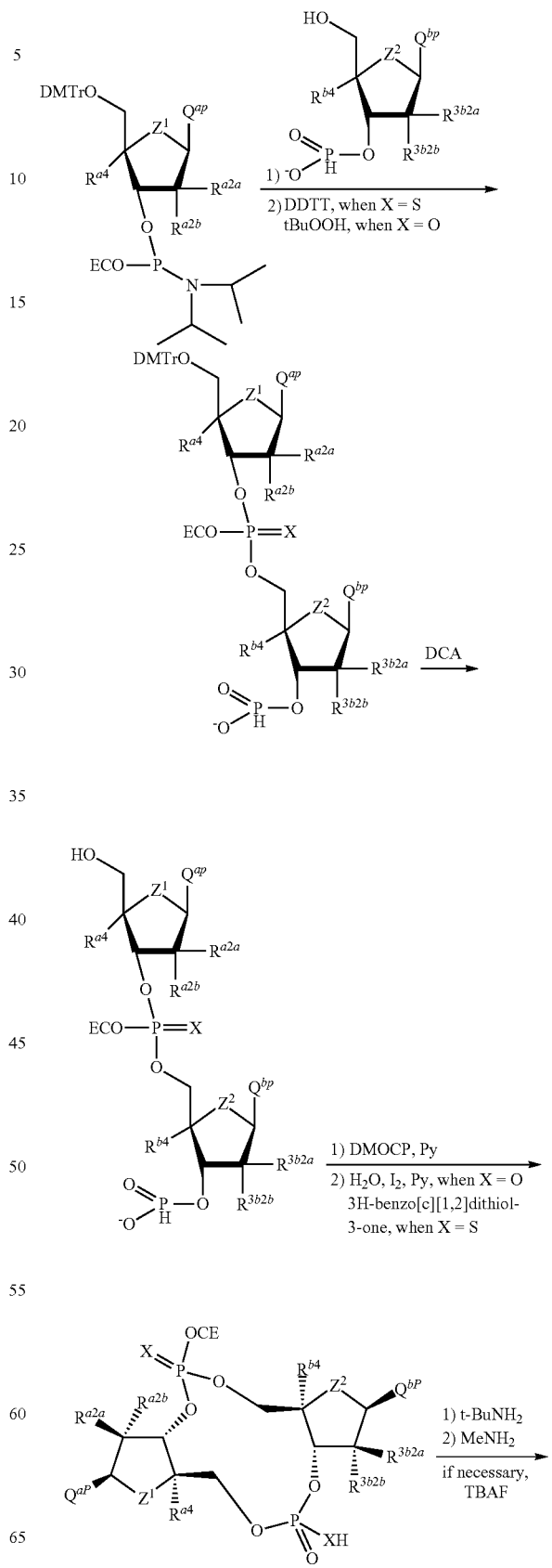

Method 17

One example for the preparation of compounds of the disclosure is detailed in Scheme 19. The sequence starts with modified ribo-nucleoside with a nucleobase of which amino group is appropriately protected with an alkyl or phenyl carbonyl group, a phosphoramidite functionality at 3'-O position, and DMTr ether at 5'-0 position. The 3-phosphoramidite of fully protected ribo-nucleoside can be reacted with 5'-hydroxyl of second modified ribo-nucleoside or thio-nucleoside containing 3'-H-phosphonate to give a phosphite triester, which can then be oxidized by DDTT or tert-butyl peroxide. After removal of DMTr under acidic condition, the cyclization can be achieved in the presence of 2-chloro-5,5-dimethyl-1,3,2-dioxaphosphinane 2-oxide. The cyclized product can be immediately reacted with 3H-benzo[c][1,2]dithiol-3-one or aqueous iodine. Treatment with t-butylamine and methylamine plus fluoride anion in case silyl protection can provide the desired cyclic dinucleotides.

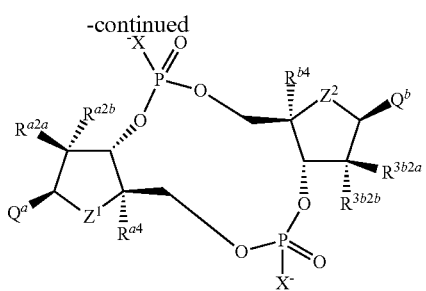

Method 18

One example for the preparation of the compounds of the disclosure is detailed in Scheme 20. The sequence starts with modified ribo-nucleoside with a nucleobase of which amino group is appropriately protected with an alkyl or phenyl carbonyl group, a phosphoramidite functionality at 2'-O position, and DMTr ether at 5'-O position. The 3-phosphoramidite of fully protected ribo-nucleoside can be reacted with 5'-hydroxyl of second modified ribo-nucleoside or thio-nucleoside containing 2'-H-phosphonate to give a phosphite triester, which is can then be oxidized by DDTT or tert-butyl peroxide. After removal of DMTr under acidic condition, the cyclization can be achieved in the presence of 2-chloro-5, 5-dimethyl-1,3,2-dioxaphosphinane 2-oxide. The cyclized product can be immediately reacted with 3H-benzo[c][1,2]dithiol-3-one or aqueous iodine. Treatment with t-butylamine and methylamine plus fluoride anion in case silyl protection can provide the desired cyclic dinucleotides.

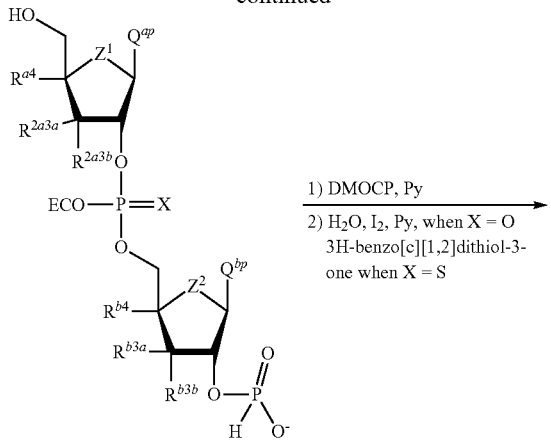

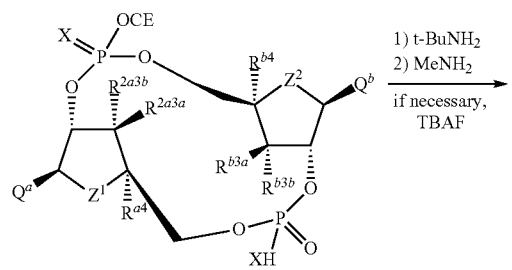

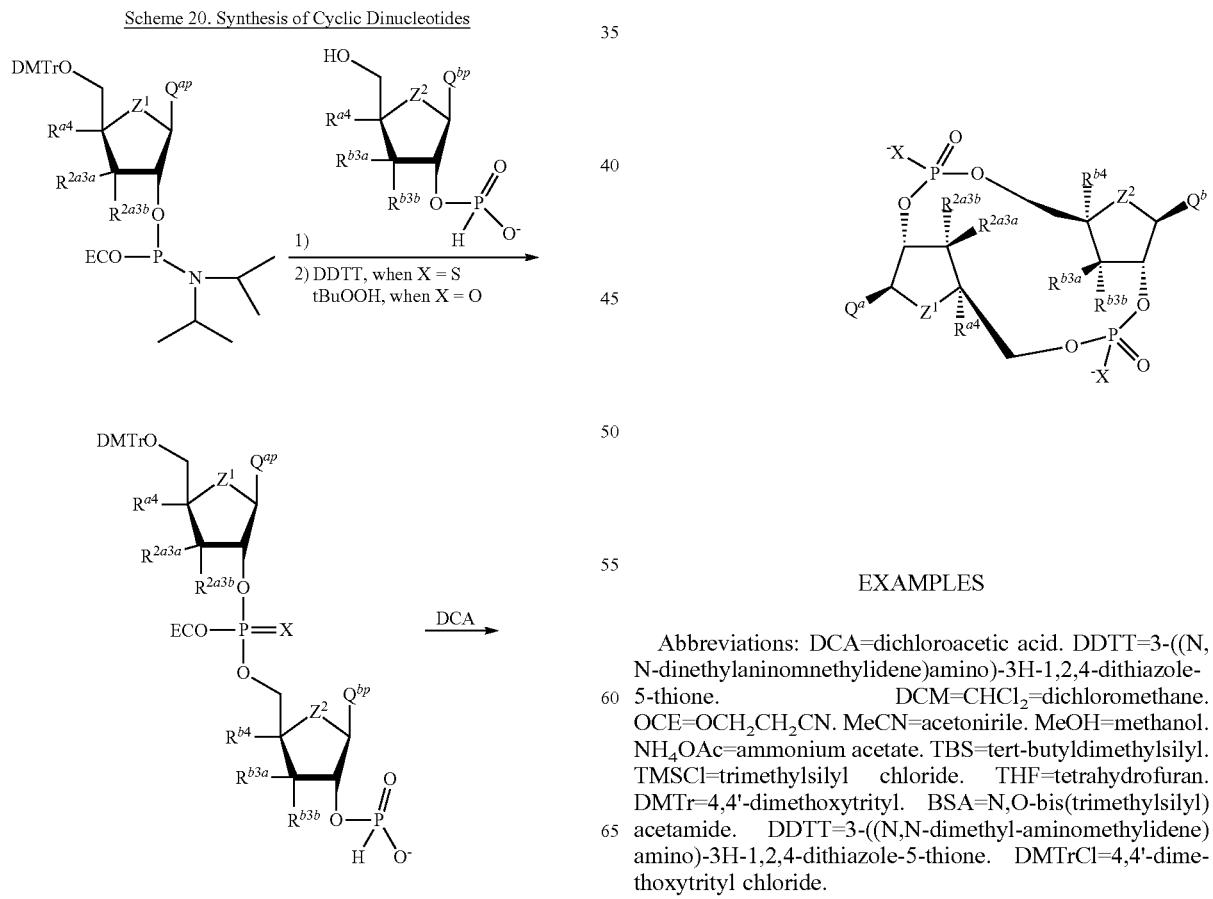

EXAMPLES

Abbreviations: DCA=dichloroacetic acid. DDTT=3-((N, N-dinethylaninomnethylidene)amino)-3H-1,2,4-dithiazole-5-thione. DCM=CHCl$_2$=dichloromethane. OCE=OCH$_2$CH$_2$CN. MeCN=acetonirile. MeOH=methanol. NH$_4$OAc=ammonium acetate. TBS=tert-butyldimethylsilyl. TMSCl=trimethylsilyl chloride. THF=tetrahydrofuran. DMTr=4,4'-dimethoxytrityl. BSA=N,O-bis(trimethylsilyl) acetamide. DDTT=3-((N,N-dimethyl-aminomethylidene) amino)-3H-1,2,4-dithiazole-5-thione. DMTrCl=4,4'-dimethoxytrityl chloride.

Intermediate Preparations

Example i: Preparation of (2R,3R,4R,5R)-5-(6-Benzamido-9H-purin-9-yl)-2-((bis(4-methoxyphenyl)(phenyl)methoxy)methyl)-4-fluorotetrahydrofuran-3-yl-(2-cyanoethyl) diisopropylphosphoramidite (1a)

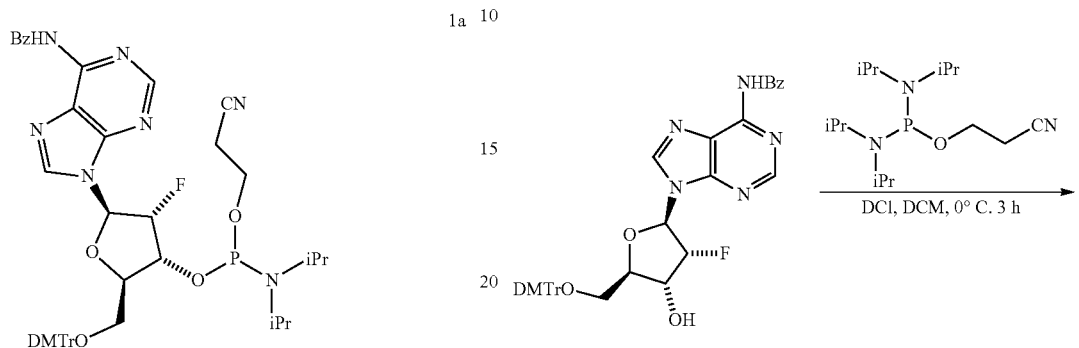

Step 1: Synthesis of N-(9-((2R,3R,4R,5R)-5-((bis(4-methoxyphenyl)(phenyl)methoxy)methyl)-3-fluoro-4-hydroxytetrahydrofuran-2-yl)-9H-purin-6-yl)benzamide

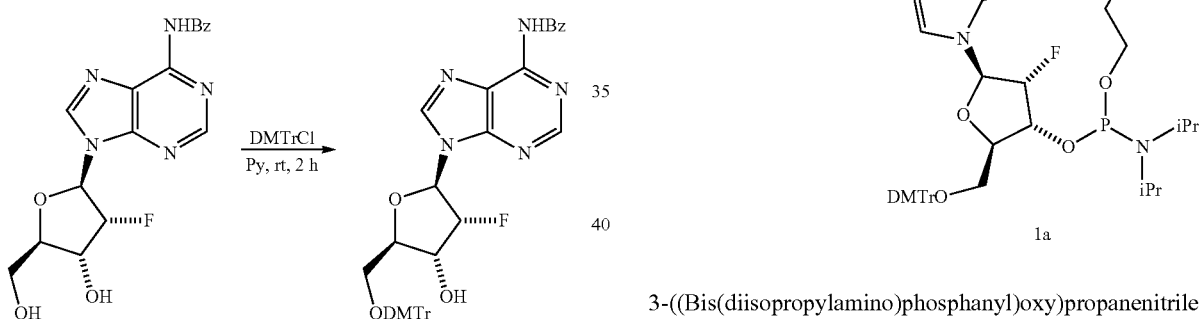

N-(9-((2R,3R,4R,5R)-3-fluoro-4-hydroxy-5-(hydroxymethyl)tetrahydrofuran-2-yl)-9H-purin-6-yl)benzamide (5.0 g, 13.4 mmol, 1.0 eq) was co-evaporated with pyridine (30 mL). DMTrCl (6.81 g, 20.1 mmol, 1.5 eq) was added to a solution of N-(9-((2R,3R,4R,5R)-3-fluoro-4-hydroxy-5-(hydroxymethyl)tetrahydrofuran-2-yl)-9H-purin-6-yl)benzamide (5.0 g, 13.4 mmol, 1.0 eq) in pyridine (35 mL) at 25° C. The mixture was stirred at 25° C. for 2 hours. Two parallel reactions were carried out. The combined mixtures were then diluted with DCM (15 mL), the organic layer was washed with sat·NaHCO$_3$ solution (20 mL) and brine (10 mL), dried over Na$_2$SO$_4$, filtered and concentrated, the crude was purified by column chromatography (petroleum ether:ethyl acetate=10:1 to 1:2) to give compound N-(9-((2R,3R,4R,5R)-5-((bis(4-methoxyphenyl)(phenyl)methoxy)methyl)-3-fluoro-4-hydroxytetrahydrofuran-2-yl)-9H-purin-6-yl)benzamide (16.0 g, 22.5 mmol, 83.9% yield, 95% purity) as a light yellow solid. LCMS (ES, m/z) 676.2 (M+H). $^1$H NMR (400 MHz, DMSO-d6) δ=11.27 (br s, 1H), 8.75 (s, 1H), 8.63 (s, 1H), 8.06 (br d, J=7.5 Hz, 2H), 7.69-7.62 (m, 1H), 7.60-7.51 (m, 2H), 7.33 (br d, J=7.3 Hz, 2H), 7.28-7.15 (m, 7H), 6.82 (dd, J=6.1, 8.6 Hz, 4H), 6.45 (d, J=20.0 Hz, 1H), 5.82-5.72 (m, 2H), 4.97-4.75 (m, 1H), 4.15 (br d, J=5.0 Hz, 1H), 3.72 (s, 6H), 3.35-3.22 (m, 2H). $^{19}$F NMR (376 MHz, DMSO-d$_6$) δ=−201.14 (s, 1F).

Step 2: (2R,3R,4R,5R)-5-(6-Benzamido-9H-purin-9-yl)-2-((bis(4-methoxyphenyl)(phenyl)methyoxy)methyl)-4-fluorotetrahydrofuran-3-yl-(2-cyanoethyl) diisopropylphosphoramidite (1a)

3-((Bis(diisopropylamino)phosphanyl)oxy)propanenitrile (6.42 g, 21.3 mmol, 6.77 mL, 1.8 eq) was added to a solution of N-(9-((2R,3R,4R,5R)-5-((bis(4-methoxyphenyl)(phenyl)methoxy)methyl)-3-fluoro-4-hydroxytetrahydrofuran-2-yl)-9H-purin-6-yl)benzamide (8.0 g, 11.8 mmol, 1.0 eq) in DCM (42 mL) at 0° C. followed by DCI (2.24 g, 18.9 mmol, 1.6 eq). The mixture was warmed to 25° C. and stirred for 3 hours. Two parallel reactions were carried out. The combined mixtures were then diluted with DCM (150 mL), the organic layer was washed with sat·NaHCO$_3$ solution (200 mL) and brine (100 mL), dried over Na$_2$SO$_4$, filtered and concentrated, the crude was purified by column chromatography to give compound 1a (18.0 g, 18.5 mmol, 78.1% yield, 90% purity) as a white solid. LCMS (ES, m/z) 876.3 (M+H). $^1$H NMR (400 MHz, DMSO-d6) δ=11.30 (br s, 1H), 8.70 (dd, J=2.9, 10.1 Hz, 2H), 8.07 (br d, J=7.3 Hz, 2H), 7.68-7.62 (m, 1H), 7.60-7.52 (m, 2H), 7.32 (br dd, J=2.6, 7.3 Hz, 2H), 7.27-7.14 (m, 7H), 6.85-6.74 (m, 4H), 6.59-6.44 (m, 1H), 6.02-5.81 (m, 1H), 5.43-5.13 (m, 1H), 4.25 (br s, 1H), 3.91-3.76 (m, 1H), 3.72 (d, J=2.8 Hz, 6H), 3.65-3.54 (m, 3H), 3.49-3.37 (m, 1H), 3.28-3.17 (m, 1H), 3.23 (dt, J=4.9, 11.0 Hz, 1H), 2.82-2.62 (m, 2H), 1.20-1.11 (m, 12H) $^{19}$F NMR (376 MHz, DMSO-d$_6$) δ=−199.12 (br dd, J=8.9, 77.0 Hz, 1F) $^{31}$P NMR (162 MHz, DMSO-d$_6$) δ=149.58 (br dd, J=7.8, 13.7 Hz, 1P).

Example ii: Preparation of N-(9-((2R,3R,4R,5R)-4-(Bis(4-methoxyphenyl)(phenyl)methoxy)-3-fluoro-5-(hydroxymethyl)tetrahydrofuran-2-yl)-9H-purin-6-yl)benzamide (1b)

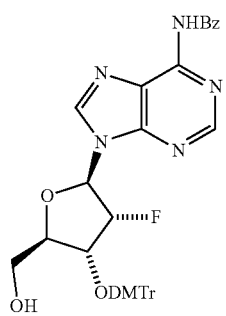

Step 1: Synthesis of N-(9-((2R,3R,4R,5R)-5-(((tert-Butyldimethylsilyl)oxy)methyl)-3-fluoro-4-hydroxytetrahydrofuran-2-yl)-9H-purin-6-yl)benzamide

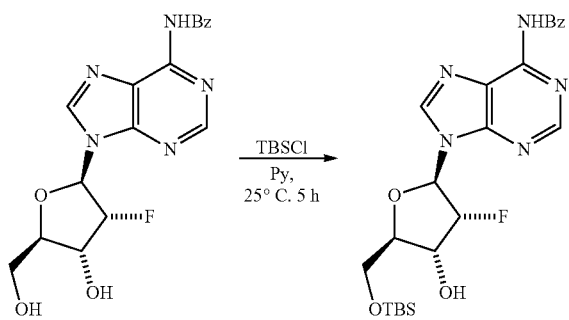

TBSCl (3.03 g, 20.1 mmol, 2.46 mL, 1.5 eq) was added to a solution of N-(9-((2R,3R,4R,5R)-3-fluoro-4-hydroxy-5-(hydroxymethyl)tetrahydrofuran-2-yl)-9H-purin-6-yl)benzamidem (5.0 g, 13.4 mmol, 1.0 eq) in pyridine (35 mL) at 25° C. The mixture was stirred at 25° C. for 5 hours. Two parallel reactions were carried out. The combined mixtures was then diluted with DCM (45 mL), and the organic layer was washed with sat·NaHCO₃ solution (40 mL) and brine (30 mL), dried over Na₂SO₄, filtered and concentrated. The crude product was purified by column chromatography to give N-(9-((2R,3R,4R,5R)-5-(((tert-butyldimethylsilyl)oxy)methyl)-3-fluoro-4-hydroxytetrahydrofuran-2-yl)-9H-purin-6-yl)benzamide (16.0 g, crude) as a light yellow solid. LCMS (ES, m/z) 488.2 (M+H)⁺.

Step 2: Synthesis of N-(9-((2R,3R,4R,5R)-4-(bis(4-methoxyphenyl)(phenyl)methoxy)-5-(((tert-butyldimethylsilyl)oxy)methyl)-3-fluorotetrahydrofuran-2-yl)-9H-purin-6-yl)benzamide

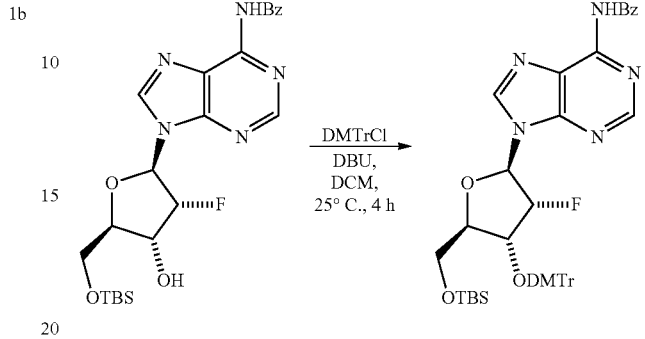

DMTrCl (6.78 g, 20.0 mmol, 1.5 eq) was added to a solution of N-(9-((2R,3R,4R,5R)-5-(((tert-butyldimethylsilyl)oxy)methyl)-3-fluoro-4-hydroxytetrahydrofuran-2-yl)-9H-purin-6-yl)benzamide (6.5 g, 13.3 mmol, 1.0 eq) in DCM (42 mL) at 25° C. followed by DBU (4.06 g, 26.66 mmol, 4.02 mL, 2.0 eq). The mixture was stirred at 25° C. for 4 hours. Two parallel reactions were carried out. The combined mixtures were then diluted with DCM (45 mL), the organic layer was washed with sat·NaHCO₃ solution (40 mL) and brine (30 mL), dried over Na₂SO₄, filtered and concentrated, the crude was purified by column chromatography to give N-(9-((2R,3R,4R,5R)-4-(bis(4-methoxyphenyl)(phenyl)methoxy)-5-(((tert-butyldimethylsilyl)oxy)methyl)-3-fluorotetrahydrofuran-2-yl)-9H-purin-6-yl)benzamide (30.0 g, crude) as a yellow solid. LCMS (ES, m/z) 790.3 (M+H)⁺.

Step 3: Synthesis of N-(9-((2R,3R,4R,5R)-4-(bis(4-methoxyphenyl)(phenyl)methoxy)-3-fluoro-5-(hydroxymethyl)tetrahydrofuran-2-yl)-9H-purin-6-yl)benzamide (1b)

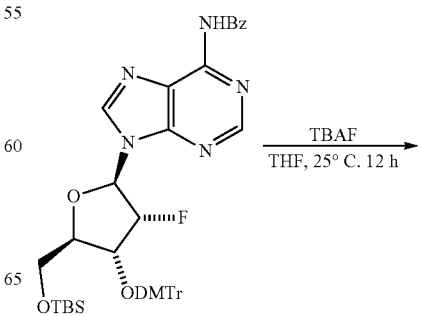

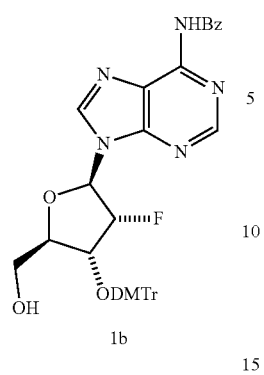

1b

TBAF (1 M, 26.6 mL, 2 eq) was added to a solution of N-(9-((2R,3R,4R,5R)-4-(bis(4-methoxyphenyl)(phenyl)methoxy)-5-(((tert-butyldimethylsilyl)oxy)methyl)-3-fluorotetrahydrofuran-2-yl)-9H-purin-6-yl)benzamide (10.5 g, 13.3 mmol, 1.0 eq) in THF (70 mL) at 25° C. The mixture was stirred at 25° C. for 12 hours. Two parallel reactions were carried out. The combined mixtures were then diluted with DCM (15 mL), the organic layer was washed with water (40 mL) and brine (10 mL), dried over $Na_2SO_4$, filtered and concentrated, the residue was purified by column chromatography to give N-(9-((2R,3R,4R,5R)-4-(bis(4-methoxyphenyl)(phenyl)methoxy)-3-fluoro-5-(hydroxymethyl)tetrahydrofuran-2-yl)-9H-purin-6-yl)benzamide (1b) (17.0 g, 22.6 mmol, 85.1% yield, 90% purity) as a light yellow solid. LCMS (ES, m/z) 676.20 (M+H)+. $^1$H NMR (400 MHz, DMSO-d6) δ=11.25 (br s, 1H), 8.73 (s, 1H), 8.60 (s, 1H), 8.06 (d, J=7.3 Hz, 2H), 7.68-7.61 (m, 1H), 7.58-7.48 (m, 4H), 7.41-7.31 (m, 6H), 7.27-7.22 (m, 1H), 6.89 (dd, J=7.2, 8.9 Hz, 4H), 6.39 (dd, J=2.6, 15.7 Hz, 1H), 4.72-4.53 (m, 2H), 3.83 (br s, 1H), 3.72 (d, J=4.8 Hz, 6H), 3.51 (br d, J=11.9 Hz, 1H), 3.32 (br dd, J=3.8, 12.4 Hz, 1H). $^{19}$F NMR (376 MHz, DMSO-d$_6$) δ=−200.74 (s, 1F).

Example iii: Preparation of N-(9-((2R,3R,4R,5R)-4-(Bis(4-methoxyphenyl)(phenyl)methoxy)-3-fluoro-5-(hydroxymethyl)tetrahydrofuran-2-yl)-6-oxo-6,9-dihydro-1H-purin-2-yl)isobutyramide (2a)

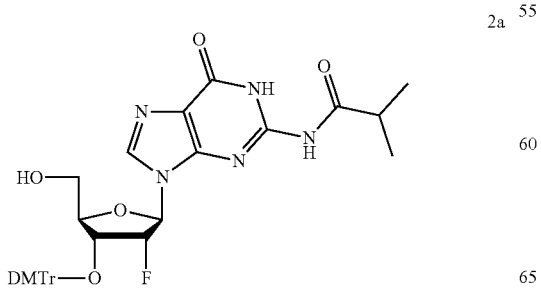

2a

Intermediate 2a was Synthesized According to Example ii as Described for Synthesis of Intermediate 1b Starting from

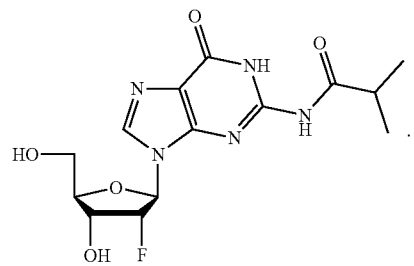

2a: LC-MS (ES, m/z): 658.30 [M+H]$^+$, $^1$H NMR (400 MHz, DMSO-d6) δ 12.14 (s, 1H), 11.71 (s, 1H), 8.15 (s, 1H), 7.50-7.43 (m, 2H), 7.38-7.18 (m, 7H), 6.94-6.79 (m, 4H), 6.09 (dd, J=13.2, 3.7 Hz, 1H), 5.13 (t, J=4.8 Hz, 1H), 4.41-4.21 (m, 2H), 3.70-3.71 (m, 7H), 3.54 (dd, J=11.6, 5.1 Hz, 1H), 3.42-3.35 (m, 1H), 2.79 (p, J=6.9 Hz, 1H), 1.13 (dd, J=8.8, 6.8 Hz, 6H); $^{19}$F-NMR (376 MHz, DMSO-d6) δ−202.87.

Example iv: Preparation of (((((2R,3R,4R,5R)-2-((bis(4-methoxyphenyl)(phenyl)methoxy)methyl)-4-fluoro-5-(2-isobutyramido-6-oxo-1,6-dihydro-9H-purin-9-yl)tetrahydrofuran-3-yl)oxy)(2-cyanoethoxy)phosphanyl)dipropylnickel (3a)

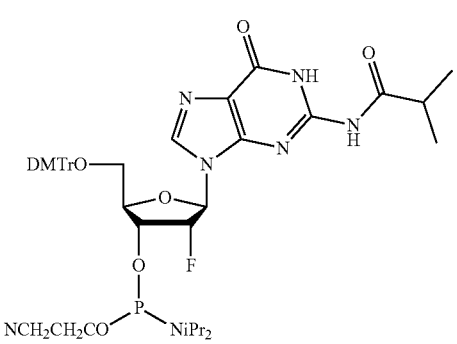

3a

Intermediate 3a was Synthesized According to Example i as Described for Synthesis of Intermediate 1a Starting from

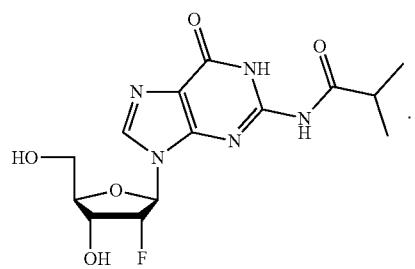

3a: ¹H NMR (400 MHz DMSO-d₆) δ 12.09 (br s, 1H), 11.65 (br s, 1H), 8.01-8.15 (m, 1H), 7.27-7.40 (m, 2H), 7.09-7.27 (m, 7H), 6.68-6.88 (m, 4H), 6.11-6.26 (m, 1H), 5.44-5.68 (m, 1H), 4.51-4.77 (m, 1H), 4.19 (d, J=4.4 Hz, 1H), 3.98 (q, J=7.2 Hz, 2H), 3.63-3.74 (m, 6H), 3.42-3.58 (m, 3H), 3.31-3.39 (m, 1H), 3.22-3.28 (m, 1H), 2.68-2.81 (m, 2H), 2.56 (t, J=6.0 Hz, 1H), 1.02-1.11 (m, 16H), 0.91 (d, J=6.8 Hz, 2H). ³¹P NMR (162 MHz DMSO-d₆) δ 150.31 (s, 1P), 149.61 (s, 1P).

Example v: Preparation of ((((2R,3R,4R,5R)-2-((bis (4-methoxyphenyl)(phenyl)methoxy)methyl)-4-fluoro-5-(2-isobutyramido-6-oxo-1,6-dihydro-9H-purin-9-yl)tetrahydrofuran-3-yl)oxy)(2-cyanoethoxy) phosphanyl)dipropylnickel (8a)

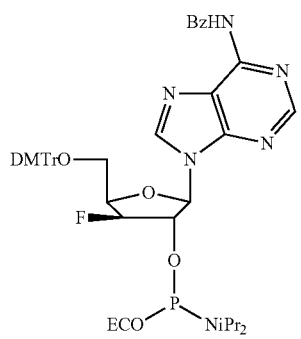

8a

Compound 8a was synthesized according to Example i from N-(9-((2R,3S,4R,5R)-5-((bis(4-methoxyphenyl)(phenyl)methoxy)methyl)-4-fluoro-3-hydroxytetrahydrofuran-2-yl)-9H-purin-6-yl)benzamide, which was prepared according to the methods described in WO2017075477A1.

Example vi: Preparation of ((((2R,3S,4R,5R)-2-(6-benzamido-9H-purin-9-yl)-5-((bis(4-methoxyphenyl)(phenyl)methoxy)methyl)-4-fluorotetrahydrofuran-3-yl)oxy)(2-cyanoethoxy)phosphanyl) dipropylnickel (10a)

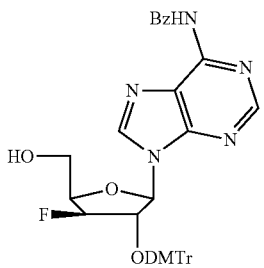

10a

Step 1: Synthesis of N-(9-((2R,3S,4R,5R)-5-(((tert-butyldimethylsilyl)oxy)methyl)-4-fluoro-3-hydroxytetrahydrofuran-2-yl)-9H-purin-6-yl)benzamide (10-2)

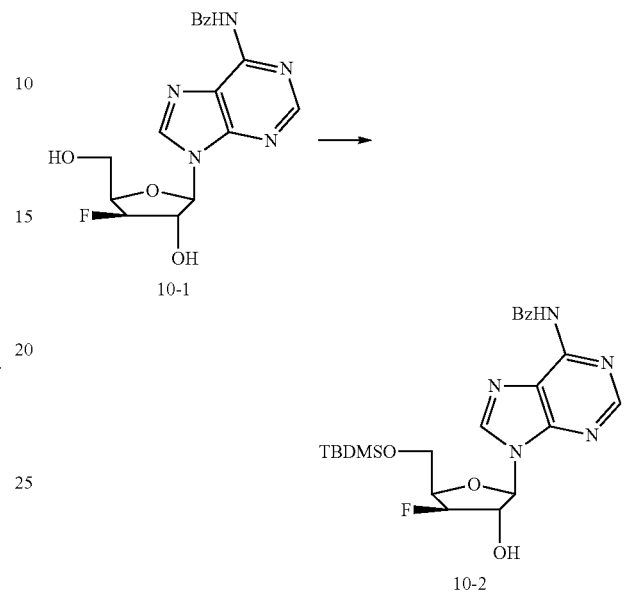

Into a 1000-mL round-bottom flask, N-[9-[(2R,3S,4R,5R)-4-fluoro-3-hydroxy-5-(hydroxymethyl)oxolan-2-yl]-9H-purin-6-yl]benzamide (35 g, 93.747 mmol, 1 equiv, prepared according to WO2017075477A1) and TBDMS-Cl (16.96 g, 112.497 mmol, 1.2 equiv) in pyridine (300 mL) were added. The resulting solution was stirred overnight at room temperature and concentrated. The residue was purified by column chromatography eluting with dichloromethane/methanol (15:1) to give 30 g of N-(9-((2R,3S,4R,5R)-5-(((tert-butyldimethylsilyl)oxy)methyl)-4-fluoro-3-hydroxytetrahydrofuran-2-yl)-9H-purin-6-yl)benzamide (10-2) as a yellow solid (66.70%).

Step 2: Synthesis of N-(9-((2R,3S,4S,5R)-3-(bis(4-methoxyphenyl)(phenyl)methoxy)-5-(((tert-butyldimethylsilyl)oxy)methyl)-4-fluorotetrahydrofuran-2-yl)-9H-purin-6-yl)benzamide (10-3)

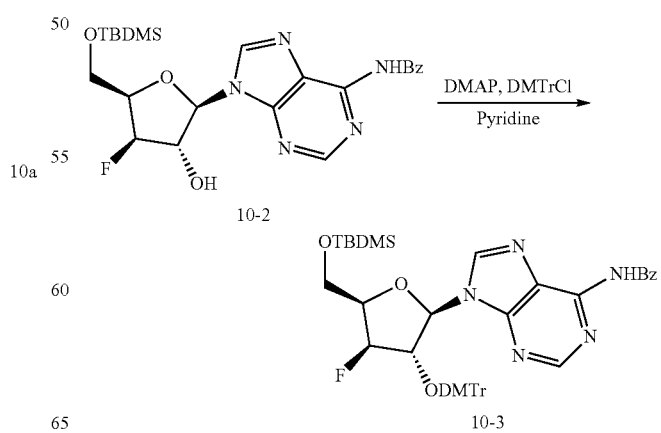

Into a 1000-mL round-bottom flask, N-[9-[(2R,3S,4R,5R)-5-[[(tert-butyldimethylsilyl)oxy]methyl]-4-fluoro-3-hydroxyoxolan-2-yl]-9H-purin-6-yl]benzamide (30 g, 61.525 mmol, 1 equiv), DMTr-Cl (41.59 g, 123.050 mmol, 2 equiv) and DMAP (15.03 g, 123.050 mmol, 2 equiv) in pyridine (500 mL) were added. The resulting solution was stirred overnight at room temperature and then quenched with 500 mL of water. The resulting solution was extracted with 2×1000 mL of dichloromethane, the organic layer was concentrated in vacuo. The residue was purified by column chromatography eluting with ethyl acetate/petroleum ether (1:1) to give 22 g of N-(9-((2R,3S,4S,5R)-3-(bis(4-methoxyphenyl)(phenyl)methoxy)-5-(((tert-butyldimethylsilyl)oxy)methyl)-4-fluorotetrahydrofuran-2-yl)-9H-purin-6-yl)benzamide (10-3) as a yellow solid (45.80%).

Step 3: Synthesis of N-[9-[(2R,3S,4S,5R)-3-[bis(4-methoxyphenyl)(phenyl)methoxy]-4-fluoro-5-(hydroxymethyl)oxolan-2-yl]-9H-purin-6-yl]benzamide (10a)

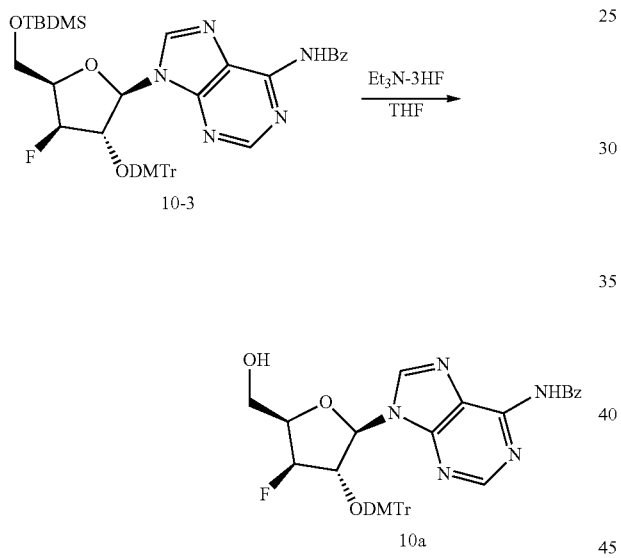

Into a 500-mL round-bottom flask, N-[9-[(2R,3S,4S,5R)-3-[bis(4-methoxyphenyl)(phenyl)methoxy]-5-[[(tert-butyldimethylsilyl)oxy]methyl]-4-fluorooxolan-2-yl]-9H-purin-6-yl]benzamide (22 g, 27.849 mmol, 1 equiv) and Et₃N-3HF (8.98 g, 55.698 mmol, 2.00 equiv) in THF (200 mL) were added. The resulting solution was stirred overnight at room temperature and concentrated. The residue was purified by column chromatography eluting with dichloromethane/ethyl acetate (2:1) to give 14.7380 g of N-[9-[(2R,3S,4S,5R)-3-[bis(4-methoxyphenyl)(phenyl)methoxy]-4-fluoro-5-(hydroxymethyl)oxolan-2-yl]-9H-purin-6-yl]benzamide as a white solid (10a, 78.32%). LCMS: (ES, m/z): 676.35 [M+H]+; ¹H NMR: (300 MHz, DMSO-d₆, ppm): δ 11.25 (s, 1H), 8.75 (s, 1H), 8.26 (s, 1H), 8.06 (d, J=7.8 Hz, 2H), 7.71-7.61 (m, 1H), 7.59-7.53 (m, 2H), 7.46-7.34 (m, 2H), 7.34-7.14 (m, 7H), 6.77 (d, J=8.8 Hz, 2H), 6.67 (d, J=8.9 Hz, 2H), 6.11 (t, J=1.9 Hz, 1H), 5.03 (t, J=5.3 Hz, 1H), 4.94 (d, J=16.5 Hz, 1H), 4.66 (d, J=52.3 Hz, 1H), 4.33 (dt, J=30.5, 6.0 Hz, 1H), 3.73-3.59 (m, 8H); ¹⁹F NMR: (300 MHz, DMSO-d₆, ppm): δ −199.21 (1F).

Example vii: Preparation of N-(9-((2R,3S,4R,5R)-3-(bis(4-methoxyphenyl)(phenyl)methoxy)-4-fluoro-5-(hydroxymethyl)tetrahydrofuran-2-yl)-9H-purin-6-yl)benzamide (12a)

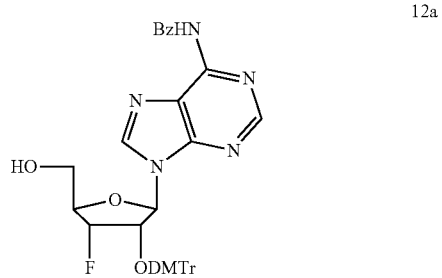

Compound 12a was prepared according to Example vi from

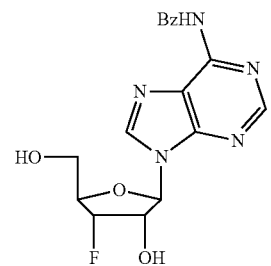

which was prepared according to procedures reported in WO2017075477A1.

Example viii: Preparation of ((((2R,3S,4R,5R)-2-(6-benzamido-9H-purin-9-yl)-5-((bis(4-methoxyphenyl)(phenyl)methoxy)methyl)-4-fluorotetrahydrofuran-3-yl)oxy)(2-cyanoethoxy)phosphanyl) dipropylnickel (14a)

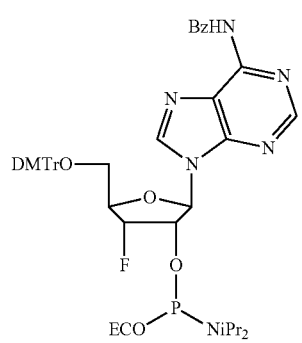

Compound 14a was synthesized according to Example i from N-(9-((2R,3S,4S,5R)-5-((bis(4-methoxyphenyl)(phenyl)methoxy)methyl)-4-fluoro-3-hydroxytetrahydrofuran-2-yl)-9H-purin-6-yl)benzamide, which was prepared according to the methods described in WO2017075477A1.

Synthesis of Compounds of the Present Disclosure

Example 1: Synthesis of 4 stereoisomers of ((2R,3R,3aR,7aR,9R,10R,10aR,14aS)-2,9-bis(6-amino-9H-purin-9-yl)-3,10-difluoro-12-mercapto-5,12-dioxidooctahydro-2H,7H-difuro[3,2-d:3',2'-j][1,3,7,9]tetraoxa[2,8]diphosphacyclododecin-5-yl) trihydroborate (Compounds A1-A4)

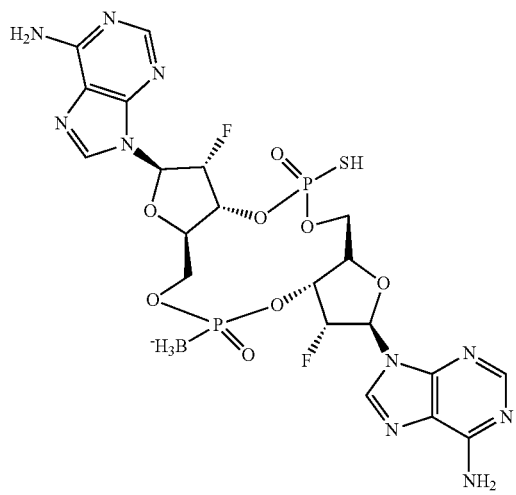

Step 1: Synthesis of (2R,3R,4R,5R)-5-(6-benzamido-9H-purin-9-yl)-2-((bis(4-methoxyphenyl)(phenyl)methoxy)methyl)-4-fluorotetrahydrofuran-3-yl-(((2R,3R,4R,5R)-5-(6-benzamido-9H-purin-9-yl)-3-(bis(4-methoxyphenyl)(phenyl)methoxy)-4-fluorotetrahydrofuran-2-yl)methyl) (2-cyanoethyl) phosphite (1c)

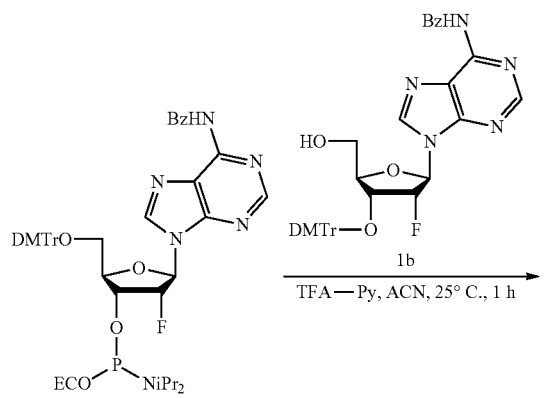

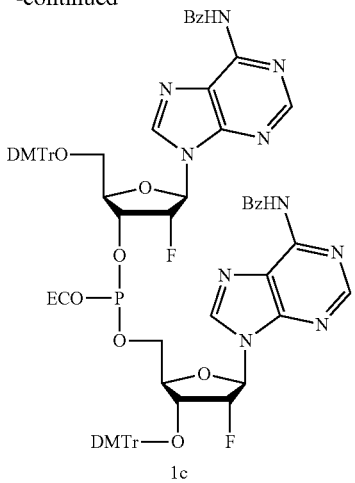

Compound 1a (5.0 g, 7.40 mmol, 1.0 eq) and compound 1b (7.13 g, 8.14 mmol, 1.1 eq) were co-evaporated with CH$_3$CN (60 mL×2). Molecular sieve 3A (5 g, 37.0 mmol, 5 eq) was added to a solution of compound 1a and compound 1b in CH$_3$CN (100 mL) at 25° C. followed by TFA-Pyridine (2.14 g, 11.1 mmol, 1.5 eq). The mixture was stirred at 25° C. for 0.5 hr. Filtered and diluted with DCM (100 mL), the organic layer was washed with sat·NaHCO$_3$ solution (100 mL×2) and brine (100 mL), dried over Na$_2$SO$_4$, filtered and concentrated to give compound 1c (12 g, crude) as a light yellow solid. LCMS (ES, m/z) 725.8 [(M+H)/2]$^+$.

Step 2: Synthesis of (((((2R,3R,4R,5R)-5-(6-benzamido-9H-purin-9-yl)-2-((bis(4-methoxyphenyl)(phenyl)methoxy)methyl)-4-fluorotetrahydrofuran-3-yl)oxy)(((2R,3R,4R,5R)-5-(6-benzamido-9H-purin-9-yl)-3-(bis(4-methoxyphenyl)(phenyl)methoxy)-4-fluorotetrahydrofuran-2-yl)methoxy)(2-cyanoethoxy)-14-phosphanyl)trihydroborate (1d)

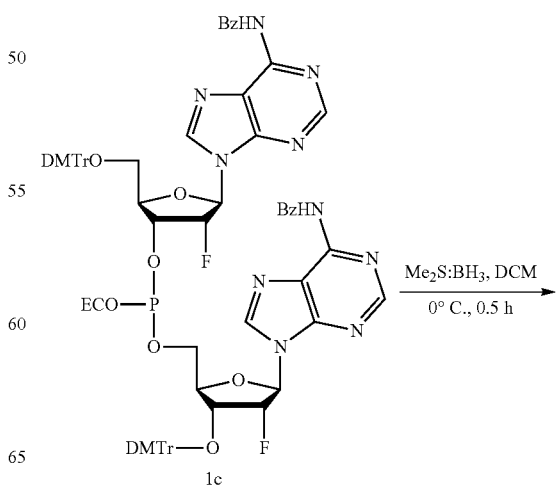

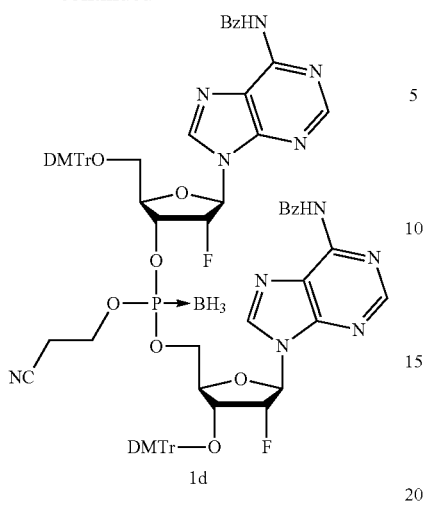

1d

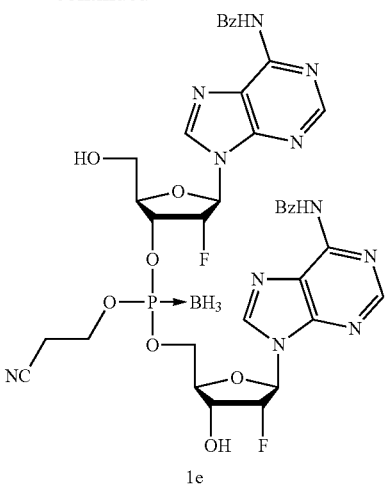

1e

BH₃-Me₂S (2 M, 4.55 mL, 3.3 eq) was added to a solution of compound 1c (4.0 g, 2.76 mmol, 1.0 eq) in DCM (28 mL) at 0° C. and stirred for 0.5 hr. Three parallel reactions were carried out. The combined mixtures were then quenched by MeOH (18 mL) and diluted with DCM (300 mL). The organic layer was washed with sat·NaHCO₃ solution (300 mL) and brine (300 mL), dried over Na₂SO₄, filtered and concentrated to give compound 1d (12.0 g, crude) as a yellow solid.

Step 3: Synthesis of (((((2R,3R,4R,5R)-5-(6-benzamido-9H-purin-9-yl)-4-fluoro-2-(hydroxymethyl)tetrahydrofuran-3-yl)oxy)(((2R,3R,4R,5R)-5-(6-benzamido-9H-purin-9-yl)-4-fluoro-3-hydroxytetrahydrofuran-2-yl)methoxy)(2-cyanoethoxy)-15-phosphanyl)trihydroborate (1c)

The solution of compound 1d (4.0 g, 2.73 mmol, 1 eq) in 80% AcOH/CH₃CN (3/1) (80 mL) was stirred at 25° C. for 12 hrs. The mixture was diluted with ethyl acetate (20 mL), the organic layer was washed with sat·NaHCO₃ solution (100 mL×2) and brine (40 mL), dried over Na₂SO₄, filtered and concentrated. After recrystallization and filtration, the resulting cake was purified by column chromatography (DCM:MeOH=100:1 to 10:1) to provide compound 1f (0.5 g, 523 μmol, 19.1% yield, 90% purity) as a white solid. LCMS (ES, m/z) 860.70 [M+H]⁺.

Step 4: Synthesis of ((2R,3R,3aR,7aR,9R,10R,10aR,14aS)-2,9-Bis(6-benzamido-9H-purin-9-yl)-5,12-bis(2-cyanoethoxy)-3,10-difluorooctahydro-2H,7H-5λ⁴-difuro[3,2-d:3',2'-j][1,3,7,9]tetraoxa[2,8]diphosphacyclododecin-5-yl)trihydroborate (1f)

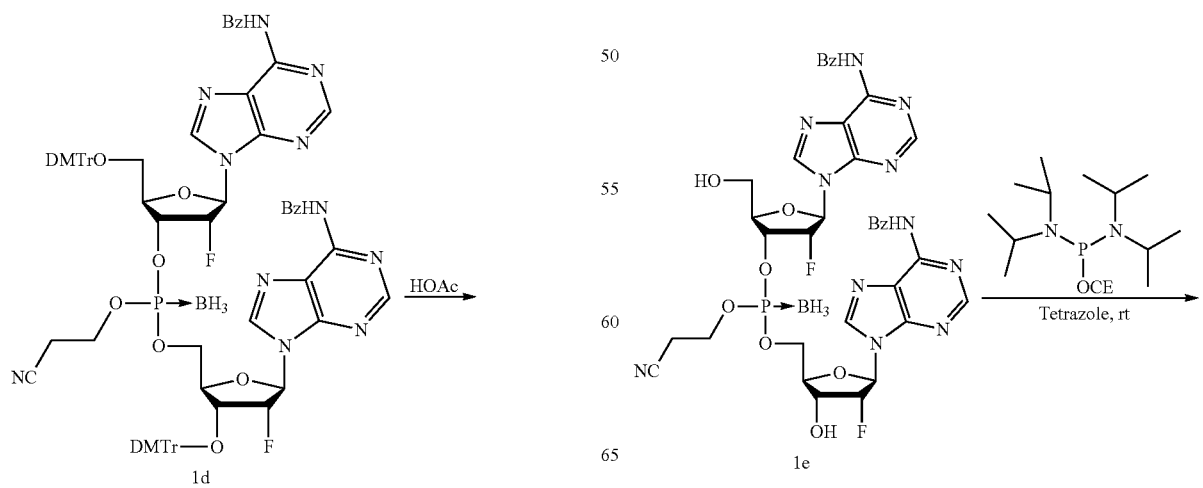

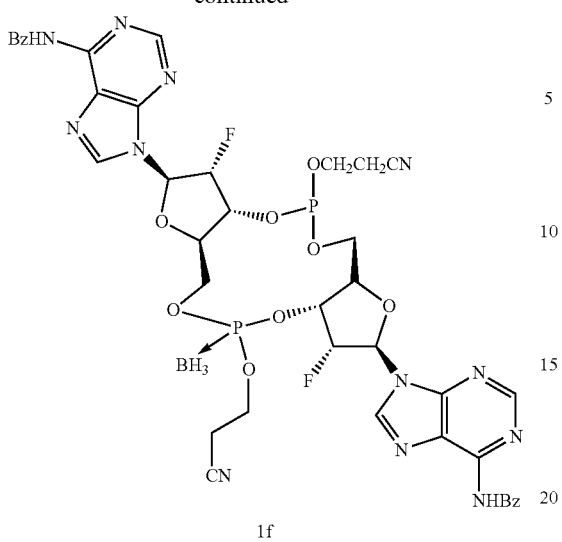

1f

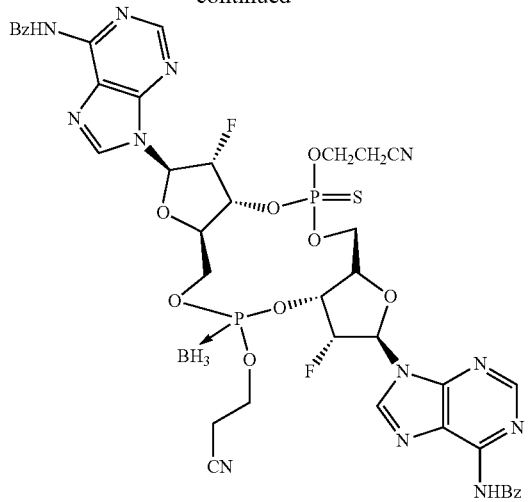

1g

To a solution of compound 1e (0.51.00 g, 581 μmol 1.16 mmol, 1.0 eq) and 2H-tetrazole (0.45 M, 7.76 mL, 600 eq) in ACN (7 mL) followed by (7.00 mL) was added 4A molecular sieve (1.00 g, 1.16 mmol, 1.00 eq), tetrazole (907 mg, 6.97 mmol, 6.00 eq) and 3-((bis(diisopropylamino)phosphanyl)oxy)propanenitrile (263 (525 mg, 872 μmol, 2771.74 mmol, 553 uL, 1.550 eq). The mixture was stirred at 25° C. for 1 hr. Diluted with EtOAc (15 mL), 2 hrs. TLC (DCM/MeOH=20/1, product: Rf=0.43) the organic layer was washed with sat·NaHCO₃ solution (20 mL×2) and brine (10 mL), dried over Na₂SO₄, filtered and concentrated to give compound 1f (40% purity) in ACN (7 mL) as a light yellow solution·reaction mixture completed. The reaction mixture was used directly to the next step. LCMS (ES, m/z) 959.6 (M+H)⁺.

Step 5: Synthesis of ((2R,3R,3aR,7aR,9R,10R, 10aR,14aS)-2,9-bis(6-benzamido-9H-purin-9-yl)-5, 12-bis(2-cyanoethoxy)-3,10-difluoro-12-sulfidoocta-hydro-2H,7H-5λ⁴-difuro[3,2-d:3',2'-j][1,3,7,9] tetraoxa[2,8]diphosphacyclododecin-5-yl) trihydroborate (1g)

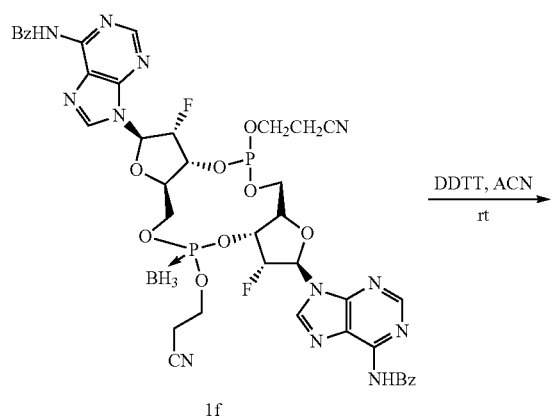

1f

DDTT (107 mg, 521 μmol, 1.0 eq) was added to the solution of compound 1f (0.5 g, 521 μmol, 1 eq) in ACN (10 mL) at 25° C. and stirred for 0.5 hr. LCMS showed compound 1f was consumed completely and desired MS was detected. Diluted with EtOAc (30 mL), the organic layer was washed with sat·NaHCO₃ solution (40 mL×2) and brine (10 mL), dried over Na₂SO₄, filtered and concentrated to give the residue which was purified by column chromatography (DCM:MeOH=200: 1 to 30: 1) to give compound 1g (0.14 g, crude) as a yellow solid. LCMS (ES, m/z) 496.4 [1/2(M+H)]⁺.

Step 6: Synthesis of Compounds A1, A2, A3, and A4

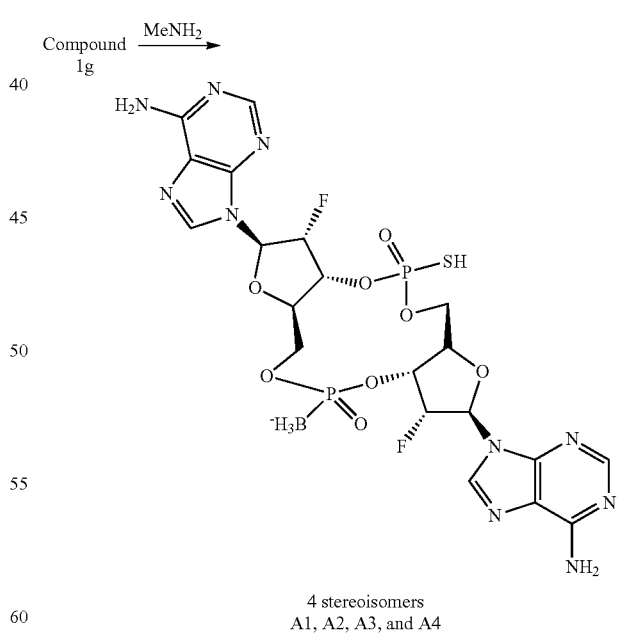

4 stereoisomers
A1, A2, A3, and A4

Compound 1g (0.14 g, 141.32 μmol, 1 eq) was dissolved in a solution of MeNH₂ in EtOH (2 mL, 30% by weigh) at 25° C. The mixture was stirred at 25° C. for 3 hours and concentrated to give the residue, which was purified by HPLC to give a mixture of two peaks. RT=1.693, 1.870 min. LCMS (ES, m/z) 677.0 (M+H)+.

Example 2: Synthesis of 4 stereoisomers of ((2R,3R,3aR,7aR,9R,10R,10aR,14aS)-9-(2-amino-6-oxo-1,6-dihydro-9H-purin-9-yl)-2-(6-amino-9H-purin-9-yl)-3,10-difluoro-12-mercapto-5,12-dioxidooctahydro-2H,7H-difuro[3,2-d:3',2'-j][1,3,7,9]tetraoxa[2,8]diphosphacyclododecin-5-yl) trihydroborate (Compounds B1-B4)

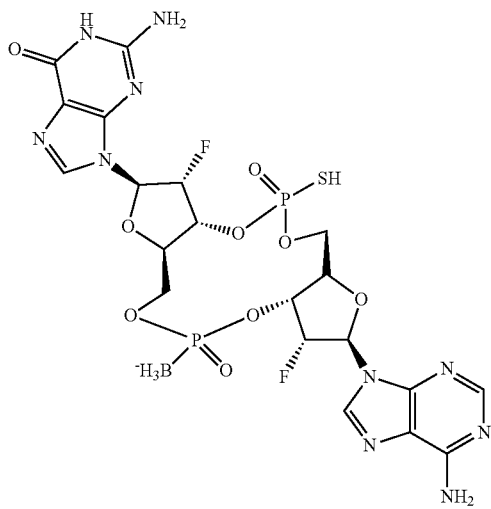

Step 1: Synthesis of (2R,3R,4R,5R)-5-(6-benzamido-9H-purin-9-yl)-2-((bis(4-methoxyphenyl)(phenyl)methoxy)methyl)-4-fluorotetrahydrofuran-3-yl (((2R,3R,4R,5R)-3-(bis(4-methoxyphenyl)(phenyl)methoxy)-4-fluoro-5-(2-isobutyramido-6-oxo-1,6-dihydro-9H-purin-9-yl)tetrahydrofuran-2-yl) methyl) (2-cyanoethyl) phosphite (2b)

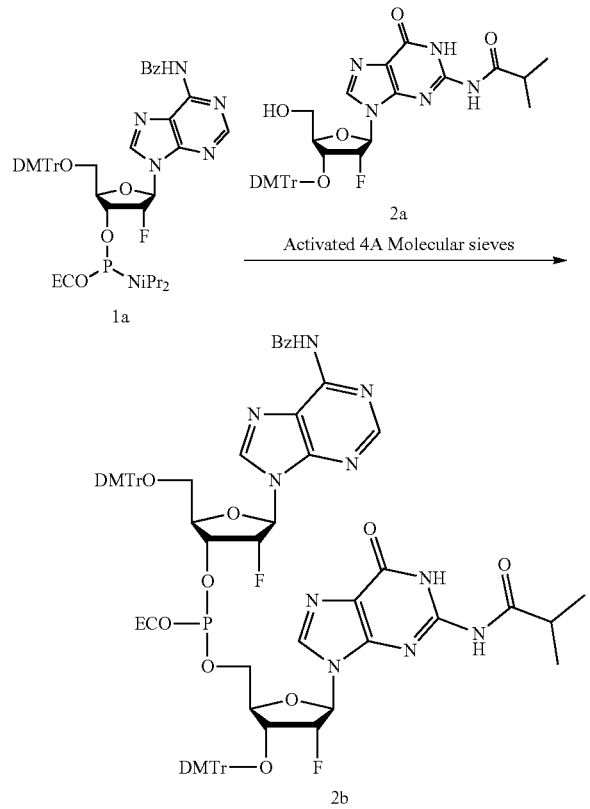

To a solution of compound 1a (7.62 g, 8.70 mmol, 1.10 eq) and compound 2a (5.20 g, 7.91 mmol, 1.00 eq) in ACN (50 mL), TFA-Py (1.0 M, 17.39 mL, 2.20 eq) was added and stirred at 25° C. for 0.5 h. Dilute with DCM (150 mL), the mixture was washed with sat·NaHCO₃ solution (150 mL) and brine (100 mL), dried over $Na_2SO_4$, filtered and concentrated in vacuo to give 2b (11.33 g) as light yellow solid, which was used in next step without further purification. LCMS (ES, m/z) 1432.5 (M+H)+.

Step 2: Synthesis of (((((2R,3R,4R,5R)-5-(6-Benzamido-9H-purin-9-yl)-2-((bis(4-methoxyphenyl)(phenyl)methoxy)methyl)-4-fluorotetrahydrofuran-3-yl)oxy)(((2R,3R,4R,5R)-3-(bis(4-methoxyphenyl)(phenyl)methoxy)-4-fluoro-5-(2-isobutyramido-6-oxo-1,6-dihydro-9H-purin-9-yl)tetrahydrofuran-2-yl)methoxy)(2-cyanoethoxy)-14-phosphanyl) trihydroborate (2c)

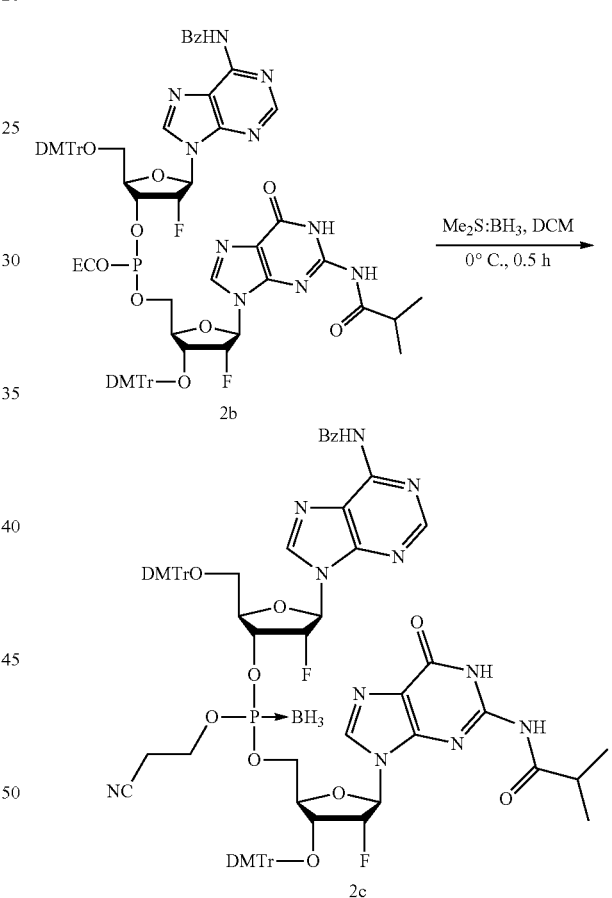

To a solution of compound 2b (11.33 g, 7.91 mmol, 1.00 eq) in DCM (15 mL) at 0° C. $BH_3\text{-}Me_2S$ (10 M, 2.61 mL, 3.30 eq) was added. The mixture was stirring at 0° C. for 0.5 hr. The mixture was quenched by MeOH (10 mL), diluted with DCM (200 mL, 100 mL), washed with sat. NaHCO₃ solution (100 mL) and brine (100 mL), dried over $Na_2SO_4$, filtered and concentrated in vacuo to give compound 2c (11.4 g, crude) as a yellow solid, which was used in next step without further purification.

Step 3: Synthesis of ((((2R,3R,4R,5R)-5-(6-Benzamido-9H-purin-9-yl)-4-fluoro-2-(hydroxymethyl)tetrahydrofuran-3-yl)oxy)(2-cyanoethoxy)(((2R,3R,4R,5R)-4-fluoro-3-hydroxy-5-(2-isobutyramido-6-oxo-1,6-dihydro-9H-purin-9-yl)tetrahydrofuran-2-yl)methoxy)-λ⁴-phosphanyl)trihydroborate (2d)

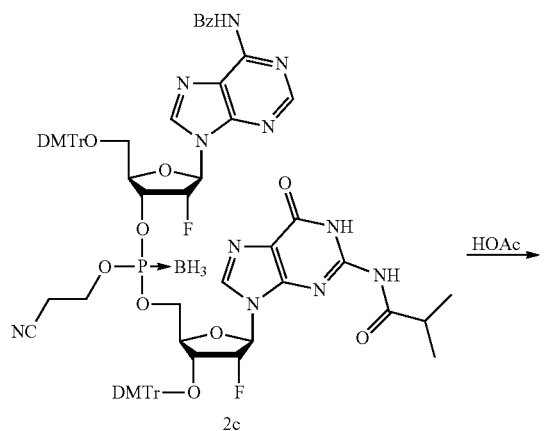

2c

Compound 2c (11.4 g, 7.91 mmol, 1.00 eq) was added to 80% AcOH/ACN (7.81 mmol, 250 mL) at 25° C. The mixture was stirred at 25° C. for 12 h, diluted with ethyl acetate (200 mL), the organic layer was washed with sat·NaHCO$_3$ solution (200 mL×2), and brine (100 mL), dried over Na$_2$SO$_4$, filtered and concentrated in vacuo to give a residue, which was purified by prep-HPLC to give compound 2d (2.50 g, 37.5% yield) as white solid. LCMS (ES, m/z) 842.3 (M+H)⁺. ¹H NMR: (300 MHz, DMSO-d$_6$, ppm): δ 12.12 (s, 1H), 11.62 (s, 1H), 11.27 (s, 1H), 8.64-8.81 (m, 2H), 8.12 (d, J=2.8 Hz, 1H), 8.05 (d, J=7.2 Hz, 2H), 7.62-7.70 (m, 1H), 7.49-7.60 (m, 2H), 6.48 (dd, J=2.4, 16.8 Hz, 1H), 6.11-6.25 (m, 1H), 5.80-6.04 (m, 2H), 5.25-5.49 (m, 3H), 4.12-4.66 (m, 7H), 3.53-3.77 (m, 2H), 3.17 (s, 4H), 2.93 (m, 2H), 2.68-2.83 (m, 1H), 1.00-1.19 (m, 6H), 0.48 (br s, 3H). ³¹P NMR: (162 MHz, DMSO-d$_6$) 115.33 (s, 1P).

Step 4: Synthesis of ((2R,3R,3aR,7aR,9R,10R,10aR,14aS)-2-(6-Benzamido-9H-purin-9-yl)-5,12-bis(2-cyanoethoxy)-3,10-difluoro-9-(2-isobutyramido-6-oxo-1,6-dihydro-9H-purin-9-yl)octahydro-2H,7H-5λ⁴-difuro[3,2-d:3',2'-j][1,3,7,9]tetraoxa[2,8]diphosphacyclododecin-5-yl)trihydroborate (2e)

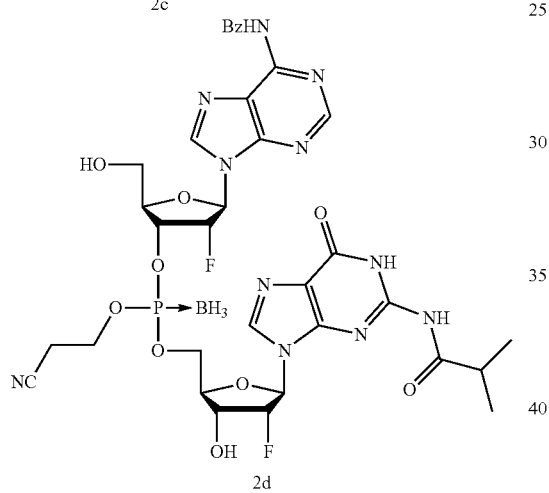

2d

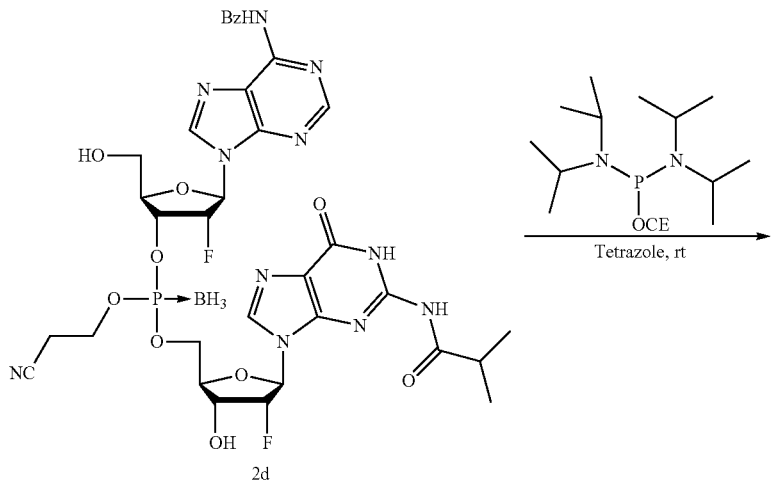

2d

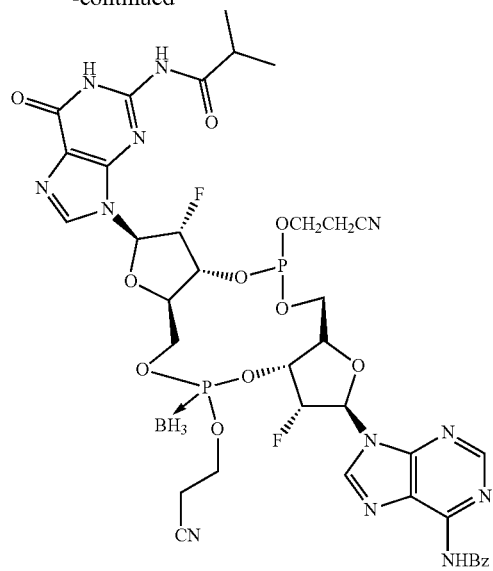

2e

To a solution of compound 2d (1.00 g, 1.19 mmol, 1.00 eq) in ACN (10 mL) were added 5-ethylsulfanyl-2H-tetrazole (0.92 g, 7.13 mmol, 6.00 eq), 3A molecular sieve (1.00 g, 1.19 mmol, 1.00 eq) and 3-((bis(diisopropylamino)phosphanyl)oxy)propanenitrile (0.53 g, 1.78 mmol, 1.50 eq). The mixture was stirred at 25° C. for 2 hrs. TLC (DCM:MeOH=10:1, product: $R_f$=0.51) indicated compound 2e was consumed completely. The light yellow solution was used directly to the next step Step 5: ((2R,3R,3aR,7aR,9R,10R,10aR,14aS)-2-(6-Benzamido-9H-purin-9-yl)-5,12-bis(2-cyanoethoxy)-3,10-difluoro-9-(2-isobutyramido-6-oxo-1,6-dihydro-9H-purin-9-yl)-12-sulfidooctahydro-2H,7H-5λ$^4$-difuro[3,2-d:3',2'-j][1,3,7,9]tetraoxa[2,8]diphosphacyclododecin-5-yl)trihydroborate (2f)

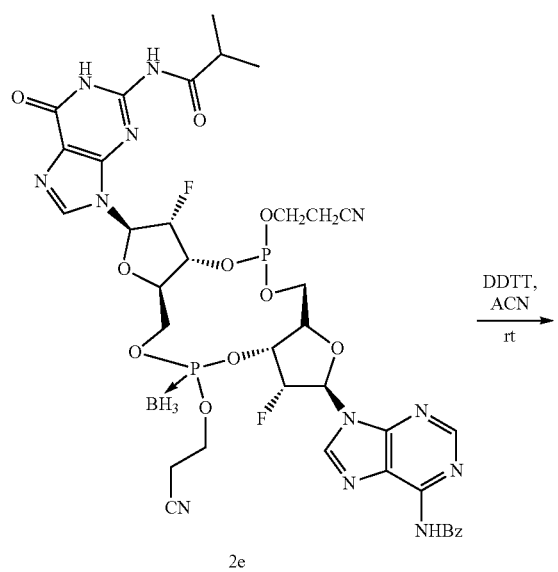

2e $\xrightarrow{\text{DDTT, ACN}}_{\text{rt}}$

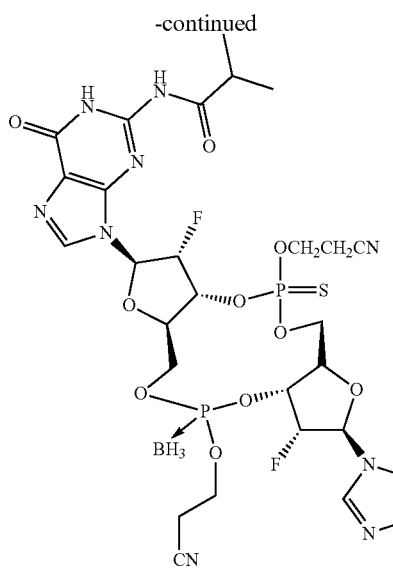

2f

To a solution of compound 2e (1.12 g, 1.19 mmol, 1.00 eq) in ACN (10 mL) was added DDTT (244 mg, 1.19 mmol, 1.00 eq). The mixture was stirred at 25° C. for 0.5 hr. The reaction mixture was diluted with sat·NaHCO$_3$ solution (50 mL×2) and extracted with ethyl acetate (50 mL, 25 mL), the organic layer was then washed with brine (50 mL), dried over Na$_2$SO$_4$, filtered and concentrated to provide a residue, which was purified by column chromatography (SiO$_2$, DCM/MeOH=200/1 to 30/1) to give compound 2f (0.40 g, crude) as a light yellow solid. LCMS (ES, m/z) 973.3 (M+H)$^+$ Step 6: Synthesis of Compounds B1, B2, B3, and B4

Compound 2f $\xrightarrow{\text{MeNH}_2}$

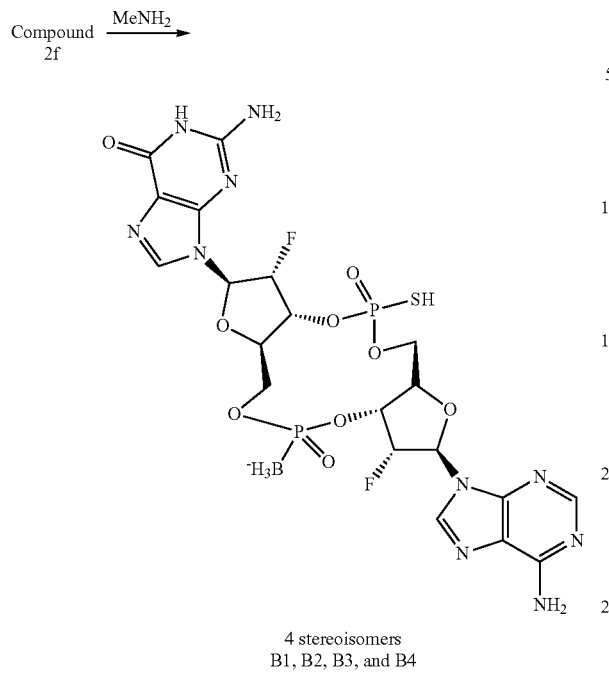

4 stereoisomers
B1, B2, B3, and B4

The solution of compound 2f (0.40 g, 411 umol, 1.00 eq) in MeNH₂ (18 mL, 30% in EtOH) was stirred at 25° C. for 3 hrs. The reaction mixture was diluted with ACN (5 mL×2) and concentrated in vacuo. The residue was purified by prep-HPLC (column: Waters Xbridge 150*25 5u; mobile phase: [water (10 mM NH₄HCO₃)-ACN]; B %: 1%-18%, 12 min) to give compounds B1 (5.0 mg), B2 (8.0 mg), B3 (0.8 mg) and B4 (12.0 mg) as white foam. B1: LCMS (ES, m/z) 691.1 (M−H)⁻; B2: LCMS (ES, m/z) 691.0 (M−H)⁻; B3: LCMS (ES, m/z) 691.0 (M−H)⁻; B4: LCMS (ES, m/z) 691.0 (M−H)⁻, ¹H NMR: (300 MHz, DMSO-d6, ppm): δ 7.87-8.34 (m, 3H), 5.96-6.37 (m, 2H), 5.02-5.78 (m, 4H), 4.33-4.63 (m, 4H), 3.99 (br s, 2H), 0.39 (br s, 3H).

Example 3: Synthesis of 4 stereoisomers of ((2R,3R,3aR,7aS,9R,10R,10aR,14aR)-2-(2-amino-6-oxo-1,6-dihydro-9H-purin-9-yl)-9-(6-amino-9H-purin-9-yl)-3,10-difluoro-12-mercapto-5,12-dioxidooctahydro-2H,7H-difuro[3,2-d:3',2'-j][1,3,7,9]tetraoxa[2,8]diphosphacyclododecin-5-yl) trihydroborate (Compounds C1-C4)

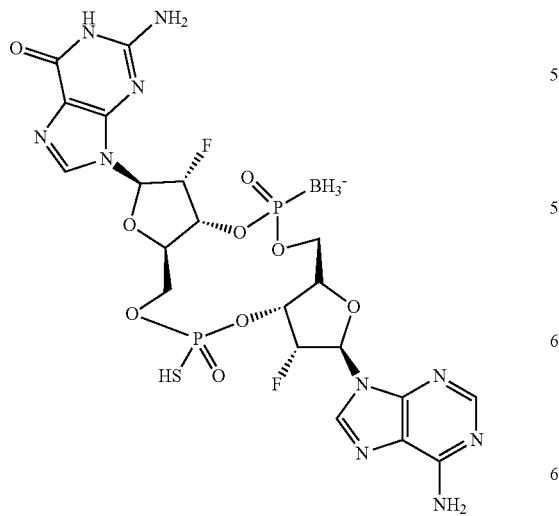

Step 1: Synthesis of ((2R,3R,4R,5R)-5-(6-Benzamido-9H-purin-9-yl)-3-(bis(4-methoxyphenyl)(phenyl)methoxy)-4-fluorotetrahydrofuran-2-yl)methyl ((2R,3R,4R,5R)-2-((bis(4-methoxyphenyl)(phenyl)methoxy)methyl)-4-fluoro-5-(2-isobutyramido-6-oxo-1,6-dihydro-9H-purin-9-yl)tetrahydrofuran-3-yl) (2-cyanoethyl) phosphite (3b)

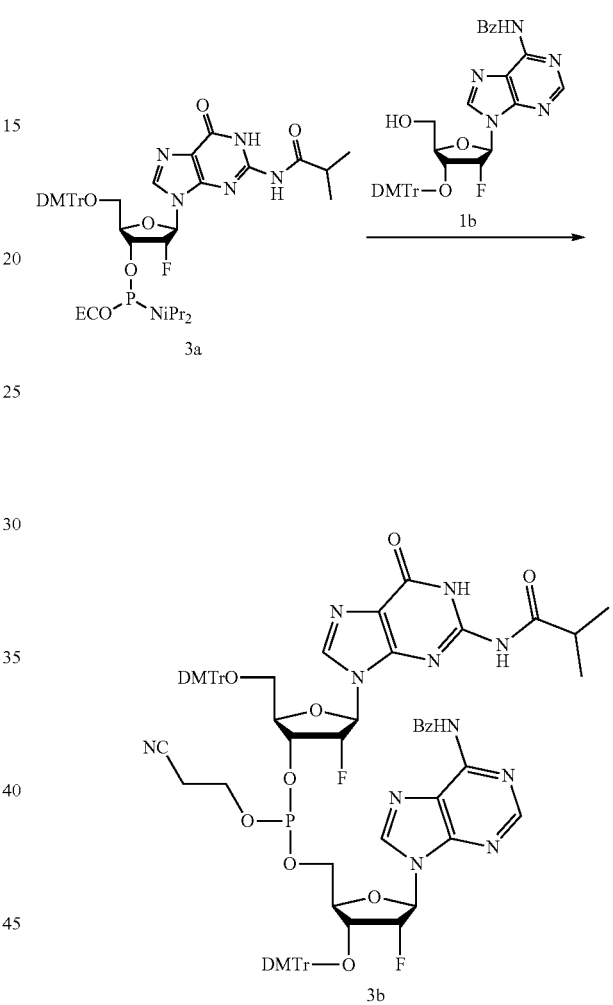

To a solution of compound 3a (6.70 g, 7.81 mmol, 1.00 eq) and compound 1b (5.28 g, 7.81 mmol, 1.00 eq) in ACN (50 mL) was added TFA-Py (1.0 M, 15.6 mL, 2.00 eq) at 25° C. and stirred for 2 h. The mixture was diluted with DCM (100 mL), the organic layer was washed with sat·NaHCO₃ solution (100 mL) and brine (80 mL), dried over Na₂SO₄, filtered and concentrated in vacuo to give a residue (11.19 g, crude) as a light yellow foam, which was used in next step without further purification. LCMS (ES, m/z) 1430.4 (M−1).

Step 2: Synthesis of ((((2R,3R,4R,5R)-5-(6-ben-zamido-9H-purin-9-yl)-3-(bis(4-methoxyphenyl)(phenyl)methoxy)-4-fluorotetrahydrofuran-2-yl)methoxy)(((2R,3R,4R,5R)-2-((bis(4-methoxyphenyl)(phenyl)methoxy)methyl)-4-fluoro-5-(2-isobutyramido-6-oxo-1,6-dihydro-9H-purin-9-yl)tetrahydrofuran-3-yl)oxy)(2-cyanoethoxy)-λ⁴-phosphanyl)trihydroborate (3c)

Step 3: Synthesis of ((((2R,3R,4R,5R)-5-(6-Benzamido-9H-purin-9-yl)-4-fluoro-3-hydroxytetrahydrofuran-2-yl)methoxy)(2-cyanoethoxy)(((2R,3R,4R,5R)-4-fluoro-2-(hydroxymethyl)-5-(2-isobutyramido-6-oxo-1,6-dihydro-9H-purin-9-yl)tetrahydrofuran-3-yl)oxy)-λ⁵-phosphanyl)trihydroborate (3d)

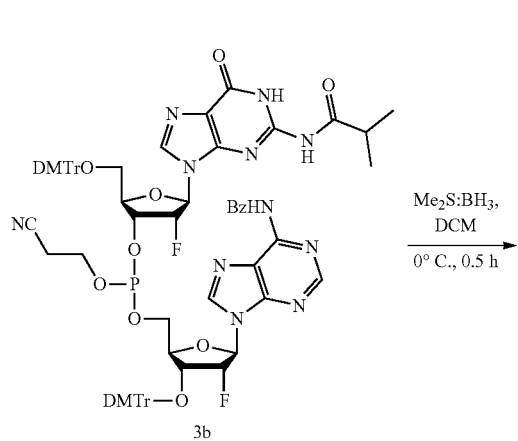

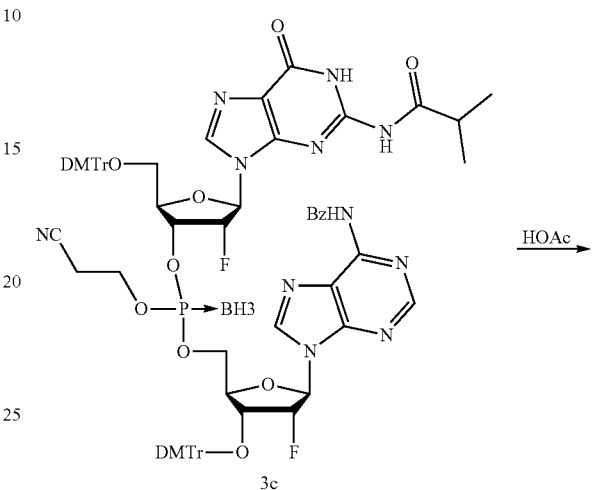

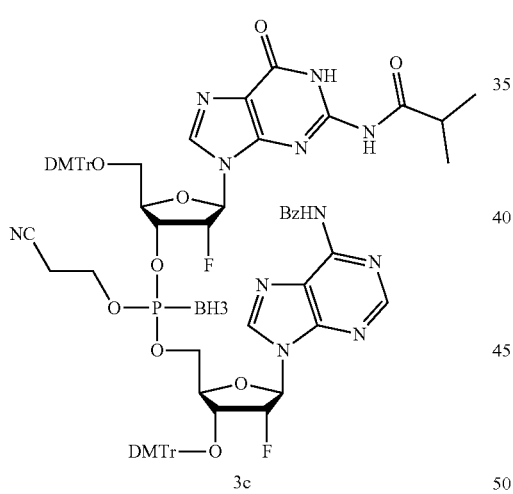

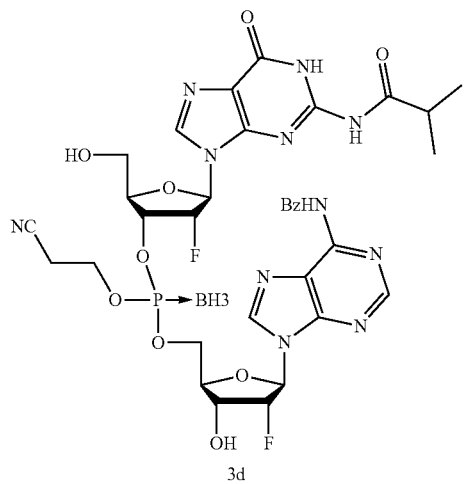

To a solution of compound 3b (11.19 g, 7.81 mmol, 1.00 eq) in DCM (100 mL) at 0° C., was added BH₃-Me₂S (10 M, 2.58 mL, 3.30 eq) and stirred at 0° C. for 0.5 hr. The mixture was quenched by MeOH (10 mL) and diluted with DCM (300 mL), the organic layer was washed with sat. NaHCO₃ solution (150 mL) and brine (100 mL), dried over Na₂SO₄, filtered and concentrated in vacuo to give a compound 3c (11.3 g, crude) as a yellow solid, which was used in next step without further purification.

To a solution of compound 3c (11.3 g, 7.81 mmol, 1.00 eq) was added 80% AcOH/ACN (7.81 mmol, 80 mL) at 25° C. and stirred for 12 h. The mixture was diluted with ethyl acetate (150 mL), the organic layer was washed with sat·NaHCO₃ solution (100 mL×2) and brine (100 mL), dried over Na₂SO₄, filtered and concentrated in vacuo to give a residue, which was purified by column chromatography (SiO₂, DCM:MeOH=100:1 to 20:1) to provide compound 3d (3.20 g, 38.4% yield) as a light yellow foam. LCMS (ES, m/z) 842.3 (M+H)⁺; ³¹P NMR (162 MHz, DMSO-d₆) 138.61 (br s, 1P), 115.18 (br s, 1P).

Step 4: Synthesis of ((2R,3R,3aR,7aS,9R,10R, 10aR,14aR)-9-(6-Benzamido-9H-purin-9-yl)-5,12-bis(2-cyanoethoxy)-3,10-difluoro-2-(2-isobu-tyramido-6-oxo-1,6-dihydro-9H-purin-9-yl)octahydro-2H,7H-5)⁴-difuro[3,2-d:3',2'-j][1,3,7,9]tetraoxa[2,8]diphosphacyclododecin-5-yl) trihydroborate (3e)

Step 5: Synthesis of ((2R,3R,3aR,7aS,9R,10R, 10aR,14aR)-9-(6-Benzamido-9H-purin-9-yl)-5,12-bis(2-cyanoethoxy)-3,10-difluoro-2-(2-isobu-tyramido-6-oxo-1,6-dihydro-9H-purin-9-yl)-$\lambda^2$-sulfidooctahydro-2H,7H-5$\lambda^4$-difuro[3,2-d:3',2'-j][1,3,7,9]tetraoxa[2,8]diphosphacyclododecin-5-yl) trihydroborate (3f)

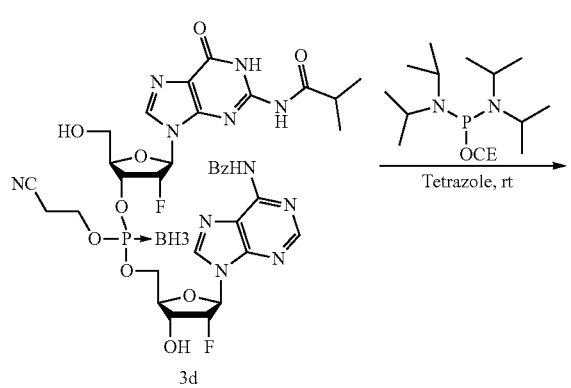

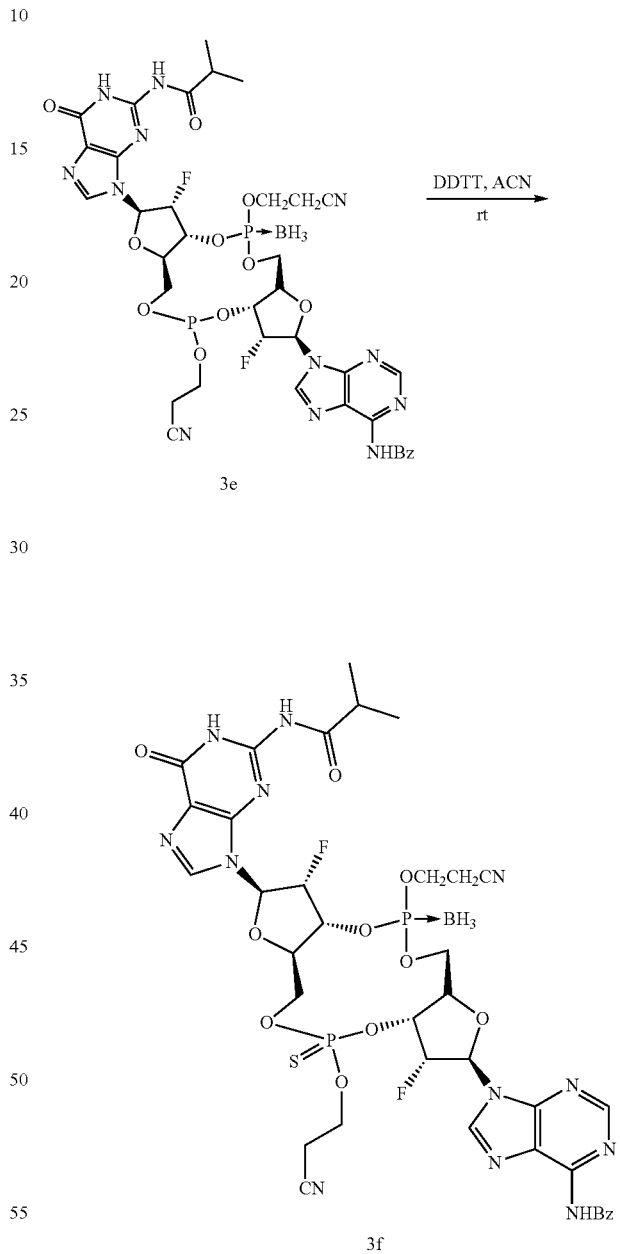

To a solution of compound 3d (1.00 g, 1.19 mmol, 1.00 eq) in ACN (10 mL) were added 5-ethylsulfanyl-2H-tetrazole (0.92 g, 7.13 mmol, 6.00 eq), 3A molecular sieve (1.00 g, 1.19 mmol, 1.00 eq) and 3-((bis(diisopropylamino)phosphanyl)oxy)propanenitrile (0.53 g, 1.78 mmol, 1.50 eq). The mixture was stirred at 25° C. for 2 hours and used directly to the next step.

To a solution of compound 3e (1.12 g, 1.19 mmol, 1.00 eq) in ACN (10 mL) was added DDTT (0.37 g, 1.79 mmol, 1.50 eq). The mixture was stirred at 25° C. for 0.5 hour and diluted with ethyl acetate, the organic layer was washed with sat·NaHCO₃ solution (50 mL×2) and brine (50 mL), dried over Na₂SO₄, filtered and concentrated. The residue was purified by column chromatography (SiO₂, DCM: MeOH=100:1 to 20:1) to give compound 3f (0.43 g, 29.7% yield) as a yellow solid. LCMS (ES, m/z) 973.3 (M+H)⁺.

Step 6: Synthesis of Compounds C1, C2, C3, and C4

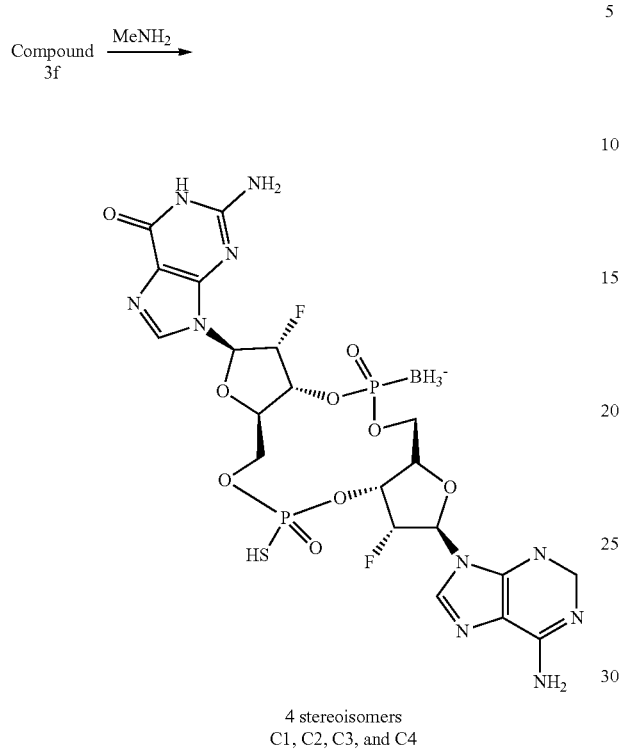

4 stereoisomers
C1, C2, C3, and C4

The mixture of compound 3f (0.35 g, 359 umol, 1.00 eq) and MeNH$_2$ (3.60 mmol, 8 mL, 30% in EtOH, 10.0 eq) was stirred at 25° C. for 3 hrs. ACN (10 mL) was added and the mixture was concentrated in vacuo. The residue was purified by prep-HPLC (column: Xamide 150*30 mm 5 um; mobile phase: [TEAB (10 mM)-ACN]; B %: 3%-30%, 10 min) to provide compounds C1 (5.0 mg), C2 (18.0 mg), C3 (9 mg) and C4 (15 mg).

C1: LCMS (ES, m/z) 691.2 (M−1)$^-$; $^1$H NMR (400 MHz, D$_2$O) δ 8.38 (s, 1H), 8.05 (s, 1H), 7.97 (s, 1H), 6.36 (d, J=16.0 Hz, 1H), 6.15 (d, J=18.4 Hz, 1H), 5.82 (d, J=3.6 Hz, 1H), 5.43-5.86 (m, 1H), 4.84-5.23 (m, 2H), 4.49 (d, J=9.2 Hz, 1H), 4.16-4.39 (m, 3H), 3.90-4.08 (m, 2H), −0.24-0.65 (m, 3H).

C2: LCMS (ES, m/z) 691.0 (M−1)$^-$; $^1$H NMR (400 MHz, D$_2$O) δ 8.06-8.21 (m, 1H), 7.65-7.75 (m, 1H), 7.58-7.65 (m, 1H), 6.03-6.14 (m, 1H), 5.88 (d, J=18.4 Hz, 1H), 5.18-5.47 (m, 2H), 4.65-4.94 (m, 2H), 4.05-4.34 (m, 4H), 3.70-3.91 (m, 2H), 0.47-0.54 (m, 3H).

C3: LCMS (ES, m/z) 691.1 (M−1)$^-$; $^1$H NMR (400 MHz, D$_2$O) δ 8.31 (d, J=4.4 Hz, 1H), 8.23 (s, 1H), 8.17 (br s, 1H), 6.28-6.41 (m, 1H), 6.18 (d, J=15.6 Hz, 1H), 5.82-6.05 (m, 1H), 5.31-5.51 (m, 1H), 5.04-5.25 (m, 2H), 4.36-4.59 (m, 4H), 3.96-4.12 (m, 2H), 0.37 (br s, 3H).

C4: LCMS (ES, m/z) 690.9 (M−1)$^-$; $^1$H NMR (400 MHz, D$_2$O) δ 7.88 (s, 1H), 7.65 (s, 1H), 7.43 (s, 1H), 5.87 (d, J=15.6 Hz, 1H), 5.72 (d, J=15.2 Hz, 1H), 4.86-5.44 (m, 4H), 4.03-4.31 (m, 4H), 3.57-3.81 (m, 2H), −0.49-0.52 (m, 3H).

Example 4: Synthesis of 4 Stereoisomers of the Compound Depicted Below (Compounds D1-D4)

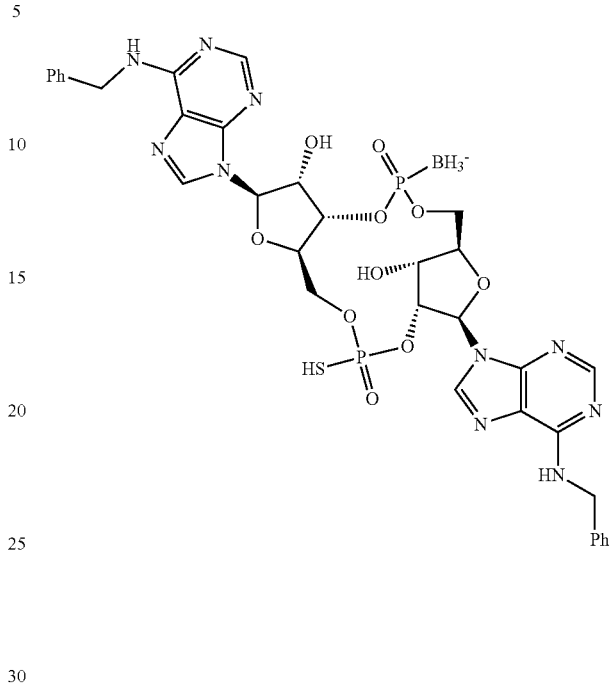

Step 1: Synthesis of 4 stereoisomers, Compounds 4b$_1$, 4b$_2$, 4b$_3$, and 4b$_4$

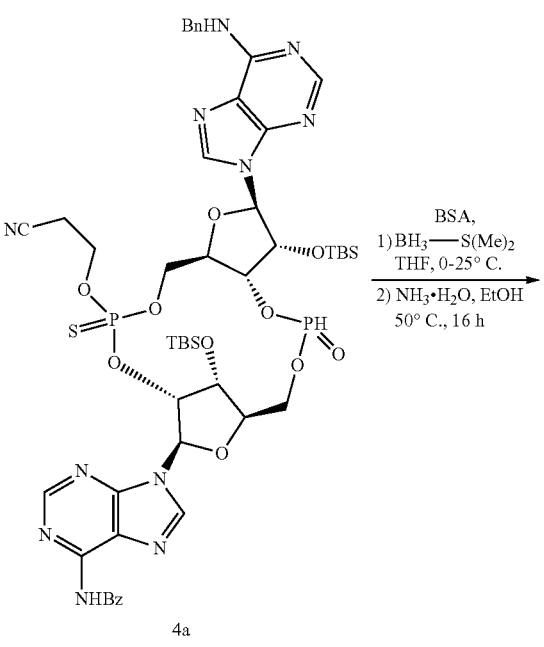

4a

-continued

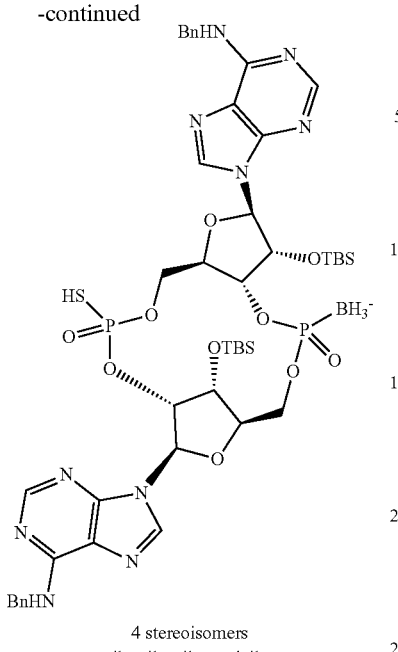

4 stereoisomers
4b₁, 4b₂, 4b₃, and 4b₄

Intermediate 4a was synthesized as described in WO2014189805A1. BSA (797.2 mg, 3.9 mmol, 968.7 uL, 3 eq) was added to a solution of 4a (1.50 g, 1.3 mmol, 1 eq) in THF (10 mL) at 15° C. and stirred for 0.5 hr. The mixture was cooled to 0° C. and BH₃-Me₂S (992 mg, 13.1 mmol, 10 eq) was added. The solution was then warmed to 25° C. and stirred for 0.5 hr. LCMS indicated compound 4a was consumed completely. The mixture was quenched by water (20 mL), extracted with DCM (10 mL, 5 mL), the organic layer was washed with brine (10 mL), dried over Na₂SO₄, filtered and concentrated. The residue was dissolved in EtOH (10 mL) at 15° C. in sealed tube. NH₃·H₂O (9.1 g, 64.9 mmol, 10.0 mL, 25% purity, 50.2 eq) was added at 15° C. and then warmed to 50° C. The mixture was stirred at 50° C. for 16 hours and concentrated. The residue was purified by prep-HPLC (column: Agela Durashell C18 150×25 5u) eluted with 40%-60% ACN in aq NH₄HCO₃(10 mM) to give compounds 4b₁ (60.0 mg, 49.3 μmol, 3.82% yield, 89.0% purity), 4b₂ (40.0 mg, 32.9 μmol, 2.55% yield, 89.0% purity), 4b₃ (68.0 mg, 55.9 μmol, 4.33% yield, 89.0% purity) and 4b₄ (50.0 mg, 41.1 μmol, 3.18% yield, 89.0% purity).

4b₁: LCMS (ES, m/z) 539.2 [(M-H)/2]⁻ RT (LCMS)=2.237 min

4b₂: LCMS (ES, m/z) 539.2 [(M-H)/2]⁻ RT (LCMS)=2.420 min

4b₃: LCMS (ES, m/z) 539.2 [(M-H)/2]⁻ RT (LCMS)=2.537 min

4b₄: LCMS (ES, m/z) 539.2 [(M-H)/2]⁻ RT (LCMS)=2.896 min

Step 2a: Synthesis of D1 and D1'

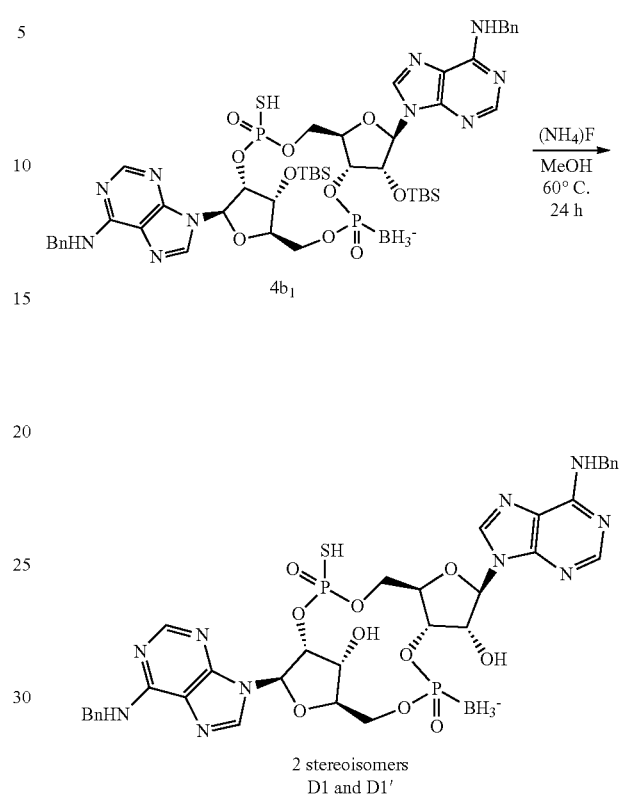

2 stereoisomers
D1 and D1'

NH₄F (41.1 mg, 1.11 mmol, 20.0 eq) was added to a solution of compound 4b₁ (60.0 mg, 55.50 μmol, 1 eq) in MeOH (1.5 mL) at 15° C. The mixture was warmed to 60° C. and stirred for 20 hrs. LC-MS showed compound 4b₁ was consumed completely. The volatile components were removed in vacuo. The residue was purified by prep-HPLC (column: Agela Durashell C18 150×25 5u) eluted with 20%-50% ACN in aq NH₄HCO₃(10 mM) to give compounds D1 (5.0 mg) and compound D1' (7.5 mg).

D1: LCMS (ES, m/z) 851.1 (M-H)⁻. $^1$H NMR (400 MHz, MeOD) δ 8.83 (s, 1H), 8.23-8.36 (m, 3H), 7.21-7.44 (m, 10H), 6.33-6.41 (m, 1H), 6.09 (d, J=4.5 Hz, 1H), 5.27-5.54 (m, 2H), 5.02 (t, J=4.6 Hz, 1H), 4.76-4.83 (m, 3H), 4.56-4.69 (m, 3H), 4.29-4.46 (m, 4H), 4.19 (br s, 1H), 3.71-4.07 (m, 3H). $^{31}$P NMR (162 MHz, MeOD) δ 114.97-123.38 (m, 1P), 61.41 (br s, 1P).

D1': LCMS (ES, m/z) 851.1 (M-H)⁻. $^1$H NMR: (400 MHz, MeOD) δ 8.13 (s, 1H), 8.03 (s, 2H), 7.91 (s, 1H), 6.95-7.20 (m, 10H), 6.14 (d, J=3.6 Hz, 1H), 5.82-5.94 (m, 1H), 5.17 (td, J=5.6, 10.7 Hz, 1H), 5.06 (ddd, J=3.8, 6.7, 10.5 Hz, 1H), 4.81-4.93 (m, 1H), 4.57-4.57 (m, 1H), 4.42-4.60 (m, 5H), 4.26-4.39 (m, 2H), 3.87-3.99 (m, 2H), 3.69-3.79 (m, 1H), 3.58-3.66 (m, 1H), 3.45-3.55 (m, 1H), 3.31-3.42 (m, 1H). $^{31}$P NMR (162 MHz, MeOD) δ 96.80-101.85 (m, 1P), 58.02 (br s, 1P).

Step 2b: Synthesis of D2 and D2'

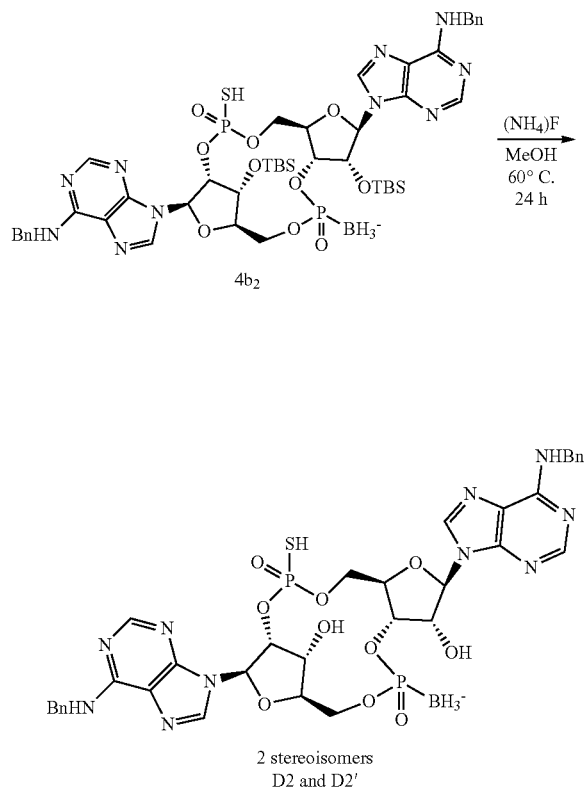

NH$_4$F (27.4 mg, 740 μmol, 20.0 eq) was added to a solution of compound 4b$_2$ (40.0 mg, 37.0 μmol, 1 eq) in MeOH (1.5 mL) at 15° C. The mixture was warmed to 60° C. and stirred for 20 hrs. LCMS showed compound 4b$_2$ was consumed completely. The volatile components were removed in vacuo. The residue was purified by prep-HPLC (column: Agela Durashell C18 150×25 5u) eluted with 20%-50% ACN in aq NH$_4$HCO$_3$ (10 mM) to give compounds D2 (6.2 mg) and D2' (3.9 mg).

D2: LCMS (ES, m/z) 851.1 (M–H)$^-$. $^1$H NMR (400 MHz, MeOD) δ 8.76 (s, 1H), 8.23-8.30 (m, 3H), 7.22-7.42 (m, 10H), 6.39 (d, J=8.3 Hz, 1H), 6.08 (d, J=3.8 Hz, 1H), 5.38-5.44 (m, 1H), 5.21-5.29 (m, 1H), 4.96 (br t, J=4.3 Hz, 1H), 4.79-4.83 (m, 3H), 4.32-4.58 (m, 5H), 4.05-4.26 (m, 3H), 3.74-3.98 (m, 3H). $^{31}$P (162 MHz, MeOD) δ 96.66 (s, 1P), δ3.79 (br s, 1P)

D2': LCMS (ES, m/z) 851.0 (M–H)$^-$. H NMR (400 MHz, MeOD) δ 8.30-8.39 (m, 1H), 8.21-8.30 (m, 2H), 8.12 (s, 1H), 7.18-7.44 (m, 10H), 6.36 (d, J=3.4 Hz, 1H), 6.12 (d, J=6.7 Hz, 1H), 5.41-5.52 (m, 1H), 5.17-5.28 (m, 1H), 4.96-5.08 (m, 1H), 4.79-4.85 (m, 5H), 4.72 (br s, 2H), 4.61 (dd, J=2.2, 4.8 Hz, 1H), 4.47 (br d, J=3.6 Hz, 1H), 4.17 (br d, J=2.5 Hz, 1H), 3.80-3.97 (m, 3H), 3.72 (br dd, J=2.9, 12.7 Hz, 1H)$^3$)P NMR (162 MHz, MeOD) δ 122.74 (s, 1P), 58.37 (br s, 1P).

Step 2c: Synthesis of D3 and D3'

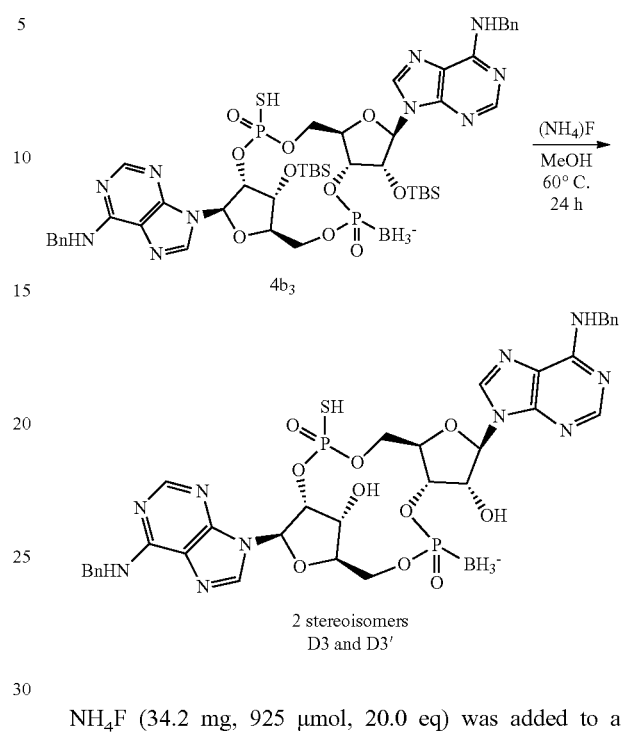

NH$_4$F (34.2 mg, 925 μmol, 20.0 eq) was added to a solution of compound 4b$_3$ (50.0 mg, 46.2 μmol, 1 eq) in MeOH (1.5 mL) at 15° C. The mixture was warmed to 60° C. and stirred for 20 hrs. LCMS showed compound 4b$_3$ was consumed completely. The volatile components were removed in vacuo. The residue was purified by prep-HPLC (column: Agela Durashell C18 150×25 5u) eluted with 18%-38% ACN in aq NH$_4$HCO$_3$ (10 mM) to give compounds D3 (7.0 mg) and D3' (11 mg).

D3: LCMS (ES, m/z) 851.1 (M–H)$^-$. $^{31}$P NMR (162 MHz, MeOD) δ 105.88 (br d, J=180.0 Hz, 1P), 62.00 (br s, 1P).

D3': LCMS (ES, m/z) 851.1 (M–H)$^-$. δ 8.23-8.38 (m, 3H), 8.07 (s, 1H), 7.23-7.44 (m, 10H), 6.11-6.21 (m, 2H), 5.27-5.42 (m, 2H), 5.18 (br s, 1H), 4.66-4.79 (m, 3H), 4.55-4.60 (m, 1H), 4.31 (br s, 1H), 4.12-4.23 (m, 2H), 3.71-3.89 (m, 3H). $^{31}$P NMR (162 MHz, MeOD) δ 116.56 (s, 1P), 57.42 (br s, 1P).

Step 2d: Synthesis of D4 and D4'

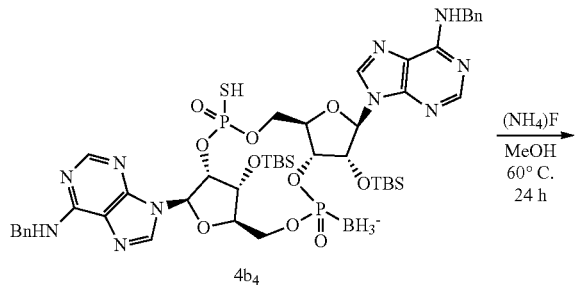

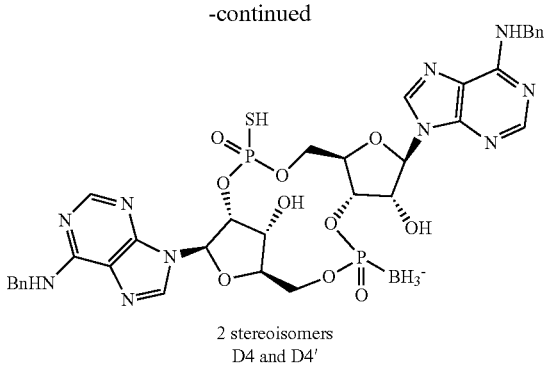

2 stereoisomers
D4 and D4'

NH$_4$F (20.5 mg, 555.0 μmol, 20.0 eq) was added to a solution of compound 4b$_4$ (30.0 mg, 27.7 μmol, 1 eq) in MeOH (1.5 mL) at 15° C. The mixture was warmed to 60° C. and stirred for 20 hrs. LCMS showed compound 4b$_4$ was consumed completely. The volatile components were removed in vacuo. The residue was purified by prep-HPLC (column: Agela Durashell C18 150×25 5u) eluted with 20%-50% ACN in aq NH$_4$HCO$_3$ (10 mM) to give compounds D4 (3.8 mg) and D4' (5.0 mg).

D4: LCMS (ES, m/z) 851.0 (M–H)$^-$. $^{31}$P NMR (162 MHz, MeOD) δ 99.29 (s, 1P), 52.54-59.84 (m, 1P).

D4': LCMS (ES, m/z) 851.0 (M–H)$^-$. $^1$H NMR (400 MHz, MeOD) δ 8.33-8.37 (m, 1H), 8.22-8.29 (m, 2H), 8.05-8.13 (m, 1H), 7.18-7.45 (m, 10H), 6.10-6.21 (m, 2H), 5.39-5.49 (m, 1H), 5.23-5.32 (m, 1H), 5.08-5.28 (m, 1H), 4.79-4.85 (m, 5H), 4.72 (br s, 2H), 4.60 (dd, J=2.3, 4.9 Hz, 1H), 4.25 (br d, J=3.6 Hz, 1H), 4.13-4.20 (m, 1H), 3.66-3.97 (m, 4H). $^{31}$P NMR (162 MHz, MeOD) δ 117.95 (s, 1P), 58.24 (br s, 1P).

Example 5: Synthesis of 2 stereoisomers of ((2R, 3R,3aR,7aR,9R,10R,10aR,14aR)-2,9-bis(6-amino-9H-purin-9-yl)-3,10-difluoro-12-hydroxy-5,12-di-oxidooctahydro-2H,7H-difuro[3,2-d:3',2'-j][1,3,7,9]tetraoxa[2,8]diphosphacyclododecin-5-yl) trihydroborate (Compounds E1 and E2)

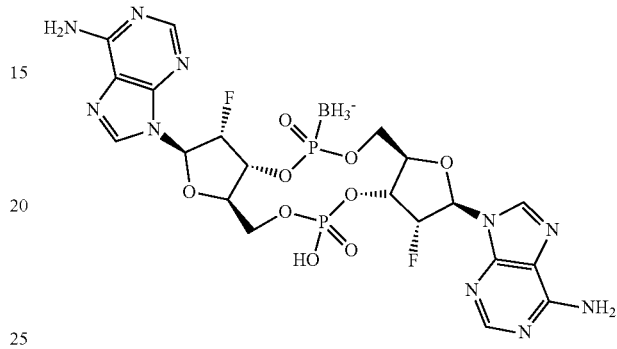

Step 1: Synthesis of ((2R,3R,3aR,7aR,9R,10R, 10aR,14aR)-2,9-bis(6-benzamido-9H-purin-9-yl)-5, 12-bis(2-cyanoethoxy)-3,10-difluoro-12-oxidoocta-hydro-2H,7H-514-difuro[3,2-d:3',2'-j][1,3,7,9]tetraoxa[2,8]diphosphacyclododecin-5-yl) trihydroborate (5a)

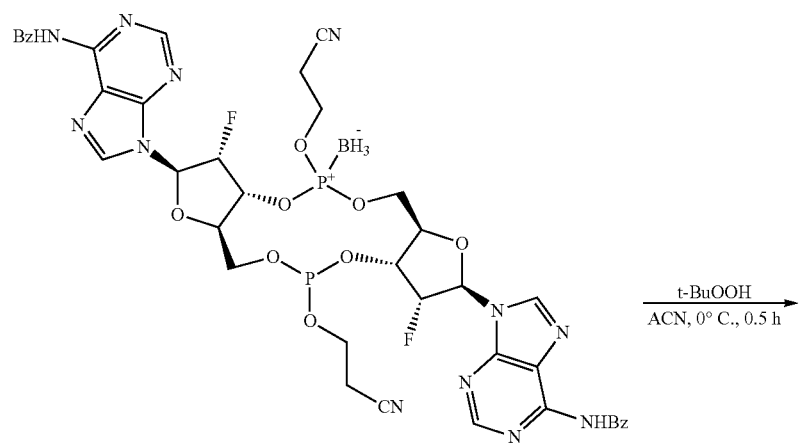

Example 1, 1f

-continued

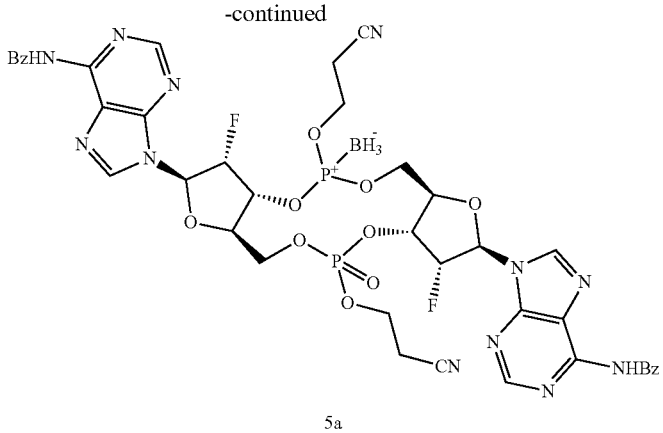

5a

To a solution of compound 1f (1.12 g, 1.17 mmol, 1.00 eq) in ACN (7.00 mL) was added t-BuOOH (5.50 M, 254 uL, 1.20 eq). The mixture was stirred at 15° C. for 0.5 hour and then quenched with sat. NaHCO₃ solution (20 mL×2). Ethyl acetate (15 mL) was added and the organic layer was washed with brine (10 mL), dried over Na₂SO₄, filtered and concentrated in vacuo. The residue was purified by column chromatography (SiO₂, DCM/MeOH=200/1 to 30/1) to give compound 5a (0.21 g, 215 umol, 18.4% yield) as white solid.

Step 2: Synthesis of Compounds E1 and E2

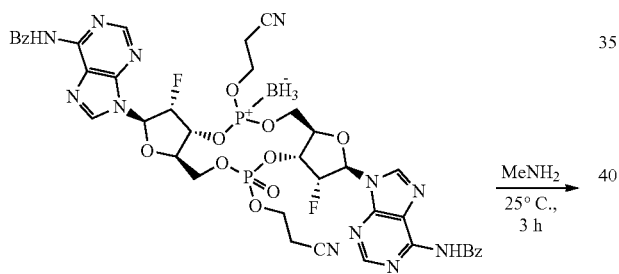

2 stereoisomers
E1 and E2

In a 10 mL round bottom flask, compound 5a (0.21 g, 215 umol, 1.00 eq) was dissolved in a solution of MeNH₂ in EtOH (2 mL, 30% by weigh) (2 mL) and stirred at 25° C. for 3 hr. ACN (5 mL×2) was added and concentrated to remove EtOH. After recrystallization with ACN at 25° C., the residue was purified by prep-HPLC column (Xtimate C18 150×25 mm×5 μm; mobile phase: [water (10 mM NH₄HCO₃)-ACN]; B %: 1%-20%, 10.5 min.) to give E1 (0.023 g, 34.8 umol, 95.0% purity) and E2 (0.027 g, 40.9 umol, 96.0% purity) as a white solid.

Compound E1: LCMS (ES, m/z) 659.1 (M−1)⁻. ¹H NMR (400 MHz, MeOD) δ 8.19 (s, 2H), 7.99 (s, 1H), 7.67 (s, 1H), 6.30-6.46 (m, 2H), 5.24-5.55 (m, 2H), 4.36-4.50 (m, 6H), 4.06 (d, J=10.0 Hz, 2H), 0.01-0.12 (m, 3H).

Compound E2: LCMS (ES, m/z) 659.1 (M−1)⁻. ¹H NMR (400 MHz, MeOD) δ 8.17 (d, J=16.8 Hz, 2H), 7.95 (d, J=8.40 Hz, 2H), 6.29 (dd, J=4.40, 4.00 Hz, 2H), 5.43-5.56 (m, 2H), 4.44-4.54 (m, 4H), 4.046-4.07 (m, 2H), 0.28-0.38 (m, 3H).

Example 6: Synthesis of 2 stereoisomers of ((2R,3R,3aR,5R,7aS,9R,10R,10aR,14aR)-2-(2-amino-6-oxo-1,6-dihydro-9H-purin-9-yl)-9-(6-amino-9H-purin-9-yl)-3,10-difluoro-12-hydroxy-5,12-dioxidooctahydro-2H,7H-difuro[3,2-d:3',2'-j][1,3,7,9]tetraoxa[2,8]diphosphacyclododecin-5-yl) trihydroborate (Compounds F1 and F2)

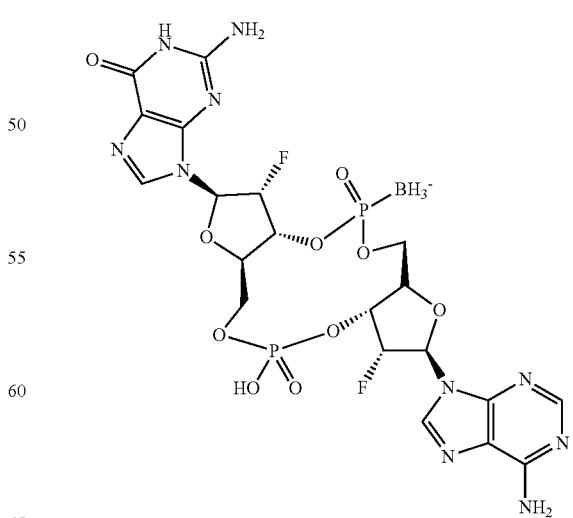

Step 1: Synthesis of ((2R,3R,3aR,7aR,9R,10R, 10aR,14aR)-2,9-bis(6-benzamido-9H-purin-9-yl)-5, 12-bis(2-cyanoethoxy)-3,10-difluoro-12-oxidoocta-hydro-2H,7H-5l4-difuro[3,2-d:3',2'-j][1,3,7,9] tetraoxa[2,8]diphosphacyclododecin-5-yl) trihydroborate (6a)

Step 2: Synthesis of Compounds F1 and F2

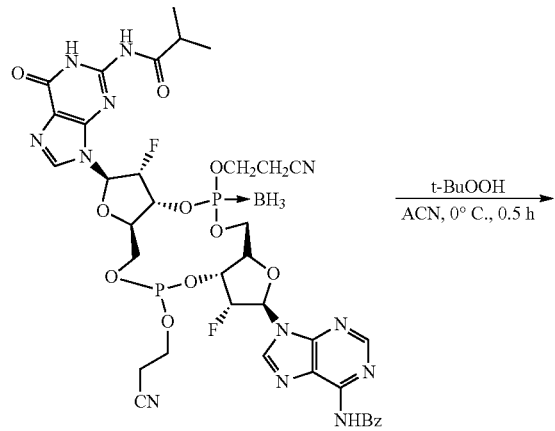

Example 3, 3e

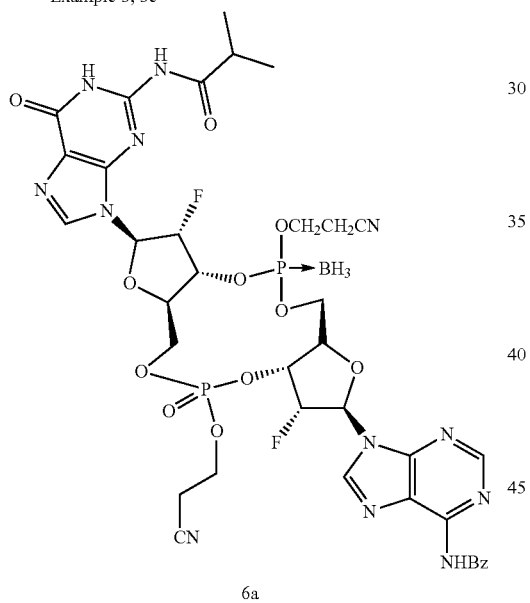

6a

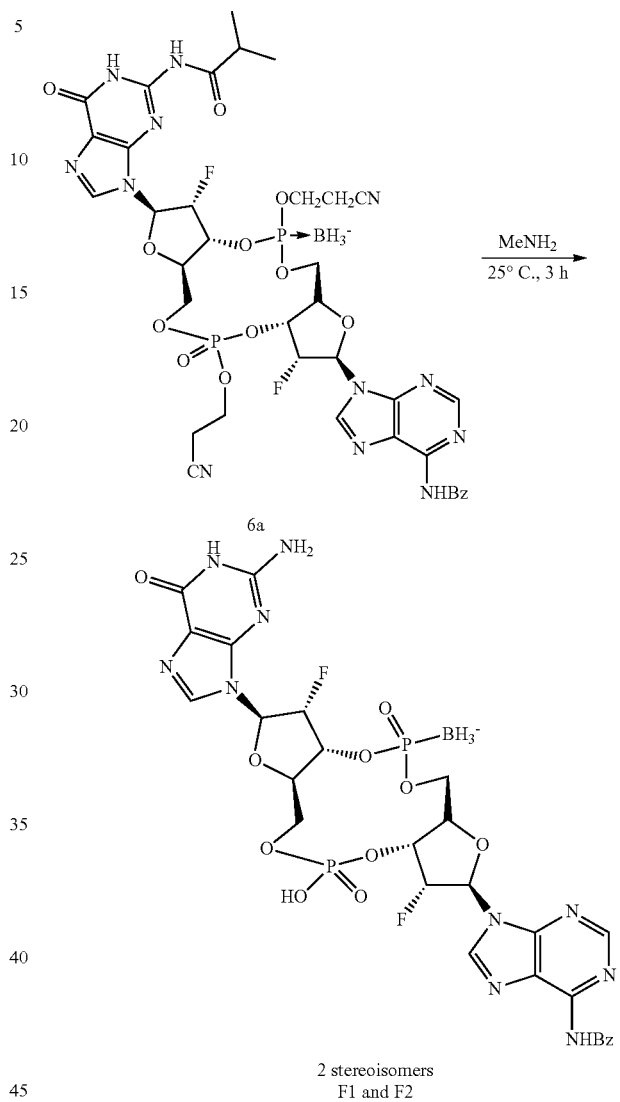

2 stereoisomers
F1 and F2

To a solution of compound 3e (1.12 g, 1.19 mmol, 1.00 eq) in ACN (10 mL) was added t-BuOOH (5.5 M, 0.324 mL, 1.50 eq). The mixture was stirred at 25° C. for 0.5 hour, diluted with ethyl acetate (15 mL), the organic layer was washed with sat·NaHCO$_3$ solution (10 mL×2) and brine (10 mL), dried over Na$_2$SO$_4$, filtered and concentrated. The residue was purified by prep-HPLC (column: Xtimate C18 10μ 250 mm*50 mm; mobile phase: [water (10 mM NH$_4$HCO$_3$)-ACN]; B %: 25%-50%, 25 min) to give compound 6a (0.25 g, 21.9% yield) as a white solid. LCMS (ES, m/z) 957.3 (M+H)$^+$.

The solution of compound 6a (0.25 g, 261 umol, 1.00 eq) and MeNH$_2$ (270.57 mg, 2.61 mmol, 4 mL, 30% in EtOH, 10.0 eq) was stirred at 25° C. for 3 hrs. ACN was added (10 mL) and the mixture was concentrated in vacuo. The residue was purified by prep-HPLC (column: Waters Xbridge 150*25 5u; mobile phase: [water (10 mM NH$_4$HCO$_3$)-ACN]; B %: 1%-5%, 12 min) to give compound F1 (13.0 mg) and F2 (15 mg) as white foam.

F1: LCMS (ES, m/z) 675.1 (M−1)$^-$; $^1$H NMR (400 MHz, MeOD) δ 7.99-8.18 (m, 1H), 7.49-7.70 (m, 2H), 5.73-6.18 (m, 2H), 5.10-5.46 (m, 2H), 4.54-4.82 (m, 1H), 4.23 (d, J=8.4 Hz, 1H), 3.98-4.16 (m, 3H), 3.70-3.89 (m, 2H), 0.09 (br s, 3H).

F2: LCMS (ES, m/z) 675.1 (M−1)$^-$; $^1$H NMR (400 MHz, MeOD) δ 8.25 (s, 1H), 8.05 (br s, 2H), 6.04-6.30 (m, 2H), 5.11-5.55 (m, 4H), 4.36-4.58 (m, 4H), 3.96-4.17 (m, 2H), 0.32 (br s, 3H).

Example 7: Synthesis of 2 stereoisomers of ((2R, 3R,3aR,5R,7aR,9R,10R,10aR,14aS)-9-(2-amino-6-oxo-1,6-dihydro-9H-purin-9-yl)-2-(6-amino-9H-purin-9-yl)-3,10-difluoro-12-hydroxy-5,12-dioxidooctahydro-2H,7H-difuro[3,2-d:3',2'-j][1,3,7,9]tetraoxa[2,8]diphosphacyclododecin-5-yl) trihydroborate (Compounds G1 and G2)

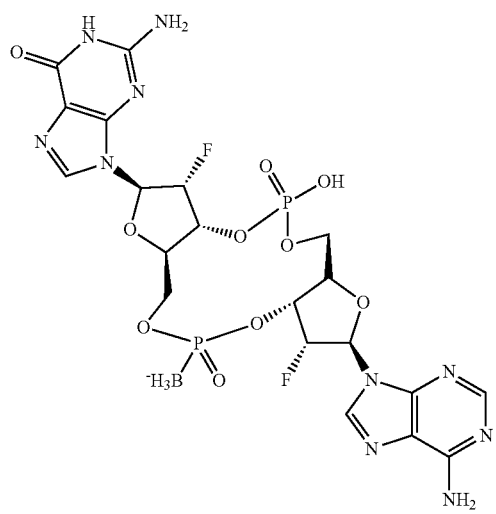

Step 1: Synthesis of ((2R,3R,3aR,7aR,9R,10R,10aR,14aS)-2-(6-benzamido-9H-purin-9-yl)-5,12-bis(2-cyanoethoxy)-3,10-difluoro-9-(2-isobutyramido-6-oxo-1,6-dihydro-9H-purin-9-yl)-12-oxidooctahydro-2H,7H-514-difuro[3,2-d:3',2'-j][1,3,7,9]tetraoxa[2,8]diphosphacyclododecin-5-yl) trihydroborate (7a)

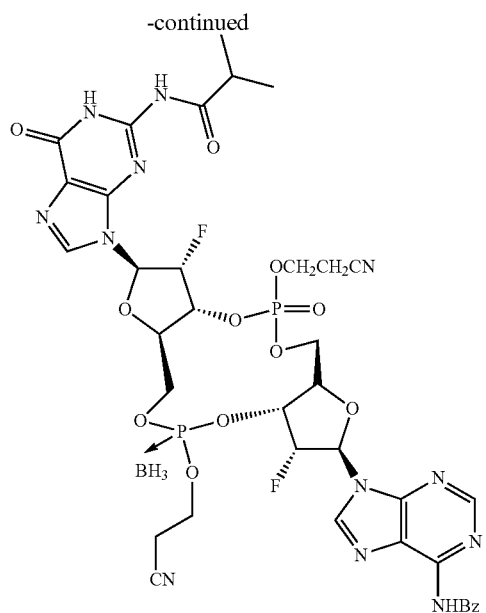

7a

To a solution of compound 2e (1.12 g, 1.19 mmol, 1.00 eq) in ACN (10 mL) was added t-BuOOH (5.5 M, 0.324 mL, 1.50 eq). The mixture was stirred at 25° C. for 0.5 hour, diluted with ethyl acetate (15 mL), the organic layer was washed with sat·NaHCO$_3$ solution (10 mL×2) and brine (10 mL), dried over Na$_2$SO$_4$, filtered and concentrated. The residue was purified by prep-HPLC (column: Waters Xbridge 150*25 5u; mobile phase: [water (10 mM NH$_4$HCO$_3$)-ACN]; B %: 30%-45%, 12 min) to give compound 7a (0.3 g) as a light yellow solid. LCMS (ES, n/z) 957.3 (M+H)$^+$.

Step 2: Synthesis of Compounds G1 and G2

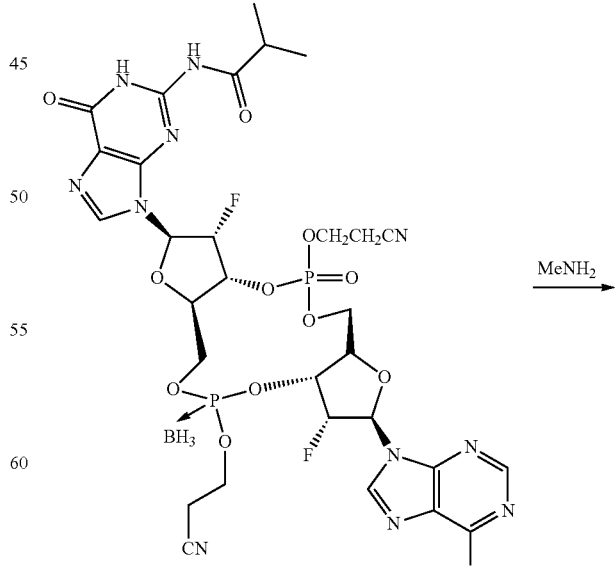

-continued

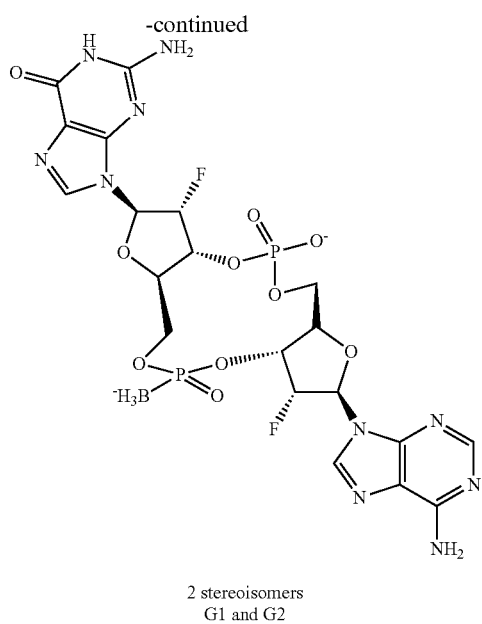

2 stereoisomers
G1 and G2

The solution of compound 7a (0.30 g, 313 umol, 1.00 eq) and MeNH₂ (8 mL, 30% in EtOH) was stirred at 25° C. for 3 hrs. ACN was added (16 mL) and the mixture was concentrated in vacuo. The residue was purified by prep-HPLC (column: Waters Xbridge 150*25 5u; mobile phase: [water (10 mM NH₄HCO₃)-ACN]; B %: 1%-20%, 12 min.) to give compound G1 (13.0 mg) and G2 (39.6 mg) as white foam.

G1: LCMS (ES, m/z) 675.0 (M−1)⁻; ¹H NMR (400 MHz, MeOD) δ 8.28 (s, 1H), 8.15 (d, J=11.6 Hz, 2H), 6.14-6.33 (m, 2H), 5.62-5.85 (m, 1H), 5.33-5.54 (m, 1H), 4.90-5.22 (m, 2H), 4.27-4.63 (m, 4H), 4.02-4.16 (m, 2H), −0.20-0.78 (m, 3H).

G2: LCMS (ES, m/z) 675.1 (M−1)⁻; ¹H NMR (400 MHz, MeOD) δ 7.88-8.41 (m, 3H), 5.90-6.36 (m, 2H), 4.98-5.77 (m, 4H), 4.26-4.60 (m, 4H), 3.85-4.16 (m, 2H), 0.39 (br s, 3H).

Example 8: Synthesis of 4 stereoisomers of the compound depicted below (Compounds H1, H2, H3 and H4)

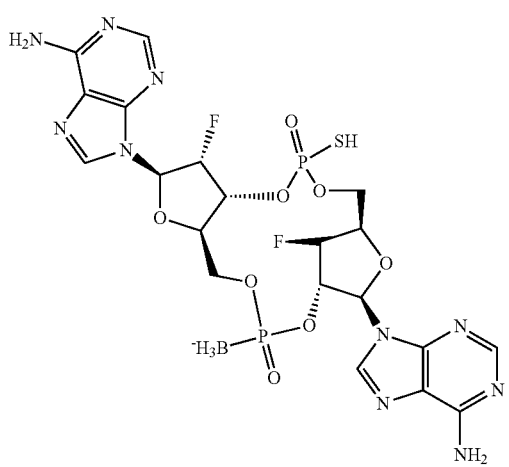

Step 1: Synthesis of (2R,3R,4R,5R)-5-(6-benzamido-9H-purin-9-yl)-2-((bis(4-methoxyphenyl)(phenyl)methoxy)methyl)-4-fluorotetrahydrofuran-3-yl (((2R,3S,4S,5R)-5-(6-benzamido-9H-purin-9-yl)-4-(bis(4-methoxyphenyl)(phenyl)methoxy)-3-fluorotetrahydrofuran-2-yl)methyl) (2-cyanoethyl) phosphite (8b)

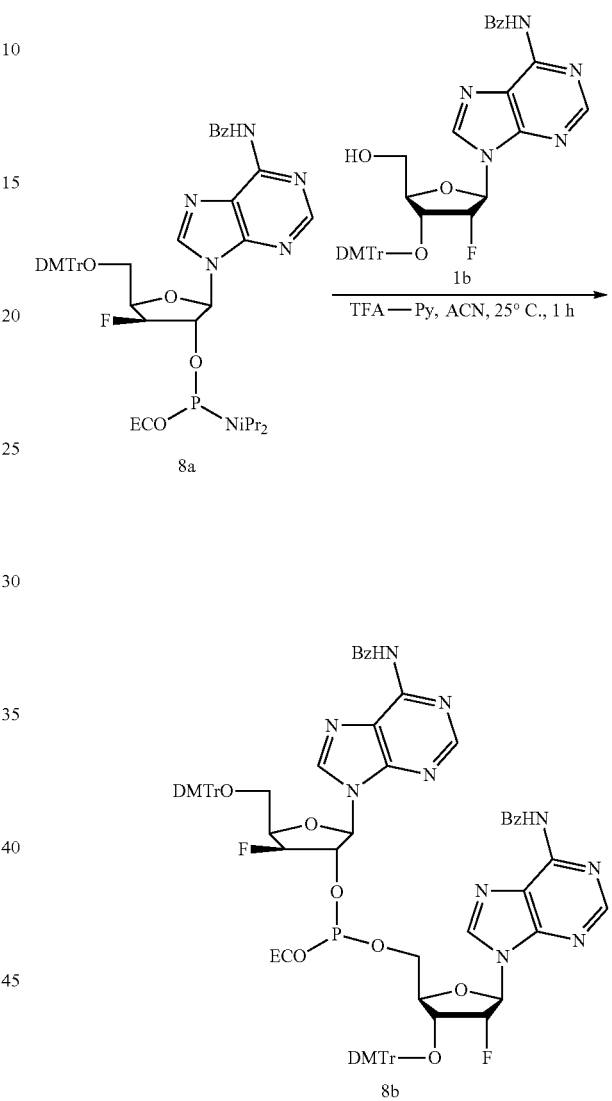

To a solution of compound 8a (6.00 g, 6.85 mmol, 1.00 eq) and compound 1b (4.63 g, 6.85 mmol, 1.00 eq) in ACN (40.0 mL) were added Molecular sieve 3A (5.00 g, 6.85 mmol, 1.00 eq) and Pyrine-TFA (1.00 M, 10.2 mL, 1.50 eq). The mixture was stirred at 25° C. for 0.5 h. The reaction mixture was diluted with DCM (60 ml), washed with a.q. NaHCO₃ (100 ml) and brine (80.0 ml), dried over Na₂SO₄, filtered and concentrated in vacuo to give compound 8b (10 g, crude) as light-yellow solid.

Step 2: Synthesis of ((((2R,3R,4R,5R)-5-(6-benzamido-9H-purin-9-yl)-4-fluoro-3-methoxytetrahydrofuran-2-yl)methoxy)(((2R,3S,4S,5R)-2-(6-benzamido-9H-purin-9-yl)-5-((bis(4-methoxyphenyl)(phenyl)methoxy)methyl)-4-fluorotetrahydrofuran-3-yl)oxy)(2-cyanoethoxy)-14-phosphanyl)trihydroborate (8c)

Step 3: Synthesis of ((((2R,3R,4R,5R)-5-(6-benzamido-9H-purin-9-yl)-4-fluoro-3-hydroxytetrahydrofuran-2-yl)methoxy)(((2R,3S,4S,5R)-2-(6-benzamido-9H-purin-9-yl)-4-fluoro-5-(hydroxymethyl)tetrahydrofuran-3-yl)oxy)(2-cyanoethoxy)-14-phosphanyl)trihydroborate (8d)

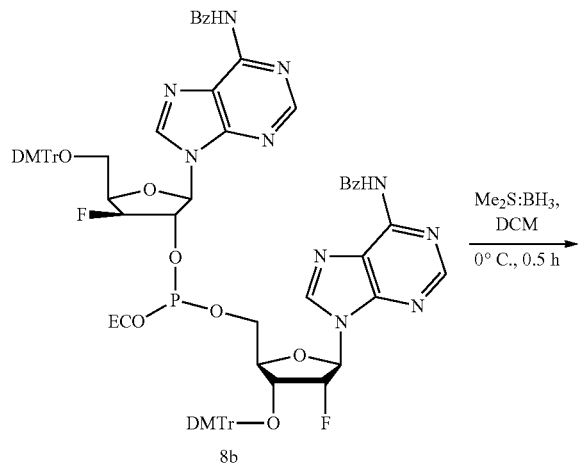

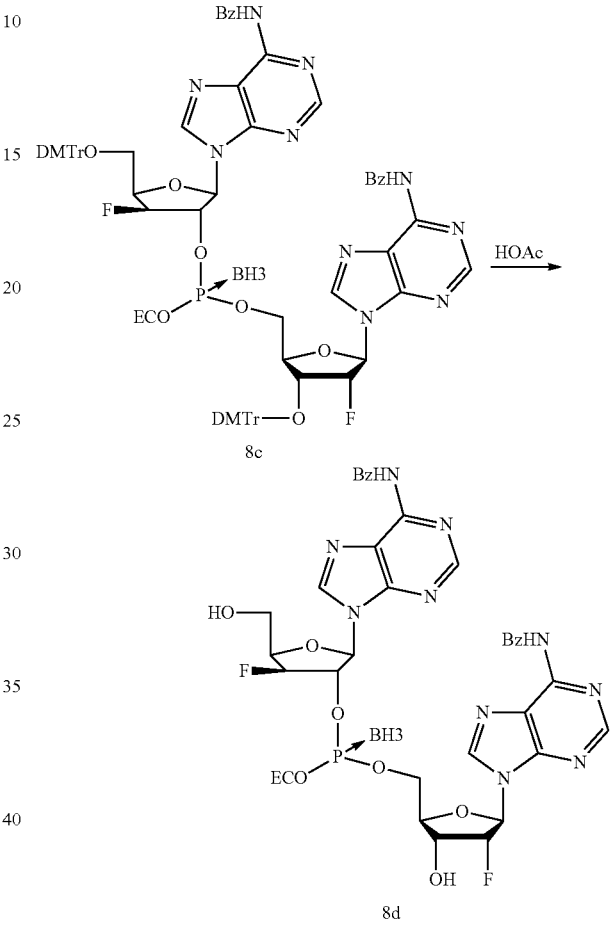

To a solution of compound 15 (10.0 g, 6.89 mmol, 1.00 eq) in DCM (100 ml) was added $BH_3$-$Me_2S$ (1.00 M, 22.7 mL, 3.30 eq). The mixture was stirred at 0° C. for 0.5 h and diluted with DCM (100 mL), the organic layer was washed with a.q. $NaHCO_3$ (100 mL×2), brine (100 mL), dried over $Na_2SO_4$, filtered and concentrated in vacuo to give compound 8c (10 g, crude), which was used in next step.

To a solution of compound 8c (10.0 g, 6.82 mmol, 1.00 eq) in ACN (20 mL) was added AcOH (1.00 M, 61.4 mL, 80.0% purity, 9.00 eq). The mixture was stirred at 25° C. for 12 h. The reaction mixture was diluted with ethyl acetate (100 mL), the organic layer was washed with a.q. $NaHCO_3$ (150 mL×2) and brine (150 mL), dried over $Na_2SO_4$, filtered and concentrated in vacuo to give a residue, after recrystallization (petroleum ether/ethyl acetate=1/1) at 25° C., the filtered solid was purified by column chromatography ($SiO_2$, DCM/MeOH=200/1 to 10/1) to give compound 8d (3.20 g, 3.72 mmol, 54.4% yield) as light yellow foam. $^1$H NMR (400 MHz, MeOD) 0.30 (br, 3H), 2.842-2.909 (m, 2H), 3.35 (s, 1H), 3.755-3.781 (m, 2H), 4.110-4.185 (m, 4H), 4.429-4.448 (m, 3H), 5.197 (s, 1H), 5.5-5.663 (m, 2H), 5.963-6.009 (m, 1H), 6.348-6.414 (m, 2H), 7.532-7.569 (m, 4H), 7.629-7.647 (m, 2H), 8.047-8.064 (m, 4H), 8.559-8.581 (m, 2H), 8.746-8.784 (m, 2H), 11.241-11.262 (d, J=8.4 Hz, 2H).

Step 4: Synthesis of Compound 8e

Compound 8d (0.5 g, 581 µmol, 1.0 eq) is co-evaporated with ACN (5 mL×2) to remove MeOH. Molecular sieve 3A (0.5 g, 581 µmol, 1 eq) is added to a solution of compound 8d (0.5 g, 581 µmol, 1.0 eq) and 2H-tetrazole (0.45 M, 7.76 mL, 6 eq) in ACN (7 mL) followed by 3-((bis(diisopropylamino)phosphanyl)oxy)propanenitrile (263 mg, 872 µmol, 277 uL, 1.5 eq). The mixture is stirred at 25° C. for 1 hr. Diluted with EtOAc (15 mL), the organic layer is washed with sat·NaHCO$_3$ solution (20 mL×2) and brine (10 mL), dried over Na$_2$SO$_4$, filtered and concentrated to give compound 8e.

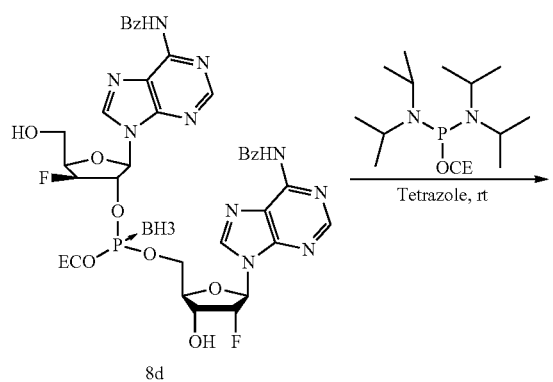

8d

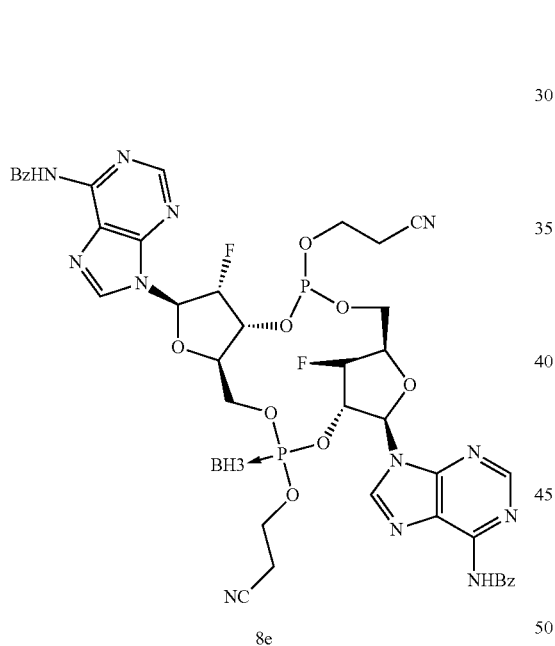

8e

To a solution of compound 8d (1.20 g, 1.39 mmol, 1.00 eq) in DMF (2.00 mL) were added molecular sieve 3A (1.20 g, 1.39 mmol, 1.00 eq), 5-ethylsulfanyl-2H-tetrazole (1.09 g, 8.37 mmol, 6.00 eq) and 3-((bis(diisopropylamino)phosphanyl)oxy)propanenitrile (672 mg, 2.23 mmol, 708 uL, 1.60 eq). After stirring at 25° C. for 2 h, the resulting mixture was used in next step.

Step 5: Synthesis of Compound 8f

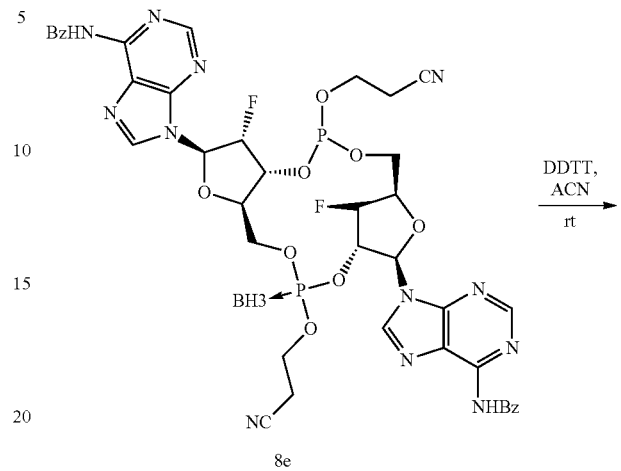

8e

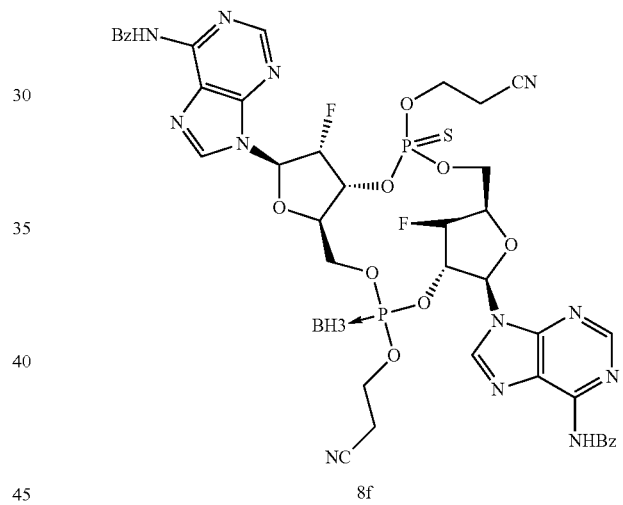

8f

DDTT (357 mg, 1.74 mmol, 1.50 eq) was added to above solution at 25° C. and stirred for 0.5 hr. The reaction mixture was filtered, the filtered solid was washed with ethyl acetate (10.0 mL, 5.00 mL), the combined organic layer was washed with sat. NaHCO$_3$ solution (20.0 mL×2) and brine (10.0 mL), dried over Na$_2$SO$_4$, filtered and concentrated. The residue was purified by column chromatography (SiO$_2$, dichloromethane/methanol=100/1 to 10/1) to give compound 8f (0.15 g, 151 umol, 13.0% yield) as a light-yellow solid. LCMS (ES, m/z) 989.1 (M−1).

Step 6: Synthesis of Compounds H1, H2, H3 and H4

Compound 8f  →  MeNH$_2$

-continued

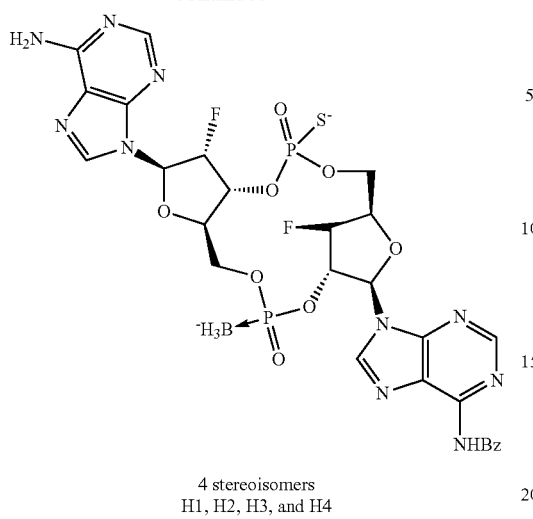

4 stereoisomers
H1, H2, H3, and H4

A solution of compound 8f (0.15 g, 151 umol, 1.00 eq) and MeNH₂ (2.00 mL) was stirred at 25° C. for 3 h. ACN (5.00 mL×2) was added and the mixture was concentrated in vacuo. After recrystallization, the filtered solid was purified by prep-HPLC column (Xtimate C18 150×25 mm×5 um; mobile phase: [water(0.04% NH₃H₂O+10 mM NH₄HCO₃)-ACN]; B %: 1%-10%, 10.5 min) to give one or more of the isomers of H1-H4 (single peak by HPLC) as a white solid (0.003 g, 4.44 umol, 2.94% yield). LCMS (ES, m/z) 675.0 (M−1)⁻.

Example 9: Synthesis of 2 Stereoisomers of the Compound Depicted Below (Compounds 11 and 12)

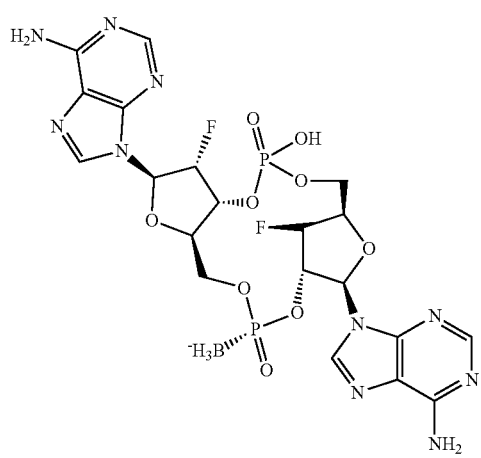

Step 1: Synthesis of Compound 9a

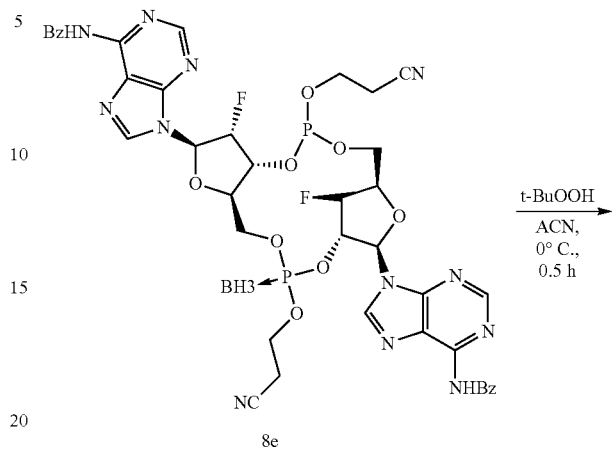

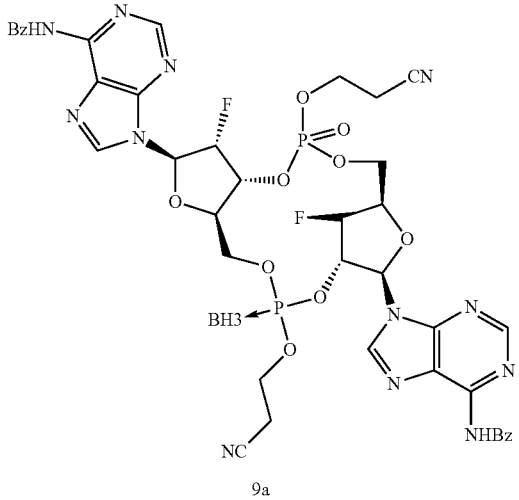

To a solution of compound 8e (2.22 g, 2.32 mmol) in DMF (2.0 mL), was added t-BuOOH (5.50 M, 718 uL, 1.70 eq). The mixture was stirred at 25° C. for 0.5 hour and then quenched with sat. NaHCO₃ solution (20 mL×2). Ethyl acetate (15 mL) was added and the organic layer was washed with brine (10 mL), dried over Na₂SO₄, filtered and concentrated in vacuo. The residue was purified by column chromatography (SiO₂, Dichloromethane/Methanol=100/1 to 10/1) to give compound 9a (0.14 g, 143 umol, 10.2% yield) as a light-yellow solid. LCMS (ES, m/z) 973.2 (M−1)⁻.

213

Step 2 Synthesis of Compounds I1 and I2

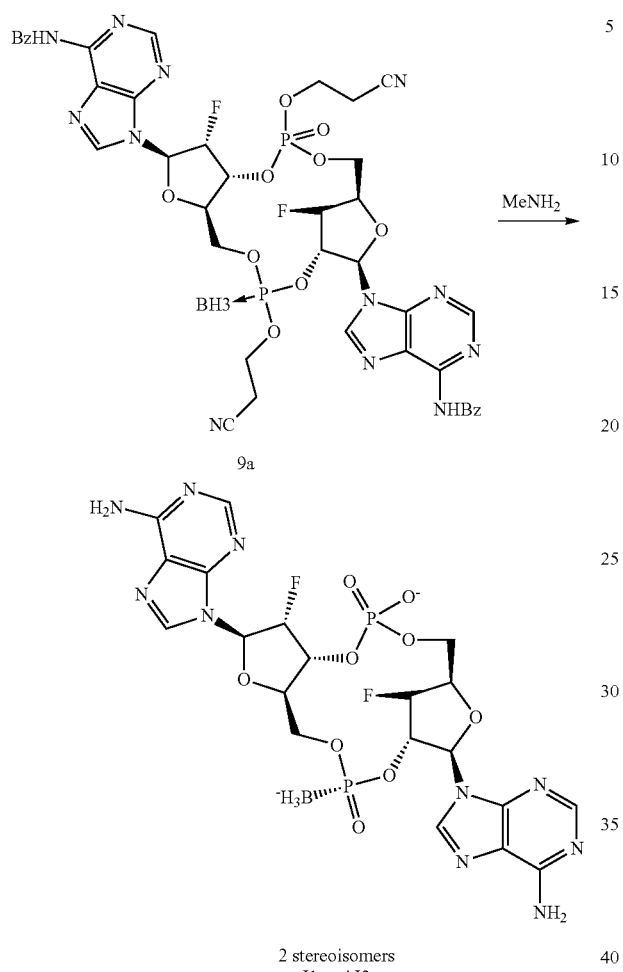

2 stereoisomers
I1 and I2

In a 10 mL round bottom flask, compound 9a (0.18 g, 184 umol, 1.00 eq) was dissolved in a solution of MeNH$_2$ in EtOH (2 mL, 30% by weigh) and stirred at 25° C. for 3 hr. ACN (5 mL×2) was added and concentrated in vacuo. After recrystallization with ACN at 25° C., the crude residue is purified by prep-HPLC column (Xtimate C18 150×25 mm×5 um; mobile phase: [water (0.04% NH$_3$H$_2$O+10 mM NH$_4$HCO$_3$)-ACN]; B %: 1%-5%, 10.5 min.) to give two isomers I1 (4 mg) and I2 (8 mg) as white solid.

I1: LCMS (ES, m/z) 659.1 (M−1)$^-$. $^1$H NMR (400 MHz D$_2$O) −1.00--0.81 (m, 2H), −0.32-0.46 (m, 1H), 4.04-4.31 (m, 8H), 4.44-4.46 (m, 2H), 4.99-5.10 (m, 2H), 5.46-5.83 (m, 2H), 6.00 (s, 1H), 6.24-6.42 (m, 2H), 7.97 (s, 1H), 8.14-8.24 (m, 2H), 8.43 (s, 1H).

I2: LCMS (ES, m/z) 659.1 (M−1)$^-$. $^1$H NMR (400 MHz D$_2$O) 1.348-1.189 (m, 3H), 3.903-4.607 (m, 10H), 4.938-5.166 (m, 2H), 5.454-5.715 (m, 2H), 5.990-6.482 (m, 3H), 7.917-8.161 (s, 1H), 8.223-8.356 (m, 3H).

214

Example 10: Synthesis of 4 Stereoisomers of the Compound Depicted Below (Compounds J1, J2, J3 and J4)

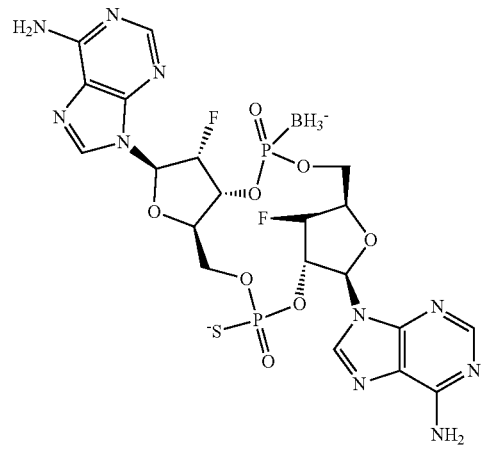

Step 1: Synthesis of (2R,3R,4R,5R)-5-(6-benzamido-9H-purin-9-yl)-2-((bis(4-methoxyphenyl)(phenyl)methoxy)methyl)-4-fluorotetrahydrofuran-3-yl (((2R,3S,4S,5R)-5-(6-benzamido-9H-purin-9-yl)-4-(bis(4-methoxyphenyl)(phenyl)methoxy)-3-fluorotetrahydrofuran-2-yl)methyl) (2-cyanoethyl) phosphite (10b)

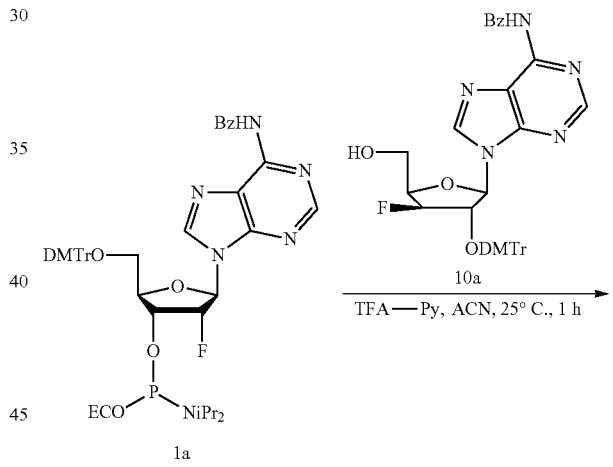

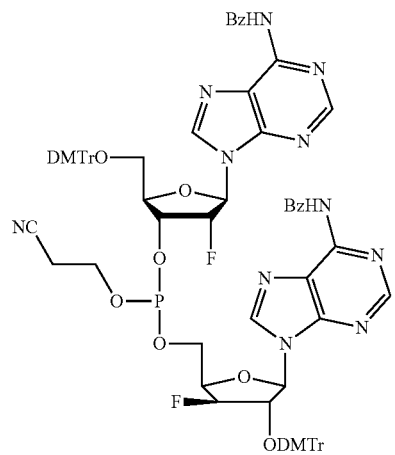

10b

Compound 10b was prepared using the same method as shown in Step 1 of Example 1.

Step 2: Synthesis of (((((2R,3R,4R,5R)-5-(6-benzamido-9H-purin-9-yl)-2-((bis(4-methoxyphenyl)(phenyl)methoxy)methyl)-4-fluorotetrahydrofuran-3-yl)oxy)(((2R,3S,4S,5R)-5-(6-benzamido-9H-purin-9-yl)-4-(bis(4-methoxyphenyl)(phenyl)methoxy)-3-fluorotetrahydrofuran-2-yl)methoxy)(2-cyanoethoxy)-14-phosphanyl)trihydroborate (10c)

Step 3: Synthesis of (((((2R,3R,4S,5R)-5-(6-benzamido-9H-purin-9-yl)-3-fluoro-4-hydroxytetrahydrofuran-2-yl)methoxy)(((2R,3R,4R,5R)-5-(6-benzamido-9H-purin-9-yl)-4-fluoro-2-(hydroxymethyl)tetrahydrofuran-3-yl)oxy)(2-cyanoethoxy)-14-phosphanyl)trihydroborate (10d)

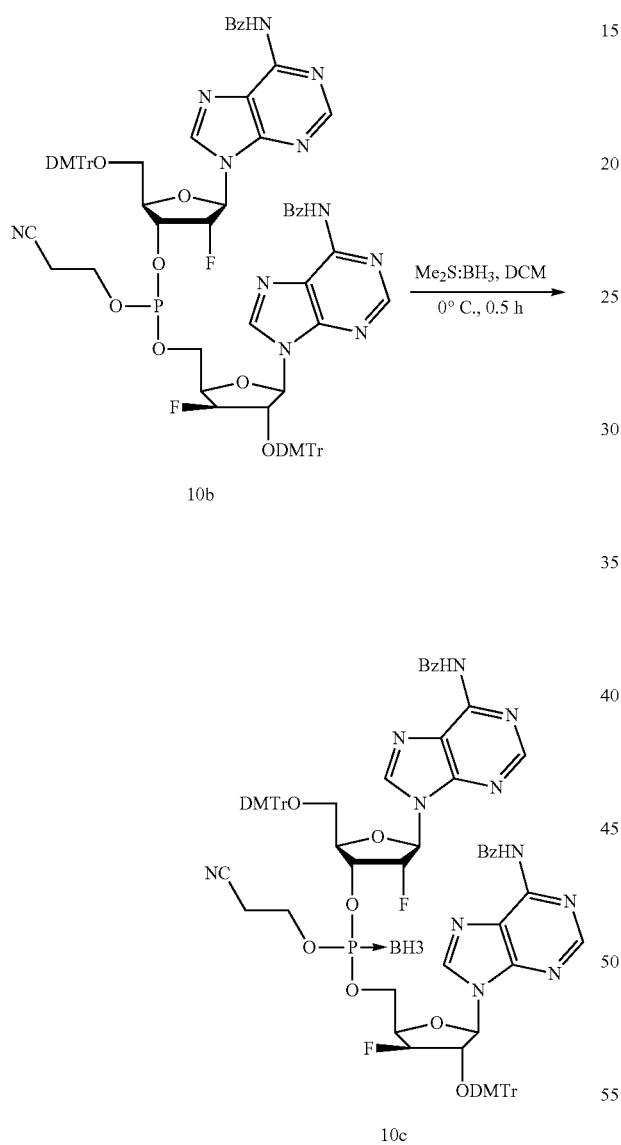

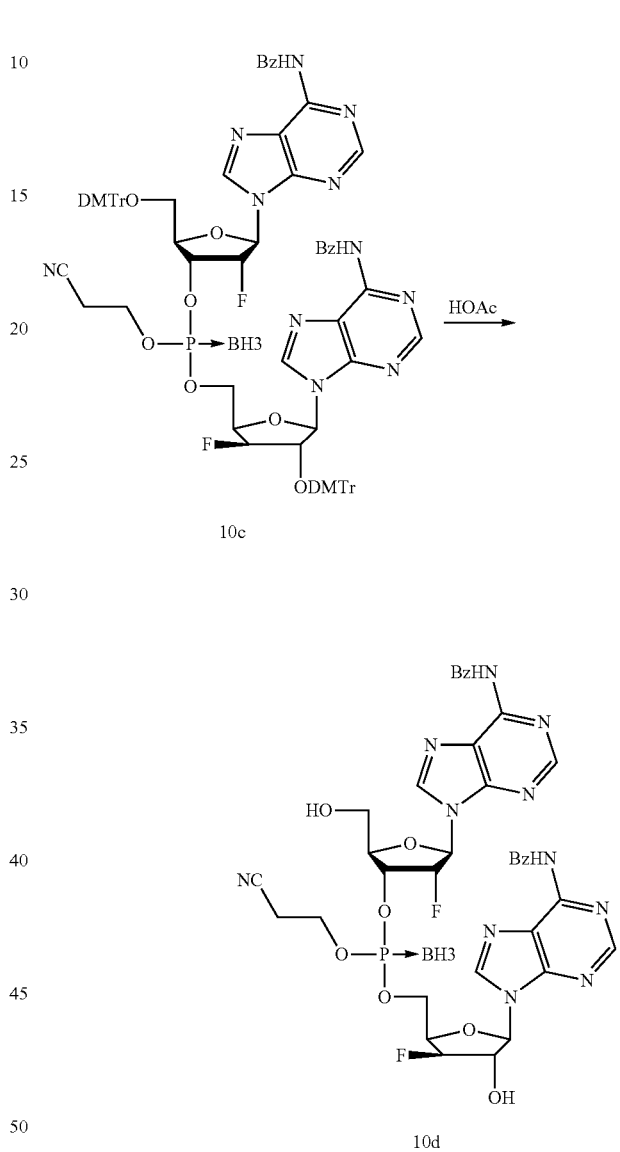

Compound 10c was prepared using the same method as shown in Step 2 of Example 1.

Compound 10d was prepared using the same method as shown in Step 3 of Example 1. $^1$H NMR (400 MHz DMSO-$d_6$) 0.527 (b rs, 3H) 2.966-2.995 (m, 2H) 3.618-3.721 (m, 1H) 4.282-4.297 (m, 1H) 4.481-4.506 (m, 3H) 4.581-4.607 (m, 1H) 4.906-4.947 (m, 1H) 5.235 (m, 1H) 5.327 (m, 1H) 5.364 (m, 2H) 5.468-5.480 (s, 2H) 5.899-6.027 (s, 1H) 6.182 (s, 1H) 6.476-6.528 (d, J=20.8 Hz, 2H) 7.535-7.573 (m, 4H) 7.633-7.650 (m, 2H) 8.044-8.063 (d, J=7.6 Hz, 4H) 8.487 (s, 1H) 8.704 (s, 1H) 8.765-8.788 (m, 2H) 11.243-11.279 (d, J=14.4 Hz, 2H).

Step 4: Synthesis of Compound 10e

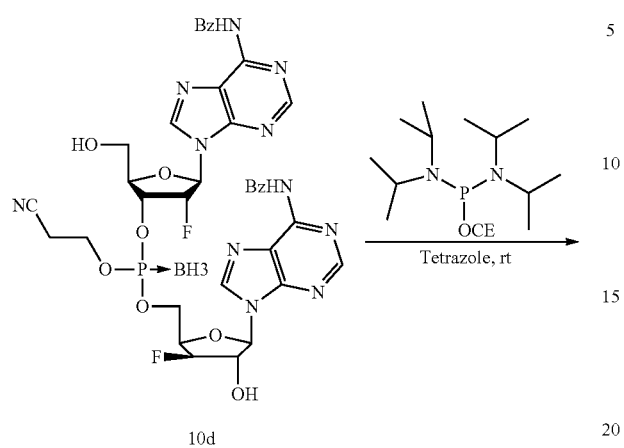

10d

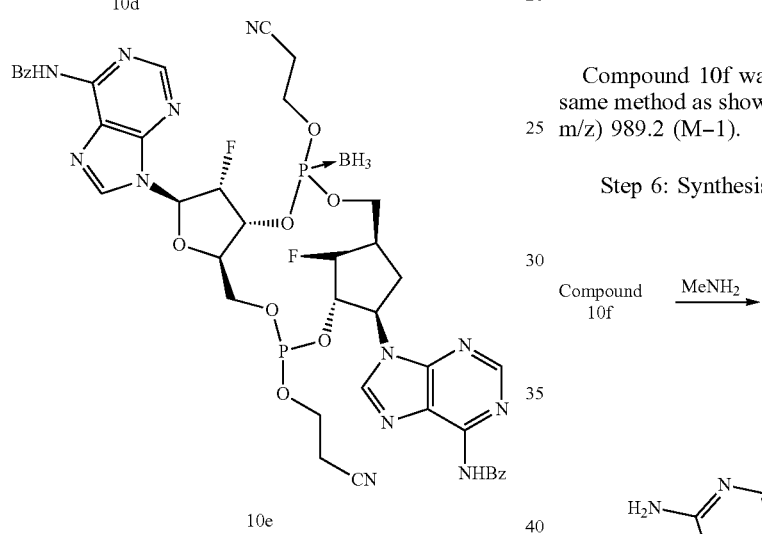

10e

Compound 10e was prepared using the same method as shown in Step 4 of Example 8.

Step 5: Synthesis of Compound 10f

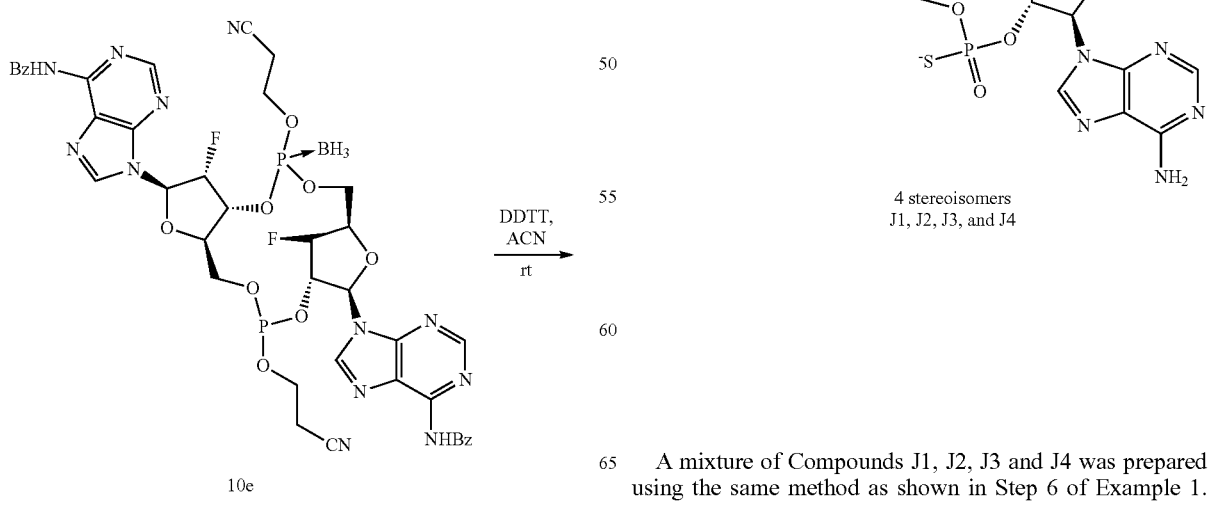

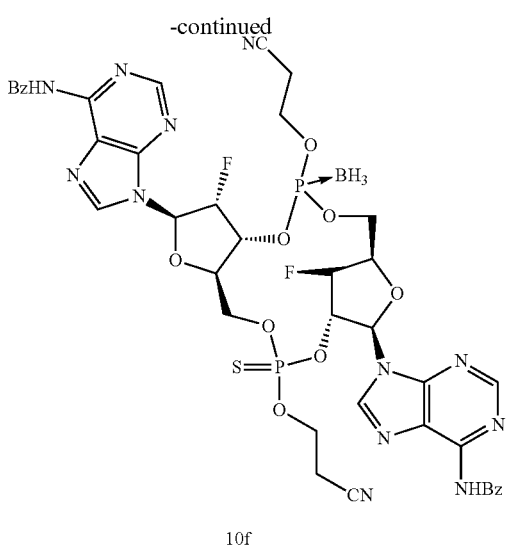

10f

Compound 10f was prepared as a white solid using the same method as shown in Step 5 of Example 8. LCMS (ES, m/z) 989.2 (M−1).

Step 6: Synthesis of Compounds J1, J2, J3 and J4

Compound 10f →(MeNH$_2$)

4 stereoisomers
J1, J2, J3, and J4

A mixture of Compounds J1, J2, J3 and J4 was prepared using the same method as shown in Step 6 of Example 1. 79% (HPLC purity); LCMS (ES, m/z) 675.0 (M−1)⁻.

Example 11: Synthesis of 2 Stereoisomers of the Compound Depicted Below (Compounds K1 and K2)

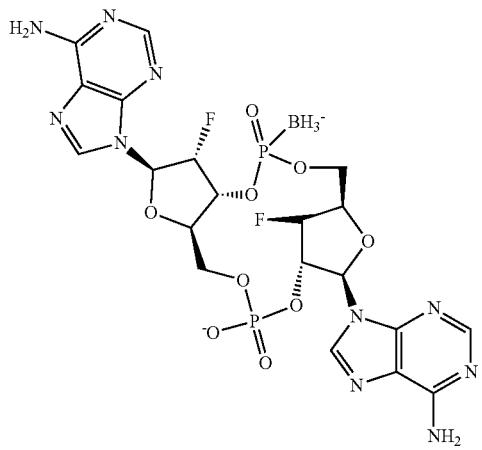

Compounds K1 and K2 were prepared according to Example 9 starting from compound 10e. The crude was purified by prep-HPLC column: Xtimate C18 150×25 mm×5 um; mobile phase: [water (0.04% NH$_3$H$_2$O+10 mM NH$_4$HCO$_3$)-ACN]; B %: 1%-10%, 10.5 min to give two isomers: K1 (5 mg) and K2 (2 mg). K1: 100% (HPLC purity), LCMS (ES, m/z) 659.1 (M−1)⁻. K2: 100% (HPLC purity), LCMS (ES, m/z) 659.1 (M−1)⁻.

Example 12: Synthesis of 4 Stereoisomers of the Compound Depicted Below (Compounds L1, L2, L3 and L4)

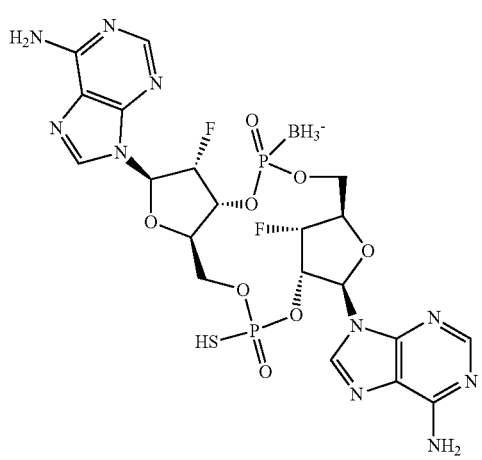

Step 1: Synthesis of (2R,3R,4R,5R)-5-(6-benzamido-9H-purin-9-yl)-2-((bis(4-methoxyphenyl)(phenyl)methoxy)methyl)-4-fluorotetrahydrofuran-3-yl (((2R,3R,4S,5R)-5-(6-benzamido-9H-purin-9-yl)-4-(bis(4-methoxyphenyl)(phenyl)methoxy)-3-fluorotetrahydrofuran-2-yl)methyl) (2-cyanoethyl) phosphite (12b)

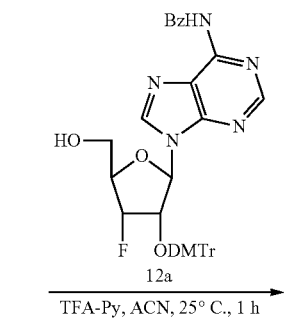

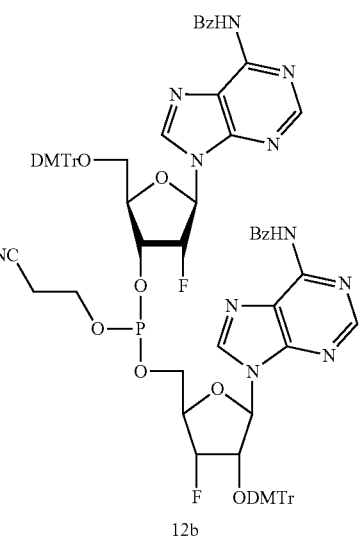

Compound 12b was prepared using the same method as shown in Step 1 of Example 1.

Step 2: Synthesis of (((((2R,3R,4R,5R)-5-(6-benzamido-9H-purin-9-yl)-2-((bis(4-methoxyphenyl)(phenyl)methoxy)methyl)-4-fluorotetrahydrofuran-3-yl)oxy)(((2R,3R,4S,5R)-5-(6-benzamido-9H-purin-9-yl)-4-(bis(4-methoxyphenyl)(phenyl)methoxy)-3-fluorotetrahydrofuran-2-yl)methoxy)(2-cyanoethoxy)-14-phosphanyl)trihydroborate (12c)

Step 3: Synthesis of (((((2R,3S,4S,5R)-5-(6-benzamido-9H-purin-9-yl)-3-fluoro-4-hydroxytetrahydrofuran-2-yl)methoxy)(((2R,3R,4R,5R)-5-(6-benzamido-9H-purin-9-yl)-4-fluoro-2-(hydroxymethyl)tetrahydrofuran-3-yl)oxy)(2-cyanoethoxy)-14-phosphanyl)trihydroborate (12d)

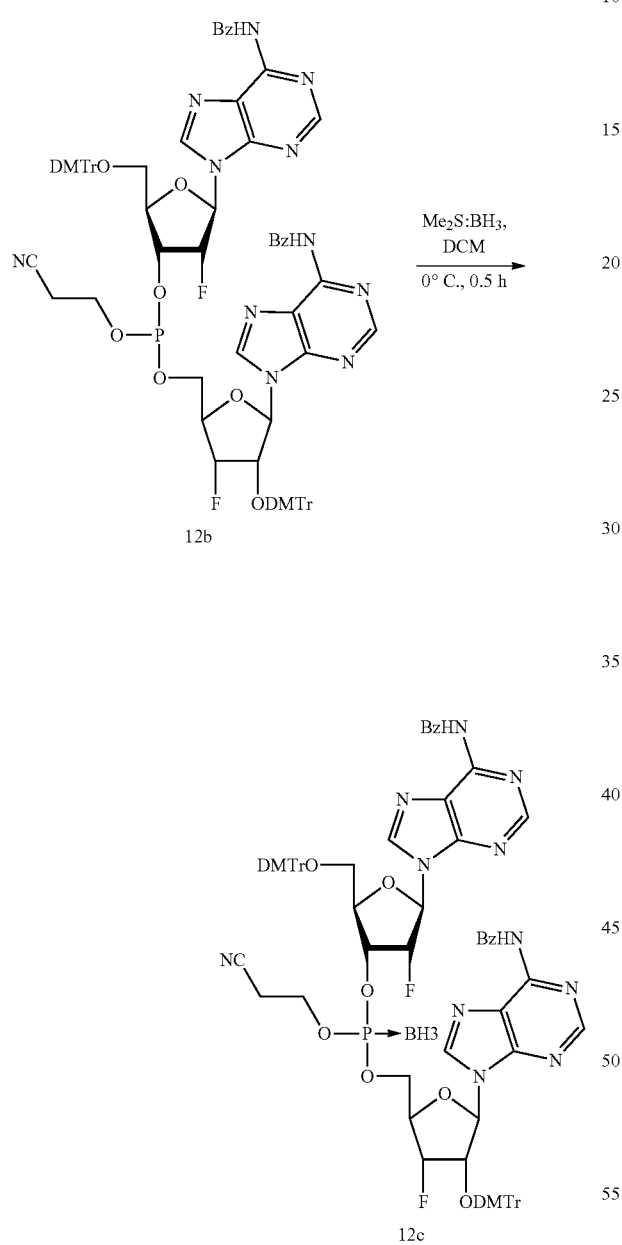

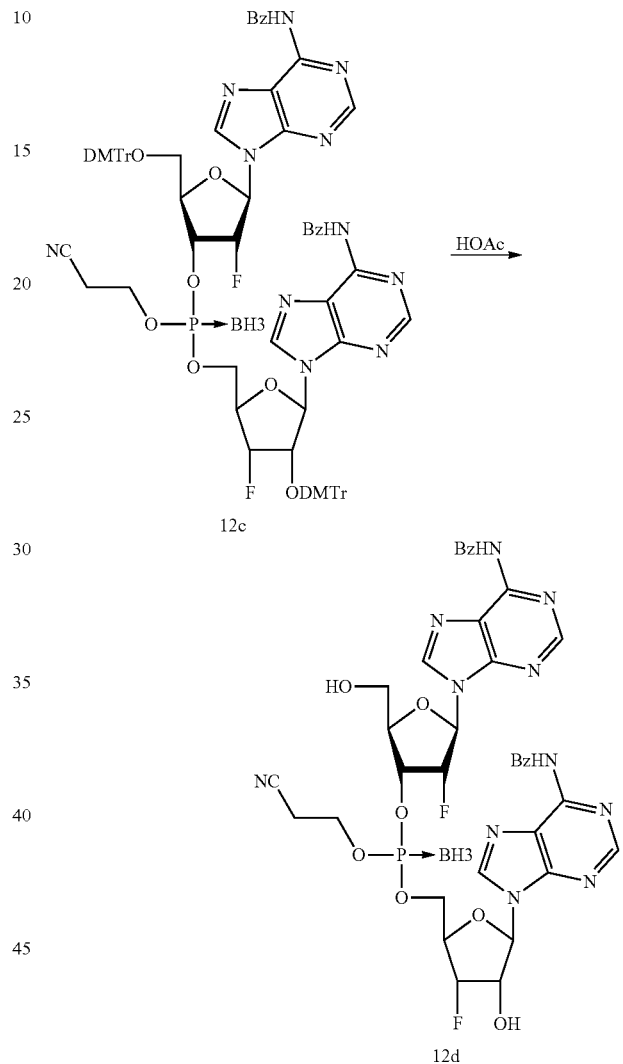

Compound 12c was prepared using the same method as shown in Step 2 of Example 1.

Compound 12d was prepared using the same method as shown in step 3 of example 1. LCMS (ES, m/z) 860.2 (M+1)+. $^1$H NMR (400 MHz DMSO-$d_6$) δ ppm 0.52 (br s, 3H), 2.93-3.00 (m, 2H), 3.64-3.65 (m, 1H), 3.72 (m, 1H), 4.26-4.30 (m, 3H), 4.47-4.48 (m, 2H), 4.56-4.62 (m, 1H), 5.24-5.25 (m, 1H), 5.32-5.34 (m, 2H), 5.38-5.39 (m, 1H), 6.18-6.20 (dd, J=24 Hz, 2H), 6.13 (m, 0.5H), 6.15 (m, 0.5H), 6.48-6.52 (m, 1H), 7.54-7.57 (m, 4H), 7.63-7.65 (m, 2H), 8.04-8.06 (d, J=8 Hz, 4H), 8.68-8.70 (m, 2H), 8.76-8.79 (m, 2H), 11.06-11.28 (m, 2H).

Step 4: Synthesis of Compound 12e

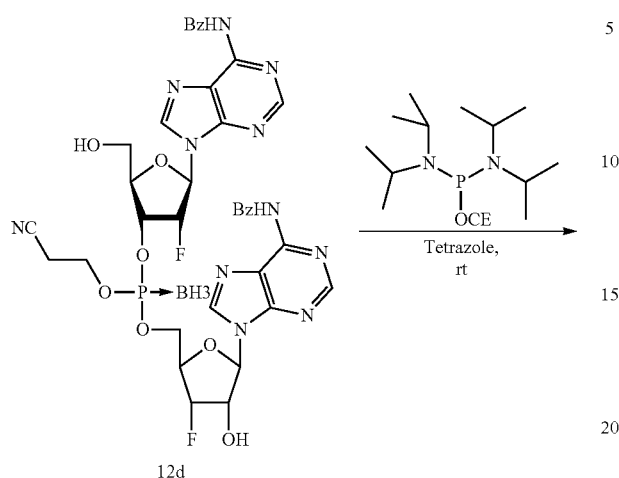

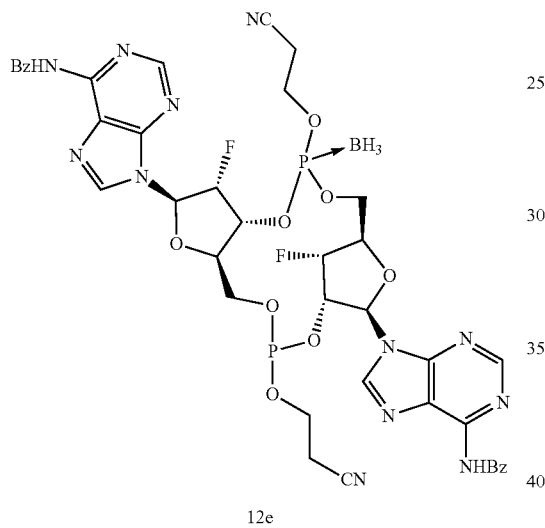

Compound 12e is prepared using the same method as shown in Step 4 of Example 1.

Step 5: Synthesis of Compound 12f

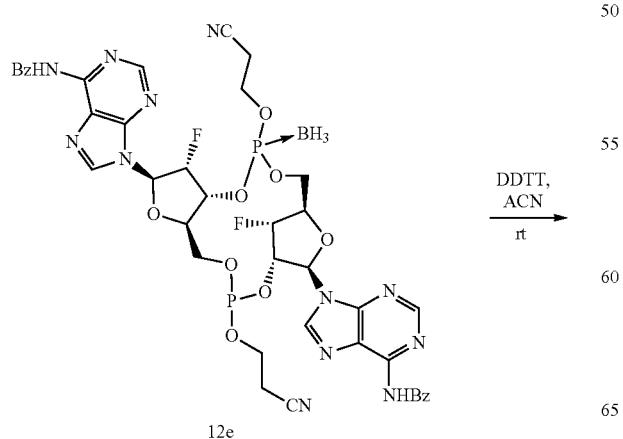

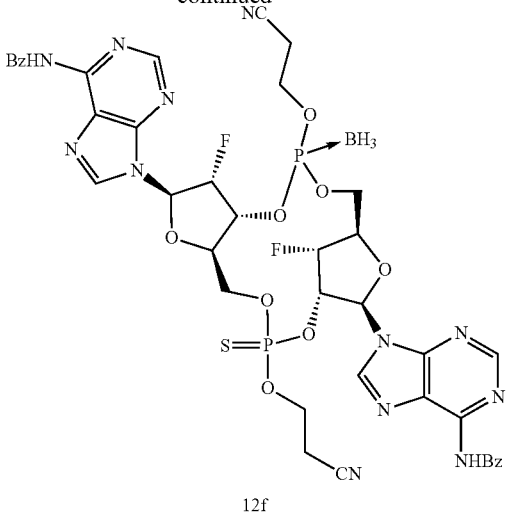

Compound 12f is prepared using the same method as shown in Step 5 of Example 1. LCMS (ES, m/z) 991.1 (M+1)$^+$.

Step 6: Synthesis of Compounds L1, L2, L3 and L4

Compound 12f $\xrightarrow{\text{MeNH}_2}$

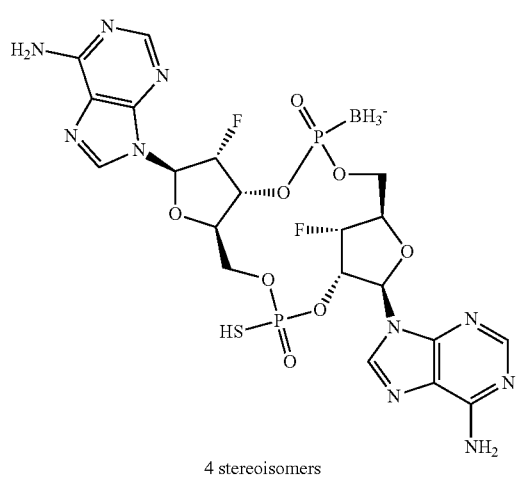

4 stereoisomers
L1, L2, L3, and L4

Compounds L1, L2, L3 and L4 are prepared using the same method as shown in Step 6 of Example 1.

Example 13: Synthesis of 2 Stereoisomers of the Compound Depicted Below (Compounds M1 and M2)

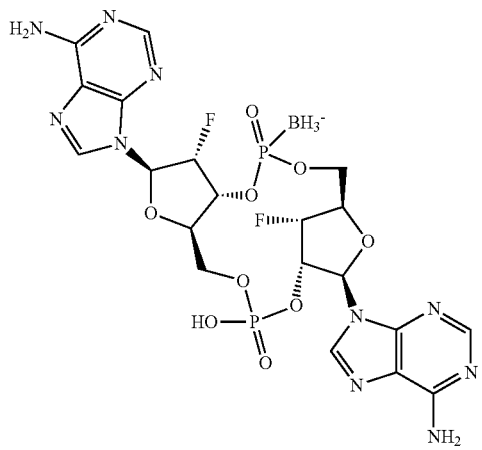

Compounds M1 and M2 are prepared according to Example 9 starting from compound 12e.

Example 14: Synthesis of 4 Stereoisomers of the Compound Depicted Below (Compounds N1, N2, N3 and N4)

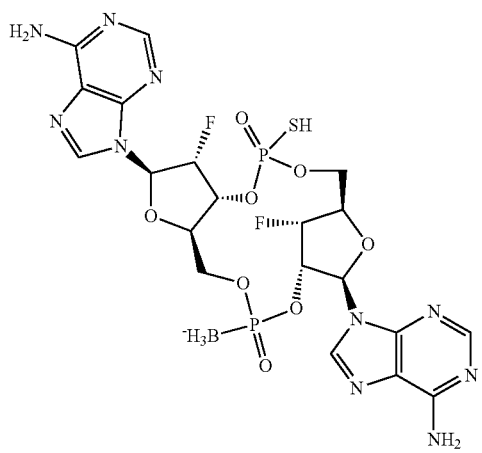

Step 1: Synthesis of ((2R,3R,4R,5R)-5-(6-benzamido-9H-purin-9-yl)-3-(bis(4-methoxyphenyl)(phenyl)methoxy)-4-fluorotetrahydrofuran-2-yl)methyl ((2R,3S,4R,5R)-2-(6-benzamido-9H-purin-9-yl)-5-((bis(4-methoxyphenyl)(phenyl)methoxy)methyl)-4-fluorotetrahydrofuran-3-yl) (2-cyanoethyl) phosphite (14b)

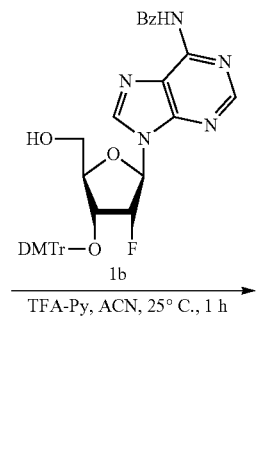

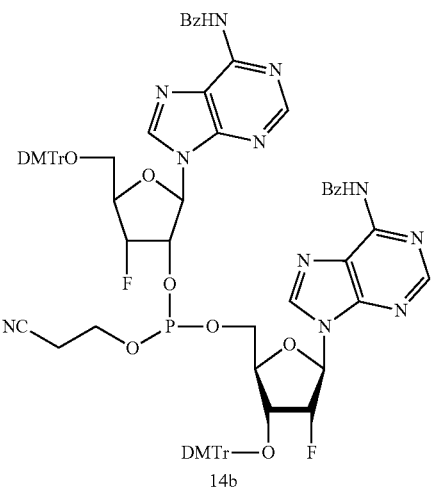

Compound 14b was prepared using the same method as shown in Step 1 of Example 1.

Step 2: Synthesis of (((((2R,3R,4R,5R)-5-(6-benzamido-9H-purin-9-yl)-3-(bis(4-methoxyphenyl)(phenyl)methoxy)-4-fluorotetrahydrofuran-2-yl)methoxy)(((2R,3S,4R,5R)-2-(6-benzamido-9H-purin-9-yl)-5-((bis(4-methoxyphenyl)(phenyl)methyl)-4-fluorotetrahydrofuran-3-yl)oxy)(2-cyanoethoxy)-14-phosphanyl)trihydroborate (14c)

Step 3: Synthesis of (((((2R,3R,4R,5R)-5-(6-benzamido-9H-purin-9-yl)-4-fluoro-3-hydroxytetrahydrofuran-2-yl)methoxy)(((2R,3S,4R,5R)-2-(6-benzamido-9H-purin-9-yl)-4-fluoro-5-(hydroxymethyl)tetrahydrofuran-3-yl)oxy)(2-cyanoethoxy)-14-phosphanyl)trihydroborate (14d)

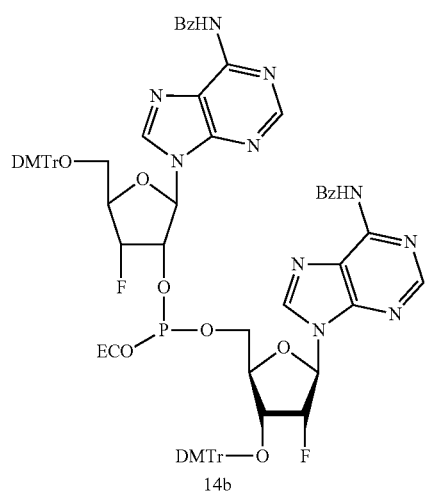

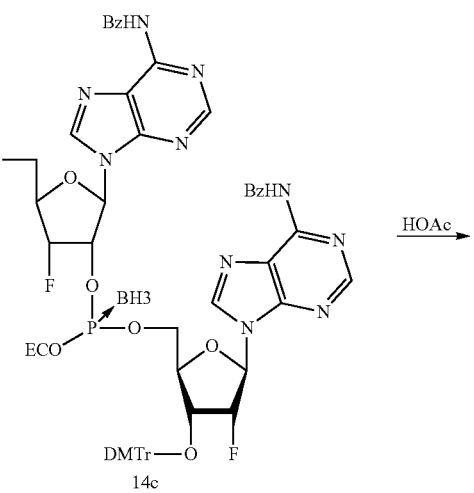

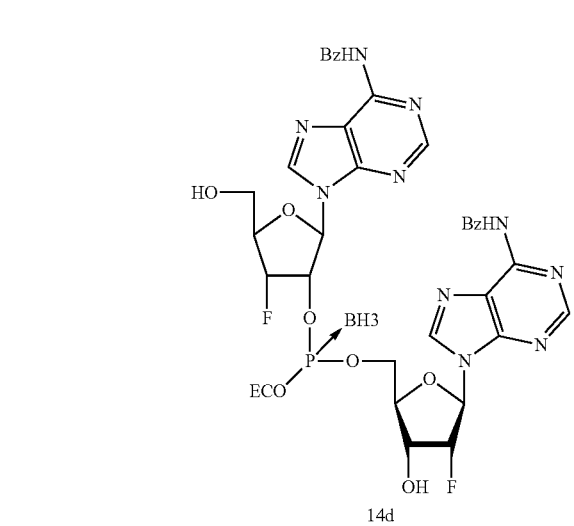

Compound 14c was prepared using the same method as shown in Step 2 of Example 1.

Compound 14d was prepared using the same method as shown in Step 3 of Example 1. LCMS (ES, m/z) 860.2 (M+1)$^+$.

Step 4: Synthesis of Compound 14e
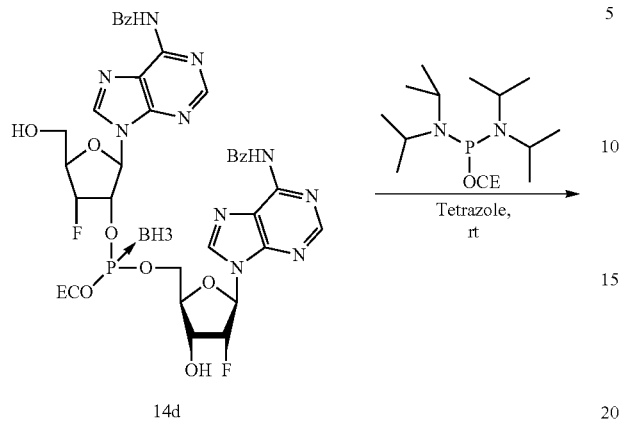
14d
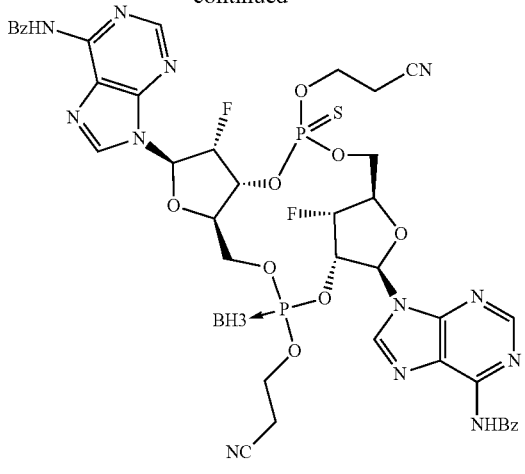
14f
Compound 14f is prepared using the same method as shown in Step 5 of Example 1.
Step 6: Synthesis of Compounds N1, N2, N3 and N4
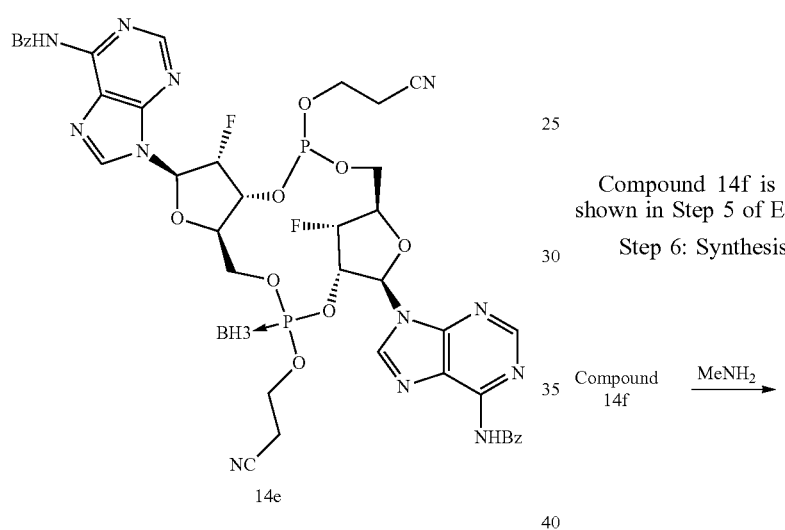
14e
Compound 14e is prepared using the same method as shown in Step 4 of Example 1.
Step 5: Synthesis of Compound 14f
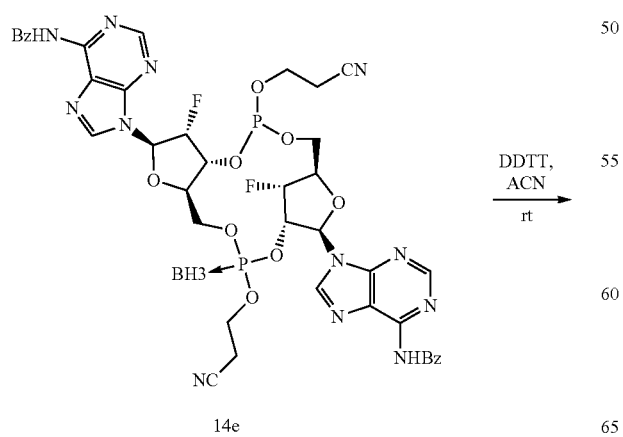
14e
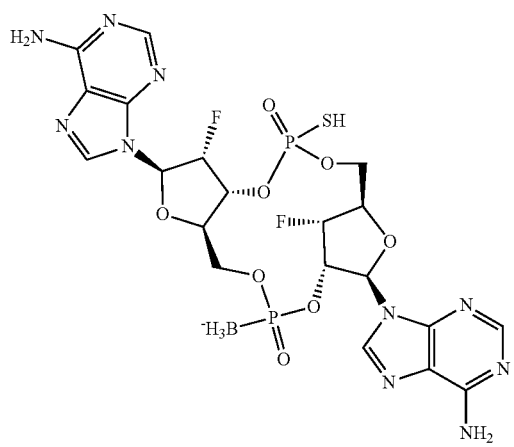
4 stereoisomers
N1, N2, N3, and N4
Compounds N1, N2, N3 and N4 are prepared using the same method as shown in Step 6 of Example 1.

Example 15: Synthesis of 2 Stereoisomers of the Compound Depicted Below (Compounds O1 and O2)

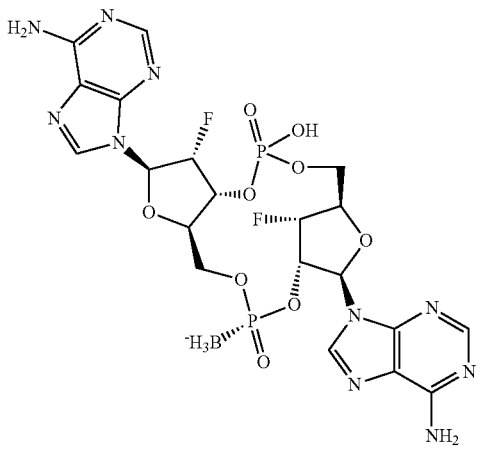

Compounds O1 and O2 are prepared according to Example 9 starting from compound 14e.

The examples provided herein are representative, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

Biological Assays

Example 16: Activation of Human STING Signaling in THP1 Cell Line

STING pathway activation by the compounds described herein was measured using THP-1 dual cells. These cells are THP1 monocytes that have been modified to be reporters for the IRF pathway, which is activated by STING agonists in these cells.

THP1-Dual cells (obtained from Invivogen) are maintained in growth medium with 100 ug/ml of Zeocin and 10 ug/ml of blasticidin at 37° C., 5% $CO_2$, the cells were passaged every 3 days by inoculating $7 \times 10^5$ cells per ml and centrifuged at 1000 rpm for 5 min. Supernatant was removed and THP-1 Dual cells were re-suspended at $5 \times 10^5$ cells/ml in fresh pre-warmed growth medium.

Compounds were dissolved in DMSO and transferred into assay plate by Echo, the final DMSO concentration was kept below 0.5%, 2'3'-cGMAP (100 ug/ml) is used as positive control. 50 ul of Cell suspension (about $2.5 \times 10^4$ cells per well) was added in 384-well plate, which was incubated for 24 hours at 37° C., 5% $CO_2$. QUANTI-Luc was prepared and used following the manufacturer's instructions, $5 \times 10^3$ cells per well were seeded in 40 μl medium and incubated overnight. Luminometer was set with the following parameters: 50u of injection, end-point measurement with a 4 second start time and 0.1 second reading time. 10 ul of THP-1 Dual cell culture medium per well was added into a 96-well white (opaque) plate, luminescence was measured and calculated.

FIG. 1 shows the biological data of compound mixture of A1, A2, A3 and A4 that assayed using above procedures and Table 1 provides the data shown in FIG. 1.

TABLE 1

THP1-Dual Cell Assay Results

| Cpd. Code in FIG. 1 | Compound ID | Con. (μM) | n = 1 | n = 2 | Average | Std |
|---|---|---|---|---|---|---|
| 1 | DMSO | 0 | 4720 | 3420 | 4070 | 460 |
| 2 | 2',3'-cGAMP | 100 ug/ml | 1054660 | 1099530 | 1077095 | 15864 |
| 3 | Mixture of | 120 | 1133220 | 1291450 | 1212335 | 55943 |
| 4 | A1, A2, A3 | 90 | 1264170 | 1220070 | 1242120 | 15592 |
| 5 | and A4 | 60 | 1194350 | 1161900 | 1178125 | 11473 |
| 6 | | 30 | 1130760 | 1198560 | 1164660 | 23971 |
| 7 | ADU-S100 | 30 | 909990 | 964820 | 937405 | 19385 |

Figure 2:
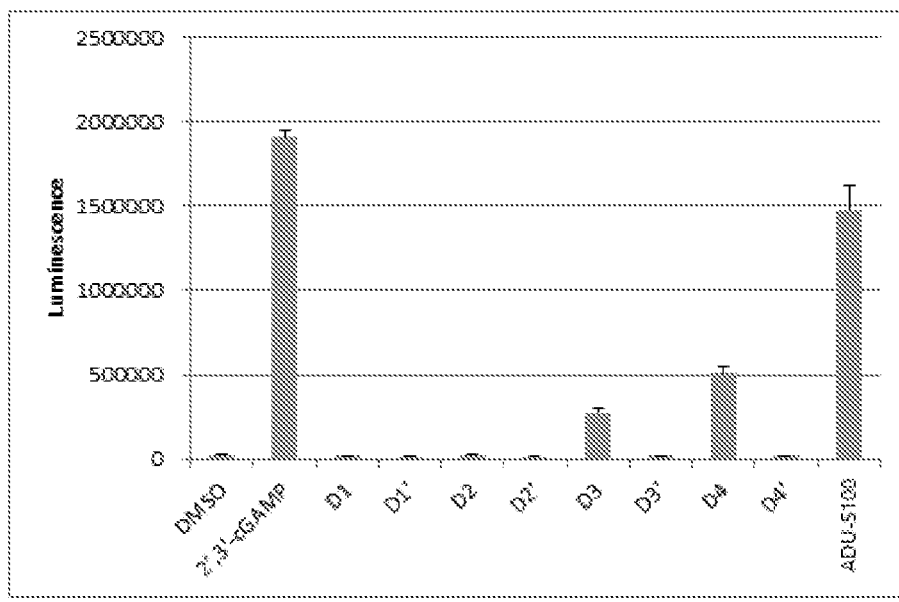
FIG. 2 shows THP1-dual cell assay results of Compounds D1, D1', D2, D2', D3, D3', D4 and D4'.

FIG. 2 shows the biological data of compounds D1, D1', D2, D2', D3, D3', D4 and D4' that assayed using above procedures and Table 2 provides the data shown in FIG. 2.

TABLE 2

THP1-Dual Cell Assay Results

| Cpd Code in FIG. 2 | Compound ID | Con. (μM) | n = 1 | n = 2 | Average | Std |
|---|---|---|---|---|---|---|
| 1 | DMSO | 0 | 27540 | 24250 | 25895 | 2326 |
| 2 | 2',3'-cGAMP | 1 mg/ml | 1883110 | 1935710 | 1909410 | 37194 |
| 3 | D1 | 30 | 22420 | 21660 | 22040 | 537 |
| 4 | D1' | 30 | 17680 | 13020 | 15350 | 3295 |
| 5 | D2 | 30 | 18350 | 29570 | 23960 | 7934 |
| 6 | D2' | 30 | 14610 | 12790 | 13700 | 1287 |
| 7 | D3 | 30 | 289010 | 258740 | 273875 | 21404 |
| 8 | D3' | 30 | 21460 | 17840 | 19650 | 2560 |
| 9 | D4 | 30 | 534040 | 486440 | 510240 | 33658 |
| 10 | D4' | 30 | 18940 | 18850 | 18895 | 64 |
| 11 | ADU-S100 | 30 | 1386020 | 1578860 | 1482440 | 136358 |

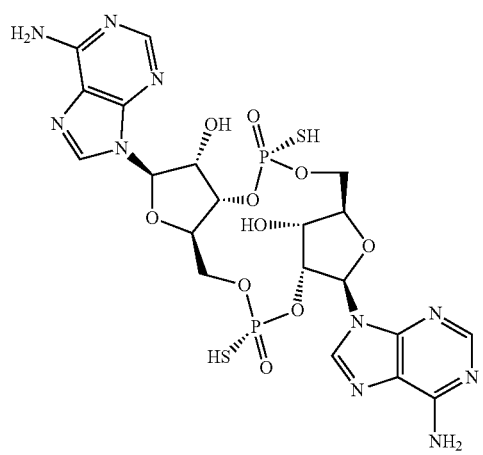 [SMILES: Nc1ncnc2c1ncn2[C@@H]1O[C@@H]2CO[P@@](=O)(S)O[C@@H]3[C@H](O)[C@@H](CO[P@@](=O)(S)O[C@H]2[C@H]1O)O[C@H]3n1cnc2c(N)ncnc21]

ADU-S100 was obtained from WUXI AppTec

THP1-Dual cells (obtained from Invivogen) are maintained in RPM11640 medium with 100 g/ml of Zeocin and 10 g/ml of blasticidin at 37° C., 5% $CO_2$, compounds were dissolved in sterile PBS (pH7.4) as 20 mM, $0.5 \times 10^6$ cells/ml of THP-1 Dual cells were incubated with indicated concentrations of a compound for 24 hours at 37° C., 5% $CO_2$ incubator. QUANTI-Luc and QUANTI-Blue were prepared and used following the manufacturer's instructions. 10 ul of cell culture supernatant were mixed with QUANTI-Luc and immediately measured using Luminometer; 20 ul of supernatant were mixed with QUANTI-Blue, and incubated at 37° C. for 30 minutes, and read at OD620. EC50 was calculated using Prism with 4-parameter dose-response curve fitting (Table 3).

TABLE 3

$EC_{50}$ in THP1 cell line

| Compound ID | $EC_{50}$ IRF3 (μM) | $ECs_{50}$ NF-kB (μM) |
|---|---|---|
| Mixture of A1, A2, A3 and A4 | 1.76 | |
| 2',3'-cGAMP | 8.05 | |
| E1 | 0.48 | 2.55 |
| E2 | 0.80 | 7.96 |
| ADU-S100 | 1.45 | 7.58 |
| F1 | 1.16 | 6.59 |
| F2 | 1.56 | 10.04 |
| G1 | 0.63 | 4.3 |
| G2 | 1.08 | 8.52 |
| I1 | 13.95 | 28.95 |
| I2 | 6.27 | 34.68 |
| K1 | 0.91 | 7.47 |
| K2 | 23.02 | 72.63 |
| C1 | 88.4 | 67.14 |
| C2 | 0.43 | 4.93 |
| C3 | 0.37 | 4.56 |
| C4 | 0.63 | 6.29 |
| B1 | 28.22 | >100 |
| B2 | 14.69 | 74.59 |
| B3 | 0.91 | 5.22 |
| B4 | 0.61 | 7.61 |
| Mixtures of H1, H2, H3, and H4 | >100 | >100 |

Example 17: Evaluation of the Effect of Compounds on STING in 293T-Dual hSTING R232 Cells 293T-Dual hSTING R232 cells were cultured in DMEM medium supplemented with 10% heat inactivated FBS, 2 mM L-glutamine, 4.5 g/L glucose, Pen-Strep (100 U/mL-100 μg/mL), 100 μg/mL Normocin, 10 μg/mL blasticidin, 100 μg/mL hygromycin B Gold and 100 μg/mL zeocin (complete medium). 100 μL of 293T-Dual hSTING R232 cells (InvivoGen) at $0.25 \times 10^6$ cells/ml were seeded in a well of a 96-well plate, and cultured at 37° C. incubator for 2 hr. A test compound with a serial of dilution was prepared in complete medium, and 50 μL of the compound were added to the corresponding well, and incubated with the cells at 37° C. incubator for 24 hr.

To determine the effect on interferon regulatory factor (IRF) activation, 20 μL of cell culture supernatant was transferred into a fresh 96-well plate, 150 μL of Quanti-Blue was added to each well and incubated at 37° C. for 25 min. OD at 620 nm was recorded, and $EC_{50}$ was calculated with 4 parameter logistic equation.

To evaluate the effect on interferon-β expression, 20 μL of cell culture supernatant were transferred into a fresh 96-half area-well white plate, 30 μL of Quanti-Luc were added to each well, and luminescence was measured immediately with a luminometer. Four parameter logistic equation was used to calculate $EC_{50}$ (Table 4).

TABLE 4

$EC_{50}$ in 293T-Dual hSTING R232 cell line

| Compound ID | IRF $EC_{50}$ (μM) | IFNb $EC_{50}$ (μM) |
|---|---|---|
| ADU-S100 | 2.57 | 2.93 |
| Mixture of A1, A2, A3 and A4 | 0.74 | 1.29 |
| 2',3'-cGAMP | 32.20 | 28.50 |
| E1 | 0.53 | 0.70 |
| E2 | 1.06 | 1.63 |
| F1 | 0.63 | 2.44 |
| F2 | 1.2 | 2.78 |
| G1 | 0.41 | 0.92 |
| G2 | 0.94 | 1.77 |
| I1 | 9.68 | 12.79 |
| I2 | 5.43 | 11.16 |
| K1 | 0.72 | 2.3 |
| K2 | 14.96 | 32.97 |
| C1 | 34.29 | 75 |
| C2 | 0.23 | 0.43 |
| C3 | 0.085 | 0.16 |
| C4 | 0.34 | 0.7 |
| B1 | 11.76 | 37.45 |
| B2 | 9.82 | 29.11 |
| B3 | 0.32 | 2.97 |
| B4 | 0.34 | 2.27 |
| Mixtures of H1, H2, H3, and H4 | 33.64 | 84.35 |

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as acknowledgment or any form of suggestion that they constitute valid prior art or form part of the common general knowledge in any country in the world.

What is claimed is:

1. A compound of formula (II-C), (II-D), or (II-F):

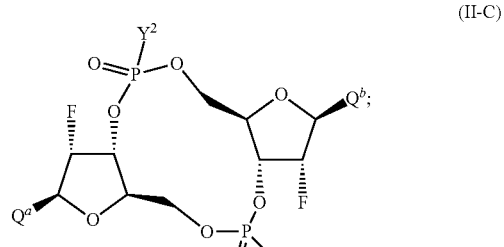

(II-C)

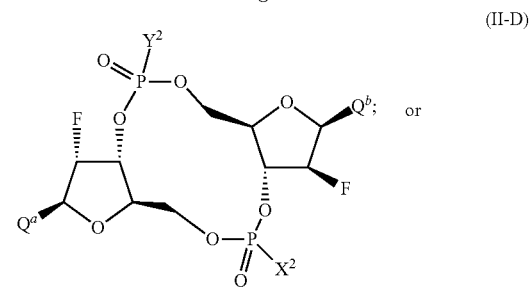

(II-D) or

-continued (II-F)

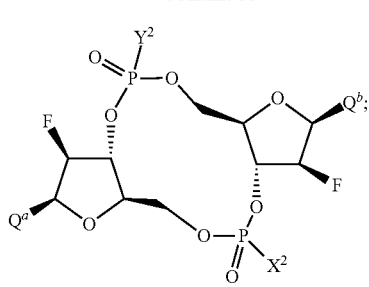

or a pharmaceutically acceptable salt or stereoisomer thereof, wherein:

$Q^a$ and $Q^b$ are each independently selected from:

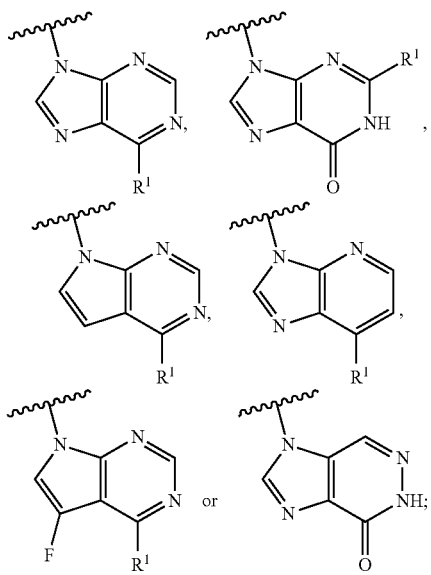

$R^1$ is each independently hydrogen, halogen, or —N($R^{c1}$)$_2$;

$R^{c1}$ is each independently H, $C_{1-6}$ alkyl, $C_{3-6}$ cycloalkyl, $C_{3-6}$ cycloalkyl-$C_{1-6}$ alkyl-, 3-6 membered heterocyclyl, (3-6 membered heterocyclyl)-$C_{1-6}$ alkyl-, 5-6 membered aryl, (5-6 membered aryl)-$C_{1-6}$ alkyl-, 5-6 membered heteroaryl, or (5-6 membered heteroaryl)-$C_{1-6}$ alkyl-; and $X^2$ and $Y^2$ are each independently SH, OH, or $BH_3^-$, wherein at least one of $X^2$ and $Y^2$ is $BH_3^-$.

2. The compound of claim 1, wherein the compound has the structure of formula (II-C) and $Q^a$ and $Q^b$ are each

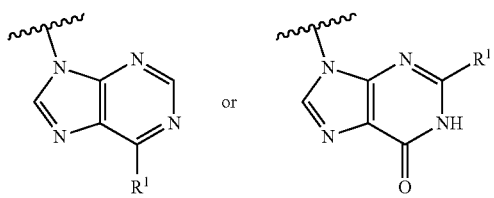

3. The compound of claim 2, wherein the compound has the structure of formula (II-C) and $Q^a$ and $Q^b$ are each

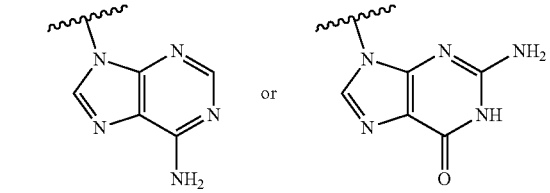

4. A pharmaceutical composition comprising a compound of claim 1, or a pharmaceutically acceptable salt or stereoisomer thereof, and one or more pharmaceutically acceptable excipients.

5. A method for modulating a stimulator of interferon gene (STING) comprising administering a therapeutically effective amount of a compound of claim 1, or a pharmaceutically acceptable salt or stereoisomer thereof to the subject in need thereof.

6. A method for treating a disease comprising administering a therapeutically effective amount of a compound of claim 1, or a pharmaceutically acceptable salt or stereoisomer thereof to the subject in need thereof, wherein the disease is selected from cancer, rheumatoid arthritis, psoriasis, acute rejection of an organ transplant, allergic asthma or Crohn's disease.

7. The compound of claim 1, wherein the compound is selected from:

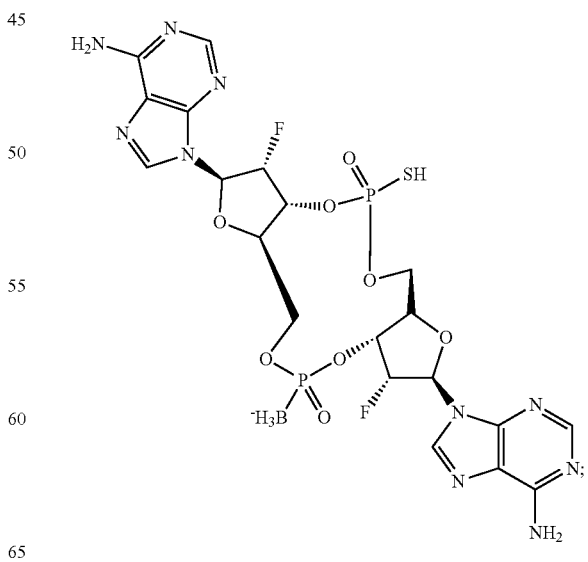

237
-continued

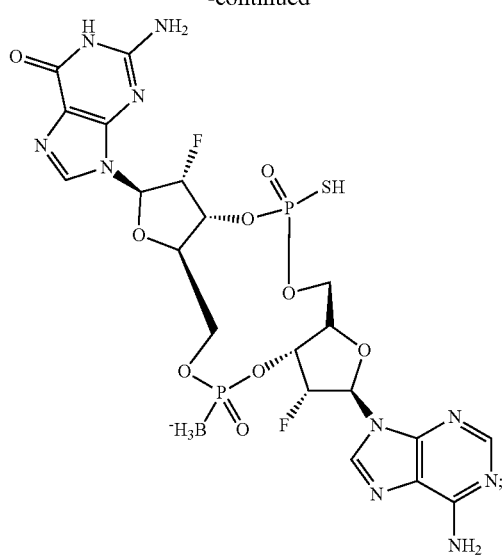

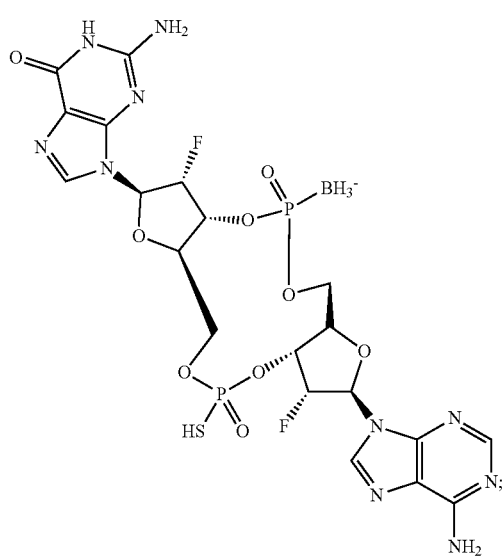

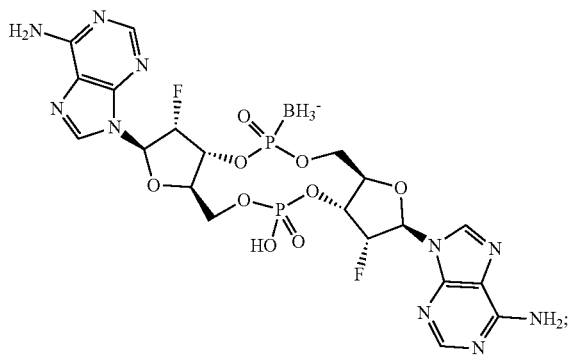

238
-continued

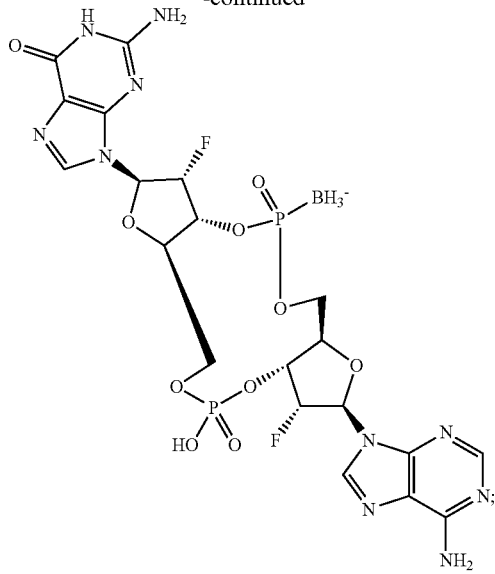

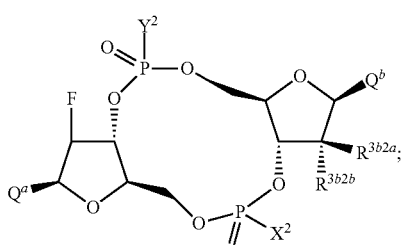

or a pharmaceutically acceptable salt or stereoisomer thereof.

8. A compound of formula (B), (B)

or a pharmaceutically acceptable salt or stereoisomer thereof, wherein:

$Q^a$ and $Q^b$ are each independently cycloalkyl, heterocyclyl, aryl, or heteroaryl, wherein the cycloalkyl, heterocyclyl, aryl, and heteroaryl can be optionally substituted with one, two, three, four, or five $R^1$;

$R^1$ is each independently hydrogen, halogen, —NO$_2$, —CN, —OR$^{cl}$, —SR$^{cl}$, —N(R$^1$)$_2$, —C(O)R$^{cl}$, —CO$_2$R$_{cl}$, —C(O)C(O)R$^{cl}$, —C(O)CH$_2$C(O)R$^{cl}$, —C(O)N(R$^{cl}$)$_2$, —C(=NR$^{cl}$)N(R$^{cl}$)$_2$, —C(=NOR$^{cl}$)R$^{cl}$, —S(O)R$^{cl}$, —S(O)$_2$R$^{cl}$, —SO$_2$N(R$^{cl}$)$_2$, —OC(O)R$^{cl}$, —N(R$^{cl}$)C(O)R$^{cl}$, —NR$^{cl}$N(R$^{cl}$)$_2$, —N(R$^{cl}$)C(=NR$^{cl}$)N(R$^{cl}$)$_2$, —N(R$^{cl}$)C(O)N(R$^{cl}$)$_2$, —N(R$^{cl}$)SO$_2$N(R$^{cl}$)$_2$, —N(R$^{cl}$)SO$_2$R$^{cl}$, —N(R$^{cl}$)SO$_2$NR$^{cl}$C(=O)OR$^{cl}$, —OC(O)N(R$^{cl}$)$_2$, or R$^{cl}$;

$R^{cl}$ is each independently H, C$_{1-12}$ alkyl, C$_{2-12}$ alkenyl, C$_{2-12}$ alkynyl, C$_{3-12}$ cycloalkyl, C$_{3-12}$ cycloalkyl-C$_{1-6}$ alkyl-, heterocyclyl, heterocyclyl-C$_{1-6}$ alkyl-, aryl, aryl-C$_{1-6}$ alkyl-, heteroaryl, or heteroaryl-C$_{1-6}$ alkyl-, wherein C$_{1-12}$ alkyl, C$_{2-12}$ alkenyl, C$_{2-12}$ alkynyl, C$_{3-12}$ cycloalkyl, C$_{3-12}$ cycloalkyl-C$_{1-6}$ alkyl-, heterocyclyl, heterocyclyl-C$_{1-6}$ alkyl-, aryl, aryl-C$_{1-6}$ alkyl-, heteroaryl, and heteroaryl-C$_{1-6}$ alkyl- can be substituted one or more substituents selected from C$_{1-6}$ alkyl, halogen, C$_{1-6}$ alkoxy, —NO$_2$, —NR$^{ns}$R$^{ns}$, —OH, =O, or COOR$^{cs}$;

$R^{ns}$ is each independently H, R$^{cs}$, R$^{cs}$—C(O)—, R$^{cs}$—S(O)$_2$—, R$^{cs}$R$^{cs}$N—C(O)—, or R$^{cs}$R$^{cs}$NS(O)$_2$—;

$R^{cs}$ is each independently H, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, or C$_2$-C$_6$ haloalkynyl; or alternatively, two R$^{cs}$ attached to the same N atom can together with the N atom form a 4-7 membered heterocyclic ring, containing up to one other heteroatom chosen from O, S, or NR$^{ns}$, wherein the 4-7 membered heterocyclic ring is optionally substituted with up to three substituents selected from hydroxyl, C$_{1-6}$ alkoxy, C$_{1-6}$ hydroxyalkyl, C$_{1-6}$ alkoxy-C$_{1-6}$ alkyl, C$_{1-6}$ alkoxy-C$_{1-6}$ alkoxy, C$_{2-6}$ hydroxyalkoxy, oxo, thiono, cyano or halo;

$R^{3b2a}$ and $R^{3b2b}$ are each independently H, halogen, —OH, or —O(C$_{1-3}$ alkyl);

$X^2$ and $Y^2$ are each independently SR$^4$, OR$^4$, NR$^4$R4, BH(OR$^7$)$_2$—, or BH(R$^b$)$_2$—; wherein, at least one of $X^2$ and $Y^2$ is BH(R$^b$)$_2^-$; and $R^4$ and $R^7$ are each independently H or CH$_3$;

$R^b$ is each independently H, CN, carboxyl, carboxyl salts, C$_{1-6}$ alkyl, alkylaryl, aryl, alkoxycarbonyl, or alkylaminocarbonyl, wherein the C$_{1-6}$ alkyl, alkylaryl, aryl, alkoxycarbonyl and alkylaminocarbonyl is each optionally substituted with up to 3 substituents selected from —OH, —P(O)(OH)$_2$, —OP(O)(OH)$_2$, —CO$_2$H, or F.

9. The compound of claim 8, wherein:
$Q^a$ and $Q^b$ are each independently selected from:

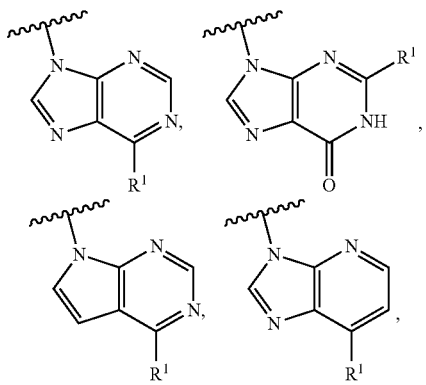

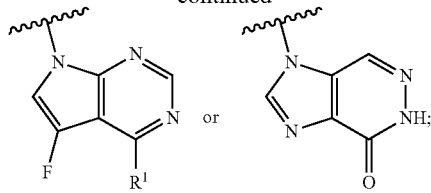

and $R^1$ is each independently hydrogen, halogen, or —N(R$^{cl}$)$_2$, and R$^{cl}$ is each independently H, C$_{1-6}$ alkyl, C$_{3-6}$ cycloalkyl, C$_{3-6}$ cycloalkyl-C$_{1-6}$ alkyl-, 3-6 membered heterocyclyl, (3-6 membered heterocyclyl)-C$_{1-6}$ alkyl-, 5-6 membered aryl, (5-6 membered aryl)-C$_{1-6}$ alkyl-, 5-6 membered heteroaryl, or (5-6 membered heteroaryl)-C$_{1-6}$ alkyl-.

10. The compound of claim 9, wherein:
$Q^a$ and $Q^b$ are each

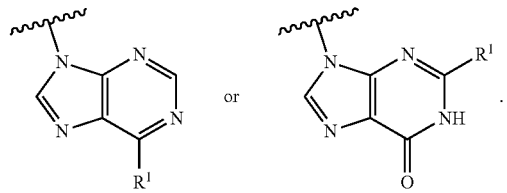

11. The compound of claim 10, wherein:
$Q^a$ and $Q^b$ are each

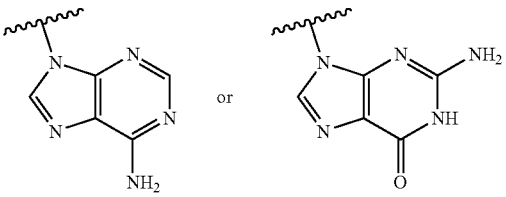

12. The compound of claim 8, wherein $R^{3b2a}$ and $R^{3b2b}$ are each independently selected from H, F or OH.

13. A pharmaceutical composition comprising a compound of claim 8, or a pharmaceutically acceptable salt or stereoisomer thereof, and one or more pharmaceutically acceptable excipients.

14. A method for modulating a stimulator of interferon gene (STING) comprising administering a therapeutically effective amount of a compound of claim 8, or a pharmaceutically acceptable salt or stereoisomer thereof to the subject in need thereof.

15. A method for treating a disease comprising administering a therapeutically effective amount of a compound of claim 8, or a pharmaceutically acceptable salt or stereoisomer thereof to the subject in need thereof;
wherein the disease is selected from cancer, rheumatoid arthritis, psoriasis, acute rejection of an organ transplant, allergic asthma or Crohn's disease.

* * * * *